US012703734B2

(12) United States Patent
Amin et al.

(10) Patent No.: US 12,703,734 B2
(45) Date of Patent: Aug. 11, 2026

(54) METHOD OF ASSESSING ACTIVITY OF RECOMBINANT ANTIGEN RECEPTORS

(71) Applicant: Juno Therapeutics, Inc., Seattle, WA (US)

(72) Inventors: Rupesh Amin, Seattle, WA (US); Aye Chen, Seattle, WA (US)

(73) Assignee: Juno Therapeutics, Inc., Seattle, WA (US)

(*) Notice: Subject to any disclaimer, the term of this patent is extended or adjusted under 35 U.S.C. 154(b) by 167 days.

(21) Appl. No.: 18/506,070

(22) Filed: Nov. 9, 2023

(65) Prior Publication Data

US 2024/0084253 A1 Mar. 14, 2024

Related U.S. Application Data

(62) Division of application No. 16/760,006, filed as application No. PCT/US2018/058781 on Nov. 1, 2018, now Pat. No. 11,851,679.

(60) Provisional application No. 62/599,672, filed on Dec. 15, 2017, provisional application No. 62/596,758, filed on Dec. 8, 2017, provisional application No. 62/580,405, filed on Nov. 1, 2017.

(51) Int. Cl.

| | |
|---|---|
| ***C07K 14/725*** | (2006.01) |
| ***A61K 40/11*** | (2025.01) |
| ***A61K 40/31*** | (2025.01) |
| ***A61K 40/32*** | (2025.01) |
| ***A61K 40/42*** | (2025.01) |
| ***A61K 40/46*** | (2025.01) |
| ***C07K 14/705*** | (2006.01) |
| ***C12N 5/0783*** | (2010.01) |
| ***C12N 15/113*** | (2010.01) |
| ***C12N 15/65*** | (2006.01) |
| ***C12N 15/86*** | (2006.01) |

(52) U.S. Cl.

CPC .......... *C07K 14/7051* (2013.01); *A61K 40/11* (2025.01); *A61K 40/31* (2025.01); *A61K 40/32* (2025.01); *A61K 40/4211* (2025.01); *A61K 40/4215* (2025.01); *A61K 40/46* (2025.01); *C12N 5/0636* (2013.01); *C12N 15/113* (2013.01); *C12N 15/65* (2013.01); *C12N 15/86* (2013.01); *A61K 2239/28* (2023.05); *C07K 2319/03* (2013.01); *C12N 2740/16043* (2013.01)

(58) Field of Classification Search

CPC ............ C07K 14/7051; C07K 2319/03; C07K 16/2803; A61K 40/11; A61K 40/31; A61K 40/32; A61K 40/46; A61K 2239/28; C12N 5/0636; C12N 15/113; C12N 15/65; C12N 15/86; C12N 2740/16043; C12Q 1/6897

USPC ..................... 435/6.1, 91.1, 91.31, 455, 458; 514/44 R, 44 A; 536/23.1, 24.5

See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,811,218 | A | 3/1989 | Hunkapiller et al. |
| 4,897,355 | A | 1/1990 | Eppstein et al. |
| 4,946,787 | A | 8/1990 | Eppstein et al. |
| 5,033,252 | A | 7/1991 | Carter |
| 5,049,386 | A | 9/1991 | Eppstein et al. |
| 5,052,558 | A | 10/1991 | Carter |
| 5,075,216 | A | 12/1991 | Innis et al. |
| 5,130,238 | A | 7/1992 | Malek et al. |
| 5,149,625 | A | 9/1992 | Church et al. |
| 5,171,534 | A | 12/1992 | Smith et al. |
| 5,219,740 | A | 6/1993 | Miller et al. |
| 5,323,907 | A | 6/1994 | Kalvelage |
| 5,356,802 | A | 10/1994 | Chandrasegaran |
| 5,374,527 | A | 12/1994 | Grossman |
| 5,405,746 | A | 4/1995 | Uhlen |
| 5,409,811 | A | 4/1995 | Tabor et al. |

(Continued)

FOREIGN PATENT DOCUMENTS

| | | |
|---|---|---|
| CN | 105777911 | 7/2016 |
| CN | 105837693 | 8/2016 |

(Continued)

OTHER PUBLICATIONS

Ashouri et al (J. Immunol., vol. 198, No. 2, pp. 657-668 (2017) (Year: 2017).*

(Continued)

*Primary Examiner* — Jane J Zara

(74) *Attorney, Agent, or Firm* — Morrison & Foerster LLP

(57) ABSTRACT

Provided herein are methods for screening for one or more activity of a recombinant receptor, including recombinant receptors containing an extracellular antigen-binding domain and an intracellular signaling domain, such as a chimeric antigen receptor (CAR). The methods include assessing activity of a cell expressing the recombinant receptor based on a detectable expression of a reporter molecule that is responsive to a signal through the intracellular signaling region of the recombinant receptor. In some embodiments, the activity assessed is an antigen-dependent or an antigen-independent activity. In some embodiments, the methods can be used to screen a plurality of reporter cells each containing a nucleic acid molecule encoding a candidate recombinant receptor, e.g. CAR, and assessing such cells or plurality of cells for one or more property or activity. The methods can be high-throughput. Also provided are reporter cells, cell compositions, nucleic acids and kits for use in the methods.

28 Claims, 22 Drawing Sheets

Specification includes a Sequence Listing.

(56) References Cited

U.S. PATENT DOCUMENTS

| | | | |
|---|---|---|---|
| 5,409,818 | A | 4/1995 | Davey et al. |
| 5,436,150 | A | 7/1995 | Chandrasegaran |
| 5,455,166 | A | 10/1995 | Walker et al. |
| 5,487,994 | A | 1/1996 | Chandrasegaran |
| 5,547,835 | A | 8/1996 | Koster |
| 5,554,517 | A | 9/1996 | Davey et al. |
| 5,622,824 | A | 4/1997 | Koster |
| 5,624,825 | A | 4/1997 | Walker et al. |
| 5,674,743 | A | 10/1997 | Ulmer |
| 5,707,804 | A | 1/1998 | Mathies et al. |
| 5,716,785 | A | 2/1998 | Van Gelder et al. |
| 5,821,058 | A | 10/1998 | Smith et al. |
| 5,846,727 | A | 12/1998 | Soper et al. |
| 5,854,033 | A | 12/1998 | Lizardi |
| 5,858,671 | A | 1/1999 | Jones |
| 5,876,934 | A | 3/1999 | Duthie et al. |
| 6,066,457 | A | 5/2000 | Hampson et al. |
| 6,087,095 | A | 7/2000 | Rosenthal et al. |
| 6,132,997 | A | 10/2000 | Shannon |
| 6,140,081 | A | 10/2000 | Barbas |
| 6,143,495 | A | 11/2000 | Lizardi |
| 6,207,453 | B1 | 3/2001 | Maass et al. |
| 6,232,107 | B1 | 5/2001 | Bryan et al. |
| 6,258,533 | B1 | 7/2001 | Jones |
| 6,410,319 | B1 | 6/2002 | Raubitschek et al. |
| 6,451,995 | B1 | 9/2002 | Cheung et al. |
| 6,453,242 | B1 | 9/2002 | Eisenberg et al. |
| 6,534,261 | B1 | 3/2003 | Cox et al. |
| 7,070,995 | B2 | 7/2006 | Jensen |
| 7,265,209 | B2 | 9/2007 | Jensen |
| 7,354,762 | B2 | 4/2008 | Jensen |
| 7,446,179 | B2 | 11/2008 | Jensen et al. |
| 7,446,190 | B2 | 11/2008 | Sadelain et al. |
| 7,446,191 | B2 | 11/2008 | Jensen |
| 8,324,353 | B2 | 12/2012 | Jensen |
| 8,339,645 | B2 | 12/2012 | Nakawaki |
| 8,389,282 | B2 | 3/2013 | Sadelain et al. |
| 8,479,118 | B2 | 7/2013 | Lyndersay et al. |
| 8,802,374 | B2 | 8/2014 | Jensen |
| 8,911,993 | B2 | 12/2014 | June et al. |
| 11,066,475 | B2 | 7/2021 | Sather et al. |
| 11,458,167 | B2 | 10/2022 | Jensen |
| 11,851,679 | B2 | 12/2023 | Rupesh et al. |
| 12,428,486 | B2 | 9/2025 | Sather et al. |
| 2002/0131960 | A1 | 9/2002 | Sadelain et al. |
| 2002/0150914 | A1 | 10/2002 | Andersen et al. |
| 2003/0223994 | A1 | 12/2003 | Hoogenboom et al. |
| 2004/0191260 | A1 | 9/2004 | Reiter et al. |
| 2005/0196768 | A1 | 9/2005 | Campbell et al. |
| 2006/0034850 | A1 | 2/2006 | Weidanz et al. |
| 2007/0099253 | A1 | 5/2007 | Erkhov et al. |
| 2007/0116690 | A1 | 5/2007 | Yang et al. |
| 2009/0226474 | A1 | 9/2009 | Weidanz et al. |
| 2009/0304679 | A1 | 12/2009 | Weidanz |
| 2010/0047805 | A1 | 2/2010 | Wang |
| 2011/0207221 | A1 | 8/2011 | Cost et al. |
| 2011/0301073 | A1 | 12/2011 | Gregory et al. |
| 2013/0149337 | A1 | 6/2013 | Cooper et al. |
| 2013/0287748 | A1 | 10/2013 | June et al. |
| 2013/0326645 | A1 | 12/2013 | Cost et al. |
| 2014/0234893 | A1 | 8/2014 | Enenkel |
| 2014/0271635 | A1 | 9/2014 | Brogdon |
| 2014/0294841 | A1 | 10/2014 | Scheinberg et al. |
| 2015/0051266 | A1 | 2/2015 | Kochenderfer |
| 2015/0283178 | A1 | 10/2015 | June et al. |
| 2016/0017286 | A1 | 1/2016 | Albelda et al. |
| 2016/0046724 | A1 | 2/2016 | Brogdon et al. |
| 2016/0051530 | A1 | 2/2016 | Thakurta et al. |
| 2016/0122747 | A1 | 5/2016 | Chen et al. |
| 2016/0237139 | A1 | 8/2016 | Pule et al. |
| 2016/0238613 | A1 | 8/2016 | Wagner |
| 2016/0297884 | A1 | 10/2016 | Kuo et al. |
| 2016/0311907 | A1 | 10/2016 | Brogdon et al. |
| 2017/0051035 | A1 | 2/2017 | Payne et al. |
| 2017/0226216 | A1 | 8/2017 | Morgan et al. |
| 2017/0281766 | A1 | 10/2017 | Wiltzius |
| 2017/0283504 | A1 | 10/2017 | Wiltzius |
| 2018/0334653 | A1 | 11/2018 | O'Neill |
| 2018/0360880 | A1 | 12/2018 | Brentjens et al. |
| 2019/0161553 | A1 | 5/2019 | Blythe et al. |
| 2020/0078404 | A1 | 3/2020 | Ports et al. |
| 2020/0292526 | A1* | 9/2020 | Hause, Jr. .......... G01N 33/6854 |
| 2021/0324100 | A1 | 10/2021 | Sather et al. |
| 2021/0393689 | A1 | 12/2021 | Sather et al. |
| 2021/0393690 | A1 | 12/2021 | Sather et al. |
| 2022/0096651 | A1 | 3/2022 | Costa et al. |
| 2023/0087953 | A1 | 3/2023 | Westoby et al. |
| 2023/0149462 | A1 | 5/2023 | Stirner et al. |
| 2023/0346734 | A1 | 11/2023 | Hudecek et al. |

FOREIGN PATENT DOCUMENTS

| | | | |
|---|---|---|---|
| EP | 2537416 | 12/2012 | |
| WO | WO 1991/016024 | 10/1991 | |
| WO | WO 1991/017424 | 11/1991 | |
| WO | WO 1996/013593 | 5/1996 | |
| WO | WO 1998/053058 | 11/1998 | |
| WO | WO 1998/053059 | 11/1998 | |
| WO | WO 1998/053060 | 11/1998 | |
| WO | WO 1999/018129 | 4/1999 | |
| WO | WO 1999/060120 | 11/1999 | |
| WO | WO 2000/014257 | 3/2000 | |
| WO | WO 2003/020763 | 3/2003 | |
| WO | WO 2003/068201 | 8/2003 | |
| WO | WO 2011/044186 | 4/2011 | |
| WO | WO 2012/129514 | 9/2012 | |
| WO | WO 2013/071154 | 5/2013 | |
| WO | WO 2013/123061 | 8/2013 | |
| WO | WO 2013/126726 | 8/2013 | |
| WO | WO 2013/166321 | 11/2013 | |
| WO | WO 2014/031687 | 2/2014 | |
| WO | WO 2014/055668 | 4/2014 | |
| WO | WO 2014/100385 | 6/2014 | |
| WO | WO 2014/144039 | 9/2014 | |
| WO | WO 2014/190273 | 11/2014 | |
| WO | WO 2015/105522 | 7/2015 | |
| WO | WO 2015/157391 | 10/2015 | |
| WO | WO 2015/158671 | 10/2015 | |
| WO | WO 2015/161276 | 10/2015 | |
| WO | WO 2016/014530 | 1/2016 | |
| WO | WO 2016/014565 | 1/2016 | |
| WO | WO 2016/014789 | 1/2016 | |
| WO | WO 2016/090320 | 6/2016 | |
| WO | WO 2016/090327 | 6/2016 | |
| WO | WO 2016/094304 | 6/2016 | |
| WO | WO 2016/130598 | 8/2016 | |
| WO | WO 2016/138034 | 9/2016 | |
| WO | WO 2016/154628 | 9/2016 | |
| WO | WO-2016138034 A1 * | 9/2016 | ............. G01N 33/53 |
| WO | WO 2016/164580 | 10/2016 | |
| WO | WO 2016/187349 | 11/2016 | |
| WO | WO 2016/210129 | 12/2016 | |
| WO | WO 2016/210262 | 12/2016 | |
| WO | WO 2017/027291 | 2/2017 | |
| WO | WO 2017/041143 | 3/2017 | |
| WO | WO 2017/058754 | 4/2017 | |
| WO | WO 2017/064084 | 4/2017 | |
| WO | WO 2017/087547 | 5/2017 | |
| WO | WO 2017/096329 | 6/2017 | |
| WO | WO 2017/130223 | 8/2017 | |
| WO | WO 2017/180993 | 10/2017 | |
| WO | WO 2017/214207 | 12/2017 | |
| WO | WO 2018/071873 | 4/2018 | |
| WO | WO 2018/075820 | 4/2018 | |
| WO | WO 2018/085731 | 5/2018 | |
| WO | WO 2018/093591 | 5/2018 | |
| WO | WO 2018/102785 | 6/2018 | |
| WO | WO 2018/102786 | 6/2018 | |
| WO | WO 2018/102787 | 6/2018 | |
| WO | WO 2018/197675 | 11/2018 | |

(56) References Cited

FOREIGN PATENT DOCUMENTS

WO WO 2018/204427 11/2018
WO WO 2019/090003 5/2019

OTHER PUBLICATIONS

Moran et al (J. Exp. Med., vol. 208, No. 6, pp. 1279-1289 (2011)), Guo et al (Molecular Therapy—Methods & Clinical Development, vol. 3, No. 15054, pp. 1-12 (2016)) (Year: 2016).*
Guo et al (Molecular Therapy—Methods & Clinical Development, vol. 3, No. 15054, pp. 1-12 (2016)) (Year: 2016).*
Yang et al (Cell, vol. 154, No. 6, pp. 1370-1379 (2013)) (Year: 2013).*
Ali et al., "T cells expressing an anti-B-cell maturation antigen chimeric antigen receptor cause remissions of multiple myeloma," Blood (2016) 128(13):1688-1700.
Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2: e93.
Anderson, "Human Gene Therapy," Science (1992) 256:808-813.
Anson et al., "An improved β-galactosidase reporter gene," J Biotechnol (2004) 108(2004):17-30.
Appleby, "New Technologies for Ultra-High Throughput Genotyping in Plants," Method Mol Biology (2009) 513:19-39.
Ashouri et al., "Endogenous Nur77 is a Specific Indicator of Antigen Receptor Signaling in Human T and B Cells," J Immunol (2017) 198(2):657-668.
Au-Yeung et al., "A sharp T-cell antigen receptor signaling threshold for T-cell proliferation," PNAS (2014) e3679-e3688.
Bergthorsdottir et al., "Signals That Initiate Somatic Hypermutation of B Cells In Vitro," J Immunol (2001) 166(4):228-2234.
Bertilaccio et al., "Low-Dose Lenalidomide Improves CAR-Based Immunotherapy in CLL by Reverting T-Cell Defects In Vivo," Blood (2013) 122(21):4171.
Boris-Lawrie et al., "Recent advances in retrovirus vector technology," Cur. Opin. Genet. Develop. (1993) 3:102-109.
Brash et al., "Strontium phosphate transfection of human cells in primary culture: stable expression of the simian virus 40 large-T-antigen gene in primary human bronchial epithelial cells," Mol. Cell Biol. (1987) 7(5): 2031-2034.
Brentjens et al., "CD19-targeted T cells rapidly induce molecular remissions in adults with chemotherapy-refractory acute lymphoblastic leukemia," Sci Transl Med. (2013) 5(177); 177ra38.
Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90(17): 8033-8037.
Carlens et al., "Ex vivo T lymphocyte expansion for retroviral transduction: influence of serum-free media on variations in cell expansion rates and lymphocyte subset distribution," Exp Hematol (2000) 28(10): 1137-1146.
Cavalieri et al., "Human T lymphocytes transduced by lentiviral vectors in the absence of TCR activation maintain an intact immune competence," Blood (2003) 102(2): 497-505.
Challita et al., "Multiple modifications in cis elements of the long terminal repeat of retroviral vectors lead to increased expression and decreased DNA methylation in embryonic carcinoma cells," J Virol (1995) 69(2):748-755.
Chang et al., "Modification of DNA ends can decrease end joining relative to homologous recombination in mammalian cells," Proc Natl Acad Sci USA (1987) 84(14):4959-4963.
Chervin et al., "Engineering higher affinity T cell receptors using a T cell display system," J Immunol Methods, (2008) 339(2): 175-84.
Chicaybam et al., "An efficient low cost method for gene transfer to T lymphocytes," PLoS ONE (2013) 8(3): e60298.
Chothia et al., "The outline structure of the T-cell alpha beta receptor," EMBO J. (1988) 7(12):3745-3755.
Clackson et al. "Making Antibody Fragments Using Phage Display Libraries," Nature (1991) 352:624-628.
Coco et al., "DNA shuffling method for generating highly recombined genes and evolved enzymes," Nature Biotechnology (2001) 19:354-359.
Cohen et al., "Recombinant antibodies with MHC-restricted, peptide-specific, T-cell receptor-like specificity: new tools to study antigen presentation and TCR-peptide-MHC interactions," J Mol Recognit. (2003) 16(5):324-332.
Cooper et al., "T-cell clones can be rendered specific for CD19: toward the selective augmentation of the graft-versus-B-lineage leukemia effect," Blood. (2003) 101:1637-1644.
Davila et al., "CD19 CAR-targeted T cells induce long-term remission and B Cell Aplasia in an immunocompetent mouse model of B cell acute lymphoblastic leukemia," PLoS ONE (2013) 8(4):e61338.
De Felipe, "Skipping the co-expression problem: the new 2A "CHYSEL" technology," Genet Vaccines Ther Sep. 13, 2004;2(1):13.
De Felipe, "Targeting of proteins derived from self-processing polyproteins containing multiple signal sequences," Traffic (2004) 5(8): 616-626.
De Haard et al., "A large non-immunized human Fab fragment phage library that permits rapid isolation and kinetic analysis of high affinity antibodies," J Biol Chem (1999) 274(26):18218-18230.
Deniger et al., "A pilor trial of the combination of vemurafenib with adoptive cell therapy in patients with metastatic melanoma," Clin Can Res (2017) 23(2):351-362.
Dillion et al., "Regulating gene expression in gene therapy," TIBTECH (1993) 11:167-175.
Duong et al., "Engineering T Cell Function Using Chimeric Antigen Receptors Identified Using a DNA Library Approach," PLOS One (2013) 8(5):e63037.
Fox et al., "Applications of Ultra-high-Throughput Sequencing," Methods Mol Biol (2009) 553:79-108.
Fraiette et al., "Immunobiology ibrutinib enhances chimeric antigen receptor T-cell engraftment and efficacy in leukemia," Blood (2016) 127:1117-1127.
Gacerez et al., "How Chimeric Antigen Receptor Design Affects Adoptive T Cell Therapy," J Cell Physiol (2016) 231(12):2590-2598.
Gomes-Silva et al., "Tonic 4-1BB Costimulation in Chimeric Antigen Receptors Impedes T Cell Survival and is Vector-Dependent," Cell Reports (2017) 21:17-26.
Griffiths et al. "Isolation of high affinity human antibodies directly from large synthetic repertoires," EMBO J (1994) 13(14):3245-3260.
Griffiths et al., "Human anti-self antibodies with high specificity from phage display libraries," EMBO Journal (1993) 12(2):725-734.
Guo et al., "Rapid cloning, expression, and functional characterization of paired alpha-beta and gamma-delta T-cell receptor chains from single-cell analysis," Mol Ther (2016) 3:15054.
Harrington et al., "Development of JCARH125: Optimization of a fully human anti-Bcma CAR for use in the treatment of multiple myeloma," Blood (2017) 130(Supp 1):1813-1813.
Harrington et al., "JCARH125: Development of an Optimized Fully Human Anti-BCMA CAR for the Treatment of Multiple Myeloma," Presented at 2017 ASH. Dec. 9-12. Poster 1813.
He et al., "Knock-in of large reporter genes in human cells via CRISPR/Cas9-induced homology-dependent and independent DNA repair," Nucleic Acids Research (2016) 44(9):e85.
Heigwer et al., "E-CRISP: fast CRISPR target site identification," Nat Methods (2014) 11(2):122-123.
Hoekstra et al., "Assessing T lymphocyte function and differentiation by genetically encoded reporter systems," Trends in Immunology (2015) 36(7):P392-400.
Holler et al., "TCRs with high affinity for foreign pMHC show self-reactivity," Nat Immunol (2003) 4(1): 55-62.
Holler et al., "In vitro Evolution of a T Cell Receptor With High Affinity for Peptide/MHC," Proc Natl Acad Sci USA (2009) 97(10):5387-5392.
Hsu et al., "DNA targeting specificity of RNA-guided Cas9 nucleases,"Nat Biotechnol (2013) 31(9):827-832.

(56) References Cited

OTHER PUBLICATIONS

Huang et al., "DNA transposons for modification of human primary T lymphocytes," Methods Mol Biol (2009) 506: 115-126.
Hudecek et al., "Receptor affinity and extracellular domain modifications affect tumor recognition by ROR1-specific chimeric antigen receptor T cells," Clin Cancer Res. Jun. 15, 2013;19(12):3153-3164.
Hudecek et al., "The nonsignaling extracellular spacer domain of chimeric antigen receptors is decisive for in vivo antitumor activity," Cancer Immunol Res (2015) 3(2):125-135.
Ibraheem et al., "Designs and applications of fluorescent protein-based biosensors," Curr Opin Chem Biol (2010) 14(1):30-36.
Imelfort et al., "De novo sequencing of plant genomes using second-generation technologies," Brief Bioinform (2009) 10:609-618.
Jensen et al., "Design and implementation of adoptive therapy with chimeric antigen receptor-modified T cells," Immunol Rev (2014) 257(1):127-144.
Jiang et al., "T cell exhaustion in the tumor microenvironment," Cell Death & Disease (2015) 6:e1792.
Johnston, et al., "Biolistic transformation: microbes to mice," Nature (1990) 346: 776-777.
Jonnalagadda et al., "Chimeric antigen receptors with mutated IgG4 Fc spacer avoid fc receptor binding and improve T cell persistence and antitumor efficacy," Mol Ther. (2015) 23(4):757-68.
Jores et al., "Resolution of hypervariable regions in T-cell receptor beta chains by a modified Wu-Kabat index of amino acid diversity," Proc Natl Acad Sci U S A. (1990) 87(23):9138-9142.
Kapustin et al., "Cryptic splice sites and split genes," Nucleic Acids Res. (2011) 39(14):5837-5844.
Khalil et al., "The future of cancer treatment: immunomodulation, CARs and combination immunotherapy," Nature Reviews Clinical Oncology (2016) 13(5):272-290.
Kim et al., "Chimeric restriction endonuclease," PNAS (1994) 91(3):883-887.
Kim et al., "Insertion and Deletion Mutants of FokO Restriction Endonuclease," J Biol Chem (1994) 269(50):31978-31982.
Kindt et al., Kuby Immunology 6th ed., W.H. Freeman and Co. (2007) p. 91.
Knappik et al., "Fully synthetic human combinatorial antibody libraries (HuCAL) based on modular consensus frameworks and CDRs randomized with trinucleotides," J Mol Biol (2000) 296(1):57-86.
Koste et al., "T-cell receptor transfer into human T cells with ecotropic retroviral vectors," Gene Therapy (2014) 21: 533-538.
Kuramitsu et al., "Lenalidomide enhances the function of chimeric antigen receptor T cells against the epidermal growth factor receptor variant III by enhancing immune synapses," Cancer Gene Therapy (2015) 22:487-495.
Kurucz et al., "A bacterially expressed single-chain Fv construct from the 2B4 T-cell receptor," PNAS (1993) 90(9): 3830-3834.
Lefranc et al., "IMGT unique numbering for immunoglobulin and T cell receptor variable domains and Ig superfamily V-like domains," Dev Comp Immunol (2003) 27(1):55-77.
Leung et al., "A method for random mutagenesis of a defined DNA segment using a modified polymerase chain reaction," J Method Cell Mol Biol (1989) 1(1):11-15.
Li et al., "Alteration of the cleavage distance of Fok I restriction endonuclease by insertion mutagenesis," PNAS (1993) 90(7):2764-2768.
Li et al., "Directed evolution of human T-cell receptors with picomolar affinities by phage display," Nat Biotechnol (2005) 23:349-354.
Li et al., "Functional domains in Fok I restriction endonuclease," Proc Natl Acad Sci USA (1992) 89(10):4275-4279.
Liu et al., "Inclusion of Strep-tag II in design of antigen receptors for T-cell immunotherapy," Nat Biotechnol (2016) 34(4): 430-434.
Lloyd et al., "Beyond the antigen receptor: editing the genome of T-cells for cancer adoptive cellular therapies," Front in Immunology (2013) 4(Article 221):1-7.
Long et al., "4-1BB costimulation ameliorates T cell exhaustion induced by tonic signaling of chimeric antigen receptors," Nat Med (2015) 21(6):581-590.
Mali et al., "RNA-Guided Human Genome Engineering via Cas9," Science (2013) 339(6121):823-826.
Mamonkin et al., "Tonic 4-1BB signaling from chimeric antigen receptors (CARs) impairs expansion of T cells due to Fas-mediated apoptosis," J Immunol (2016) 196(1 Suppl) 143:7.
Manuri et al., "PiggyBac transposon/transposase system to generate CD19-specific T cells for the treatment of B-lineage malignancies," Hum Gene Ther (2010) 21(4): 427-437.
Margulies et al., "Genome Sequencing in Open Microfabricated High Density Picoliter Reactors," Nature (2005) 437(7057):376-380.
Marks et al., "By-passing immunization. Human antibodies from V-gene libraries displayed on phage," J Mol Biol (1991) 222(3):581-597.
Miller et al., "Improved retroviral vectors for gene transfer and expression," Biotechniques (1989) 7(9):980-982.
Miller et al., "Retrovirus packaging cells," Human Gene Therapy (1990) 1: 5-14.
Miller, "Human Gene Therapy Comes of Age," Nature (1992) 357:455-460.
Mitani, "Delivering therapeutic genes-matching approach and application," TIBTECH (1993) 11:162-166.
Moran et al., "T cell receptor signal strength in Treg and iNKT cell development demonstrated by a novel fluorescent reporter mouse," JEM (2011) 208(6):1279-1289.
Morozova et al., "Applications of next-generation sequencing technologies in functional genomics," Genomics (2008) 92(5):255-264.
Nabel et al., "Direct gene transfer for immunotherapy and immunization," Trends Biotechnol (1993) 11(5):211-215.
NCBI-GEN E—"TNFRSF17 TNF receptor superfamily member 17 [*Homo sapiens* (human)]" pp. 1-6 (Sep. 25, 2023, 10:06 AM).
Ormhoj et al., "CARs in the Lead Against Multiple Myeloma," Curr Hematol Malig Resp (2017) 12(2):119-125.
Otahal et al., "Lenalidomide enhances antitumor functions of chimeric antigen receptor modified T cells," Oncoimmunology (2015) 5(4):e1115940.
Park et al., "Treating cancer with genetically engineered T cells," Trends Biotechnol. (2011) 29(11): 550-557.
Portolano et al., "Lack of promiscuity in autoantigen-specific H and L chain combinations as revealed by human H and L chain "roulette"," J. Immunol. (1993) 150:880-887.
Preynyak et al., "Codon optimality is a major determinant of mRNA stability," Cell (2015) 160:1111-1124.
Pritchard et al., "A Genereal model of error-prone PCR," J Theroretical Biol (2005) 234:497-509.
Qian et al., "Progress of Engineering Chimeric Antigen Receptor in Tumor Therapy," Letters in Biotechnology. (2017) 28:2; 188-195 (Article in Chinese) English abstract provided.
Qin et al., "Incorporation of a hinge domain improves the expansion of chimeric antigen receptor T cells," J Hematol Oncol. (2017) 10(1):68.
Reidhaar-Olson et al., "Random mutagenesis of protein sequences using oligonucleotide cassettes," Methods Enzymol (1991) 208:564-586.
Ronaghi et al., "Real-time DNA sequencing using detection of pyrophosphate release," Anal Biochem (1996) 242(1):84-89.
Ruella et al., "Dual CD19 and CD123 targeting prevents antigen-loss relapses after CD19-directed immunotherapies," J Clin Invest (2016) 126(10):3814-3826.
Sadelain et al., "The basic principles of chimeric antigen receptor design," Cancer Discov. (2013) 3(4): 388-398.
Saiki et al., "Primer-directed enzymatic amplification of DNA with a thermostable DNA polymerase," Science (1988) 239(4839):487-491.
Sander et al., "CRISPR-Cas systems for editing, regulating and targeting genomes," Nat Biotechnol (2014) 32(4):347-355.
Sanjana et al., "Improved vectors and genome-wide libraries for CRISPR screening," Nat Methods (2014) 11(8):783-784.

(56) References Cited

OTHER PUBLICATIONS

Sarkar et al., "Access to a messenger RNA sequence or its protein product is not limited by tissue or species specificity," Science (1989) 244(4902):331-334.
Scarpa et al., "Characterization of recombinant helper retroviruses from Moloneybased vectors in ecotropic and amphotropic packaging cell lines," Virology (1991) 180: 849-852.
Schlueter et al., "Specificity and binding properties of a single-chain T cell receptor," J Mol Biol. (1996) 256(5): 859-69.
Schuler et al., SYFPEITHI, Database for Searching and T-Cell Epitope Prediction. in Immunoinformatics Methods in Molecular Biology, (2007) 409(1): 75-93.
Sharma et al., "Efficient sleeping beauty DNA transposition from DNA minicircles," Molec Ther Nucl Acids (2013) 2: e74.
Shendure et al., "Accurate multiplex polony sequencing of an evolved bacterial genome,"Science (2005) 309:1728-1732.
Singh et al., "ProPred: prediction of HLA-DR binding sites," Bioinformatics. (2001) 17(12): 1236-1237.
Smith et al., "Development and evaluation of a human single chain variable fragment (scFv) derived BCMA targeted CAR T cell vector leads to a high overall response rate in patients with advanced MM," Blood 130(Suppl_1):742.
Soo Hoo et al., "Characterization of a single-chain T-cell receptor expressed in *Escherichia coli*," Proc Natl Acad Sci U S A. (1992) 89(10): 4759-4763.
Stemmer, "Rapid evolution of a protein in vitro by DNA shuffling," Nature (1994) 370:389-391.
Swarts et al., "DNA-guided DNA interference by a prokaryotic Argonaute," Nature (2014) 507(7491):258-261.
Thaker et al., "TCR and CD28 activate the transcription factor NF-B in T-cells viadistinct adaptor signaling complexes," Immunology Letters (2015) 163:113-119.
Turtle et al., "Engineered T cells for anti-cancer therapy," Curr. Opin. Immunol. (2012) 24(5): 633-639.
Ullenhag et al., "Clinical and immune effects of lenalidomide in combination with gemcitabine in patients with advanced pancreatic cancer," PLOS One (2017) 12(1):e0169736.
Van Brunt et al., "Molecular Farming: Transgenic Animals as Bioreactors," Biotechnology (N Y) (1988) 6(10):1149-1154.
Van Tendeloo et al., "High-level transgene expression in primary human T lymphocytes and adult bone marrow CD34+ cells via electroporation-mediated gene delivery," Gene Therapy (2000) 7(16): 1431-1437.
Verhoeyen et al., "Lentiviral vector gene transfer into human T cells," Methods Mol Biol. (2009) 506: 97-114.
Vigne et al., "Third-generation adenovectors for gene therapy," Restorative Neurology and Neuroscience (1995)8:35-36.
Wang et al., "Lenalidomide enhances the function of CS1 chimeric antigen receptor redirected-T cells against multiple myeloma," Blood (2016) 128-812.
Wang et al., "Phenotypic and functional attributes of lentivirus-modified CD19-specific human CD8+ central memory T cells manufactured at clinical scale," J Immunother (2012) 35(9): 689-701.
Wu et al., "Adoptive T-cell therapy using autologous tumor-infiltrating lymphocytes for metastatic melanoma: current status and future outlook," Cancer (2012) 18(2): 160-175.
Wulfing et al., "Correctly folded T-cell receptor fragments in the periplasm of *Escherichia coli*. Influence of folding catalysts," J Mol Biol. (1994) 242(5): 655-69.
Yanagi et al., "Transcripts from a single full-length cDNA clone of hepatitis C virus are infectious when directly transfected into the liver of achimpanzee," PNAS (1997) 94(16):8738-8743.
Yang et al., One-step generation of Mice carrying reporter and conditional alleles by CRISPR/Cas-mediated genome engineering (including supplemental information) Cell (2013) 154(6):1370.
Yu et al., "Progress towards gene therapy for HIV infection," Gene Ther (1994) 1(1):13-26.
Yudushkin et al., "Imaging T-cell receptor activation reveals accumulation of tyrosine-phosphorylated CD3ζ in the endosomal compartment," PNAS (2010) 107:22128-22133.
Zheng et al., "Enhancing adoptive cell therapy of cancer through targete delivery of small-molecule immunomodulators to internalizing or noninternalizing receptors," ACS NANO (2017) 11(3):3089-3100.
Zheng et al., "Protein L: a novel reagent for the detection of chimeric antigen receptor (CAR) expression by flow cytometry," J Transl Med (2012) 10:29, 6 pages.
Zoller et al., "Oligonucleotide-directed mutagenesis using M13-derived vectors: an efficient and general procedure for the production of point mutations in any fragment of DNA," Nucl Acids Res (1982) 10(20):6487-6504.
Akbar et al., "A compact vocabulary of paratope-epitope interactions enables predictability of antibody-antigen binding," Cell Reports (Mar. 16, 2021) 34(11):108856, 21 pages.
Beckman et al., "Antibody constructs in cancer therapy: protein engineering strategies to improve exposure in solid tumors," Cancer (Jan. 8, 2007, e-pub. Dec. 11, 2006) 109(2):170-179.
Brittain, "X-ray Diffraction III: Pharmaceutical Applications of X-ray Powder Diffraction," Spectroscopy (Jul. 2001) 16(7):14-18, p. 15.
Cespedes et al., "Mouse models in oncogenesis and cancer therapy," Clin Transl Oncol (May 2006) 8(5):318-329.
Dennis, "Off by a whisker," Nature (Aug. 17, 2006) 442 (7104):739-741.
Fujimori et al., "A Modeling Analysis of Monoclonal Antibody Percolation Through Tumors: A Binding-Site Barrier," J Nucl Med (Jul. 1990) 31(7):1191-1198.
Hagner et al., "CC-122, a pleiotropic pathway modifier, mimics an interferon response and has antitumor activity in DLBCL," Blood (Aug. 6, 2015, e-pub. May 22, 2015) 126(6):779-789.
Huang et al., "Genetic Engineering Antibody," South China University of Technology Press (Dec. 1997): p. 63. English translation provided.
Huang et al., "Recombinant immunotherapeutics: current state and perspectives regarding the feasibility of the market," Appl. Microbiol. Biotechnol. (Jun. 2010, e-pub. Apr. 27, 2010) 87:401-410.
Lo et al., "Conformational epitope matching and prediction based on protein surface spiral features," BMC Genomics (May 31, 2021) 22:116, 16 pages.
Marks et al., "How repertoire data are changing antibody science," J. Biol. Chem. (Jul. 17, 2020, e-pub. May 14, 2020) 295(29):9823-9837.
Rudnick et al., "Affinity and Avidity in Antibody-Based Tumor Targeting." Cancer Biother Radiopharm (Apr. 2009) 24(2):155-161.
Tai et al., "Targeting B-cell maturation antigen in multiple myeloma," Immunotherapy (2015) 7(11):1187-1199.
Talmadge et al., "Murine Models to Evaluate Novel and Conventional Therapeutic Strategies for Cancer," Am J Pathol (Mar. 2007) 170(3):793-804.
Thurber et al., "Antibody tumor penetration: transport opposed by systemic and antigen-mediated clearance," Adv Drug Deliv Rev (Sep. 2008, e-pub. Apr. 24, 2008) 60(12):1421-1434.
Vajda et al., "Progress toward improved understanding of antibody maturation," Current Opinion in Structural Biology (Apr. 2021, e-pub. Feb. 17, 2021) 67:226-231.
Voskoglou-Nomikos et al., "Clinical Predictive Value of the in Vitro Cell Line, Human Xenograft, and Mouse Allograft Preclinical Cancer Models[1]," Clin Can Res (Sep. 15, 2003) 9:4227-4239.
U.S. Appl. No. 19/310,817, filed Aug. 26, 2025, by Sather et al. (Copy not provided). (Copy not submitted herewith pursuant to the waiver of 37 C.F. R. § 1.98(a)(2)(iii) issued by the Office on Sep. 21, 2004).

* cited by examiner

SEQUENCE LISTING

```
Sequence total quantity: 77
SEQ ID NO: 1           moltype = DNA  length = 2603
FEATURE                Location/Qualifiers
misc_feature           1..2603
                       note = Human Nur77 DNA NCBI Reference Sequence:
                        NM_001202233.1
source                 1..2603
                       mol_type = other DNA
                       organism = Homo sapiens
SEQUENCE: 1
ttcctggtgt aagctttggt atggatggtg gccgtctccc tacagactgg gagctgttag  60
agggcaggga tcctagctga cacatctatg tcctcgcctt ggttggaggc ctccaccatg  120
gacagaggcc aggccctgcc cctcccaggc agcctggctc cttctgctgg gccctgaagg  180
cagacgggat aatgtggttg gccaaggcct gttggtccat ccagagtgag atgccctgta  240
tccaagccca atatgggaca ccagcaccga gtccgggacc ccgtgaccac ctggcaagcg  300
accccctgac ccctgagttc atcaagccca ccatggacct ggccagcccc gaggcagccc  360
ccgctgcccc cactgccctg cccagcttca gcaccttcat ggacggctac acaggagagt  420
ttgacacctt cctctaccag ctgccaggaa cagtccagcc atgctcctca gcctcctcct  480
cggcctcctc cacatcctcg tcctcagcca cctcccctgc ctctgcctcc ttcaagttcg  540
aggacttcca ggtgtacggc tgctaccccg gcccctgag cggcccagtg gatgaggccc  600
tgtcctccag tggctctgac tactatggca gcccctgctc ggccccgtcg ccctccacgc  660
ccagcttcca gccgccccag ctctctccct gggatggctc cttcggccac ttctcgccca  720
gccagactta cgaaggcctg cgggcatgga cagagcagct gcccaaagcc tctgggcccc  780
cacagcctcc agccttcttt tccttcagtc ctcccaccgg ccccagcccc agcctggccc  840
agagccccct gaagttgttc ccctcacagg ccacccacca gctggggag ggagagagct  900
attccatgcc tacggccttc ccaggtttgg cacccacttc tccacacctt gagggctcgg  960
ggatactgga tacacccgtg acctcaacca aggcccggag cggggcccca ggtggaagtg  1020
aaggccgctg tgctgtgtgt ggggacaacg cttcatgcca gcattatggt gtccgcacat  1080
gtgagggctg caagggcttc ttcaagcgca cagtgcagaa aaacgccaag tacatctgcc  1140
tggctaacaa ggactgccct gtggacaaga ggcggcgaaa ccgctgccag ttctgccgct  1200
tccagaagtg cctggcggtg ggcatggtga aggaagttgt ccgaacagac agcctgaagg  1260
ggcggcgggg ccggctacct tcaaaaccca agcagccccc agatgcctcc cctgccaatc  1320
tcctcacttc cctggtccgt gcacacctgg actcagggcc cagcactgcc aaactggact  1380
actccaagtt ccaggagctg gtgctgcccc actttgggaa ggaagatgct ggggatgtac  1440
agcagttcta cgacctgctc tccggttctc tggaggtcat ccgcaagtgg gcggagaaga  1500
tccctggctt tgctgagctg tcaccggctg accaggacct gttgctggag tcggccttcc  1560
tggagctctt catcctccgc ctggcgtaca ggtctaagcc aggcgagggc aagctcatct  1620
tctgctcagg cctggtgcta caccggctgc agtgtgcccg tggcttcggg gactggattg  1680
acagtatcct ggccttctca aggtccctgc acagcttgct tgtcgatgtc cctgccttcg  1740
cctgcctctc tgcccttgtc ctcatcaccg accggcatgg gctgcaggag ccgcggcggg  1800
```

-continued

```
tggaggagct gcagaaccgc atcgccagct gcctgaagga gcacgtggca gctgtggcgg  1860
gcgagcccca gccagccagc tgcctgtcac gtctgttggg caaactgccc gagctgcgga  1920
ccctgtgcac ccagggcctg cagcgcatct tctacctcaa gctggaggac ttggtgcccc  1980
ctccacccat cattgacaag atcttcatgg acacgctgcc cttctgaccc ctgcctggga  2040
acacgtgtgc acatgcgcac tctcatatgc caccccatgt gcctttagtc cacggacccc  2100
cagagcaccc ccaagcctgg gcttgagctg cagaatgact ccaccttctc acctgctcca  2160
ggaggtttgc agggagctca agcccttggg gagggggatg ccttcatggg ggtgacccca  2220
cgatttgtct tatcccccc agcctggccc cggcctttat gtttttttgta agataaaccg  2280
tttttaacac atagcgccgt gctgtaaata agcccagtgc tgctgtaaat acaggaagaa  2340
agagcttgag gtgggagcgg ggctgggagg aagggatggg ccccgccttc ctgggcagcc  2400
tttccagcct cctgctggct ctctcttcct accctccttc cacatgtaca taaactgtca  2460
ctctaggaag aagacaaatg acagattctg acatttatat ttgtgtattt tcctggattt  2520
atagtatgtg acttttctga ttaatatatt taatatattg aataaaaaat agacatgtag  2580
ttggaactga aaaaaaaaaa aaa                                           2603

SEQ ID NO: 2           moltype = AA  length = 610
FEATURE                Location/Qualifiers
REGION                 1..610
                       note = Human Nur77 NCBI Reference Sequence: NP_001189162.1
source                 1..610
                       mol_type = protein
                       organism = Homo sapiens
SEQUENCE: 2
MWLAKACWSI QSEMPCIQAQ YGTPAPSPGP RDHLASDPLT PEFIKPTMDL ASPEAAPAAP  60
TALPSFSTFM DGYTGEFDTF LYQLPGTVQP CSSASSSASS TSSSSATSPA SASFKFEDFQ  120
VYGCYPGPLS GPVDEALSSS GSDYYGSPCS APSPSTPSFQ PPQLSPWDGS FGHFSPSQTY  180
EGLRAWTEQL PKASGPPQPP AFFSFSPPTG PSPSLAQSPL KLFPSQATHQ LGEGESYSMP  240
TAFPGLAPTS PHLEGSGILD TPVTSTKARS GAPGGSEGRC AVCGDNASCQ HYGVRTCEGC  300
KGFFKRTVQK NAKYICLANK DCPVDKRRRN RCQFCRFQKC LAVGMVKEVV RTDSLKGRRG  360
RLPSKPKQPP DASPANLLTS LVRAHLDSGP STAKLDYSKF QELVLPHFGK EDAGDVQQFY  420
DLLSGSLEVI RKWAEKIPGF AELSPADQDL LLESAFLELF ILRLAYRSKP GEGKLIFCSG  480
LVLHRLQCAR GFGDWIDSIL AFSRSLHSLL VDVPAFACLS ALVLITDRHG LQEPRRVEEL  540
QNRIASCLKE HVAAVAGEPQ PASCLSRLLG KLPELRTLCT QGLQRIFYLK LEDLVPPPPI  600
IDKIFMDTLP                                                          610

SEQ ID NO: 3           moltype = RNA  length = 20
FEATURE                Location/Qualifiers
misc_feature           1..20
                       note = Synthetic
misc_feature           1..20
                       note = Human Nur77 gRNA 1 targeting domain
source                 1..20
                       mol_type = other RNA
                       organism = synthetic construct
SEQUENCE: 3
catgaagatc ttgtcaatga                                               20

SEQ ID NO: 4           moltype = RNA  length = 19
FEATURE                Location/Qualifiers
misc_feature           1..19
                       note = Synthetic
misc_feature           1..19
                       note = Human Nur77 gRNA 2 targeting domain
source                 1..19
                       mol_type = other RNA
                       organism = synthetic construct
SEQUENCE: 4
tgcacacgtg ttcccaggc                                                19

SEQ ID NO: 5           moltype = DNA  length = 54
FEATURE                Location/Qualifiers
misc_feature           1..54
                       note = Synthetic
misc_feature           1..54
                       note = T2A DNA
source                 1..54
                       mol_type = other DNA
                       organism = synthetic construct
SEQUENCE: 5
gaaggcagag gctctctcct cacatgtggg gatgttgaag aaaatccagg tccc         54

SEQ ID NO: 6           moltype = AA  length = 18
FEATURE                Location/Qualifiers
REGION                 1..18
                       note = Synthetic
REGION                 1..18
                       note = T2A protein
source                 1..18
                       mol_type = protein
```

```
                        organism = synthetic construct
SEQUENCE: 6
EGRGSLLTCG DVEENPGP                                                18

SEQ ID NO: 7            moltype = DNA  length = 1422
FEATURE                 Location/Qualifiers
misc_feature            1..1422
                        note = Synthetic
misc_feature            1..1422
                        note = tdTomato DNA
source                  1..1422
                        mol_type = other DNA
                        organism = synthetic construct
SEQUENCE: 7
gtgagcaagg gcgaggaggt gatcaaggag tttatgagat tcaaagtccg gatggagggc  60
agcatgaacg gacatgagtt cgaaattgag ggagaaggcg agggacgacc ttacgaggga  120
acacagaccg ccaaactgaa agtgacaaaa ggcggacctc tgccatttgc ttgggacatc  180
ctgagtccac agttcatgta tggctctaag gcttacgtga aacaccctgc cgatattccc  240
gactacaaaa aactgagttt ccctgaaggc ttcaaatggg aacgagtgat gaactttgag  300
gacggaggcc tggtgacagt gacacaggac tctagtctcc aggacggcac actcatctac  360
aaagtgaaaa tgaggggcac caatttccct cccgatggac ctgtcatgca gaaaaaaaca  420
atgggatggg aggcttctac cgaacgactg tacccacggg atggagtgct gaaaggcgag  480
atccatcagg cactgaaact gaaggatggc ggccattacc tggtcgagtt caaaaccatc  540
tatatggcca aaaaacccgt ccagctgcct ggctactatt acgtggatac caaactggac  600
attacctctc acaatgaaga ctacacaatc gtcgagcagt acgagaggag tgagggccga  660
caccacctct tcctcgggca tggcaccggc agcaccggca gcggcagctc cggcaccgct  720
agttccgagg acaacaacat ggccgtcatc aaagagttca tgcgcttcaa ggtgcgcatg  780
gagggctcca tgaacggcca cgagttcgag atcgagggcg agggcgaggg ccgcccctac  840
gagggcaccc agaccgccaa gctgaaggtg accaagggcg gccccctgcc cttcgcctgg  900
gacatcctgt ccccccagtt catgtacggc tccaaggcgt acgtgaagca ccccgccgac  960
atccccgatt acaagaagct gtccttcccc gagggcttca agtgggagcg cgtgatgaac  1020
ttcgaggacg gcggtctggt gaccgtgacc caggactcct ccctgcagga cggcacgctg  1080
atctacaagg tgaagatgcg cggcaccaac ttcccccccg acggccccgt aatgcagaag  1140
aagaccatgg gctgggaggc ctccaccgag cgcctgtacc cccgcgacgg cgtgctgaag  1200
ggcgagatcc accaggccct gaagctgaag gacggcggcc actacctggt ggagttcaag  1260
accatctaca tggccaagaa gcccgtgcaa ctgcccggct actactacgt ggacaccaag  1320
ctggacatca cctcccacaa cgaggactac accatcgtgg aacagtacga gcgctccgag  1380
ggccgccacc acctgttcct gtacggcatg gacgagctgt ac                     1422

SEQ ID NO: 8            moltype = AA  length = 474
FEATURE                 Location/Qualifiers
REGION                  1..474
                        note = Synthetic
REGION                  1..474
                        note = tdTomato protein
source                  1..474
                        mol_type = protein
                        organism = synthetic construct
SEQUENCE: 8
VSKGEEVIKE FMRFKVRMEG SMNGHEFEIE GEGEGRPYEG TQTAKLKVTK GGPLPFAWDI  60
LSPQFMYGSK AYVKHPADIP DYKKLSFPEG FKWERVMNFE DGGLVTVTQD SSLQDGTLIY  120
KVKMRGTNFP PDGPVMQKKT MGWEASTERL YPRDGVLKGE IHQALKLKDG GHYLVEFKTI  180
YMAKKPVQLP GYYYVDTKLD ITSHNEDYTI VEQYERSEGR HHLFLGHGTG STGSGSSGTA  240
SSEDNNMAVI KEFMRFKVRM EGSMNGHEFE IEGEGEGRPY EGTQTAKLKV TKGGPLPFAW  300
DILSPQFMYG SKAYVKHPAD IPDYKKLSFP EGFKWERVMN FEDGGLVTVT QDSSLQDGTL  360
IYKVKMRGTN FPPDGPVMQK KTMGWEASTE RLYPRDGVLK GEIHQALKLK DGGHYLVEFK  420
TIYMAKKPVQ LPGYYYVDTK LDITSHNEDY TIVEQYERSE GRHHLFLYGM DELY        474

SEQ ID NO: 9            moltype = DNA  length = 140
FEATURE                 Location/Qualifiers
misc_feature            1..140
                        note = Human Nur77 final exon and 3' UTR sequence
source                  1..140
                        mol_type = other DNA
                        organism = Homo sapiens
SEQUENCE: 9
ctcaagctgg aggacttggt gccccctcca cccatcattg acaagatctt catggacacg  60
ctgcccttct gacccctgcc tgggaacacg tgtgcacatg cgcactctca tatgccaccc  120
catgtgcctt tagtccacgg                                              140

SEQ ID NO: 10           moltype = DNA  length = 140
FEATURE                 Location/Qualifiers
misc_feature            1..140
                        note = Human Nur77 final exon and 3' UTR sequence
                         complement strand
source                  1..140
                        mol_type = other DNA
                        organism = Homo sapiens
SEQUENCE: 10
```

```
gagttcgacc tcctgaacca cgggggaggt gggtagtaac tgttctagaa gtacctgtgc  60
gacgggaaga ctggggacgg acccttgtgc acacgtgtac gcgtgagagt atacggtggg  120
gtacacggaa atcaggtgcc                                              140

SEQ ID NO: 11          moltype = AA  length = 357
FEATURE                Location/Qualifiers
REGION                 1..357
                       note = Synthetic
REGION                 1..357
                       note = EGFRt
source                 1..357
                       mol_type = protein
                       organism = synthetic construct
SEQUENCE: 11
MLLLVTSLLL CELPHPAFLL IPRKVCNGIG IGEFKDSLSI NATNIKHFKN CTSISGDLHI  60
LPVAFRGDSF THTPPLDPQE LDILKTVKEI TGFLLIQAWP ENRTDLHAFE NLEIIRGRTK  120
QHGQFSLAVV SLNITSLGLR SLKEISDGDV IISGNKNLCY ANTINWKKLF GTSGQKTKII  180
SNRGENSCKA TGQVCHALCS PEGCWGPEPR DCVSCRNVSR GRECVDKCNL LEGEPREFVE  240
NSECIQCHPE CLPQAMNITC TGRGPDNCIQ CAHYIDGPHC VKTCPAGVMG ENNTLVWKYA  300
DAGHVCHLCH PNCTYGCTGP GLEGCPTNGP KIPSIATGMV GALLLLLVVA LGIGLFM     357

SEQ ID NO: 12          moltype = DNA  length = 48
FEATURE                Location/Qualifiers
misc_feature           1..48
                       note = CD33 leader sequence
source                 1..48
                       mol_type = other DNA
                       organism = Homo sapiens
SEQUENCE: 12
atgccgctgc tgctactgct gcccctgctg tgggcagggg ctctagag               48

SEQ ID NO: 13          moltype = AA  length = 16
FEATURE                Location/Qualifiers
REGION                 1..16
                       note = CD33 leader sequence
source                 1..16
                       mol_type = protein
                       organism = Homo sapiens
SEQUENCE: 13
MPLLLLLPLL WAGALE                                                  16

SEQ ID NO: 14          moltype = DNA  length = 15
FEATURE                Location/Qualifiers
misc_feature           1..15
                       note = Synthetic
misc_feature           1..15
                       note = CD33 barcode region
variation              4
                       note = n = C, G, or T
variation              10
                       note = n = A, C, or T
variation              13
                       note = n = A, C, G, or T
source                 1..15
                       mol_type = other DNA
                       organism = synthetic construct
SEQUENCE: 14
gctntgggcn ggngc                                                   15

SEQ ID NO: 15          moltype = DNA  length = 48
FEATURE                Location/Qualifiers
misc_feature           1..48
                       note = Synthetic
misc_feature           1..48
                       note = CD33 leader sequence
variation              30
                       note = n = C, G, or T
variation              36
                       note = n = A, C, T
variation              39
                       note = n = A, C, G, or T
source                 1..48
                       mol_type = other DNA
                       organism = synthetic construct
SEQUENCE: 15
atgccgctgc tgctactgct gcccctgctn tgggcnggng ctctagag               48

SEQ ID NO: 16          moltype = DNA  length = 76
FEATURE                Location/Qualifiers
```

-continued

```
misc_feature           1..76
                       note = Synthetic
misc_feature           1..76
                       note = CD33 barcode in vector containing NheI, XbaI and
                        BsmBI sites
variation              52
                       note = n = C, G, or T
variation              58
                       note = n = is A, C, or T
variation              61
                       note = n = A, C, G, or T
source                 1..76
                       mol_type = other DNA
                       organism = synthetic construct
SEQUENCE: 16
aggctagcgg cgcgccgcca ccatgccgct gctgctactg ctgcccctgc tntgggcngg  60
ngctctagag agacgg                                                  76

SEQ ID NO: 17          moltype = DNA  length = 76
FEATURE                Location/Qualifiers
misc_feature           1..76
                       note = Synthetic
misc_feature           1..76
                       note = CD33 barcode in vector containing NheI, XbaI and
                        BsmBI sites complement strand
variation              52
                       note = n = G, C, or A
variation              58
                       note = n = T, G, or A
variation              61
                       note = n = A, C, G, or T
source                 1..76
                       mol_type = other DNA
                       organism = synthetic construct
SEQUENCE: 17
tccgatcgcc gcgcggcggt ggtacggcga cgacgatgac gacggggacg abacccgncc  60
ncgagatctc tctgcc                                                  76

SEQ ID NO: 18          moltype = DNA  length = 66
FEATURE                Location/Qualifiers
misc_feature           1..66
                       note = Synthetic
misc_feature           1..66
                       note = Hinge-CD28 TM in vector containing RsrII site
source                 1..66
                       mol_type = other DNA
                       organism = synthetic construct
SEQUENCE: 18
cggaccgccc tgccctccct gccctatgtt ttgggtgctg gtcgtggtcg gaggggtgct  60
ggcctg                                                             66

SEQ ID NO: 19          moltype = DNA  length = 67
FEATURE                Location/Qualifiers
misc_feature           1..67
                       note = Synthetic
misc_feature           1..67
                       note = Hinge-CD28 TM in vector containing RsrII site
                        complement strand
source                 1..67
                       mol_type = other DNA
                       organism = synthetic construct
SEQUENCE: 19
gcctrggcgg gacgggaggg acgggataca aaacccacga ccagcaccag cctccccacg  60
accggac                                                            67

SEQ ID NO: 20          moltype = AA  length = 12
FEATURE                Location/Qualifiers
REGION                 1..12
                       note = Synthetic
REGION                 1..12
                       note = IgG4 hinge spacer (short spacer)
source                 1..12
                       mol_type = protein
                       organism = synthetic construct
SEQUENCE: 20
ESKYGPPCPP CP                                                      12

SEQ ID NO: 21          moltype = DNA  length = 36
FEATURE                Location/Qualifiers
```

-continued

```
misc_feature           1..36
                       note = Synthetic
misc_feature           1..36
                       note = IgG4 hinge spacer (short spacer)
source                 1..36
                       mol_type = other DNA
                       organism = synthetic construct
SEQUENCE: 21
gaatctaagt acggaccgcc ttgtcctcca tgtcct                            36

SEQ ID NO: 22          moltype = AA  length = 119
FEATURE                Location/Qualifiers
REGION                 1..119
                       note = Synthetic
REGION                 1..119
                       note = Hinge-CH3 spacer (medium spacer)
source                 1..119
                       mol_type = protein
                       organism = synthetic construct
SEQUENCE: 22
ESKYGPPCPP CPGQPREPQV YTLPPSQEEM TKNQVSLTCL VKGFYPSDIA VEWESNGQPE  60
NNYKTTPPVL DSDGSFFLYS RLTVDKSRWQ EGNVFSCSVM HEALHNHYTQ KSLSLSLGK   119

SEQ ID NO: 23          moltype = DNA  length = 357
FEATURE                Location/Qualifiers
misc_feature           1..357
                       note = Synthetic
misc_feature           1..357
                       note = Hinge-CH3 spacer (medium spacer)
source                 1..357
                       mol_type = other DNA
                       organism = synthetic construct
SEQUENCE: 23
gaatctaagt acggaccgcc ttgtcctcca tgtcctggcc agccaagaga accccaggtg  60
tacacactgc ctccaagcca agaggaaatg accaagaacc aggtgtccct gacctgcctg  120
gtcaagggct tctacccttc cgatatcgcc gtggaatggg agagcaatgg ccagcctgag  180
aacaactaca agaccacacc tcctgtgctg gacagcgacg gctcattctt cctgtacagc  240
cggctgaccg tggacaagag cagatggcaa gagggcaacg tgttcagctg cagcgtgatg  300
cacgaggccc tgcacaacca ctacacccag aagtctctga gcctgagcct gggcaag     357

SEQ ID NO: 24          moltype = AA  length = 228
FEATURE                Location/Qualifiers
REGION                 1..228
                       note = Synthetic
REGION                 1..228
                       note = Hinge-CH2-CH3 spacer
source                 1..228
                       mol_type = protein
                       organism = synthetic construct
SEQUENCE: 24
ESKYGPPCPP CPAPPVAGPS VFLFPPKPKD TLMISRTPEV TCVVVDVSQE DPEVQFNWYV  60
DGVEVHNAKT KPREEQFQST YRVVSVLTVL HQDWLNGKEY KCKVSNKGLP SSIEKTISKA  120
KGQPREPQVY TLPPSQEEMT KNQVSLTCLV KGFYPSDIAV EWESNGQPEN NYKTTPPVLD  180
SDGSFFLYSR LTVDKSRWQE GNVFSCSVMH EALHNHYTQK SLSLSLGK               228

SEQ ID NO: 25          moltype = DNA  length = 684
FEATURE                Location/Qualifiers
misc_feature           1..684
                       note = Synthetic
misc_feature           1..684
                       note = Hinge-CH2-CH3 spacer
source                 1..684
                       mol_type = other DNA
                       organism = synthetic construct
SEQUENCE: 25
gaatctaagt acggaccgcc ttgtcctcca tgtcctgctc ctccagttgc cggaccttcc  60
gtgttcctgt ttcctccaaa gcctaaggac accctgatga tcagcagaac ccctgaagtg  120
acctgcgtgg tggtggacgt gtcccaagag gatcctgagg tgcagttcaa ctggtatgtg  180
gacggcgtgg aagtgcacaa cgccaagacc aagcctagag aggaacagtt ccagagcacc  240
tacagagtgg tgtccgtgct gacagtgctg caccaggatt ggctgaacgg caaagagtac  300
aagtgcaagg tgtccaacaa gggcctgcct agcagcatcg agaaaaccat cagcaaggcc  360
aagggccagc caagagaacc ccaggtgtac acactgcctc caagccaaga ggaaatgacc  420
aagaaccagg tgtccctgac ctgcctggtc aagggcttct acccttccga tatcgccgtg  480
gaatgggaga gcaatggcca gcctgagaac aactacaaga ccacacctcc tgtgctggac  540
agcgacggct cattcttcct gtacagccgg ctgaccgtgg acaagagcag atggcaagag  600
ggcaacgtgt tcagctgcag cgtgatgcac gaggccctgc acaaccacta cacccagaag  660
tctctgagcc tgagcctggg caag                                         684

SEQ ID NO: 26          moltype = AA  length = 282
```

-continued

```
FEATURE                Location/Qualifiers
REGION                 1..282
                       note = Synthetic
REGION                 1..282
                       note = IgD-hinge-Fc
source                 1..282
                       mol_type = protein
                       organism = synthetic construct
SEQUENCE: 26
RWPESPKAQA SSVPTAQPQA EGSLAKATTA PATTRNTGRG GEEKKKEKEK EEQEERETKT  60
PECPSHTQPL GVYLLTPAVQ DLWLRDKATF TCFVVGSDLK DAHLTWEVAG KVPTGGVEEG  120
LLERHSNGSQ SQHSRLTLPR SLWNAGTSVT CTLNHPSLPP QRLMALREPA AQAPVKLSLN  180
LLASSDPPEA ASWLLCEVSG FSPPNILLMW LEDQREVNTS GFAPARPPPQ PGSTTFWAWS  240
VLRVPAPPSP QPATYTCVVS HEDSRTLLNA SRSLEVSYVT DH                    282

SEQ ID NO: 27          moltype = AA  length = 27
FEATURE                Location/Qualifiers
REGION                 1..27
                       note = CD28 (amino acids 153-179 of Accession No. P10747)
source                 1..27
                       mol_type = protein
                       organism = Homo sapiens
SEQUENCE: 27
FWVLVVVGGV LACYSLLVTV AFIIFWV                                     27

SEQ ID NO: 28          moltype = AA  length = 66
FEATURE                Location/Qualifiers
REGION                 1..66
                       note = CD28 (amino acids 114-179 of Accession No. P10747)
source                 1..66
                       mol_type = protein
                       organism = Homo sapiens
SEQUENCE: 28
IEVMYPPPYL DNEKSNGTII HVKGKHLCPS PLFPGPSKPF WVLVVVGGVL ACYSLLVTVA  60
FIIFWV                                                            66

SEQ ID NO: 29          moltype = AA  length = 41
FEATURE                Location/Qualifiers
REGION                 1..41
                       note = CD28 (amino acids 180-220 of P10747)
source                 1..41
                       mol_type = protein
                       organism = Homo sapiens
SEQUENCE: 29
RSKRSRLLHS DYMNMTPRRP GPTRKHYQPY APPRDFAAYR S                     41

SEQ ID NO: 30          moltype = AA  length = 41
FEATURE                Location/Qualifiers
REGION                 1..41
                       note = Synthetic
REGION                 1..41
                       note = CD28 (LL to GG)
source                 1..41
                       mol_type = protein
                       organism = synthetic construct
SEQUENCE: 30
RSKRSRGGHS DYMNMTPRRP GPTRKHYQPY APPRDFAAYR S                     41

SEQ ID NO: 31          moltype = AA  length = 42
FEATURE                Location/Qualifiers
REGION                 1..42
                       note = 4-1BB (amino acids 214-255 of Q07011.1)
source                 1..42
                       mol_type = protein
                       organism = Homo sapiens
SEQUENCE: 31
KRGRKKLLYI FKQPFMRPVQ TTQEEDGCSC RFPEEEEGGC EL                    42

SEQ ID NO: 32          moltype = AA  length = 112
FEATURE                Location/Qualifiers
REGION                 1..112
                       note = Synthetic
REGION                 1..112
                       note = CD3 zeta
source                 1..112
                       mol_type = protein
                       organism = synthetic construct
SEQUENCE: 32
RVKFSRSADA PAYQQGQNQL YNELNLGRRE EYDVLDKRRG RDPEMGGKPR RKNPQEGLYN  60
```

-continued

```
ELQKDKMAEA YSEIGMKGER RRGKGHDGLY QGLSTATKDT YDALHMQALP PR         112

SEQ ID NO: 33          moltype = AA  length = 112
FEATURE                Location/Qualifiers
REGION                 1..112
                       note = Synthetic
REGION                 1..112
                       note = CD3 zeta
source                 1..112
                       mol_type = protein
                       organism = synthetic construct
SEQUENCE: 33
RVKFSRSAEP PAYQQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PR         112

SEQ ID NO: 34          moltype = AA  length = 112
FEATURE                Location/Qualifiers
REGION                 1..112
                       note = Synthetic
REGION                 1..112
                       note = CD3 zeta
source                 1..112
                       mol_type = protein
                       organism = synthetic construct
SEQUENCE: 34
RVKFSRSADA PAYKQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PR         112

SEQ ID NO: 35          moltype = DNA  length = 721
FEATURE                Location/Qualifiers
misc_feature           1..721
                       note = Synthetic
misc_feature           1..721
                       note = Super-fold green fluorescent protein nucleic acid
source                 1..721
                       mol_type = other DNA
                       organism = synthetic construct
SEQUENCE: 35
atggtgtcca agggcgaaga actgtttacc ggcgtggtgc ccatcctggt ggaactggat  60
ggggatgtga acggccacaa gttcagcgtc agaggcgaag gcgaagggga tgccacaaac  120
ggcaagctga ccctgaagtt catctgcacc accggaaagc tgcccgtgcc ttggcctaca  180
ctggtcacca cactgacata cggcgtgcag tgctttagca gatacccga ccatatgaag  240
cagcacgact tcttcaagag cgccatgcct gagggctacg tgcaagagag aaccatcacc  300
ttcaaggacg acggcaccta caagacacgg gccgaagtga agtttgaggg cgacaccctg  360
gtcaaccgga tcgagctgaa gggcatcgac ttcaaagagg acggcaacat cctgggccac  420
aagctcgagt acaacttcaa cagccacaac gtgtacatca ccgccgacaa gcagaagaac  480
ggcatcaagg ccaacttcaa gatccggcac aacgtcgagg atggctctgt gcagctggcc  540
gatcactacc agcagaacac acccatcgga gatggcccag tgctgctgcc cgataaccac  600
tacctgagca cacagagcaa gctgagcaag gaccccaacg agaagcggga ccacatggtg  660
ctgctggaat ttgtgacagc cgccggaatc acccacggca tggacgagct gtataagata  720
a                                                                 721

SEQ ID NO: 36          moltype = AA  length = 239
FEATURE                Location/Qualifiers
REGION                 1..239
                       note = Synthetic
REGION                 1..239
                       note = Super-fold green fluorescent protein amino acid
source                 1..239
                       mol_type = protein
                       organism = synthetic construct
SEQUENCE: 36
MVSKGEELFT GVVPILVELD GDVNGHKFSV RGEGEGDATN GKLTLKFICT TGKLPVPWPT  60
LVTTLTYGVQ CFSRYPDHMK QHDFFKSAMP EGYVQERTIT FKDDGTYKTR AEVKFEGDTL  120
VNRIELKGID FKEDGNILGH KLEYNFNSHN VYITADKQKN GIKANFKIRH NVEDGSVQLA  180
DHYQQNTPIG DGPVLLPDNH YLSTQSKLSK DPNEKRDHMV LLEFVTAAGI THGMDELYK   239

SEQ ID NO: 37          moltype = AA  length = 184
FEATURE                Location/Qualifiers
REGION                 1..184
                       note = Human BCMA; GenBank No. BAB60895.1
source                 1..184
                       mol_type = protein
                       organism = Homo sapiens
SEQUENCE: 37
MLQMAGQCSQ NEYFDSLLHA CIPCQLRCSS NTPPLTCQRY CNASVTNSVK GTNAILWTCL  60
GLSLIISLAV FVLMFLLRKI SSEPLKDEFK NTGSGLLGMA NIDLEKSRTG DEIILPRGLE  120
YTVEECTCED CIKSKPKVDS DHCFPLPAME EGATILVTTK TNDYCKSLPA ALSATEIEKS  180
ISAR                                                              184
```

```
SEQ ID NO: 38          moltype = AA  length = 185
FEATURE                Location/Qualifiers
REGION                 1..185
                       note = Mouse BCMA; NCBI No. NP_035738.1
source                 1..185
                       mol_type = protein
                       organism = Mus musculus
SEQUENCE: 38
MAQQCFHSEY FDSLLHACKP CHLRCSNPPA TCQPYCDPSV TSSVKGTYTV LWIFLGLTLV  60
LSLALFTISF LLRKMNPEAL KDEPQSPGQL DGSAQLDKAD TELTRIRAGD DRIFPRSLEY  120
TVEECTCEDC VKSKPKGDSD HFFPLPAMEE GATILVTTKT GDYGKSSVPT ALQSVMGMEK  180
PTHTR                                                              185

SEQ ID NO: 39          moltype = AA  length = 183
FEATURE                Location/Qualifiers
REGION                 1..183
                       note = Cynomolgus BCMA; GenBank No. EHH60172.1
source                 1..183
                       mol_type = protein
                       organism = Macaca fascicularis
SEQUENCE: 39
MLQMARQCSQ NEYFDSLLHD CKPCQLRCSS TPPLTCQRYC NASMTNSVKG MNAILWTCLG  60
LSLIISLAVF VLTFLLRKMS SEPLKDEFKN TGSGLLGMAN IDLEKGRTGD EIVLPRGLEY  120
TVEECTCEDC IKNKPKVDSD HCFPLPAMEE GATILVTTKT NDYCNSLSAA LSVTEIEKSI  180
SAR                                                                183

SEQ ID NO: 40          moltype = DNA  length = 544
FEATURE                Location/Qualifiers
misc_feature           1..544
                       note = Synthetic
misc_feature           1..544
                       note = Ef1alpha promoter with HTLV1 enhancer
source                 1..544
                       mol_type = other DNA
                       organism = synthetic construct
SEQUENCE: 40
ggatctgcga tcgctccggt gcccgtcagt gggcagagcg cacatcgccc acagtccccg  60
agaagttggg gggaggggtc ggcaattgaa ccggtgccta gagaaggtgg cgcggggtaa  120
actgggaaag tgatgtcgtg tactggctcc gcctttttcc cgagggtggg ggagaaccgt  180
atataagtgc agtagtcgcc gtgaacgttc tttttcgcaa cgggtttgcc gccagaacac  240
agctgaagct tcgaggggct cgcatctctc cttcacgcgc ccgccgccct acctgaggcc  300
gccatccacg ccggttgagt cgcgttctgc cgcctcccgc ctgtggtgcc tcctgaactg  360
cgtccgccgt ctaggtaagt ttaaagctca ggtcgagacc gggcctttgt ccggcgctcc  420
cttggagcct acctagactc agccggctct ccacgctttg cctgaccctg cttgctcaac  480
tctacgtctt tgtttcgttt tctgttctgc gccgttacag atccaagctg tgaccggcgc  540
ctac                                                               544

SEQ ID NO: 41          moltype = DNA  length = 347
FEATURE                Location/Qualifiers
misc_feature           1..347
                       note = Synthetic
misc_feature           1..347
                       note = MND promoter
source                 1..347
                       mol_type = other DNA
                       organism = synthetic construct
SEQUENCE: 41
gaacagagaa acaggagaat atgggccaaa caggatatct gtggtaagca gttcctgccc  60
cggctcaggg ccaagaacag ttggaacagc agaatatggg ccaaacagga tatctgtggt  120
aagcagttcc tgccccggct cagggccaag aacagatggt ccccagatgc ggtcccgccc  180
tcagcagttt ctagagaacc atcagatgtt tccagggtgc cccaaggacc tgaaatgacc  240
ctgtgcctta tttgaactaa ccaatcagtt cgcttctcgc ttctgttcgc gcgcttctgc  300
tccccgagct ctatataagc agagctcgtt tagtgaaccg tcagatc                347

SEQ ID NO: 42          moltype = AA  length = 22
FEATURE                Location/Qualifiers
REGION                 1..22
                       note = Synthetic
REGION                 1..22
                       note = P2A
source                 1..22
                       mol_type = protein
                       organism = synthetic construct
SEQUENCE: 42
GSGATNFSLL KQAGDVEENP GP                                           22

SEQ ID NO: 43          moltype = AA  length = 19
FEATURE                Location/Qualifiers
```

-continued

```
REGION                  1..19
                        note = Synthetic
REGION                  1..19
                        note = P2A
source                  1..19
                        mol_type = protein
                        organism = synthetic construct
SEQUENCE: 43
ATNFSLLKQA GDVEENPGP                                              19

SEQ ID NO: 44           moltype = AA  length = 20
FEATURE                 Location/Qualifiers
REGION                  1..20
                        note = Synthetic
REGION                  1..20
                        note = E2A
source                  1..20
                        mol_type = protein
                        organism = synthetic construct
SEQUENCE: 44
QCTNYALLKL AGDVESNPGP                                             20

SEQ ID NO: 45           moltype = AA  length = 22
FEATURE                 Location/Qualifiers
REGION                  1..22
                        note = Synthetic
REGION                  1..22
                        note = F2A
source                  1..22
                        mol_type = protein
                        organism = synthetic construct
SEQUENCE: 45
VKQTLNFDLL KLAGDVESNP GP                                          22

SEQ ID NO: 46           moltype = AA  length = 28
FEATURE                 Location/Qualifiers
REGION                  1..28
                        note = CD28 TM
source                  1..28
                        mol_type = protein
                        organism = Homo sapiens
SEQUENCE: 46
MFWVLVVVGG VLACYSLLVT VAFIIFWV                                    28

SEQ ID NO: 47           moltype = DNA  length = 927
FEATURE                 Location/Qualifiers
misc_feature            1..927
                        note = Nur77 genomic sequence corresponding to left
                         homology arm (chr12:52,058,015-52,058,941 hg38 assembly)
source                  1..927
                        mol_type = other DNA
                        organism = Homo sapiens
SEQUENCE: 47
aatctcacta tgttgcccga gctggtctcg aactcctggg ctcaaatgat cctcctgtct  60
cagcctccta aagtgctggg attacaggtg tgagccacca cgcctagccc ttcactgtga  120
cttctgacag tgcagatcag attggttgtg cctgttttgg actttatgta aatgtagttc  180
tgcaggatgg aatctggtgt tgaatgcaga ggttttcaga tttctctgtt ttttaaagga  240
aagaatccac cctcgttcat tttttcactt aaattgcaca ggggacccaa cgatatagaa  300
cacaatcaga ggtactctgg gctgagggag tgctgagttc tgaggctggg tttctcagaa  360
cagtctagat tttaaaaacc caatgatcta gccagaaaac gtaggttagg attttatttc  420
ccgtttgtga ccctgggcaa gtcattagcc tcctgggcct cgggttctca cttggagtat  480
gaggataatg agggttactg cttctcagac ttgtgacgat gcttactaat ggccaacatg  540
tgaatgcgct tttgtgaagt gccagcagag catgaggggt ggtcaggggc agcagtttta  600
ggggcctggg ggaggctggg gctttggggg cctggttctc agatgtacag ctaatcctgt  660
acccttcccg cagaccggca tgggctgcag gagccgcggc gggtggagga gctgcagaac  720
cgcatcgcca gctgcctgaa ggagcacgtg gcagctgtgg cgggcgagcc ccagccagcc  780
agctgcctgt cacgtctgtt gggcaaactg cccgagctgc ggaccctgtg cacccagggc  840
ctgcagcgta tcttctacct caagctggag gacttggtgc cccctccacc catcattgac  900
aagatcttca tggacacgct gcccttc                                     927

SEQ ID NO: 48           moltype = AA  length = 16
FEATURE                 Location/Qualifiers
REGION                  1..16
                        note = Synthetic
REGION                  1..16
                        note = CD33 leader re-generated XbaI/NheI digested sequence
source                  1..16
                        mol_type = protein
                        organism = synthetic construct
```

```
SEQUENCE: 48
MPLLLLLPLL WAGALA                                                  16

SEQ ID NO: 49           moltype = DNA  length = 927
FEATURE                 Location/Qualifiers
misc_feature            1..927
                        note = Nur77 left homology arm (chr12:52,058,015-52,058,941
                         hg38 assembly), with silent mutations
source                  1..927
                        mol_type = other DNA
                        organism = Homo sapiens
SEQUENCE: 49
aatctcacta tgttgcccga gctggtctcg aactcctggg ctcaaatgat cctcctgtct  60
cagcctccta aagtgctggg attacaggtg tgagccacca cgcctagccc ttcactgtga  120
cttctgacag tgcagatcag attggttgtg cctgttttgg actttatgta aatgtagttc  180
tgcaggatgg aatctggtgt tgaatgcaga ggttttcaga tttctctgtt ttttaaagga  240
aagaatccac cctcgttcat tttttcactt aaattgcaca ggggacccaa cgatatagaa  300
cacaatcaga ggtactctgg gctgagggag tgctgagttc tgaggctggg tttctcagaa  360
cagtctagat tttaaaaacc caatgatcta gccagaaaac gtaggttagg attttatttc  420
ccgtttgtga ccctgggcaa gtcattagcc tcctgggcct cgggttctca cttggagtat  480
gaggataatg agggttactg cttctcagac ttgtgacgat gcttactaat ggccaacatg  540
tgaatgcgct tttgtgaagt gccagcagag catgaggggt ggtcaggggc agcagtttta  600
ggggcctggg ggaggctggg gctttggggg cctggttctc agatgtacag ctaatcctgt  660
acccttcccg cagaccggca tggctgcag gagccgcggc gggtggagga gctgcagaac  720
cgcatcgcca gctgcctgaa ggagcacgtg gcagctgtgg cgggcgagcc ccagccagcc  780
agctgcctgt cacgtctgtt gggcaaactg cccgagctgc ggaccctgtg cacccagggc  840
ctgcagcgta tcttctacct caagctggag gacttggtgc cccctccacc tatcatcgac  900
aagatcttca tggacacgct gcccttc                                      927

SEQ ID NO: 50           moltype = DNA  length = 975
FEATURE                 Location/Qualifiers
misc_feature            1..975
                        note = Nur77 right homology arm
                         (chr12:52,058,950-52,059,924 hg38 assembly)
source                  1..975
                        mol_type = other DNA
                        organism = Homo sapiens
SEQUENCE: 50
gcctgggaac acgtgtgcac atgcgcactc tcatatgcca ccccatgtgc ctttagtcca  60
cggaccccca gagcaccccc aagcctgggc ttgagctgca gaatgactcc accttctcac  120
ctgctccagg aggtttgcag ggagctcaag cccttgggga gggggatgcc ttcatggggg  180
tgaccccacg atttgtctta tccccccag cctggccccg gcctttatgt tttttgtaag  240
ataaaccgtt tttaacacat agcgccgtgc tgtaaataag cccagtgctg ctgtaaatac  300
aggaagaaag agcttgaggt gggagcgggg ctgggaggaa gggatgggcc ccgccttcct  360
gggcagcctt tccagcctcc tgctggctct ctcttcctac cctccttcca catgtacata  420
aactgtcact ctaggaagaa gacaaatgac agattctgac atttatattt gtgtattttc  480
ctggatttat agtatgtgac ttttctgatt aatatattta atatattgaa taaaaaatag  540
acatgtagtt ggaactgaga ttcagtctgt ctctgatgcc ccctccccac tcccccacca  600
gacacacccc atcattacat aagagatggg ctgctcaaga tgaaacttgg atgttaccag  660
cctgagctgt caggcctcag tgtactcatt tgtaaaaggc ggataataat gacacctgct  720
tcacgaggtt gttatgcaaa gcacttagac taatttctaa cacgtgggaa gcctgcatta  780
gctgtgcctg gctagctgtg cctggctcat tgctggggtc tgcagtggct gactagccca  840
ggggtcactg cagggcccta gcaatagact tagccgcaga tctcagggtt gtcatgtttc  900
ctaaactgga catatattct ctgattcttg atttccacat ccataaaaca agaatagacc  960
cagcctcaca gagct                                                   975

SEQ ID NO: 51           moltype = DNA  length = 3341
FEATURE                 Location/Qualifiers
misc_feature            1..3341
                        note = Synthetic
misc_feature            1..3341
                        note = Nur77 knock-in construct sequence
source                  1..3341
                        mol_type = other DNA
                        organism = synthetic construct
SEQUENCE: 51
cagcctccta aagtgctggg attacaggtg tgagccacca cgcctagccc ttcactgtga  60
cttctgacag tgcagatcag attggttgtg cctgttttgg actttatgta aatgtagttc  120
tgcaggatgg aatctggtgt tgaatgcaga ggttttcaga tttctctgtt ttttaaagga  180
aagaatccac cctcgttcat tttttcactt aaattgcaca ggggacccaa cgatatagaa  240
cacaatcaga ggtactctgg gctgagggag tgctgagttc tgaggctggg tttctcagaa  300
cagtctagat tttaaaaacc caatgatcta gccagaaaac gtaggttagg attttatttc  360
ccgtttgtga ccctgggcaa gtcattagcc tcctgggcct cgggttctca cttggagtat  420
gaggataatg agggttactg cttctcagac ttgtgacgat gcttactaat ggccaacatg  480
tgaatgcgct tttgtgaagt gccagcagag catgaggggt ggtcaggggc agcagtttta  540
ggggcctggg ggaggctggg gctttggggg cctggttctc agatgtacag ctaatcctgt  600
acccttcccg cagaccggca tggctgcag gagccgcggc gggtggagga gctgcagaac  660
cgcatcgcca gctgcctgaa ggagcacgtg gcagctgtgg cgggcgagcc ccagccagcc  720
agctgcctgt cacgtctgtt gggcaaactg cccgagctgc ggaccctgtg cacccagggc  780
```

-continued

```
ctgcagcgta tcttctacct caagctggag gacttggtgc cccctccacc tatcatcgac  840
aagatcttca tggacacgct gcccttcgga tccggagaag gcagaggctc tctcctcaca  900
tgtggggatg ttgaagaaaa tccaggtccc ggtgtgagca agggcgagga ggtgatcaag  960
gagtttatga gattcaaagt ccggatggag ggcagcatga acggacatga gttcgaaatt  1020
gagggagaag gcgagggacg accttacgag ggaacacaga ccgccaaact gaaagtgaca  1080
aaaggcggac ctctgccatt tgcttgggac atcctgagtc cacagttcat gtatggctct  1140
aaggcttacg tgaaacaccc tgccgatatt cccgactaca aaaaactgag tttccctgaa  1200
ggcttcaaat gggaacgagt gatgaacttt gaggacggag gcctggtgac agtgacacag  1260
gactctagtc tccaggacgg cacactcatc tacaaagtga aatgaggggg caccaatttc  1320
cctcccgatg gacctgtcat gcagaaaaaa acaatgggat gggaggcttc taccgaacga  1380
ctgtacccac gggatggagt gctgaaaggc gagatccatc aggcactgaa actgaaggat  1440
ggcggccatt acctggtcga gttcaaaacc atctatatgg ccaaaaaacc cgtccagctg  1500
cctggctact attacgtgga taccaaactg gacattacct ctcacaatga agactacaca  1560
atcgtcgagc agtacgagag gagtgagggc cgacaccacc tcttcctcgg gcatggcacc  1620
ggcagcaccg gcagcggcag ctccggcacc gctagttccg aggacaacaa catggccgtc  1680
atcaaagagt tcatgcgctt caaggtgcgc atggagggct ccatgaacgg ccacgagttc  1740
gagatcgagg gcgagggcga gggccgcccc tacgagggca cccagaccgc caagctgaag  1800
gtgaccaagg gcggcccccct gcccttcgcc tgggacatcc tgtcccccca gttcatgtac  1860
ggctccaagg cgtacgtgaa gcaccccgcc gacatccccg attacaagaa gctgtccttc  1920
cccgagggct tcaagtggga gcgcgtgatg aacttcgagg acggcggtct ggtgaccgtg  1980
acccaggact cctccctgca ggacggcacg ctgatctaca aggtgaagat gcgcggcacc  2040
aacttccccc ccgacggccc cgtaatgcag aagaagacca tgggctggga ggcctccacc  2100
gagcgcctgt accccgcga cggcgtgctg aagggcgaga tccaccaggc cctgaagctg  2160
aaggacggcg gccactacct ggtggagttc aagaccatct acatggccaa gaagcccgtg  2220
caactgcccg gctactacta cgtggacacc aagctggaca tcacctccca caacgaggac  2280
tacaccatcg tggaacagta cgagcgctcc gagggccgcc accacctgtt cctgtacggc  2340
atggacgagc tgtacaaatg actcgagcct gggaacacgt gtgcacatgc gcactctcat  2400
atgccacccc atgtgccttt agtccacgga cccccagagc acccccaagc ctgggcttga  2460
gctgcagaat gactccacct tctcacctgc tccaggaggt ttgcagggag ctcaagccct  2520
tggggagggg gatgccttca tgggggtgac cccacgattt gtcttatccc ccccagcctg  2580
gccccggcct ttatgttttt tgtaagataa accgttttta acacatagcg ccgtgctgta  2640
aataagccca gtgctgctgt aaatacagga agaaagagct tgaggtggga gcggggctgg  2700
gaggaaggga tgggccccgc cttcctgggc agcctttcca gcctcctgct ggctctctct  2760
tcctaccctc cttccacatg tacataaact gtcactctag gaagaagaca aatgacagat  2820
tctgacattt atatttgtgt attttcctgg atttatagta tgtgactttt ctgattaata  2880
tatttaatat attgaataaa aaatagacat gtagttggaa ctgagattca gtctgtctct  2940
gatgcccct ccccactccc ccaccagaca caccccatca ttacataaga gatgggctgc  3000
tcaagatgaa acttggatgt taccagcctg agctgtcagg cctcagtgta ctcatttgta  3060
aaaggcggat aataatgaca cctgcttcac gaggttgtta tgcaaagcac ttagactaat  3120
ttctaacacg tgggaagcct gcattagctg tgcctggcta gctgtgcctg gctcattgct  3180
ggggtctgca gtggctgact agcccagggg tcactgcagg gccctagcaa tagacttagc  3240
cgcagatctc agggttgtca tgtttcctaa actggacata tattctctga ttcttgattt  3300
ccacatccat aaaacaagaa tagacccagc ctcacagagc t                       3341

SEQ ID NO: 52          moltype = AA  length = 84
FEATURE                Location/Qualifiers
REGION                 1..84
                       note = Nur77 final exon
source                 1..84
                       mol_type = protein
                       organism = Homo sapiens
SEQUENCE: 52
RHGLQEPRRV EELQNRIASC LKEHVAAVAG EPQPASCLSR LLGKLPELRT LCTQGLQRIF  60
YLKLEDLVPP PPIIDKIFMD TLPF                                        84

SEQ ID NO: 53          moltype = DNA  length = 1431
FEATURE                Location/Qualifiers
misc_feature           1..1431
                       note = Synthetic
misc_feature           1..1431
                       note = tdTomato DNA sequence (GenBank: AY678269.1)
source                 1..1431
                       mol_type = other DNA
                       organism = synthetic construct
SEQUENCE: 53
atggtgagca agggcgagga ggtcatcaaa gagttcatgc gcttcaaggt gcgcatggag  60
ggctccatga acggccacga gttcgagatc gagggcgagg gcgagggccg cccctacgag  120
ggcacccaga ccgccaagct gaaggtgacc aagggcggcc ccctgccctt cgcctgggac  180
atcctgtccc cccagttcat gtacggctcc aaggcgtacg tgaagcaccc cgccgacatc  240
cccgattaca agaagctgtc cttccccgag ggcttcaagt gggagcgcgt gatgaacttc  300
gaggacggcg gtctggtgac cgtgacccag gactcctccc tgcaggacgg cacgctgatc  360
tacaaggtga agatgcgcgg caccaacttc ccccccgacg gccccgtaat gcagaagaag  420
accatgggct gggaggcctc caccgagcgc ctgtaccccc gcgacggcgt gctgaagggc  480
gagatccacc aggccctgaa gctgaaggac ggcggccact acctggtgga gttcaagacc  540
atctacatgg ccaagaagcc cgtgcaactg cccggctact actacgtgga caccaagctg  600
gacatcacct cccacaacga ggactacacc atcgtggaac agtacgagcg ctccgagggc  660
cgccaccacc tgttcctggg gcatggcacc ggcagcaccg gcagcggcag ctccggcacc  720
gcctcctccg aggacaacaa catggccgtc atcaaagagt tcatgcgctt caaggtgcgc  780
atggagggct ccatgaacgg ccacgagttc gagatcgagg gcgagggcga gggccgcccc  840
```

```
tacgagggca cccagaccgc caagctgaag gtgaccaagg gcggccccct gcccttcgcc  900
tgggacatcc tgtcccccca gttcatgtac ggctccaagg cgtacgtgaa gcaccccgcc  960
gacatccccg attacaagaa gctgtccttc cccgagggct tcaagtggga gcgcgtgatg  1020
aacttcgagg acggcggtct ggtgaccgtg acccaggact cctccctgca ggacggcacg  1080
ctgatctaca aggtgaagat gcgcggcacc aacttccccc ccgacggccc cgtaatgcag  1140
aagaagacca tgggctggga ggcctccacc gagcgcctgt acccccgcga cggcgtgctg  1200
aagggcgaga tccaccaggc cctgaagctg aaggacggcg gccactacct ggtggagttc  1260
aagaccatct acatggccaa gaagcccgtg caactgcccg gctactacta cgtggacacc  1320
aagctggaca tcacctccca caacgaggac tacaccatcg tggaacagta cgagcgctcc  1380
gagggccgcc accacctgtt cctgtacggc atggacgagc tgtacaagta a           1431

SEQ ID NO: 54          moltype = AA  length = 476
FEATURE                Location/Qualifiers
REGION                 1..476
                       note = Synthetic
REGION                 1..476
                       note = tdTomato protein sequence (GenBank: AAV52169.1)
source                 1..476
                       mol_type = protein
                       organism = synthetic construct
SEQUENCE: 54
MVSKGEEVIK EFMRFKVRME GSMNGHEFEI EGEGEGRPYE GTQTAKLKVT KGGPLPFAWD  60
ILSPQFMYGS KAYVKHPADI PDYKKLSFPE GFKWERVMNF EDGGLVTVTQ DSSLQDGTLI  120
YKVKMRGTNF PPDGPVMQKK TMGWEASTER LYPRDGVLKG EIHQALKLKD GGHYLVEFKT  180
IYMAKKPVQL PGYYYVDTKL DITSHNEDYT IVEQYERSEG RHHLFLGHGT GSTGSGSSGT  240
ASSEDNNMAV IKEFMRFKVR MEGSMNGHEF EIEGEGEGRP YEGTQTAKLK VTKGGPLPFA  300
WDILSPQFMY GSKAYVKHPA DIPDYKKLSF PEGFKWERVM NFEDGGLVTV TQDSSLQDGT  360
LIYKVKMRGT NFPPDGPVMQ KKTMGWEAST ERLYPRDGVL KGEIHQALKL KDGGHYLVEF  420
KTIYMAKKPV QLPGYYYVDT KLDITSHNED YTIVEQYERS EGRHHLFLYG MDELYK      476

SEQ ID NO: 55          moltype = DNA  length = 72
FEATURE                Location/Qualifiers
misc_feature           1..72
                       note = Synthetic
misc_feature           1..72
                       note = T2A DNA
source                 1..72
                       mol_type = other DNA
                       organism = synthetic construct
SEQUENCE: 55
ctcgagggcg gcggagaggg cagaggaagt cttctaacat gcggtgacgt ggaggagaat  60
cccggcccta gg                                                      72

SEQ ID NO: 56          moltype = AA  length = 24
FEATURE                Location/Qualifiers
REGION                 1..24
                       note = Synthetic
REGION                 1..24
                       note = T2A protein
source                 1..24
                       mol_type = protein
                       organism = synthetic construct
SEQUENCE: 56
LEGGGEGRGS LLTCGDVEEN PGPR                                         24

SEQ ID NO: 57          moltype = DNA  length = 336
FEATURE                Location/Qualifiers
misc_feature           1..336
                       note = Synthetic
misc_feature           1..336
                       note = CD3 zeta DNA
source                 1..336
                       mol_type = other DNA
                       organism = synthetic construct
SEQUENCE: 57
cgggtgaagt tcagcagaag cgccgacgcc cctgcctacc agcagggcca gaatcagctg  60
tacaacgagc tgaacctggg cagaagggaa gagtacgacg tcctggataa gcggagaggc  120
cgggaccctg agatgggcgg caagcctcgg cggaagaacc cccaggaagg cctgtataac  180
gaactgcaga aagacaagat ggccgaggcc tacagcgaga tcggcatgaa gggcgagcgg  240
aggcggggca agggccacga cggcctgtat cagggcctgt ccaccgccac caaggatacc  300
tacgacgccc tgcacatgca ggccctgccc ccaagg                            336

SEQ ID NO: 58          moltype = AA  length = 229
FEATURE                Location/Qualifiers
REGION                 1..229
                       note = Synthetic
REGION                 1..229
                       note = Hinge-CH2-CH3 spacer (long spacer)
source                 1..229
```

-continued

```
                         mol_type = protein
                         organism = synthetic construct
SEQUENCE: 58
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGK             229

SEQ ID NO: 59            moltype = AA  length = 122
FEATURE                  Location/Qualifiers
REGION                   1..122
                         note = Synthetic
REGION                   1..122
                         note = SJ25C1 VH
source                   1..122
                         mol_type = protein
                         organism = synthetic construct
SEQUENCE: 59
EVKLQQSGAE LVRPGSSVKI SCKASGYAFS SYWMNWVKQR PGQGLEWIGQ IYPGDGDTNY  60
NGKFKGQATL TADKSSSTAY MQLSGLTSED SAVYFCARKT ISSVVDFYFD YWGQGTTVTV  120
SS                                                                122

SEQ ID NO: 60            moltype = AA  length = 108
FEATURE                  Location/Qualifiers
REGION                   1..108
                         note = Synthetic
REGION                   1..108
                         note = SJ25C1 VL
source                   1..108
                         mol_type = protein
                         organism = synthetic construct
SEQUENCE: 60
DIELTQSPKF MSTSVGDRVS VTCKASQNVG TNVAWYQQKP GQSPKPLIYS ATYRNSGVPD  60
RFTGSGSGTD FTLTITNVQS KDLADYFCQQ YNRYPYTSGG GTKLEIKR               108

SEQ ID NO: 61            moltype = AA  length = 245
FEATURE                  Location/Qualifiers
REGION                   1..245
                         note = Synthetic
REGION                   1..245
                         note = SJ25C1 scFv
source                   1..245
                         mol_type = protein
                         organism = synthetic construct
SEQUENCE: 61
EVKLQQSGAE LVRPGSSVKI SCKASGYAFS SYWMNWVKQR PGQGLEWIGQ IYPGDGDTNY  60
NGKFKGQATL TADKSSSTAY MQLSGLTSED SAVYFCARKT ISSVVDFYFD YWGQGTTVTV  120
SSGGGGSGGG GSGGGGSDIE LTQSPKFMST SVGDRVSVTC KASQNVGTNV AWYQQKPGQS  180
PKPLIYSATY RNSGVPDRFT GSGSGTDFTL TITNVQSKDL ADYFCQQYNR YPYTSGGGTK  240
LEIKR                                                             245

SEQ ID NO: 62            moltype = AA  length = 120
FEATURE                  Location/Qualifiers
REGION                   1..120
                         note = Synthetic
REGION                   1..120
                         note = FMC63 VH
source                   1..120
                         mol_type = protein
                         organism = synthetic construct
SEQUENCE: 62
EVKLQESGPG LVAPSQSLSV TCTVSGVSLP DYGVSWIRQP PRKGLEWLGV IWGSETTYYN  60
SALKSRLTII KDNSKSQVFL KMNSLQTDDT AIYYCAKHYY YGGSYAMDYW GQGTSVTVSS  120

SEQ ID NO: 63            moltype = AA  length = 107
FEATURE                  Location/Qualifiers
REGION                   1..107
                         note = Synthetic
REGION                   1..107
                         note = FMC63 VL
source                   1..107
                         mol_type = protein
                         organism = synthetic construct
SEQUENCE: 63
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEIT                107

SEQ ID NO: 64            moltype = AA  length = 245
FEATURE                  Location/Qualifiers
```

-continued

```
REGION                 1..245
                       note = Synthetic
REGION                 1..245
                       note = FMC63 scFv
source                 1..245
                       mol_type = protein
                       organism = synthetic construct
SEQUENCE: 64
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEITGST SGSGKPGSGE  120
GSTKGEVKLQ ESGPGLVAPS QSLSVTCTVS GVSLPDYGVS WIRQPPRKGL EWLGVIWGSE  180
TTYYNSALKS RLTIIKDNSK SQVFLKMNSL QTDDTAIYYC AKHYYYGGSY AMDYWGQGTS  240
VTVSS                                                             245

SEQ ID NO: 65          moltype = DNA  length = 20
FEATURE                Location/Qualifiers
misc_feature           1..20
                       note = Human Nur77 gRNA target 1
source                 1..20
                       mol_type = other DNA
                       organism = Homo sapiens
SEQUENCE: 65
tcattgacaa gatcttcatg                                             20

SEQ ID NO: 66          moltype = DNA  length = 19
FEATURE                Location/Qualifiers
misc_feature           1..19
                       note = Human Nur77 gRNA target 2
source                 1..19
                       mol_type = other DNA
                       organism = Homo sapiens
SEQUENCE: 66
gcctgggaac acgtgtgca                                              19

SEQ ID NO: 67          moltype = AA  length = 10
FEATURE                Location/Qualifiers
REGION                 1..10
                       note = Synthetic
REGION                 1..10
                       note = Linker
REPEAT                 5..9
                       note = SGGGG is repeated 5 times
source                 1..10
                       mol_type = protein
                       organism = synthetic construct
SEQUENCE: 67
PGGGSGGGGP                                                        10

SEQ ID NO: 68          moltype = AA  length = 17
FEATURE                Location/Qualifiers
REGION                 1..17
                       note = Synthetic
REGION                 1..17
                       note = Linker
source                 1..17
                       mol_type = protein
                       organism = synthetic construct
SEQUENCE: 68
GSADDAKKDA AKKDGKS                                                17

SEQ ID NO: 69          moltype = DNA  length = 1189
FEATURE                Location/Qualifiers
misc_feature           1..1189
                       note = EF1alpha promoter (GenBank: J04617.1)
source                 1..1189
                       mol_type = other DNA
                       organism = Homo sapiens
SEQUENCE: 69
cgtgaggctc cggtgcccgt cagtgggcag agcgcacatc gcccacagtc cccgagaagt  60
tggggggagg ggtcggcaat tgaaccggtg cctagagaag gtggcgcggg gtaaactggg  120
aaagtgatgt cgtgtactgg ctccgccttt ttcccgaggg tgggggagaa ccgtatataa  180
gtgcagtagt cgccgtgaac gttctttttc gcaacgggtt tgccgccaga acacaggtaa  240
gtgccgtgtg tggttcccgc gggcctggcc tctttacggg ttatggccct tgcgtgcctt  300
gaattacttc cacgcccctg gctgcagtac gtgattcttg atcccgagct tcgggttgga  360
agtgggtggg agagttcgag gccttgcgct taaggagccc cttcgcctcg tgcttgagtt  420
gaggcctggc ctgggcgctg gggccgccgc gtgcgaatct ggtggcacct tcgcgcctgt  480
ctcgctgctt tcgataagtc tctagccatt taaaattttt gatgacctgc tgcgacgctt  540
tttttctggc aagatagtct tgtaaatgcg ggccaagatc tgcacactgg tatttcggtt  600
tttggggccg cgggcggcga cggggcccgt gcgtcccagc gcacatgttc ggcgaggcgg  660
```

-continued

```
ggcctgcgag cgcggccacc gagaatcgga cgggggtagt ctcaagctgg ccggcctgct  720
ctggtgcctg gcctcgcgcc gccgtgtatc gccccgccct gggcggcaag gctggcccgg  780
tcggcaccag ttgcgtgagc ggaaagatgg ccgcttcccg gccctgctgc agggagctca  840
aaatggagga cgcggcgctc gggagagcgg gcgggtgagt cacccacaca aaggaaaagg  900
gcctttccgt cctcagccgt cgcttcatgt gactccacgg agtaccgggc gccgtccagg  960
cacctcgatt agttctcgag cttttggagt acgtcgtctt taggttgggg ggaggggttt  1020
tatgcgatgg agtttcccca cactgagtgg gtggagactg aagttaggcc agcttggcac  1080
ttgatgtaat tctccttgga atttgccctt tttgagtttg gatcttggtt cattctcaag  1140
cctcagacag tggttcaaag tttttttctt ccatttcagg tgtcgtgaa             1189

SEQ ID NO: 70          moltype = DNA  length = 1205
FEATURE                Location/Qualifiers
misc_feature           1..1205
                       note = Synthetic
misc_feature           1..1205
                       note = EF1alpha promoter
source                 1..1205
                       mol_type = other DNA
                       organism = synthetic construct
SEQUENCE: 70
cgtgaggctc cggtgcccgt cagtgggcag agcgcacatc gcccacagtc cccgagaagt  60
tggggggagg ggtcggcaat tgaaccggtg cctagagaag gtggcgcggg gtaaactggg  120
aaagtgatgt cgtgtactgg ctccgccttt ttcccgaggg tgggggagaa ccgtatataa  180
gtgcactagt cgccgtgaac gttctttttc gcaacgggtt tgccgccaga acacaggtaa  240
gtgccgtgtg tggttcccgc gggcctggcc tctttacggg ttatggccct tgcgtgcctt  300
gaattacttc cacctggctg cagtacgtga ttcttgatcc cgagcttcgg gttggaagtg  360
ggtgggagag ttcgtggcct tgcgcttaag gagccccttc gcctcgtgct tgagttgtgg  420
cctggcctgg gcgctggggc cgccgcgtgc gaatctggtg gcaccttcgc gcctgtctcg  480
ctgctttcga taagtctcta gccatttaaa atttttgatg acctgctgcg acgctttttt  540
tctggcaaga tagtcttgta aatgcgggcc aagatcagca cactggtatt tcggtttttg  600
gggccgcggg cggcgacggg gcccgtgcgt cccagcgcac atgttcggcg aggcggggcc  660
tgcgagcgcg gccaccgaga atcggacggg ggtagtctca agctgcccgg cctgctctgg  720
tgcctggcct cgcgccgccg tgtatcgccc cgccctgggc ggcaaggctg gcccggtcgg  780
caccagttgc gtgagcggaa agatggccgc ttcccggccc tgctgcaggg agcacaaaat  840
ggaggacgcg gcgctcggga gagcgggcgg gtgagtcacc cacacaaagg aaaagggcct  900
ttccgtcctc agccgtcgct tcatgtgact ccacggagta ccgggcgccg tccaggcacc  960
tcgattagtt ctccagcttt tggagtacgt cgtctttagg ttggggggag gggttttatg  1020
cgatggagtt tccccacact gagtgggtgg agactgaagt taggccagct tggcacttga  1080
tgtaattctc cttggaattt gcccttttttg agtttggatc ttggttcatt ctcaagcctc  1140
agacagtggt tcaaagtttt tttcttccat ttcaggtgtc gtgaaaacta cccctaaaag  1200
ccaaa                                                              1205

SEQ ID NO: 71          moltype = DNA  length = 181
FEATURE                Location/Qualifiers
misc_feature           1..181
                       note = Synthetic
misc_feature           1..181
                       note = MND promoter
source                 1..181
                       mol_type = other DNA
                       organism = synthetic construct
SEQUENCE: 71
gggtctctct ggttagacca gatctgagcc tgggagctct ctggctaact agggaaccca  60
ctgcttaagc ctcaataaag cttgccttga gtgcttcaag tagtgtgtgc ccgtctgttg  120
tgtgactctg gtaactagag atccctcaga cccttttagt cagtgtggaa aatctctagc  180
a                                                                  181

SEQ ID NO: 72          moltype = DNA  length = 66
FEATURE                Location/Qualifiers
misc_feature           1..66
                       note = Synthetic
misc_feature           1..66
                       note = GMCSFR alpha chain leader sequence
source                 1..66
                       mol_type = other DNA
                       organism = synthetic construct
SEQUENCE: 72
atgcttctcc tggtgacaag ccttctgctc tgtgagttac cacacccagc attcctcctg  60
atccca                                                             66

SEQ ID NO: 73          moltype = AA  length = 22
FEATURE                Location/Qualifiers
REGION                 1..22
                       note = Synthetic
REGION                 1..22
                       note = GMCSFR alpha chain leader
source                 1..22
                       mol_type = protein
                       organism = synthetic construct
```

-continued

```
SEQUENCE: 73
MLLLVTSLLL CELPHPAFLL IP                                    22

SEQ ID NO: 74          moltype = AA  length = 18
FEATURE                Location/Qualifiers
REGION                 1..18
                       note = Synthetic
REGION                 1..18
                       note = CD8 alpha chain leader sequence
source                 1..18
                       mol_type = protein
                       organism = synthetic construct
SEQUENCE: 74
MALPVTALLL PLALLLHA                                         18

SEQ ID NO: 75          moltype = AA  length = 21
FEATURE                Location/Qualifiers
REGION                 1..21
                       note = Synthetic
REGION                 1..21
                       note = CD8 alpha chain leader sequence
source                 1..21
                       mol_type = protein
                       organism = synthetic construct
SEQUENCE: 75
MALPVTALLL PLALLLHAAR P                                     21

SEQ ID NO: 76          moltype = AA  length = 335
FEATURE                Location/Qualifiers
REGION                 1..335
                       note = Synthetic
REGION                 1..335
                       note = EGFRt
source                 1..335
                       mol_type = protein
                       organism = synthetic construct
SEQUENCE: 76
RKVCNGIGIG EFKDSLSINA TNIKHFKNCT SISGDLHILP VAFRGDSFTH TPPLDPQELD  60
ILKTVKEITG FLLIQAWPEN RTDLHAFENL EIIRGRTKQH GQFSLAVVSL NITSLGLRSL  120
KEISDGDVII SGNKNLCYAN TINWKKLFGT SGQKTKIISN RGENSCKATG QVCHALCSPE  180
GCWGPEPRDC VSCRNVSRGR ECVDKCNLLE GEPREFVENS ECIQCHPECL PQAMNITCTG  240
RGPDNCIQCA HYIDGPHCVK TCPAGVMGEN NTLVWKYADA GHVCHLCHPN CTYGCTGPGL  300
EGCPTNGPKI PSIATGMVGA LLLLLVVALG IGLFM                         335

SEQ ID NO: 77          moltype = AA  length = 112
FEATURE                Location/Qualifiers
REGION                 1..112
                       note = Synthetic
REGION                 1..112
                       note = CD3zeta ITAM mutant
source                 1..112
                       mol_type = protein
                       organism = synthetic construct
SEQUENCE: 77
RVKFSRSADA PAYQQGQNQL FNELNLGRRE EFDVLDKRRG RDPEMGGKPR RKNPQEGLFN  60
ELQKDKMAEA FSEIGMKGER RRGKGHDGLF QGLSTATKDT FDALHMQALP PR          112
```

METHOD OF ASSESSING ACTIVITY OF RECOMBINANT ANTIGEN RECEPTORS

CROSS-REFERENCE TO RELATED APPLICATIONS

This application is a divisional of U.S. application Ser. No. 16/760,006 filed Apr. 28, 2020, which is a U.S. National Stage application under 35 U.S.C. § 371 of International Patent Application PCT/US2018/058781, filed internationally on Nov. 1, 2018, which claims priority from U.S. provisional application No. 62/580,405, filed Nov. 1, 2017, entitled "METHOD OF ASSESSING ACTIVITY OF RECOMBINANT ANTIGEN RECEPTORS," U.S. provisional application No. 62/596,758, filed Dec. 8, 2017, entitled "METHOD OF ASSESSING ACTIVITY OF RECOMBINANT ANTIGEN RECEPTORS," and U.S. provisional application No. 62/599,672, filed Dec. 15, 2017, entitled "METHOD OF ASSESSING ACTIVITY OF RECOMBINANT ANTIGEN RECEPTORS," the contents of which are incorporated by reference in their entirety.

INCORPORATION BY REFERENCE OF SEQUENCE LISTING

The present application is being filed along with a Sequence Listing in electronic format. The Sequence Listing is provided as a file entitled 73504-20074.00.XML, created Nov. 9, 2023, which is 146,884 in size. The information in the electronic format of the Sequence Listing is incorporated by reference in its entirety.

FIELD

The present disclosure relates to a method for screening for one or more activity of a recombinant receptor, including recombinant receptors that contain an extracellular antigen-binding domain and an intracellular signaling domain, such as a chimeric antigen receptor (CAR). The methods include assessing or determining activity of a cell expressing the recombinant receptor based on a detectable or measurable expression of a reporter molecule that is responsive to a signal through the intracellular signaling region of the recombinant receptor. In some embodiments, the activity assessed is an antigen-dependent or an antigen-independent activity. In some embodiments, the methods can be used to screen a plurality of reporter cells each containing a nucleic acid molecule encoding a candidate recombinant receptor, e.g. CAR, and assessing such cells or plurality of cells for one or more property or activity. The methods can be high-throughput. Also provided are reporter cells, such as reporter T cells, cell compositions, nucleic acids and kits for use in the methods.

BACKGROUND

Adoptive cell therapies that utilize recombinantly expressed antigen receptors (e.g. chimeric antigen receptors (CARs)) to recognize tumor antigens represent an attractive therapeutic modality for the treatment of cancers and other diseases. Improved strategies are needed to identify CARs that have particular properties or activities, such as properties and activities suited for use as therapeutic molecules, including in connection with adoptive immunotherapy, for use in treating cancer, infectious diseases and autoimmune diseases. Provided are methods, cells, and nucleic acids, e.g., vectors, and compositions and/or a plurality of cells or nucleic acids, e.g., vectors, for use in the methods that meet such needs.

SUMMARY

Provided in some aspects are reporter T cells containing a nucleic acid sequence encoding a reporter molecule operably linked to a transcriptional regulatory element or a variant thereof, of a Nur77, wherein the transcriptional regulatory element optionally is a transcriptional regulatory element within an endogenous Nur77 locus in the T cell. Provided in some aspects are reporter T cells containing a nucleic acid sequence encoding a reporter molecule operably linked to a transcriptional regulatory element of the endogenous locus encoding Nur77. In some embodiments, the reporter T cell further contains a recombinant receptor comprising an intracellular signaling region, optionally a chimeric antigen receptor (CAR). In some embodiments, the transcriptional regulatory element is a promoter, an enhancer or a response element or a portion thereof.

In some embodiments, the reporter T cell includes a nucleic acid sequence encoding a reporter molecule operably linked to a transcriptional regulatory element of the endogenous locus encoding Nur77. In some embodiments, the reporter T cell further contains a recombinant receptor comprising an intracellular signaling region, optionally a chimeric antigen receptor (CAR). In some embodiments, the transcriptional regulatory element is a promoter, an enhancer or a response element or a portion thereof. In some embodiments, the nucleic acid sequence encoding the reporter molecule is present within the genome of the cell or integrated at or near the endogenous locus encoding Nur77.

In some embodiments, provided herein are reporter T cells wherein the nucleic acid sequence encoding the reporter molecule is integrated or is targeted for integration by a) inducing a genetic disruption at one or more target site(s) at or near the endogenous locus encoding Nur77; and b) introducing a template polynucleotide for homology directed repair (HDR). In some embodiments, the genetic disruption is induced by a DNA binding protein or DNA-binding nucleic acid that specifically binds to or hybridizes to the target site, optionally a fusion protein containing a DNA-targeting protein and a nuclease or an RNA-guided nuclease. In some embodiments, the fusion protein containing a DNA-targeting protein and a nuclease or the RNA-guided nuclease is or includes a zinc finger nuclease (ZFN), a TAL-effector nuclease (TALEN), or a CRISPR-Cas9 combination that specifically binds to, recognizes, or hybridizes to the target site. In some embodiments, the RNA-guided nuclease includes a guide RNA (gRNA) having a targeting domain that is complementary to the target site.

In some embodiments of any of the reporter T cells described herein, the nucleic acid encoding the reporter is present within the genome at a site that is at or near the final exon of the endogenous locus encoding Nur77. In some embodiments, the one or more target site(s) comprise, and/or the nucleic acid is present within the genome at a site comprising, the nucleic acid sequence TCATTGACAAGATCTTCATG (SEQ ID NO:65) and/or GCCTGGGAACACGTGTGCA (SEQ ID NO:66). In some embodiments, the template polynucleotide includes the structure [5' homology arm]-[nucleic acid sequence encoding the reporter molecule]-[3' homology arm]. In some embodiments, the 5' homology arm and/or 3' homology arm includes nucleic acid sequences homologous to nucleic acid sequences present at and/or surrounding the one or more target site(s). In some embodiments, the 5' homology arm includes nucleic acid sequences that are homologous to nucleic acid sequences 5' of the one or more target site(s). In some embodiments, the 3' homology arm includes nucleic acid sequences that are homologous to nucleic acid sequences 3' of the one or more target site(s). In some embodiments, the 5' homology arm and 3' homology arm independently is between about 50 and 100, 100 and 250, 250 and 500, 500 and 750, 750 and 1000, 1000 and 2000 base pairs in length.

In some embodiments of any of the reporter T cells described herein, the nucleic acid sequence encoding the reporter molecule is present within the genome of the cell or is targeted for integration in-frame with the endogenous Nur77 coding sequence, optionally separated by a nucleic acid sequence encoding a ribosome skip element selected from among a T2A, a P2A, a E2A or a F2A. In some embodiments, the reporter molecule is or includes a fluorescent protein, a luciferase, a 0-galactosidase, a chloramphenicol acetyltransferase (CAT), a β-glucuronidase (GUS), or a modified form thereof. In some embodiments, the reporter molecule includes a fluorescent protein, optionally a red fluorescent protein (RFP), optionally tdTomato. In some embodiments, the reporter molecule includes the sequence of amino acids set forth in SEQ ID NO:8 or 54, or a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NO: 8 or 54.

In some embodiments of any of the reporter T cells described herein, the T cell is an immortalized cell line. In some embodiments, the T cell line is a Jurkat cell line or a derivative thereof, optionally Jurkat T cell clone E6-1.

Provided in some aspects are a plurality of reporter T cells, containing one or more reporter T cells of any of the embodiments described herein. In some embodiments, each of said reporter T cells comprises a recombinant receptor, and the recombinant receptor present in the one or more reporter T cell is distinct from the recombinant receptor present in at least one of the other reporter T cells in the plurality.

Provided in some aspects are methods for assessing activity of a recombinant receptor, involving: a) incubating one or more of any of the reporter T cells or any of the plurality of reporter T cells described herein, each of said reporter T cells containing a recombinant receptor comprising an intracellular signaling region and a binding domain, wherein the incubating is carried out in the presence or absence of an agent that binds to the binding domain of the recombinant receptor and/or an agent that induces or is capable of inducing a signal through the intracellular signaling region of the recombinant receptor; and b) assessing the one or more reporter T cells for expression of the reporter molecule. In some embodiments of the methods described herein, the recombinant receptor is a chimeric antigen receptor (CAR).

Provided in some embodiments are methods for assessing activity of a recombinant receptor that is a chimeric antigen receptor (CAR) that involve: a) incubating one or more reporter T cells each containing i) a recombinant receptor that is a CAR containing an intracellular signaling region and a binding domain, and ii) a reporter molecule, wherein the expression of said reporter molecule is responsive to a signal through the intracellular signaling region of the recombinant receptor, wherein the incubating is carried out in the presence or absence of an agent that binds to the binding domain of the recombinant receptor and/or an agent that induces or is capable of inducing a signal through the intracellular signaling region of the recombinant receptor; and b) assessing the one or more reporter T cells for expression of the reporter molecule. In some embodiments of the methods described herein, the one or more reporter T cells contains a plurality of reporter T cells. In some embodiments, the recombinant receptor present in the one or more reporter T cell is distinct from the recombinant receptor present in at least one of the other reporter T cells in the plurality.

Provided in some embodiments are methods of generating a plurality of reporter T cells that involve: a) producing a plurality of polynucleotides each encoding a recombinant receptor, wherein each polynucleotide includes i) a vector backbone containing a nucleic acid sequence encoding an intracellular signaling region and ii) a nucleic acid sequence encoding a binding domain; and b) introducing one of the plurality of polynucleotides encoding a recombinant receptor into a reporter T cell containing a reporter molecule, wherein the expression of said reporter molecule is responsive to a signal through the intracellular signaling region, and the encoded recombinant receptor present in the reporter T cell is distinct from the encoded recombinant receptor present in at least one of the other reporter T cells in the plurality.

Provided in other embodiments are methods for assessing activity of a recombinant receptor that involve: a) incubating one or more reporter T cells from any of the plurality of reporter T cells of described herein in the presence or absence of an agent that binds to the binding domain of the recombinant receptor and/or an agent that induces or is capable of inducing a signal through an intracellular signaling region of the recombinant receptor; and b) assessing the one or more reporter T cells for expression of the reporter molecule.

In some embodiments of any of the methods described herein, the agent contains a target antigen or epitope specifically recognized by the recombinant receptor. In some embodiments, incubating is carried out in the absence of the agent, thereby assessing tonic signaling and/or antigen independent activity of the recombinant receptor. In some embodiments, incubating is carried out in the presence of the agent, thereby assessing antigen-specific activity of the recombinant receptor.

In some embodiments of any of the methods described herein, the method includes assessing expression of the recombinant receptor on the surface of the cell. In some embodiments of any of the methods described herein, the method further includes identifying one or more reporter T cells among the plurality that express the recombinant receptor on the surface of the cell, express the reporter molecule in the presence of the agent and/or do not express the reporter molecule in the absence of the agent.

Provided in other embodiments are methods for screening recombinant receptors that involve: a) producing a plurality of polynucleotides each encoding a recombinant receptor that is a chimeric antigen receptor (CAR), wherein each polynucleotide includes i) a vector backbone containing a nucleic acid sequence encoding an intracellular signaling region and ii) a nucleic acid sequence encoding a binding domain; b) introducing one of the plurality of polynucleotides encoding a recombinant receptor into a reporter T cell containing a reporter molecule, wherein the expression of said reporter molecule is responsive to a signal through the intracellular signaling region, and the encoded recombinant receptor present in the reporter T cell is distinct from the encoded recombinant receptor present in at least one of the other reporter T cells in the plurality; c) incubating one or more reporter T cells from the plurality of reporter T cells in the presence or absence of an agent that binds to the binding domain of the recombinant receptor and/or an agent that induces or is capable of inducing a signal through an intracellular signaling region of the recombinant receptor; d) assessing the one or more reporter T cells for expression of the reporter molecule and/or expression of the recombinant receptor on the surface of the cell; and e) identifying one or more reporter T cells among the plurality that express the recombinant receptor on the surface of the cell, express the reporter molecule in the presence of the agent and/or do not express the reporter molecule in the absence of the agent.

In some embodiments of any of the methods described herein, the agent includes a target antigen or epitope specifically recognized by the recombinant receptor.

In some embodiments of any of the methods described herein, incubating is carried out in the absence of the agent, thereby assessing tonic signaling and/or antigen independent activity of the recombinant receptor. In some embodiments, incubating is carried out in the presence of the agent, thereby assessing antigen-specific activity of the recombinant receptor.

In some embodiments of any of the methods described herein, the intracellular signaling region includes an intracellular signaling domain. In some embodiments, the intracellular signaling domain is or includes a primary signaling domain, a signaling domain that is capable of inducing a primary activation signal in a T cell, a signaling domain of a T cell receptor (TCR) component, and/or a signaling domain containing an immunoreceptor tyrosine-based activation motif (ITAM). In some embodiments, the intracellular signaling domain is or includes an intracellular signaling domain of a CD3 chain, optionally a CD3-zeta (CD3ζ) chain, or a signaling portion thereof. In some embodiments, the intracellular signaling region further includes a costimulatory signaling region.

In some embodiments of any of the methods described herein, the costimulatory signaling region includes an intracellular signaling domain of a T cell costimulatory molecule or a signaling portion thereof. In some embodiments, the costimulatory signaling region includes an intracellular signaling domain of a CD28, a 4-1BB or an ICOS or a signaling portion thereof.

In some embodiments of any of the methods described herein, the reporter molecule is encoded by a nucleic acid sequence under the operable control of a regulatory element that is responsive to the quality and/or strength of the signal through the intracellular signaling region and/or binding and/or recognition of the recombinant receptor to a target antigen or epitope. In some embodiments, the regulatory element is or includes a transcriptional regulatory element, optionally promoter, an enhancer or a response element or a portion thereof. In some embodiments, the regulatory element is or includes a transcriptional regulatory element of a gene whose expression is induced and/or is upregulated upon signal through the intracellular signaling region of the recombinant receptor and/or binding and/or recognition of the recombinant receptor to a target antigen or epitope. In some embodiments, the gene is Nur77 and the regulatory element is or includes a transcriptional regulatory element of the Nur77 gene.

In some embodiments of any of the methods described herein, the transcriptional regulatory element includes the Nur77 promoter or portion thereof containing a response element or elements recognized by a transcription factor. In some embodiments, the regulatory element includes a response element or elements recognized by a transcription factor that is activated upon signal through the intracellular signaling region and/or binding and/or recognition of the recombinant receptor to a target antigen or epitope, optionally containing an immunoreceptor tyrosine-based activation motif (ITAM). In some embodiments, the transcription factor is selected from among NFAT family transcription factors or NFκB family of transcription factors. In some embodiments, the transcription factor is NFAT or NFκB. In some of any embodiments, the regulatory element is a transcriptional regulatory element or a variant thereof of a Nur77, wherein the transcriptional regulatory element optionally is a transcriptional regulatory element within an endogenous Nur77 locus in the T cell. In some embodiments, the regulatory element is a transcriptional regulatory element of the endogenous locus encoding Nur77, optionally a promoter, an enhancer or a response element of the endogenous locus encoding Nur77. In some embodiments, the nucleic acid sequence encoding the reporter molecule is present within the genome of the cell or integrated at or near the endogenous locus encoding Nur77.

In some embodiments of any of the methods described herein, the nucleic acid sequence encoding the reporter molecule is integrated or is targeted for integration by a) inducing a genetic disruption at one or more target site(s) at or near the endogenous locus encoding Nur77; and b) introducing a template polynucleotide for homology directed repair (HDR). In some embodiments, genetic disruption is induced by a DNA binding protein or DNA-binding nucleic acid that specifically binds to or hybridizes to the target site, optionally a fusion protein containing a DNA-targeting protein and a nuclease or an RNA-guided nuclease. In some embodiments, the fusion protein containing a DNA-targeting protein and a nuclease or the RNA-guided nuclease is or includes a zinc finger nuclease (ZFN), a TAL-effector nuclease (TALEN), or a CRISPR-Cas9 combination that specifically binds to, recognizes, or hybridizes to the target site.

In some embodiments of any of the methods described herein, the RNA-guided nuclease includes a guide RNA (gRNA) having a targeting domain that is complementary to the target site. In some embodiments, the nucleic acid encoding the reporter is present within the genome at a site that is at or near the final exon of the endogenous locus encoding Nur77. In some embodiments, the one or more target site(s) comprise, and/or the nucleic acid is present within the genome at a site comprising, the nucleic acid sequence TCATTGACAAGATCTTCATG (SEQ ID NO:65) and/or GCCTGGGAACACGTGTGCA (SEQ ID NO:66). In some embodiments, the template polynucleotide includes the structure [5' homology arm]-[nucleic acid sequence encoding the reporter molecule]-[3' homology arm]. In some embodiments, the 5' homology arm and/or 3' homology arm includes nucleic acid sequences homologous to nucleic acid sequences present at and/or surrounding the one or more target site(s). In some embodiments, the 5' homology arm includes nucleic acid sequences that are homologous to nucleic acid sequences 5' of the one or more target site(s). In some embodiments, the 3' homology arm includes nucleic acid sequences that are homologous to nucleic acid sequences 3' of the one or more target site(s). In some embodiments, the 5' homology arm and 3' homology arm independently is between about 50 and 100, 100 and 250, 250 and 500, 500 and 750, 750 and 1000, 1000 and 2000 base pairs in length.

In some embodiments of any of the methods described herein, the nucleic acid sequence encoding the reporter molecule is present within the genome of the cell or is targeted for integration in-frame with the endogenous Nur77 coding sequence, optionally separated by a nucleic acid sequence encoding a ribosome skip element selected from among a T2A, a P2A, a E2A or a F2A. In some embodiments, the reporter molecule is or includes a fluorescent protein, a luciferase, a β-galactosidase, a chloramphenicol acetyltransferase (CAT), a β-glucuronidase (GUS), or a modified form thereof. In some embodiments, the reporter molecule includes a fluorescent protein, optionally a red fluorescent protein (RFP), optionally tdTomato. In some embodiments, the reporter molecule includes the sequence of amino acids set forth in SEQ ID NO:8 or 54, or a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NO: 8 or 54.

In some embodiments of any of the methods described herein, the polynucleotide encoding the recombinant receptor includes a vector backbone. In some embodiments, the vector backbone includes a nucleic acid sequence encoding the intracellular signaling region. In some embodiments, the encoded intracellular signaling region includes an intracellular signaling domain. In some embodiments, the intracellular signaling domain is or includes a primary signaling domain, a signaling domain that is capable of inducing a primary activation signal in a T cell, a signaling domain of a T cell receptor (TCR) component, and/or a signaling domain containing an immunoreceptor tyrosine-based activation motif (ITAM). In some embodiments, the intracellular signaling domain is or includes an intracellular signaling domain of a CD3 chain, optionally a CD3-zeta (CD3ζ) chain, or a signaling portion thereof.

In some embodiments of any of the methods described herein, the polynucleotide encoding the recombinant receptor includes a vector backbone, wherein the vector backbone further includes one or more site(s) for introduction of a nucleic acid sequence encoding a binding domain or a portion thereof. In some embodiments, the one or more site(s) for introduction of a nucleic acid sequence encoding a binding domain or a portion thereof includes a restriction site. In some embodiments, the restriction site is a restriction site that does not occur or occurs 1, 2 or 3 or fewer times within an endogenous human $V_H$ or $V_L$ gene. In some of any embodiments, the vector backbone comprises one or more site(s) for introduction of a nucleic acid sequence encoding a $V_H$ region of the binding domain. In some of any embodiments, the encoded $V_H$ region of the binding domain is distinct from the encoded $V_H$ region in the binding domain of the recombinant receptor present in at least one of the other reporter T cells in the plurality. In some of any embodiments, the vector backbone comprises one or more site(s) for introduction of a nucleic acid sequence encoding a $V_L$ region of the binding domain. In some of any embodiments, the encoded $V_H$ region of the binding domain is distinct from the encoded $V_H$ region in the binding domain of the recombinant receptor present in at least one of the other reporter T cells in the plurality. In some of any embodiments, the vector backbone comprises one or more site(s) for introduction of a nucleic acid sequence encoding a $V_H$ region and a $V_L$ region of the binding domain. In some of any embodiments, the encoded $V_H$ region and/or $V_L$ region of the binding domain is distinct from the encoded $V_H$ region and/or $V_L$ region in the binding domain of the recombinant receptor present in at least one of the other reporter T cells in the plurality.

In some embodiments, the vector backbone further includes a nucleic acid sequence encoding a transmembrane domain disposed between the one or more site(s) for introduction of a nucleic acid sequence encoding a binding domain and the nucleic acid sequence encoding the intracellular signaling region. In some embodiments, the encoded intracellular signaling region further includes a costimulatory signaling region. In some embodiments, the costimulatory signaling region includes an intracellular signaling domain of a T cell costimulatory molecule or a signaling portion thereof. In some embodiments, the costimulatory signaling region includes an intracellular signaling domain of a CD28, a 4-1BB or an ICOS or a signaling portion thereof. In some embodiments, the costimulatory signaling region is between the transmembrane domain and the intracellular signaling region.

In some embodiments of any of the methods described herein, the vector backbone further includes a nucleic acid sequence encoding a leader sequence. In some embodiments, the leader sequence is derived from the leader sequence of human CD33. In some embodiments, the nucleic acid sequences encoding the leader sequence includes a molecular barcode. In some embodiments, each molecular barcode is distinct from at least one of the molecular barcodes present in the plurality of polynucleotides. In some embodiments, the molecular barcode includes the sequence GCTBTGGGCHGGNGC (SEQ ID NO:14), wherein B=C or G or T; H=A or C or T; and N=A or C or G or T.

In some embodiments of any of the methods described herein, the vector backbone further includes regulatory elements for expression of components of the recombinant receptor. In some embodiments, the regulatory element for expression is a promoter. In some embodiments, the promoter is selected from among an RNA pol I, pol II or pol III promoter. In some embodiments, the promoter is selected from: (1) a pol III promoter that is a U6 or H1 promoter; or (2) a pol II promoter that is a CMV, SV40 early region or adenovirus major late promoter. In some embodiments, the promoter is or includes a human elongation factor 1 alpha (EF1α) promoter or an MND promoter or a modified form thereof. In some embodiments, the promoter is an inducible promoter or a repressible promoter. In some embodiments, the promoter includes a Lac operator sequence, a tetracycline operator sequence, a galactose operator sequence or a doxycycline operator sequence, or is an analog thereof or is capable of being bound by or recognized by a Lac repressor or a tetracycline repressor, or an analog thereof. In some embodiments, the promoter includes a Lac operator sequence, a tetracycline operator sequence, a galactose operator sequence or a doxycycline operator sequence.

In some embodiments of any of the methods described herein, the vector backbone further includes a nucleic acid sequence encoding a spacer and/or a hinge region. In some embodiments, the encoded spacer is derived from an immunoglobulin or a portion thereof. In some embodiments, the encoded spacer is derived from a hinge of IgG4 or IgG1, a hinge of IgG4 linked to a $C_H3$ domain, or a hinge of IgG4 linked to a $C_H2$ and $C_H3$ domains. In some embodiments, the encoded spacer includes the sequence of amino acids set forth in SEQ ID NO: 20, 22 or 24, or a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NO: 20, 22 or 24.

In some embodiments of any of the methods described herein, the vector further includes a nucleic acid sequence encoding one or more marker(s) that optionally is or includes a transduction marker and/or a selection marker. In some embodiments, the transduction marker includes a fluorescent protein, a cell surface protein or a modified form thereof. In some embodiments, the selection marker includes a Puromycin resistance gene, a Hygromycin resistance gene, a Blasticidin resistance gene, a Neomycin resistance gene, a Geneticin resistance gene or a Zeocin resistance gene or a modified form thereof.

In some embodiments of any of the methods described herein, the vector backbone further includes a nucleic acid sequence encoding an internal ribosome entry site (IRES) or a ribosome skip element selected from among a T2A, a P2A, a E2A or a F2A separating the nucleic acid sequences encoding one or more components of the recombinant receptor and/or markers. In some embodiments, the vector backbone is capable of accepting an insert containing nucleic acid sequences encoding one of a plurality of binding domains. In some embodiments, the binding domain is or includes an antibody or an antibody fragment thereof, which optionally is a single chain fragment. In some embodiments, the fragment includes antibody variable regions joined by a flexible linker. In some embodiments, the fragment includes an scFv. In some of any embodiments, the fragment comprises a heavy chain variable ($V_H$) region and a light chain variable ($V_L$) region, optionally joined by a flexible linker. In some of any embodiments, the $V_H$ region is amino-terminal to the $V_L$ region. In some of any embodiments, the $V_H$ region is carboxy-terminal to the $V_L$ region.

In some embodiments of any of the methods described herein, the vector backbone is a viral vector. In some embodiments, the viral vector is a retroviral vector. In some embodiments, the viral vector is a lentiviral vector. In some embodiments, the lentiviral vector is derived from HIV-1.

In some embodiments of any of the methods described herein, the plurality of nucleic acid sequences encoding a binding domain includes at least 2, 5, 10, 25, 50, 100, 500, $10^3$, $10^4$, $10^5$, $10^6$ or more different nucleic acid sequences. In some embodiments, the plurality of polynucleotides encoding a recombinant receptor includes at least 2, 5, 10, 25, 50, 100, 500, $10^3$, $10^4$, $10^5$, $10^6$ or more different polynucleotides. In some of any embodiments, the plurality of reporter T cells comprises at least 2, 5, 10, 25, 50, 100, 500, $10^3$, $10^4$, $10^5$, $10^6$ or more different reporter T cells.

In some embodiments of any of the methods described herein, the T cell is an immortalized cell line. In some embodiments, the T cell line is a Jurkat cell line or a derivative thereof, optionally Jurkat T cell clone E6-1.

Provided in some embodiments, are a plurality of reporter T cells, containing one or more of the reporter T cells generated by any of the methods described herein.

Provided in other aspects are a plurality of polynucleotides encoding a recombinant receptor, containing one or more of the polynucleotides encoding a recombinant receptor assessed in any of the methods described herein.

In some embodiments, the reporter T cell is identified by a method described in any of the embodiments provided herein. In some embodiments, a polynucleotide encoding a recombinant receptor present in the reporter T cell is identified by a method of any of the embodiments provided herein. In some embodiments, a binding domain, encoded by the polynucleotide encoding the recombinant receptor present in the reporter T cell identified by a method of any of the embodiments provided herein. In some embodiments, a recombinant receptor, encoded by the polynucleotide encoding the recombinant receptor present in the reporter T cell identified by a method of any of the embodiments provided herein.

In some aspects, provided is a vector backbone that includes a) regulatory elements for expression of components of a recombinant receptor, b) a nucleic acid sequence encoding a leader sequence containing a molecular barcode, c) one or more site(s) for introduction of a nucleic acid sequence encoding a binding domain or a portion thereof; d) a nucleic acid sequence encoding a spacer, e) a nucleic acid sequence encoding an intracellular signaling region, and optionally f) a nucleic acid sequence encoding one or more marker(s).

In some embodiments, the vector backbone is capable of accepting an insert containing nucleic acid sequences encoding one of a plurality of binding domains. In some embodiments of any of the vector backbones described herein, the binding domain is or includes an antibody or an antibody fragment thereof, which optionally is a single chain fragment. In some embodiments, the fragment includes antibody variable regions joined by a flexible linker. In some embodiments, the fragment includes an scFv. In some of any embodiments, the fragment comprises a heavy chain variable ($V_H$) region and a light chain variable ($V_L$) region, optionally joined by a flexible linker. In some of any embodiments, the $V_H$ region is amino-terminal to the $V_L$ region. In some of any embodiments, the $V_H$ region is carboxy-terminal to the $V_L$ region.

In some of any embodiments, the vector backbone comprises one or more site(s) for introduction of a nucleic acid sequence encoding a $V_H$ region of the binding domain. In some of any embodiments, the vector backbone comprises one or more site(s) for introduction of a nucleic acid sequence encoding a $V_L$ region of the binding domain. In some of any embodiments, the vector backbone comprises one or more site(s) for introduction of a nucleic acid sequence encoding a $V_H$ region and a $V_L$ region of the binding domain.

In some embodiments, the regulatory element for expression is a promoter. In some embodiments, the promoter is selected from among an RNA pol I, pol II or pol III promoter. In some embodiments, the promoter is selected from: a pol III promoter that is a U6 or H1 promoter; or a pol II promoter that is a CMV, SV40 early region or adenovirus major late promoter. In some embodiments, the promoter is or includes a human elongation factor 1 alpha (EF1a) promoter or an MND promoter or a modified form thereof. In some embodiments, the promoter is an inducible promoter or a repressible promoter. In some embodiments, the promoter includes a Lac operator sequence, a tetracycline operator sequence, a galactose operator sequence or a doxycycline operator sequence, or is an analog thereof or is capable of being bound by or recognized by a Lac repressor or a tetracycline repressor, or an analog thereof. In some embodiments, the promoter includes a Lac operator sequence, a tetracycline operator sequence, a galactose operator sequence or a doxycycline operator sequence.

In some embodiments of any of the vector backbones described herein, the leader sequence is derived from the leader sequence of human CD33. In some embodiments, the nucleic acid sequences encoding the leader sequence includes a molecular barcode. In some embodiments, each molecular barcode is distinct from at least one of the molecular barcodes present in the plurality of polynucleotides. In some embodiments, the molecular barcode includes the sequence GCTBTGGGCHGGNGC (SEQ ID NO:14), wherein B=C or G or T; H=A or C or T; and N=A or C or G or T.

In some embodiments of any of the vector backbones described herein, the one or more site(s) for introduction of a nucleic acid sequence encoding a binding domain includes a restriction site. In some embodiments, the restriction site is a restriction site that does not occur or occurs 1, 2 or 3 or fewer times within an endogenous human $V_H$ or $V_L$ gene. In some embodiments, the encoded spacer is derived from an immunoglobulin or a portion thereof. In some embodiments, the encoded spacer is derived from a hinge of IgG4 or IgG1, a hinge of IgG4 linked to a $C_H3$ domain, or a hinge of IgG4 linked to a $C_H2$ and $C_H3$ domains. In some embodiments, the encoded spacer includes the sequence of amino acids set forth in SEQ ID NO: 20, 22 or 24, or a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NO: 20, 22 or 24.

In some embodiments of any of the vector backbones described herein, the encoded intracellular signaling region includes an intracellular signaling domain. In some embodiments, the intracellular signaling domain is or includes a primary signaling domain, a signaling domain that is capable of inducing a primary activation signal in a T cell, a signaling domain of a T cell receptor (TCR) component, and/or a signaling domain containing an immunoreceptor tyrosine-based activation motif (ITAM). In some embodiments, the intracellular signaling domain is or includes an intracellular signaling domain of a CD3 chain, optionally a CD3-zeta (CD3ζ) chain, or a signaling portion thereof. In some embodiments, the vector backbone further includes a nucleic acid sequence encoding a transmembrane domain disposed between the one or more site(s) for introduction of a nucleic acid sequence encoding a binding domain and the nucleic acid sequence encoding the intracellular signaling region. In some embodiments, the encoded intracellular signaling region further includes a costimulatory signaling region. In some embodiments, the costimulatory signaling region includes an intracellular signaling domain of a T cell costimulatory molecule or a signaling portion thereof. In some embodiments, the costimulatory signaling region includes an intracellular signaling domain of a CD28, a 4-1BB or an ICOS or a signaling portion thereof. In some embodiments, the costimulatory signaling region is between the transmembrane domain and the intracellular signaling region.

In some embodiments of any of the vector backbones described herein, the one or more marker(s) is or includes a transduction marker and/or a selection marker. In some embodiments, the transduction marker includes a fluorescent protein, a cell surface protein or a modified form thereof. In some embodiments, the selection marker includes a Puromycin resistance gene, a Hygromycin resistance gene, a Blasticidin resistance gene, a Neomycin resistance gene, a Geneticin resistance gene or a Zeocin resistance gene or a modified form thereof. In some embodiments, the vector backbone further includes a nucleic acid sequence encoding an internal ribosome entry site (IRES) or a ribosome skip element selected from among a T2A, a P2A, a E2A or a F2A separating the nucleic acid sequences encoding one or more components of the recombinant receptor and/or markers.

In some embodiments of any of the vector backbones described herein, the vector backbone is a viral vector. In some embodiments, the viral vector is a retroviral vector. In some embodiments, the viral vector is a lentiviral vector. In some embodiments, the lentiviral vector is derived from HIV-1.

Also provided are reporter cells comprising a nucleic acid sequence encoding a reporter molecule operably linked to a transcriptional regulatory element of the endogenous locus encoding Nur77 and a polynucleotide encoding a recombinant receptor, wherein the polynucleotide comprises i) any of the vector backbones provided herein and ii) a nucleic acid sequence encoding a binding domain.

Also provided is a plurality of reporter T cells, comprising one or more of any one of the reporter T cells provided herein. In some of any such embodiments, the recombinant receptor present in the one or more reporter T cell is distinct from the recombinant receptor present in at least one of the other reporter T cells in the plurality.

Provided in some aspects are kits that include the reporter T cell of any of the embodiments described herein; and optionally instructions for use. Provided in other aspects are kits that include the vector backbone of any of the embodiments described herein; and optionally instructions for use. Also provided are kits that include the reporter T cell of any of the embodiments described herein; the vector backbone of any of the embodiments described herein; and optionally instructions for use.

BRIEF DESCRIPTION OF THE DRAWINGS

FIG. 7C) of tdTomato+ cells, as assessed by flow cytometry, among reporter cells expressing anti-BCMA CAR #1, incubated with increasing concentrations (0, 0.1, 0.25, 1, 2.5, 10, 25 and 100 μg/mL) of huBCMA and cynoBCMA coated on 96-well flat-bottom plates.

DETAILED DESCRIPTION

Figure 1:
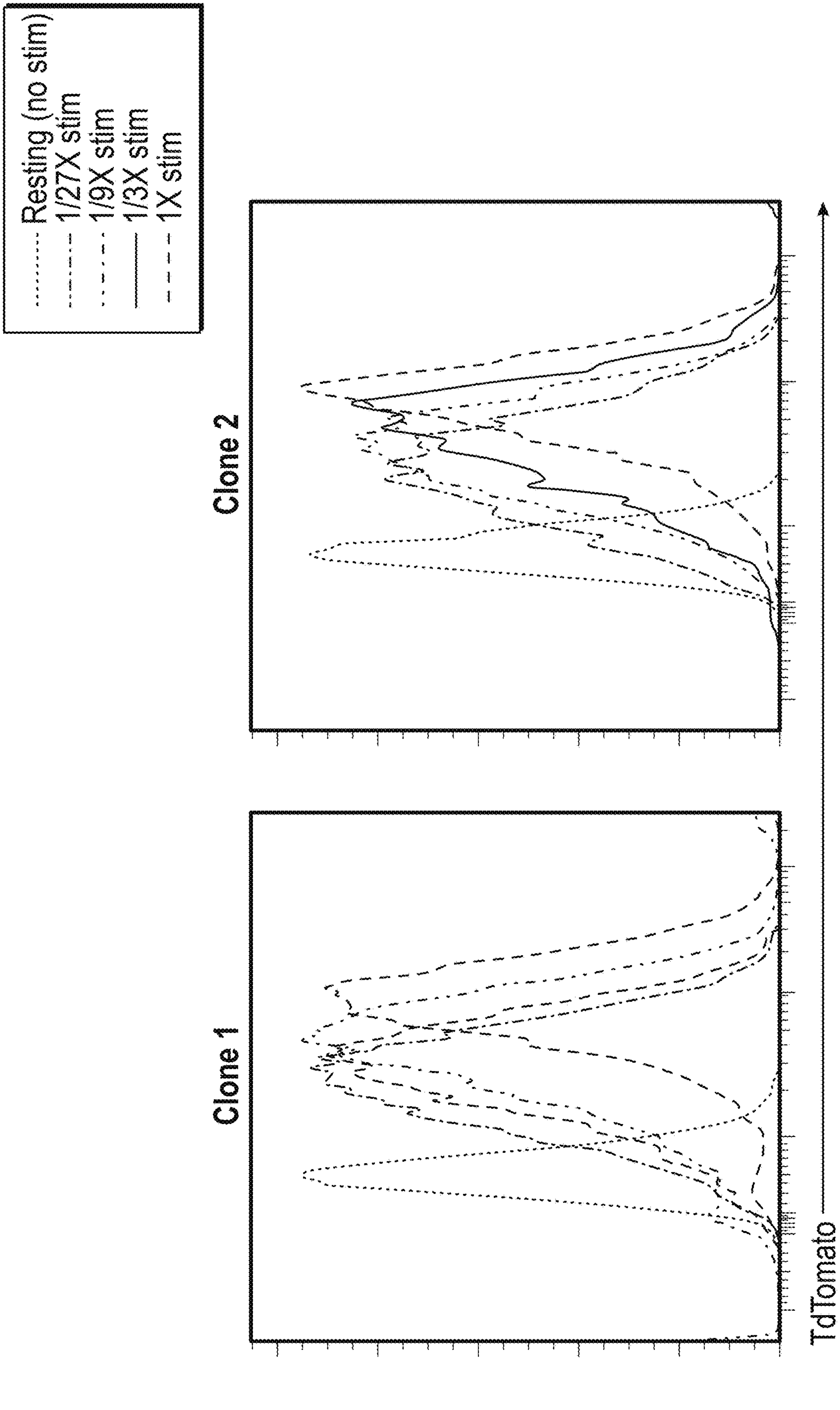
FIG. 1 depicts the expression level of tdTomato in the Jurkat Nur77-tdTomato reporter cells, as detected by flow cytometry, following stimulation with a three-fold serial dilution of PMA/ionomycin, at 80 nM PMA and 1.34 μM ionomycin (1× stim), and 3-fold (⅓× stim), 9-fold (1/9× stim) and 27-fold dilution (1/27× stim) compared to resting (no stimulation).

Provided herein are cells and methods for assessing activity of a recombinant receptor. Also provided are cells, such as reporter cells, and nucleic acid molecules, e.g., vector backbones, that can be used in the methods provided herein. In some embodiments, the methods employ a reporter cell, e.g., a reporter T cell, that contains a reporter that is responsive to a signal through the intracellular signaling region of the recombinant receptor, such as a primary activation signal in a T cell, a signaling domain of a T cell receptor (TCR) component, and/or a signaling domain comprising an immunoreceptor tyrosine-based activation motif (ITAM). In some embodiments, the methods can be used to assess the activity of a plurality of recombinant receptors, e.g., a plurality of candidate recombinant receptors. In some embodiments, the methods can be used as or can include a screening method.

Also provided are methods of generating a plurality of reporter cells, e.g., to be used to assess a plurality of recombinant receptors. In some embodiments, also provided are vector backbones to facilitate the generation and assessment of a plurality of recombinant receptors, from one or more sequences, e.g., a library, encoding particular components of the recombinant receptor to be tested, e.g., a binding domain and/or a signaling region. Also provided are vector backbones, cells, cell compositions, articles of manufacture and kits for use in the methods provided herein. Also provided are a plurality of polynucleotides, such as a library of polynucleotides, and a plurality of cells, such as a library of cells, that encode or express a plurality of recombinant receptors. Also provided are methods for screening such plurality of recombinant receptors or plurality of cells.

In some embodiments, the provided cells, e.g., reporter T cells, contain a reporter that is responsive to a signal through the intracellular signaling region of the recombinant receptor. In some embodiments, the methods involve the use of such cells. In some embodiments, the recombinant receptor to be assessed or tested includes signaling regions such as a primary activation signal in a T cell, a signaling domain of a T cell receptor (TCR) component, and/or a signaling domain comprising an immunoreceptor tyrosine-based activation motif (ITAM). In some embodiments, the reporter T cell comprises a nucleic acid sequence encoding a reporter molecule operably linked to a transcriptional regulatory element of the endogenous locus encoding Nur77. In some embodiments, the reporter T cell contains a reporter molecule knocked-in at the endogenous Nur77 locus, such that the expression of the reporter is controlled by the endogenous transcriptional regulatory elements of the Nur77 gene.

T cell-based therapies, such as adoptive T cell therapies (including those involving the administration of cells expressing chimeric receptors specific for a disease or disorder of interest, such as chimeric antigen receptors (CARs) and/or other recombinant antigen receptors, as well as other adoptive immune cell and adoptive T cell therapies) can be effective in the treatment of cancer and other diseases and disorders. In certain contexts, available approaches to assess the activity of the recombinant receptors and/or screen and identify receptors and/or cells that possess desired properties or characteristics, e.g., activity or function, may not be satisfactory in one or more of these aspects. For example, in some contexts, assessing binding of a binding molecule, e.g., an antibody or an antigen-binding fragment thereof, to a specific antigen, in some cases does not correlate to physiological and functional activity when expressed as a part of a recombinant receptor. Also, in some contexts, recombinant receptors can exhibit antigen-independent activity or signaling (also known as "tonic signaling"), which could lead to undesirable effects, such as due to increased differentiation and/or exhaustion of T cells that express the recombinant receptor. In some aspects, such activities may limit the T cell's activity, effect or potency. In some cases, during engineering and ex vivo expansion of the cells for recombinant receptor expression, the cells may exhibit phenotypes indicative of exhaustion, due to tonic signaling through the recombinant receptor. Thus, in some contexts, the ability to efficiently and reliably assess the extent of tonic signaling can be a useful tool for determining the potential or likely activity, effect or potency of the T cell that expresses the recombinant receptor. Improved strategies are needed to assess the activity of recombinant receptor-expressing cells, in particular, tonic signaling.

Improved strategies are also needed to assess different parameters or activities of a recombinant receptor simultaneously and/or in a large scale. In some aspects, it is desirable to assess and/or compare different components of recombinant receptors, such as binding domains, spacers, costimulatory signaling regions and other components of a recombinant receptor, such as a CAR. The provided embodiments provide a platform to easily and robustly assess and screen CARs, including CARs that differ in one or more components in order to identify features of a CAR that are likely to improve in vivo efficacy when administered to a subject.

The provided embodiments, in some contexts, are based on the observation that the expression of the endogenous Nur77 gene is cell intrinsic, and/or is not substantially affected or influenced by other signaling pathways, such as cytokine signaling or toll like receptor (TLR) signaling (see, e.g., Ashouri et al., (2017) J. Immunol. 198:657-668), which may act in a cell extrinsic manner and may not depend on signaling through the recombinant receptor. In some contexts, Nur77 expression is sensitive to a primary activation signal in a T cell, signals from a signaling domain of a T cell receptor (TCR) component, and/or a signaling domain comprising an immunoreceptor tyrosine-based activation motif (ITAM). In some contexts, the response of Nur77 reporter is dose-responsive to signals through the signaling regions. In some embodiments, expression of the reporter, among other parameters, can be assessed after incubation of the reporter T cells in the presence or absence of an agent that binds to the binding domain of the recombinant receptor and/or an agent that induces or is capable of inducing a signal through the intracellular signaling region of the recombinant receptor. Further, in some embodiments, the provided reporter T cells contain nucleic acid sequences encoding the reporter molecule knocked into the endogenous Nur77 locus, providing a stable reporter cell line that can generate consistent results, e.g., not dependent on the location of random genomic integration or copy number and/or loss of reporter. Such reporter cells can be used to screen numerous recombinant receptors, simultaneously with consistent readouts.

In some contexts, Nur77 expression can also be used to assess antigen-independent activity and/or tonic signaling, such as by assessing the reporter expression after incubation in the absence of an agent that binds to the binding domain of a recombinant receptor and/or an agent that induces or is capable of inducing a signal through the intracellular signaling region of a recombinant receptor. Thus, in some embodiments, the reporter cells, such as reporter T cells containing the Nur77 reporter, can be utilized to assess both antigen-dependent activity and antigen-independent signaling of a recombinant receptor.

In some embodiments, provided are vector backbones that can be used in the methods provided herein. In some embodiments, the vector backbones can be used to facilitate the generation and assessment of a plurality of recombinant receptors, from one or more sequences, e.g., a library, encoding particular components of the recombinant receptor to be tested, e.g., a binding domain and/or a signaling region. The provided backbones can be used to rapidly and efficiently generate a plurality of polynucleotides expressing recombinant receptors, from common sequences contained in the backbone of the vector encoding components of the recombinant receptor, e.g., CAR, and a site for insertion of different components, e.g., binding domains. In some embodiments, the vector backbones can facilitate the expression of a plurality of candidate binding domains in the format of a recombinant receptor, e.g., CAR, and generation of a plurality of cells, e.g., reporter T cells, to rapidly and easily assess and/or screen to identify cells expressing recombinant receptors with desired characteristics. The provided embodiments permit bivalent expression of the binding domains in the context of a recombinant receptor, e.g., a CAR, and physiological expression and assessment. In some embodiments, such vector backbones can be utilized to engineer reporter cells, such as any reporter T cells described herein, to generate one or more reporter T cells, e.g., plurality of reporter T cells, that can be used to rapidly and efficiently assess the activity of the recombinant receptors.

In some contexts, the provided embodiments, including the cells, methods, kits and articles of manufacture, can be adapted to different types of recombinant receptors, such as recombinant T cell receptors (TCRs), or other binding domain libraries.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. ASSESSING ACTIVITY OF RECOMBINANT RECEPTORS

Provided herein are cells, methods, vectors, polynucleotides, pluralities of cells, pluralities of polynucleotides, kits and articles of manufacture, including those related to assessing the activity of recombinant receptors, e.g., chimeric antigen receptors (CARs). Among the provided embodiments are those that can be used to assess and/or screen different recombinant receptors, such as candidate receptors, and encoding nucleic acids thereof, for example, in a low-, medium- or high-throughput manner. In some cases, the provided embodiments facilitate the assessment of an antigen-independent signal through the recombinant receptor and/or antigen-specific activity of the recombinant receptor.

In some embodiments, provided are cells, such as reporter T cells, for assessing activity of the recombinant receptor. In some embodiments, the reporter T cell comprises a reporter molecule, wherein the expression of a reporter molecule is responsive to a signal through the intracellular signaling region of the recombinant receptor. In some embodiments, the provided cells include reporter T cells. In some embodiments, the reporter T cells contain a nucleic acid sequence encoding a reporter molecule operably linked to a transcriptional regulatory element or a variant thereof of a Nur77, wherein the transcriptional regulatory element optionally is a transcriptional regulatory element within an endogenous Nur77 locus in the T cell. In some aspects the provided cells such as provided reporter T cells contain a nucleic acid sequence encoding a reporter molecule operably linked to a transcriptional regulatory element, such as a transcriptional regulatory element of the endogenous locus encoding Nur77. In some embodiments, the provided cells can be used to assess activity of one or more recombinant receptors, e.g., for screening a plurality or a library of candidate recombinant receptors.

Provided embodiments also include methods of assessing activity of a recombinant receptor such as those using any of the provided cells or constructs. In some embodiments, the recombinant receptor is a CAR. In some embodiments, the methods involve incubating one or more reporter T cells, such as T cells each comprising i) a recombinant receptor, such as a recombinant receptor that is a CAR comprising an intracellular signaling region and ii) a reporter molecule, wherein the expression of said reporter molecule is responsive to a signal through the intracellular signaling region of the recombinant receptor, wherein the incubating is carried out in the presence and/or absence of an agent that binds to the binding domain of the recombinant receptor and/or an agent that induces or is capable of inducing a signal through the intracellular signaling region of the recombinant receptor; and assessing the one or more reporter T cells for expression of the reporter molecule. In some embodiments, the methods can employ any of the cells, e.g., reporter T cells, described herein.

Also among the provided embodiments are methods of generating a plurality of reporter cells such as reporter T cells such as those cells provided herein. In some embodiments, the methods involve a) producing a plurality of polynucleotides each encoding a recombinant receptor (e.g., a recombinant receptor containing an intracellular signaling region), wherein each polynucleotide comprises i) a vector backbone comprising a nucleic acid sequence encoding an intracellular signaling region and ii) a nucleic acid sequence encoding a binding domain; and b) introducing one of the plurality of polynucleotides encoding a recombinant receptor into a reporter T cell comprising a reporter molecule, wherein the expression of said reporter molecule is responsive to a signal through the intracellular signaling region, and the encoded recombinant receptor present in the reporter T cell is distinct from the encoded recombinant receptor present in at least one of the other reporter T cells in the plurality. In some embodiments, the such plurality of reporter T cells generated using the methods, can be subsequently used in or subject to any of the methods of assessing activity described herein.

Also provided are methods of screening recombinant receptors. In some embodiments, the methods of screening can involve one or more steps of: a) producing a plurality of polynucleotides each encoding a recombinant receptor that is a chimeric antigen receptor (CAR), wherein each polynucleotide comprises i) a vector backbone comprising a nucleic acid sequence encoding an intracellular signaling region and ii) a nucleic acid sequence encoding a binding domain; b) introducing one of the plurality of polynucleotides encoding a recombinant receptor into a reporter T cell comprising a reporter molecule, wherein the expression of said reporter molecule is responsive to a signal through the intracellular signaling region, and the encoded recombinant receptor present in the reporter T cell is distinct from the encoded recombinant receptor present in at least one of the other reporter T cells in the plurality; c) incubating one or more reporter T cells from the plurality of reporter T cells in the presence or absence of an agent that binds to the binding domain of the recombinant receptor and/or an agent that induces or is capable of inducing a signal through an intracellular signaling region of the recombinant receptor; d) assessing the one or more reporter T cells for expression of the reporter molecule and/or expression of the recombinant receptor on the surface of the cell; and e) identifying one or more reporter T cells among the plurality that express the recombinant receptor on the surface of the cell, express the reporter molecule in the presence of the agent and/or do not express the reporter molecule in the absence of the agent.

In any of the embodiments provided herein, the incubating can be carried out in the absence of the agent, thereby assessing antigen-independent signal through the recombinant receptor. In any of the embodiments provided herein, the incubating can be carried out in the presence of the agent, thereby assessing antigen-specific activity of the recombinant receptor.

In some embodiments, the methods also involve assessing other characteristics and/or properties of the recombinant receptor, e.g., surface expression or functional T cell activity.

In some embodiments, also provided are pluralities (and/or libraries) of reporter T cells that include one or more of any of the reporter T cells generated by the methods described herein. In some embodiments, also provided are pluralities (and/or libraries) of polynucleotides encoding a recombinant receptor, comprising one or more of the polynucleotides encoding a recombinant receptors assessed or identified in any of the methods provided herein.

In some embodiments, also provided are reporter T cells, polynucleotides encoding a recombinant receptor, binding domain, or recombinant receptor identified by, or present in the cell identified by any of the methods provided herein.

In some embodiments, also provided are vector backbones for use in any of the methods provided herein. In some embodiments, the vector backbone can include any one or more of: a) regulatory elements for expression of components of a recombinant receptor, b) a nucleic acid sequence encoding a leader sequence comprising a molecular barcode, c) one or more site(s) for introduction of a nucleic acid sequence encoding a binding domain, d) a nucleic acid sequence encoding a spacer, e) a nucleic acid sequence encoding an intracellular signaling region, and/or f) a nucleic acid sequence encoding one or more marker(s). In some embodiments, any of the provided vector backbone can be used to facilitate the generation, assessment and/or screening of one or a plurality of candidate recombinant receptors, expressed in a cell, e.g., reporter T cell.

Also provided are kits and article of manufacture, containing any of the reporter T cells and/or any of the vector backbone described herein. In some embodiments, the kits and article of manufacture can be employed in any of the methods provided herein.

II. CELLS FOR ASSESSING ACTIVITY AND/OR SCREENING

Provided herein are cells, such as T cell lines, that contain a reporter molecule that is capable of being expressed upon signal through the intracellular signaling region of the recombinant receptor. Also provided are methods of using such cells, e.g., methods of assessing activity of a recombinant receptor using such cells. In some embodiments, the methods provided herein include assessing activity, e.g., signaling, of a recombinant receptor, e.g., CAR, in a T cell. In some embodiments, the methods include screening for expression and/or activity of a recombinant receptor, e.g., CAR, in T cells, such as in a plurality of T cells. In some embodiments of the methods provided herein, the activity is assessed in T cells, such as a T cell line. In some embodiments, the T cell comprises a reporter molecule, e.g., a reporter molecule that is capable of being expressed upon signal through the intracellular signaling region of the recombinant receptor and/or binding and/or recognition of the recombinant receptor to a target antigen or epitope. In some embodiments, provided are reporter T cells, such as reporter T cell lines, comprising a nucleic acid sequence encoding a reporter molecule operably linked to a transcriptional regulatory element of the endogenous locus encoding Nur77.

A. Cells and Cell Lines

In some embodiments, provided are T cells, such as T cells comprising a reporter molecule or reporter T cells. In some embodiments of the methods provided herein, T cell, such as a reporter T cell, is employed to assess activity e.g., signaling and/or activation, of the recombinant receptor, e.g., CAR. In some embodiments, the T cell is a T cell line, such as a Jurkat-derived cell line. In some embodiments, provided are reporter T cells that are derived from a T cell line. In some embodiment, the T cell is a T cell line containing a reporter molecule, such as a reporter molecule capable of producing a detectable signal upon signal through the intracellular signaling region of a recombinant receptor. Also provided are compositions containing any of the cells, such as reporter T cells, described herein.

In some aspects, the T cells or T cell compositions into which the nucleic acid molecules encoding the candidate recombinant receptors are introduced, can be referred to as "host cells" or "host cell lines." In some embodiments, the host cell is a T cell. The terms "host cell," "host cell line," and "host cell culture" are used interchangeably and refer to cells into which exogenous nucleic acid molecules have been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

In some embodiments, the cell or cell line is an immortalized cell line and/or a clonal cell line. In some embodiments, the cell or cell line is a transformed cell line. In some embodiments, the cell or cell line is a T cell line. In some embodiments, the cell or cell line is a cell line capable of transmitting, transducing, and/or mediating signaling through CD3. For example, the cell or cell line contains or expresses components of the T cell receptor (TCR) signaling pathway containing CD3 or can transduce a TCR complex containing CD3. In some embodiments, the cell contains or expresses components of the signaling pathways for transmission of signals from a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM). In some embodiments, the cell or cell line is H9 human T lymphocyte (ATCC, HTB-176) or Jurkat human T cell leukemia cell line (ATCC, TIB-152).

In some embodiments, the cell is a cell line, such as a cell line available from private and commercial sources, such as American Type Culture Collection (ATCC); National Institute of General Medical Sciences (NIGMS); ASHI Repository; the European Collection of Cell Cultures (ECACC); or the International Histocompatibility Working (IHW) Group Cell and DNA bank. In some cases, cell lines are commercially available. In some embodiments, the cells are cell lines or derived from cell lines, e.g., T cell lines. In some embodiments, the cell line is a T lymphocyte or T lymphoblast cell line. For example, the cell or cell line is Jurkat, Clone E6-1 (ATCC, PTS-TIB-152™, TIB-152™); 31E9 (ATCC, HB-11052™); CCRF-CEM (ATCC, CCL-119™, CRM-CCL-119D™, CRM-CCL-119™, PTS-CCL-119™); CCRF-HSB-2 (ATCC, CCL-120.1™); CEM/C1 (ATCC, CRL-2265™); CEM/C2 (ATCC, CRL-2264™); CEM-CM3 (ATCC, TIB-195™); FeT-1C (ATCC, CRL-11968™); FeT-J (ATCC, CRL-11967™); J.CaM1.6 (ATCC, CRL-2063™); J.RT3-T3.5 (ATCC, TIB-153™); J45.01 (ATCC, CRL-1990™); Loucy (ATCC, CRL-2629™); MOLT-3 (ATCC, CRL-1552™); MYA-1 (ATCC, CRL-2417™); SUP-T1

(ATCC, CRL-1942™); TALL-104 (ATCC, CRL-11386™); I9.2; I2.1; D1.1; J.gamma1 subline or J-Lat. In some embodiments, the cell or cell line is Jurkat, Clone E6-1 (ATCC, PTS-TIB-152™, TIB-152™).

In some embodiments, the T cells include one or more nucleic acid molecules introduced via genetic engineering, and thereby express recombinant or genetically engineered products of such nucleic acid molecules. In some embodiments, the nucleic acid molecules are heterologous, i.e., normally not present in a cell or sample obtained from the cell, such as one obtained from another organism or cell, which, for example, is not ordinarily found in the cell being engineered and/or an organism from which such cell is derived. In some embodiments, the nucleic acid molecules are not naturally occurring, such as a nucleic acid not found in nature, including one comprising chimeric combinations of nucleic acid molecules encoding various domains from multiple different cell types. In some embodiments, the T cells into which one of a plurality of recombinant receptors are introduced, transfected and/or transduced are T hybridoma cells.

Also provided are plurality of T cells or composition of T cells. In some embodiments, the provided plurality of T cells or composition of T cells comprise any of the T cells described herein, such as reporter T cells. In some embodiments, the provided plurality of T cells or composition of T cells (e.g., reporter T cells) that have been engineered to express a recombinant receptor, e.g., a CAR. In some cases, the engineering is performed by introducing one of a plurality of polynucleotide or nucleic acid molecules encoding recombinant receptors, e.g., CARs. In some embodiments, each of the plurality of T cells comprises one or more T cells, e.g., reporter T cells, containing a recombinant receptor, wherein the encoded recombinant receptor, e.g., CAR, is distinct from the recombinant receptor, e.g., CAR, in other T cells in the plurality. In some embodiments, each of the plurality of polynucleotide encoding the candidate recombinant receptor, e.g., CAR, is introduced into a separate composition containing one or more T cells (alternative called a “population of T cells”). In some embodiments, by individually introducing each polynucleotide into a separate composition of cells, the identity of the candidate recombinant receptor, e.g., CAR, is preserved.

Alternatively, in some embodiments, the plurality of polynucleotides encoding the candidate recombinant receptor, e.g., CAR, are pooled, and the pool of polynucleotides is introduced into a composition of cells. In such embodiments, the identity of particular encoded recombinant receptor, e.g., CAR, can be determined in a subsequent confirmation step, e.g., by sequencing or other method of confirmation, e.g., by determining the sequence of one or more molecular barcodes present in the cell.

In some embodiments, cells of a plurality of T cells are assessed and/or screened in accord with the provided methods.

B. Reporters

In some embodiments, the cell lines, e.g. T cell lines, contain a reporter molecule whose expression is responsive to a signal through the intracellular signaling region of the recombinant receptor, i.e. hereinafter also called “reporter cells,” such as “reporter T cells”. In some embodiments, the provided cells, such as reporter T cells, contain a reporter molecule whose expression is responsive to a signal through the intracellular signaling region of the recombinant receptor. In some embodiments, the expression of the reporter molecule is responsive to signals through a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM). In some embodiments, expression of the reporter molecule is responsive to signals through an intracellular signaling domain of a CD3 chain, optionally a CD3-zeta (CD3ζ) chain, or a signaling portion thereof and/or a costimulatory signaling region, such as an intracellular signaling domain of a T cell costimulatory molecule or a signaling portion thereof.

In some embodiments, the provided T cells, e.g., reporter T cells, and/or any of the T cells used to assess a candidate recombinant receptor, e.g., CAR and/or to which the polynucleotides encoding a candidate recombinant receptor, e.g., CAR are introduced, contain nucleic acid sequences encoding one or more reporter molecules capable of producing a detectable signal upon signaling through the intracellular signaling region of the recombinant receptor. In some embodiments, for generating a plurality of T cells that express an exogenous candidate recombinant receptor, e.g., CAR, each T cell contains (1) a reporter capable of producing a detectable signal upon signaling through the intracellular signaling region of the recombinant receptor and (2) a polynucleotide encoding a candidate recombinant receptor, e.g., CAR. In some embodiments, the T cells or plurality of T cells contain more than one reporter.

In some embodiments of the methods, assessing the activity of the recombinant receptor, CAR, includes assessing expression of nucleic acid sequences encoding a reporter, for example, determining the presence or absence of the detectable signal in or from T cells, e.g., T cells in a plurality of T cells, in the presence or absence of an agent that binds to the binding domain of the recombinant receptor and/or an agent that induces or is capable of inducing a signal through the intracellular signaling region of the recombinant receptor. In some embodiments, the agent comprises a target antigen or epitope specifically recognized or specifically bound by the recombinant receptor.

In some embodiments, the detectable signal comprises a signal that is altered compared to the signal produced by the reporter molecule in the reporter cell in the absence of the recombinant receptor in the cell, and/or in the presence or absence of an agent that binds to the binding domain of the recombinant receptor and/or an agent that induces or is capable of inducing a signal through the intracellular signaling region of the recombinant receptor. In some embodiments, the detectable signal is induced or expressed, increased, decreased, repressed, changed in color or changed in location in the cell compared to the signal produced by the reporter in the absence of the recombinant receptor in the cell, and/or in the presence or absence of an agent that binds to the binding domain of the recombinant receptor and/or an agent that induces or is capable of inducing a signal through the intracellular signaling region of the recombinant receptor. In some embodiments, the expression of the reporter molecule is responsive to the quality and/or strength of the signal through the intracellular signaling region and/or binding and/or recognition of the recombinant receptor to a target antigen or epitope. Thus, in some embodiments, the reporter capable of producing a detectable signal upon signal through the intracellular signaling region of the recombinant receptor, can be used in low-, medium- or high-throughput screening methods to determine the activity, e.g., signaling activity and/or functional activity of the exogenous recombinant receptor, e.g., CAR, introduced into the T cells or plurality of T cells.

In some embodiments, T cells or plurality of T cells, that are engineered to express the candidate recombinant receptor, e.g., CAR contain a reporter that is capable of producing a detectable signal or read-out upon binding of the agent, e.g., specific antigen, to the recombinant receptor, e.g., CAR. In some embodiments, the reporter is capable of being detected, such as expressed or induced, in the cell upon signaling through the intracellular signaling region and/or binding and/or recognition of the recombinant receptor to a target antigen or epitope and/or upon cell signaling transduced through an intracellular signaling region containing CD3 or a portion thereof. In general, a signal, such as a T cell receptor activation signal, is induced or initiated upon binding of an agent, e.g., specific antigen or epitope, which leads to the cross-linking and activation of the signaling complex that contains CD3. The signal, in some cases, then can initiate further downstream signaling and expression of various intracellular compounds associated with antigen or epitope binding and/or activation signaling, e.g., T cell activation signaling. In some embodiments, T cell activation through the CD3 complex can lead to induction of signal transduction pathways in the T cell resulting in production of cellular signaling and expression of products (e.g., interleukin-2) by that T cell.

In some embodiments, a "reporter molecule" or "reporter" is any molecule that is or can produce a detectable signal that is altered compared to the signal from or produced by the reporter in the absence of an exogenous recombinant receptor, e.g., CAR, and/or in the presence or absence of an agent that binds to the binding domain of the recombinant receptor and/or an agent that induces or is capable of inducing a signal through the intracellular signaling region of the recombinant receptor, and/or in the absence of T cell activation, e.g., T cell activation through the intracellular signaling region of the recombinant receptor. In some embodiments, the detectable signal is induced or expressed, increased, decreased, repressed, changed in color or changed in location in the cell compared to the signal produced by the reporter in the absence of T cell activation and/or in the absence of the recombinant receptor in the cell. In some embodiments, the reporter is or can produce a detectable signal in the cell that can include light emission (e.g. fluorescence), FRET, concentration of a biochemical second messenger, i.e. molecule (e.g. calcium), protein or gene expression in the cell or protein secretion from the cell (e.g. IL-2). Various reporter systems of T cell function, including T cell activation, are known (see e.g. Hoekstra et al. (2015) Trends in Immunol, 36:392-400).

In some embodiments, the reporter of antigen or epitope binding and/or activity of a receptor, e.g., signaling or activation, is heterologous and/or exogenous to the cell, i.e. normally not present in a cell. In some embodiments, the T cells containing the recombinant receptor, e.g., CAR, can optionally contain a heterologous or exogenous reporter as a read-out of activity and/or signaling of the recombinant receptor, antigen and/or antigen or epitope binding and/or signal or activity through the intracellular signaling region of the recombinant receptor, e.g., CAR. In some embodiments, the read-out or reporter of antigen and/or antigen or epitope binding and/or signal or activity through the intracellular signaling region of the recombinant receptor, e.g., CAR is endogenous to the cell, such as a reporter associated with the induction of signal transduction pathways in the cells, such as the production of cytokine or other protein products, which can occur by T cell activation.

In some embodiments, the reporter is a detectable moiety, such as a light-emitting protein or bioluminescent protein, that can be detectable and can be monitored visually, or by using a spectrophotometer, luminometer, fluorometer or other related methods. In some embodiments, the reporter is a detectable moiety, such as an enzyme that produces bioluminescence, e.g., enzymes that can convert a substrate that emits light, e.g., luciferase or variants thereof. Non-limiting examples of light emitting proteins or enzymes that produce bioluminescence include, for example, luciferase, fluorescent proteins, such as red, blue and green fluorescent proteins (see, e.g., U.S. Pat. No. 6,232,107, which provides GFPs from *Renilla* species and other species), the lacZ gene from *E. coli*, alkaline phosphatase, secreted embryonic alkaline phosphatase (SEAP), chloramphenicol acetyl transferase (CAT). Exemplary light-emitting reporter genes include luciferase (luc), β-galactosidase, chloramphenicol acetyltransferase (CAT), β-glucuronidase (GUS), and fluorescent protein and variants thereof, such as green fluorescent protein (GFP), enhanced green fluorescent protein (EGFP), such as super-fold GFP (sfGFP), red fluorescent protein (RFP), such as tdTomato, mCherry, mStrawberry, AsRed2, DsRed or DsRed2, cyan fluorescent protein (CFP), blue green fluorescent protein (BFP), enhanced blue fluorescent protein (EBFP), and yellow fluorescent protein (YFP), and variants thereof, including species variants, monomeric variants, and codon-optimized and/or enhanced variants of the fluorescent proteins. Luciferases and variants thereof can include luciferases from the firefly (Photinus pyralis), sea pansy (*Renilla reniformis*), *Photobacterium* species (*Vibrio fischeri, Vibrio haweyi* and *Vibrio harveyi*), dinoflagellates, marine copepod (*Metridia longa*), deep sea shrimp (Oplophorus) and Jack-O-Lantern mushroom (*Omphalotus olearius*), and variants thereof, including codon-optimized and/or enhanced variants. In some embodiments, the reporter molecule is a red fluorescent protein (RFP), optionally tdTomato (amino acid sequence set forth in SEQ ID NO: 8 or 54, encoded by nucleic acid sequence set forth in SEQ ID NO:7 or 53).

In some embodiments, the reporter molecule can be a hormone or cytokines or other such well-known genes that can be induced or expressed in a T cell upon antigen or epitope binding and/or activity of a receptor, e.g., signaling or activation. The expression of these reporter genes can also be monitored by measuring levels of mRNA transcribed from these genes.

In some embodiments, a reporter, such as a detectable moiety, can be directly associated with a particular recombinant receptor, e.g., CAR, or downstream signal induced by activation of the recombinant receptor, e.g., CAR, following antigen or epitope binding, thereby providing a direct read-out of activity of the reporter, e.g., signaling or cell activation. In some embodiments, the detectable signal in the cell induced upon antigen or epitope binding and/or signal or activity through the intracellular signaling region of the recombinant receptor, is a change in location of the detectable moiety in the cell compared to its location in the cell in the absence of binding of the antigen receptor to a recognized antigen or epitope, and/or signal or activity through the intracellular signaling region of the recombinant receptor. In some aspects, a particular recombinant receptor, e.g., CAR, can be engineered with, such as operably fused to, a detectable moiety whose activity is turned on and/or can be otherwise visualized upon engagement or binding to an antigen, such as an epitope. In some cases, engagement of the recombinant receptor, e.g., CAR, can result in internalization of the receptor, which can be monitored. In some embodiments, a transcription factor or other signaling molecule whose expression is induced in response to signal or activity through the intracellular signaling region of the recombinant receptor can be engineered with, such as operably fused to, a detectable moiety whose activity is turned on and/or can be otherwise visualized upon engagement of binding to an antigen or epitope. In some cases, signal or activity through the intracellular signaling region of the recombinant receptor, such as T cell activation and/or signaling, can result in translocation of the signal-specific transcription factor from the cytosol to the nucleus, which can be monitored. In some embodiments, the detectable moiety can be any as described, such as a fluorescent, enzymatic or luminescent protein.

In some embodiments, fluorescence resonance energy transfer (FRET) based systems can be used that monitor changes in the interactions between two molecules in the cell. FRET systems that can monitor TCR engagement and/or T cell activation are known (see e.g., Zal and Gascoigne (2004) *Curr. Opin. Immunol.,* 16:674-83; Yudushkin and Vale (2010) *PNAS,* 107:22128-22133; Ibraheem et al. (2010) *Curr. Opin. Chem. Biol.,* 14:30-36).

In some embodiments of the methods and cells provided herein, the reporter molecule is associated with, under operable control of and/or regulated by a T cell activation factor. In some embodiments, the reporter molecule is encoded by a nucleic acid sequence under the operable control of a T cell activation factor, e.g., a regulatory element that is responsive to the quality and/or strength of the signal through the intracellular signaling region and/or binding and/or recognition of the recombinant receptor to a target antigen or epitope. In some embodiments, a "T cell activation factor" is a molecule or factor or portion thereof that is responsive to antigen or epitope binding by a receptor, e.g. T cell receptor (TCR) present or expressed on a T cell or to a signal transduced through a components of the TCR complex of a T cell, or a recombinant receptor comprising intracellular signaling regions that comprise a component of the TCR complex or a portion thereof. In some embodiments, the T cell activation factor can be a canonical factor or a portion thereof that is part of the normal downstream signaling pathway of T cells. In some embodiments, the read-out of T cell activation is a reporter encoded by a construct containing a T cell activation factor operably connected to the reporter molecule capable of detectable expression. In some embodiments, antigen or epitope binding and/or signal or activity through the intracellular signaling region of the recombinant receptor, e.g., CAR induces signaling that induces the T cell activation factor to express the reporter. Detectable expression of the reporter molecule can then be monitored as an indicator of T cell activation.

In some embodiments, the T cell activation factor is or contains one or more regulatory elements, such as one or more transcriptional control elements, of a target gene whose expression depends on or is associated with activation of components of the TCR complex, whereby the regulatory domain or element is recognized by a transcription factor to drive expression of such gene. In some cases, the T cell activation factor, such as a regulatory domain or element, can be or contain all or a portion of an endogenous regulatory region of a particular gene locus, e.g. the T cell activation factor is derived from a target gene locus. In some embodiments, the T cell activation factor is or contains a promoter, enhancer or other response element or portion thereof, recognized by a transcription factor to drive expression of a gene whose activity is normally turned on by T cell activation. In some embodiments, the T cell activation factor can be a regulatory domain or region (e.g. promoter, enhancer or other response element) of a transcription factor whose activity is turned on by T cell activation. In some embodiments, the T cell activation factor is responsive to one or more of the quality and/or strength of the signal through the intracellular signaling region and/or binding and/or recognition of the recombinant receptor to a target antigen or epitope. In some embodiments, the regulatory element is responsive to one or more of the state of the recombinant receptor binding to an antigen or epitope, T cell activation, signal strength of the recombinant receptor and/or quality of the signaling through the intracellular signaling region of the recombinant receptor, e.g., CAR. In some embodiments, the T cell activation factor is or comprises a transcriptional regulatory element of a gene whose expression is induced and/or is upregulated upon binding of the recombinant receptor binding to an antigen or epitope, T cell activation, signal strength of the recombinant receptor and/or quality of the signaling through the intracellular signaling region of the recombinant receptor, e.g., CAR.

Typically, a T cell activation factor is operably associated with a detectable readout of T cell activation, such as a reporter that is expressed from the cell and can be detected. Thus, for example, the expression of the reporter, instead of or in addition to the endogenous gene, can be induced upon T cell activation. The T cell activation factor, alone or together with a detectable readout, can be endogenous, exogenous or heterologous to the cell.

In some embodiments, the T cell activation factor can be a regulatory element, such as a transcriptional regulatory element, such as promoter, enhancer or response element or elements, that contain a binding site for a T cell transcription factor, and that thereby is associated with the downstream activity of a T cell transcription factor. In some embodiments, the transcription factor is nuclear factor of activated T cells (NFAT), C/EBP, STAT1, STAT2, or NFκB. In some embodiments, the T cell activation factor contains a response element or elements recognized by a nuclear factor of activated T cells (NFAT), C/EBP, STAT1, STAT2, and NFκB. In some embodiments, the T cell activation factor can contain a regulatory element or elements recognized by or responsive to one or two, and in some cases three or more, unique transcription factors.

In some cases, the T cell activation factor contains a binding site, such as a response element, recognized by only a single transcription factor that is selectively activated by signaling through components of the TCR complex induced through receptor engagement following antigen or epitope binding to the recombinant receptor, e.g., CAR. In some embodiments, the T cell activation factor comprises a response element or elements recognized by a transcription factor that is activated upon stimulation of T cells through an endogenous TCR complex. For example, generally regulatory regions of genes contain multiple regulatory elements that can be responsive to more than one signaling pathway in a cell. In contrast, an artificial regulatory region or artificial promoter that contains a regulatory element or elements recognized by a transcription factor selectively activated by signaling only through the components of the TCR complex can increase the specificity of the reporter system so that it is responsive only to T cell activation. In some embodiments, the T cell activation factor contains a regulatory element or elements recognized by NFAT. In some embodiments, the T cell activation factor contains a regulatory element or elements recognized by NFκB.

In some embodiments, the T cell activation factor is associated with NFAT activity and/or NFAT-regulated signal transduction. The NFAT family of transcription factors plays a role in the transcriptional regulation of cytokine genes and other genes involved in the immune response, including in response to T cell activation. Dimerization of NFAT polypeptides and their subsequent binding to target DNA typically results in an increase in the transcription of a target gene. NFAT target genes include cytokines (e.g., GM-CSF, IFN-γ, interleukins-2, -4, -5, and -13) and lymphocyte markers (e.g., CD40L and CTLA-4). NFAT polypeptides also are able to recognize and transactivate NF-κB-like consensus sequences that are found in the promoters responsive genes, such as TNF-α, IL-8, E-selectin, GM-CSF and IL-2. Generally, the expression of an NFAT target gene is increased when one or more consensus NFAT DNA binding sequences are adjacent to DNA binding sequences of their transcriptional binding partners. In some embodiments, the T cell activation factor can be a regulatory element, such as a promoter, enhancer or response element, that contains a binding site and/or is recognized by NFAT and that can drive the expression of a reporter operably connected thereto.

In some embodiments, the T cell activation factor is associated with the activity of NF-κB and/or NF-κB-mediated signal transduction. Activation of NF-κB is dependent on stimulation of the TCR (i.e. via CD3 signaling) and co-stimulation via CD28, and can be regulated by ligation of both CD3 and CD28. While CD28 or CD3 signaling can induce NF-κB transcription, co-ligation of CD28 with TCR signaling (i.e. CD3 signaling) can produce greater transcriptional activity (Thaker et al. (2015) Immunology Letters, 163:113-119). In some embodiments, the T cell activation factor can be a transcriptional regulatory element, such as a promoter, enhancer or response element, that contains a binding site and/or that is recognized by NF-κB and that can drive the expression of a reporter operably connected thereto. In some cases, a T cell activation factor that contains a regulatory element responsive to NF-κB signaling can be an indicator of the quality of T cell signaling and the presence of both TCR-mediated signaling and costimulatory signaling.

In some embodiments, the T cell activation factor contains a regulatory domain or element, or portion thereof, of an endogenous gene locus whose expression normally depends on, is induced and/or is upregulated upon T cell signaling. For example, the regulatory domain or element can be a promoter or portion thereof of an endogenous gene locus. In some embodiments, the promoter or portion thereof can contain a binding site and/or be recognized by one or more transcription factors. In some embodiments, the T cell activation factor is or contains the IL-2 promoter or a portion thereof that can drive expression of a gene reporter operably connected thereto. In some embodiments, the gene is a cytokine and the T cell activation factor is or comprises a transcriptional regulatory element or portion thereof of the cytokine gene. In some embodiments, the cytokine is IL-2. In some embodiments, the IL-2 promoter or portion thereof contains an NFAT response element or elements and/or an NFκB response element or elements. In some embodiments, the T cell activation factor is an IL-2 promoter or a portion thereof that generally contains at least a binding site for NFκB, and thus can be an indicator of the quality of T cell activation.

In some embodiments, the T cell activation factor can be a transcriptional regulatory element, such as a promoter or enhancer or other response element, that is or is part of the endogenous gene loci regulating expression of a T cell transcription factor, which are genes whose expression can be induced by T cell signaling or activation. In some embodiments, the transcription factor is nuclear factor of activated T cells (NFAT), nerve growth factor IB (also known as Nur77, NR4A1), C/EBP, STAT1, STAT2, and NFκB.

In some embodiments, the reporter molecule is encoded by a nucleic acid sequence under the operable control of a T cell activation factor, such as a regulatory element that is responsive to the quality and/or strength of the signal through an antigen receptor such as a TCR complex. In some aspects the T cell activation factor is responsive to the quality and/or strength of signal through the intracellular signaling region of, and/or in response to the binding to and/or recognition of a recombinant receptor (such as the receptor being screened or assessed, such as the recombinant receptor expressed by the cell) a target antigen or epitope. In some aspects, the T cell activation factor is or contains a transcriptional regulatory element or elements associated with the expression of the orphan nuclear hormone receptor Nur77 (also called Nr4a1, nerve growth factor IB (NGFIB), GFRP1; Gfrp; HMR; Hbr-1; Hbr1; Hmr; N10; NAK-1; NGFI-B; NGFIB; NP10; Ngfi-b; Orphan nuclear receptor HMR; ST-59; TIS1; TR3; TR3 orphan receptor; early response protein NAK1; growth factor-inducible nuclear protein N10; hormone receptor; immediate early gene transcription factor NGFI-B; nerve growth factor IB nuclear receptor variant 1; nerve growth factor induced protein I-B; nerve growth factor-induced protein I-B; neural orphan nuclear receptor NUR77; nhr-6; nr4a1; nuclear hormone receptor NUR/77; nuclear protein N10; nuclear receptor subfamily 4 group A member 1; orphan nuclear receptor NGFI-B; orphan nuclear receptor NR4A1; orphan nuclear receptor TR3; steroid receptor TR3; testicular receptor 3; zgc:92434; exemplary human Nur77 DNA sequence set forth in SEQ ID NO:1, encoding the polypeptide set forth in SEQ ID NO:2).

Nur77 generally is encoded by an immediate-early response gene induced in response to signaling through, or activation of signal from, the endogenous T cell receptor (TCR) complex, engagement of the endogenous TCR and/or via molecules containing immunoreceptor tyrosine-based activation motif (ITAM) that are involved in the signal from the TCR complex, e.g., CD3-zeta signaling regions. Nur77 gene product itself generally can bind to regulatory elements associated with the promoters of several genes to induce downstream expression of genes. The level or extent of expression of Nur77 can serve as an indicator for strength of T cell signals, e.g., TCR signals (Moran et al. (2011) JEM, 208:1279-1289). Thus, in some embodiments, expression of a reporter molecule operably connected to a transcriptional regulatory element or elements of the Nur77 gene locus, or portion thereof, can provide an indicator of the strength of T cells signaling. Further, Nur77 expression is generally not affected or influenced by other signaling pathways such as cytokine signaling or toll-like receptor (TLR) signaling (see, e.g., Ashouri et al., (2017) J. Immunol. 198:657-668), which may act in a cell extrinsic manner and may not depend on signaling through the recombinant receptor. In some embodiments, the T cell activation factor is a Nur77 promoter or enhancer or a portion thereof, or is a molecule or gene that contains a Nur77 response element or elements.

In some of any of the embodiments, the reporter T cells contain a nucleic acid sequence encoding a reporter molecule operably linked to a transcriptional regulatory element of a Nur77, or a variant thereof. In some of any of such embodiments, the variant of the transcriptional regulatory element is a variant nucleic acid sequence that exhibits at least 85%, 86%, 87%, 88%, 89%, 90%, 91%, 92%, 93%, 94%, 95%, 96%, 97%, 98%, 99% or more sequence identity to a transcriptional regulatory element within an endogenous Nur77 locus in the T cell. In some of any of such embodiments, the variant of the transcriptional regulatory element is a functional variant, having a nucleic acid sequence that exhibits at least 85%, 86%, 87%, 88%, 89%, 90%, 91%, 92%, 93%, 94%, 95%, 96%, 97%, 98%, 99% or more sequence identity to a transcriptional regulatory element within an endogenous Nur77 locus in the T cell and is responsive to signaling through, or signal from, the endogenous T cell receptor (TCR) complex, engagement of the endogenous TCR and/or via molecules containing immunoreceptor tyrosine-based activation motif (ITAM) that are involved in the signal from the TCR complex, e.g., CD3-zeta signaling regions; and/or is responsive to a signal through the intracellular signaling region of the recombinant receptor, wherein the incubating is carried out in the presence or absence of an agent that binds to the binding domain of the recombinant receptor and/or an agent that induces or is capable of inducing a signal through the intracellular signaling region of the recombinant receptor.

Figure 12:
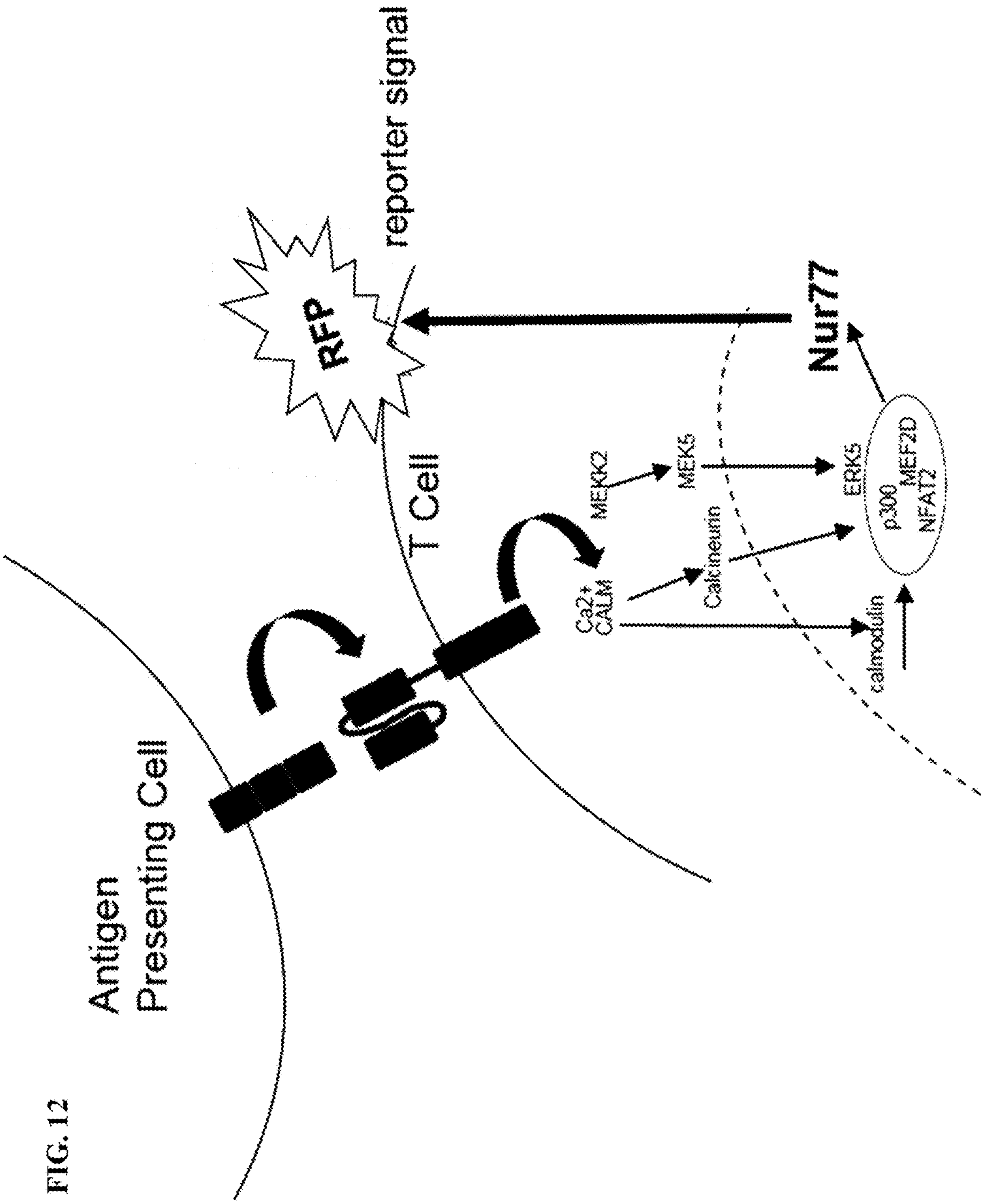
FIG. 12 depicts a schematic of reporter signal induced by an exemplary Nur77 reporter cell line in response to engagement of a receptor, e.g. chimeric antigen receptor, such as with an antigen or a ligand.

In some embodiments, the transcriptional regulatory element contains the Nur77 promoter or portion thereof containing a response element or elements recognized by a transcription factor. In some embodiments, the reporter molecule under operable control of a T cell activation factor, such as the Nur77 promoter, allows for determination of a signaling threshold and/or temporal threshold, i.e. magnitude and/or duration, of signaling from the TCR and/or a recombinant receptor that contains intracellular signaling regions derived from components of the TCR. In some embodiments, an exemplary reporter cell line containing a Nur77-tdTomato knock-in reporter was generated. A schematic of an exemplary reporter cell line, containing the Nur77 reporter and signaling components is shown in FIG. 12.

In some embodiments, a construct or vector is generated that contains nucleic acid sequences encoding a reporter molecule under the operable control of a T cell activation factor, e.g., Nur77 promoter, capable of being activated or induced upon antigen or epitope binding and/or signal or activity through the intracellular signaling region of the recombinant receptor, e.g., CAR, to a recognized an antigen or an epitope thereof. In some embodiments, “a reporter construct” comprises a nucleic acid that encodes a reporter molecule operatively linked to sequences for a T cell activation factor or factors that is/are capable of inducing its expression. In some embodiments, an advantage of using a T cell activation factor reporter construct is that the detectable expression of the reporter molecule provides a simple and efficient read-out of T cell activity, since the T cell activation factor can be specifically responsive to antigen or epitope binding and/or signal or activity through the intracellular signaling region of the recombinant receptor, e.g., CAR. In some embodiments, the reporter construct does not respond, i.e. there is no detectable expression of the reporter, in the absence of signals through the intracellular signaling region and/or antigen or epitope binding by the recombinant receptor, such as in the presence of IL-2 or other inflammatory stimuli that may not reflect specific binding of the recombinant receptor to the antigen or epitope.

Reporter constructs are known or can be generated by recombinant DNA techniques. In some embodiments, the nucleic acid sequences encoding a reporter molecule is cloned into an expression plasmid, such as a mammalian expression vector, for example pcDNA or other mammalian expression vector. In some embodiments, the nucleic acid sequences encoding a reporter molecule is cloned into a retroviral vector, e.g. lentiviral vector.

In some embodiments, the nucleic acid sequences encoding a reporter molecule is integrated into a genomic location in the cell, e.g., an endogenous genomic location. In some embodiments, the nucleic acid sequences encoding a reporter molecule can be integrated into a genomic location for its expression to be associated with, under operable control of and/or regulated by the regulatory elements present in the endogenous genomic location of a particular gene whose expression can be responsive to the quality and/or strength of the signal through the intracellular signaling region and/or binding and/or recognition of the recombinant receptor to a target antigen or epitope, and/or T cell signaling or T cell activation. In some embodiments, the nucleic acid sequences encoding a reporter molecule can be integrated into an endogenous genomic location, placed under the operative control of a transcriptional regulatory element of a gene whose expression is induced and/or is upregulated upon signal through the intracellular signaling region of the recombinant receptor and/or binding and/or recognition of the recombinant receptor to a target antigen or epitope. In some embodiments, the nucleic acid sequences encoding a reporter molecule can be integrated into an endogenous genomic location for co-expression with the endogenous gene encoded at the location, which is under operable control of a T cell activation factor, e.g., a promoter, an enhancer or a response element or a portion thereof, capable of being activated or induced upon antigen or epitope binding and/or signal or activity through the intracellular signaling region of the recombinant receptor, e.g., CAR, to a recognized an antigen or an epitope thereof and/or T cell signaling or T cell activation. In some embodiments, the endogenous gene is Nur77. In some embodiments, the T cell activation factor is the Nur77 promoter, enhancer or response element or a portion thereof. In some embodiments, the nucleic acid sequences encoding a reporter molecule is targeted for integration in-frame with the coding sequence, coding region and/or open reading frame (ORF) of the endogenous gene, e.g., the endogenous Nur77 gene, separated by sequences encoding a self-cleavage element, e.g., T2A.

In some embodiments, the nucleic acid sequences encoding a reporter molecule is integrated into a genomic location, at the same time generating a mutation, deletion, elimination, knockout, disruption or a reduction in expression of the gene(s) at or near the site of integration. For example, the T cell activation reporter can be “knocked-in” at a genomic locus where a mutation, deletion, elimination, knockout, disruption or a reduction in expression can be desired. In some embodiments, the nucleic acid sequences encoding a reporter molecule is integrated into a genomic location, without generating a deletion, elimination, knockout, disruption or a reduction in expression of the gene(s) at or near the site of integration.

In some embodiments, the T cells or plurality of T cells provided herein or the T cells or plurality of T cells used in the methods provided herein can contain more than one reporters. In some embodiments, the T cells or plurality of T cells can contain two different reporters. In such embodiments, the plurality of T cell can contain T cells that contain polynucleotides encoding the candidate recombinant receptor, e.g., CAR and a first reporter, and the plurality of T cell can further include T cells that contain a second reporter and not comprising the polynucleotides encoding the candidate recombinant receptor, e.g., CAR.

1. Exemplary Reporter T Cells

In some embodiments, the provided reporter T cells or the reporter T cells used in the methods provided herein, contain nucleic acid sequences encoding a reporter molecule is present within the genome of the cell or is targeted for integration into an endogenous genomic location, such that the expression of the reporter can be associated with, under operable control of and/or regulated by the regulatory elements present in the endogenous genomic location of a particular gene whose expression can be responsive to the quality and/or strength of the signal through the intracellular signaling region and/or binding and/or recognition of the recombinant receptor to a target antigen or epitope, and/or T cell signaling or T cell activation. In some embodiments, the reporter T cell is generated by inducing a genetic disruption at one or more target site(s) at or near the endogenous locus of interest; and introducing a template polynucleotide for homology directed repair (HDR). In some embodiments, the reporter T cells contain a targeted knock-in of nucleic acid sequences encoding a reporter molecule at an endogenous locus that is linked to a T cell activation factor, such as a regulatory element that is responsive to the quality and/or strength of the signal through an endogenous T cell receptor (TCR) and/or binding and/or recognition of the TCR to a target antigen or epitope.

In some embodiments, the reporter T cell is generated by inducing a targeted genetic disruption, e.g., generation of a DNA break, using gene editing methods, followed by HDR for a targeted knock-in of the nucleic acid sequences encoding a reporter molecule at the endogenous locus linked to a T cell activation factor, such as the Nur77 promoter, enhancer or response element or a portion thereof. In some embodiments, the nucleic acid sequences encoding a reporter molecule is present within the genome of the cell or is targeted for integration in-frame with the coding sequence, coding region and/or open reading frame (ORF) of the endogenous gene, e.g., the endogenous Nur77 gene. Thus, in some exemplary embodiments, the reporter T cell is generated by inducing a genetic disruption at one or more target site(s) at or near the endogenous locus encoding Nur77; and introducing a template polynucleotide for HDR.

In some embodiments, the genetic disruption is induced by a DNA binding protein or DNA-binding nucleic acid that specifically binds to or hybridizes to the target site, optionally a fusion protein comprising a DNA-targeting protein and a nuclease or an RNA-guided nuclease. In some embodiments, the fusion protein comprising a DNA-targeting protein and a nuclease or the RNA-guided nuclease is or comprises a zinc finger nuclease (ZFN), a TAL-effector nuclease (TALEN), or a CRISPR-Cas9 combination that specifically binds to, recognizes, or hybridizes to the target site. In some embodiments, the RNA-guided nuclease comprises a guide RNA (gRNA) having a targeting domain that is complementary to the target site.

In some embodiments, the introduction of a genetic disruption or cleavage involve the use of one or more agent(s) capable of introducing a genetic disruption, a cleavage, a double strand break (DSB) and/or a nick at a target site in the genomic DNA, thereby activating and/or recruiting various cellular DNA repair mechanisms, which can utilize the template polynucleotide, containing homology arm sequences, a DNA repair template, to effectively copy and integrate the nucleic acid sequences encoding the reporter molecule, at or near the site of the targeted genetic disruption by HDR, based on homology between the endogenous gene sequence surrounding the target site and the 5' and/or 3' homology arms included in the template polynucleotide.

In some embodiments, the one or more agent(s) capable of introducing a genetic disruption or cleavage comprises a DNA binding protein or DNA-binding nucleic acid that specifically binds to or hybridizes to a target site in the genome, e.g., at or near the Nur77 gene. In some aspects, the targeted cleavage, e.g., DNA break, at or near the endogenous gene encoding Nur77 is achieved using a protein or a nucleic acid is coupled to or complexed with a gene editing nuclease, such as in a chimeric or fusion protein. In some embodiments, the one or more agent(s) capable of introducing a genetic disruption or cleavage comprises a fusion protein comprising a DNA-targeting protein and a nuclease or an RNA-guided nuclease.

In some embodiments, introducing a genetic disruption or cleavage is carried out by gene editing methods, such as using a zinc finger nuclease (ZFN), TALEN or a CRISPR/Cas system with an engineered guide RNA that cleaves the target site(s), e.g., target site(s) at or near the Nur77 gene.

In some embodiments, the agent capable of introducing a targeted cleavage comprises various components, such as a fusion protein comprising a DNA-targeting protein and a nuclease or an RNA-guided nuclease. In some embodiments, the targeted cleavage is carried out using a DNA-targeting molecule that includes a DNA-binding protein such as one or more zinc finger protein (ZFP) or transcription activator-like effectors (TALEs), fused to a nuclease, such as an endonuclease. In some embodiments, the targeted cleavage is carried out using RNA-guided nucleases such as a clustered regularly interspaced short palindromic nucleic acid (CRISPR)-associated nuclease (Cas) system (including Cas and/or Cfp1). In some embodiments, the targeted cleavage is carried using agents capable of introducing a genetic disruption or cleavage, such as sequence-specific or targeted nucleases, including DNA-binding targeted nucleases and gene editing nucleases such as zinc finger nucleases (ZFN) and transcription activator-like effector nucleases (TALENs), and RNA-guided nucleases such as a CRISPR-associated nuclease (Cas) system, specifically engineered and/or designed to be targeted to the at least one target site(s), sequence of a gene or a portion thereof.

In some embodiments, the one or more agent(s) specifically targets the at least one target site(s), e.g., at or near the Nur77 gene. In some embodiments, the agent comprises a ZFN, TALEN or a CRISPR/Cas9 combination that specifically binds to, recognizes, or hybridizes to the target site(s). In some embodiments, the CRISPR/Cas9 system includes an engineered crRNA/tracr RNA ("single guide RNA") to guide specific cleavage. In some embodiments, the agent comprises nucleases based on the Argonaute system (e.g., from *T. thermophilus*, known as 'TtAgo', (Swarts et at (2014) Nature 507(7491): 258-261).

Zinc finger proteins (ZFPs), transcription activator-like effectors (TALEs), and CRISPR system binding domains can be "engineered" to bind to a predetermined nucleotide sequence, for example via engineering (altering one or more amino acids) of the recognition helix region of a naturally occurring ZFP or TALE protein. Engineered DNA binding proteins (ZFPs or TALEs) are proteins that are non-naturally occurring. Rational criteria for design include application of substitution rules and computerized algorithms for processing information in a database storing information of existing ZFP and/or TALE designs and binding data. See, e.g., U.S. Pat. Nos. 6,140,081; 6,453,242; and 6,534,261; see also WO 98/53058; WO 98/53059; WO 98/53060; WO 02/016536 and WO 03/016496 and U.S. Publication No. 20110301073. Exemplary ZFNs, TALEs, and TALENs are described in, e.g., Lloyd et al., Frontiers in Immunology, 4(221): 1-7 (2013).

A zinc finger protein (ZFP) or zinc finger domain thereof is a protein or domain within a larger protein that binds DNA in a sequence-specific manner through one or more zinc fingers, regions of amino acid sequence within the binding domain whose structure is stabilized through coordination of a zinc ion. Among the ZFPs are artificial ZFP domains targeting specific DNA sequences, typically 9-18 nucleotides long, generated by assembly of individual fingers. ZFPs include those in which a single finger domain is approximately 30 amino acids in length and contains an alpha helix containing two invariant histidine residues coordinated through zinc with two cysteines of a single beta turn, and having two, three, four, five, or six fingers. Generally, sequence-specificity of a ZFP may be altered by making amino acid substitutions at the four helix positions (−1, 2, 3, and 6) on a zinc finger recognition helix. Thus, for example, the ZFP or ZFP-containing molecule is non-naturally occurring, e.g., is engineered to bind to a target site of choice.

In some cases, the DNA-targeting molecule is or comprises a zinc-finger DNA binding domain fused to a DNA cleavage domain to form a zinc-finger nuclease (ZFN). For example, fusion proteins comprise the cleavage domain (or cleavage half-domain) from at least one Type IIS restriction enzyme and one or more zinc finger binding domains, which may or may not be engineered. In some cases, the cleavage domain is from the Type IIS restriction endonuclease FokI, which generally catalyzes double-stranded cleavage of DNA, at 9 nucleotides from its recognition site on one strand and 13 nucleotides from its recognition site on the other. See, e.g., U.S. Pat. Nos. 5,356,802; 5,436,150 and 5,487,994; Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31,978-31,982.

Many gene-specific engineered zinc fingers are available commercially. For example, Sangamo Biosciences (Richmond, CA, USA) has developed a platform (CompoZr) for zinc-finger construction in partnership with Sigma-Aldrich (St. Louis, MO, USA), allowing investigators to bypass zinc-finger construction and validation altogether, and provides specifically targeted zinc fingers for thousands of targets. See, e.g., Gaj et al., Trends in Biotechnology, 2013, 31(7), 397-405. In some cases, commercially available zinc fingers are used or are custom designed.

In some embodiments, the Nur77 gene can be targeted for cleavage using clustered regularly interspaced short palindromic repeats (CRISPR) and CRISPR-associated (Cas) proteins. See Sander and Joung, Nature Biotechnology, 32(4): 347-355. In some embodiments, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), and/or other sequences and transcripts from a CRISPR locus.

In some aspects, the CRISPR/Cas nuclease or CRISPR/Cas nuclease system includes a non-coding guide RNA (gRNA), which sequence-specifically binds to DNA, and a Cas protein (e.g., Cas9), with nuclease functionality. In some embodiments, the CRISPR/Cas nuclease system comprises at least one of: a guide RNA (gRNA) having a targeting domain that is complementary with a target site of a Nur77 gene; or at least one nucleic acid encoding the gRNA.

In general, a guide sequence, e.g., guide RNA, is any polynucleotide sequences comprising at least a sequence portion, e.g., targeting domain, that has sufficient complementarity with a target site sequence, such as a target site in the Nur77 gene in humans, to hybridize with the target sequence at the target site and direct sequence-specific binding of the CRISPR complex to the target sequence. In some embodiments, in the context of formation of a CRISPR complex, "target site" (also known as "target position," "target DNA sequence" or "target location") generally refers to a sequence to which a guide sequence is designed to have complementarity, where hybridization between the target sequence and a domain, e.g., targeting domain, of the guide RNA promotes the formation of a CRISPR complex. Full complementarity is not necessarily required, provided there is sufficient complementarity to cause hybridization and promote formation of a CRISPR complex. Generally, a guide sequence is selected to reduce the degree of secondary structure within the guide sequence. Secondary structure may be determined by any suitable polynucleotide folding algorithm.

In some aspects, a CRISPR enzyme (e.g. Cas9 nuclease) in combination with (and optionally complexed with) a guide sequence is delivered to the cell. For example, one or more elements of a CRISPR system is derived from a type I, type II, or type III CRISPR system. For example, one or more elements of a CRISPR system are derived from a particular organism comprising an endogenous CRISPR system, such as *Streptococcus pyogenes, Staphylococcus aureus* or *Neisseria meningitides*.

In some embodiments, a guide RNA (gRNA) specific to the target site (e.g. the Nur77 gene) is used to guide RNA-guided nucleases, e.g., Cas, to introduce a DNA break at the target site or target position. Methods for designing gRNAs and exemplary targeting domains can include those described in, e.g., in International PCT Publication No. WO2015/161276. Targeting domains can be incorporated into the gRNA that is used to target Cas9 nucleases to the target site or target position. Methods for selection and validation of target sequences as well as off-target analyses are described, e.g., in Mali et al., 2013 Science 339(6121): 823-826; Hsu et al. Nat Biotechnol, 31(9): 827-32; Fu et al., 2014 Nat Biotechnol; Heigwer et al., 2014 Nat Methods 11(2):122-3; Bae et al., 2014 Bioinformatics; Xiao A et al., 2014 Bioinformatics. A genome-wide gRNA database for CRISPR genome editing is publicly available, which contains exemplary single guide RNA (sgRNA) sequences targeting constitutive exons of genes in the human genome or mouse genome (see e.g., genescript.com/gRNA-database.html; see also, Sanjana et al. (2014) Nat. Methods, 11:783-4). In some aspects, the gRNA sequence is or comprises a sequence with minimal off-target binding to a non-target site or position.

In some exemplary embodiments, the target site is at or near the final exon of the endogenous locus encoding Nur77. In some exemplary embodiments, the target site is at or near the final exon of the endogenous locus encoding Nur77 but prior to the stop codon of the endogenous locus encoding Nur77. In some embodiments, the one or more target site(s) comprise the nucleic acid sequence TCATTGACAAGATCTTCATG (SEQ ID NO:65) and/or GCCTGGGAACACGTGTGCA (SEQ ID NO:66). In some embodiments, the gRNA comprises a targeting domain sequence selected from CAUGAAGAUCUUGUCAAUGA (SEQ ID NO:3) or UGCACACGUGUUCCCAGGC (SEQ ID NO:4).

In some embodiments, induction of genetic disruption or cleavage is carried out by delivering or introducing one or more agent(s) capable of introducing a genetic disruption or cleavage, e.g., Cas9 and/or gRNA components, to a cell, using any of a number of known delivery method or vehicle for introduction or transfer to cells, for example, using lentiviral delivery vectors, or any of the known methods or vehicles for delivering Cas9 molecules and gRNAs. Exemplary methods are described in, e.g., Wang et al. (2012) J. Immunother. 35(9): 689-701; Cooper et al. (2003) Blood. 101:1637-1644; Verhoeyen et al. (2009) Methods Mol Biol. 506: 97-114; and Cavalieri et al. (2003) Blood. 102(2): 497-505. In some embodiments, nucleic acid sequences encoding one or more components of one or more agent(s) capable of introducing a genetic disruption or cleavage, e.g., DNA break, is introduced into the cells, e.g., by any methods for introducing nucleic acids into a cell described herein or known. In some embodiments, a vector encoding components of one or more agent(s) capable of introducing a genetic disruption or cleavage such as a CRISPR guide RNA and/or a Cas9 enzyme can be delivered into the cell.

In some embodiments, the one or more agent(s) capable of introducing a genetic disruption or cleavage, e.g., a Cas9/gRNA system, is introduced into the cell as a ribonucleoprotein (RNP) complex. RNP complexes include a sequence of ribonucleotides, such as an RNA or a gRNA molecule, and a protein, such as a Cas9 protein or variant thereof. For example, the Cas9 protein is delivered as RNP complex that comprises a Cas9 protein and a gRNA molecule targeting the target sequence, e.g., using electroporation or other physical delivery method. In some embodiments, the RNP is delivered into the cell via electroporation or other physical means, e.g., particle gun, calcium phosphate transfection, cell compression or squeezing. In some embodiments, the RNP can cross the plasma membrane of a cell without the need for additional delivery agents (e.g., small molecule agents, lipids, etc.).

In some embodiments, a template polynucleotide comprising nucleic acid sequences encoding the reporter molecule is introduced into the cell. In some embodiments, a template polynucleotide is introduced into the engineered cell, prior to, simultaneously with, or subsequent to introduction of agent(s) capable of inducing a targeted genetic disruption. In the presence of a targeted genetic disruption, e.g., DNA break, the template polynucleotide can be used as a DNA repair template, to effectively copy and integrate the transgene, e.g., nucleic acid sequences encoding the reporter molecule, at or near the site of the targeted genetic disruption by HDR, based on homology between the endogenous gene sequence surrounding the target site and the 5' and/or 3' homology arms included in the template polynucleotide. In some embodiments, the gene editing and HDR steps are performed simultaneously and/or in one experimental reaction. In some embodiments, the gene editing and HDR steps are performed consecutively or sequentially, in one or consecutive experimental reaction(s). In some embodiments, the gene editing and HDR steps are performed in separate experimental reactions, simultaneously or at different times.

In some embodiments, HDR can be utilized for targeted integration of one or more transgene at one or more target site in the genome, e.g., the Nur77 gene. In some embodiments, the nuclease-induced HDR can be used to alter a target sequence, integrate a transgene, e.g., nucleic acid sequences encoding a reporter molecule, at a particular target location.

Alteration of nucleic acid sequences at the target site can occur by HDR with an exogenously provided template polynucleotide (also referred to as donor polynucleotide or template sequence). For example, the template polynucleotide provides for alteration of the target sequence, such as insertion of the transgene contained within the template polynucleotide. In some embodiments, a plasmid or a vector can be used as a template for homologous recombination. In some embodiments, a linear DNA fragment can be used as a template for homologous recombination. In some embodiments, a single stranded template polynucleotide can be used as a template for alteration of the target sequence by alternate methods of homology directed repair (e.g., single strand annealing) between the target sequence and the template polynucleotide. Template polynucleotide-effected alteration of a target sequence depends on cleavage by a nuclease, e.g., a targeted nuclease such as CRISPR/Cas9. Cleavage or genetic disruption by the nuclease can comprise a double strand break or two single strand breaks.

In some embodiments, "recombination" refers to a process of exchange of genetic information between two polynucleotides. In some embodiments, "homologous recombination (HR)" refers to the specialized form of such exchange that takes place, for example, during repair of double-strand breaks in cells via homology-directed repair mechanisms. This process requires nucleotide sequence homology, uses a template polynucleotide to template repair of a target DNA (i.e., the one that experienced the double-strand break, e.g., target site in the endogenous gene), and is variously known as "non-crossover gene conversion" or "short tract gene conversion," because it leads to the transfer of genetic information from the template polynucleotide to the target. In some embodiments, such transfer can involve mismatch correction of heteroduplex DNA that forms between the broken target and the template polynucleotide, and/or "synthesis-dependent strand annealing," in which the template polynucleotide is used to resynthesize genetic information that will become part of the target, and/or related processes. Such specialized HR often results in an alteration of the sequence of the target molecule such that part or all of the sequence of the template polynucleotide is incorporated into the target polynucleotide.

In some embodiments, a template polynucleotide, e.g., polynucleotide containing transgene, is integrated into the genome of a cell via homology-independent mechanisms. The methods comprise creating a double-stranded break (DSB) in the genome of a cell and cleaving the template polynucleotide molecule using a nuclease, such that the template polynucleotide is integrated at the site of the DSB. In some embodiments, the template polynucleotide is integrated via non-homology dependent methods (e.g., NHEJ). Upon in vivo cleavage the template polynucleotides can be integrated in a targeted manner into the genome of a cell at the location of a DSB. The template polynucleotide can include one or more of the same target sites for one or more of the nucleases used to create the DSB. Thus, the template polynucleotide may be cleaved by one or more of the same nucleases used to cleave the endogenous gene into which integration is desired. In some embodiments, the template polynucleotide includes different nuclease target sites from the nucleases used to induce the DSB. As described above, the genetic disruption of the target site or target position can be created by any mechanisms, such as ZFNs, TALENs, CRISPR/Cas9 system, or TtAgo nucleases.

In canonical HDR, a double-stranded template polynucleotide is introduced, comprising a homologous sequence to the target site that will either be directly incorporated into the target site or used as a template to insert the transgene near the target site. After resection at the genetic disruption or cleavage, repair can progress by different pathways, e.g., by the double Holliday junction model (or double strand break repair, DSBR, pathway) or the synthesis-dependent strand annealing (SDSA) pathway. In some embodiments, other DNA repair pathways such as single strand annealing (SSA), single-stranded break repair (SSBR), mismatch repair (MMR), base excision repair (BER), nucleotide excision repair (NER), intrastrand cross-link (ICL), translesion synthesis (TLS), error-free postreplication repair (PRR) can be employed by the cell to repair a double-stranded or single-stranded break created by the nucleases.

Targeted integration results in the transgene being integrated into a specific gene or locus in the genome. The transgene may be integrated anywhere at or near one of the at least one target site(s) or site in the genome. In some embodiments, the transgene is present within the genome of the cell or present within the genome of the cell or integrated at or near one of the at least one target site(s), for example, within 300, 250, 200, 150, 100, 50, 10, 5, 4, 3, 2, 1 or fewer base pairs upstream or downstream of the site of cleavage, such as within 100, 50, 10, 5, 4, 3, 2, 1 base pairs of either side of the target site, such as within 50, 10, 5, 4, 3, 2, 1 base pairs of either side of the target site.

The genetic disruption or cleavage at the target site should be sufficiently close to the site for targeted integration such that an alteration is produced in the desired region, e.g., insertion of transgene occurs. In some embodiments, the distance is not more than 10, 25, 50, 100, 200, 300, 350, 400 or 500 nucleotides. In some embodiments, it is believed that the genetic disruption or cleavage should be sufficiently close to the site for targeted integration such that the genetic disruption or cleavage is within the region that is subject to exonuclease-mediated removal during end resection. In some embodiments, the targeting domain is configured such that a cleavage event, is positioned within 1, 2, 3, 4, 5, 10, 15, 20, 25, 30, 35, 40, 45, 50, 60, 70, 80, 90, 100, 150, 200, 300, 350, 400 or 500 nucleotides of the region desired to be altered, e.g., site for targeted insertion, such as between about 0 and about 200 bp (e.g., 0 to 175, 0 to 150, 0 to 125, 0 to 100, 0 to 75, 0 to 50, 0 to 25, 25 to 200, 25 to 175, 25 to 150, 25 to 125, 25 to 100, 25 to 75, 25 to 50, 50 to 200, 50 to 175, 50 to 150, 50 to 125, 50 to 100, 50 to 75, 75 to 200, 75 to 175, 75 to 150, 75 to 125, 75 to 100 bp) away from the site for targeted integration. The genetic disruption or cleavage can be positioned upstream or downstream of the region desired to be altered, e.g., site for targeted insertion. In some embodiments, a break is positioned within the region desired to be altered, e.g., within a region defined by at least two mutant nucleotides. In some embodiments, a break is positioned immediately adjacent to the region desired to be altered, e.g., immediately upstream or downstream of site for targeted integration.

A template polynucleotide having homology with sequences at or near one or more target site(s) in the endogenous DNA can be used to alter the structure of a target DNA, e.g., targeted insertion of the transgene, e.g., nucleic acid sequences encoding a reporter molecule. In some embodiments, the template polypeptide contains homology sequences (e.g., homology arms) flanking the transgene, e.g., nucleic acid sequences encoding a reporter molecule, such as any reporter molecules described herein, for targeted insertion. In some embodiments, the homology sequences target the transgene at or near the Nur77 locus. In some embodiments, the template polynucleotide includes additional sequences (coding or non-coding sequences) between the homology arms, such as a regulatory sequences, such as promoters and/or enhancers, splice donor and/or acceptor sites, internal ribosome entry site (IRES), sequences encoding ribosome skipping elements (e.g., 2A peptides), markers and/or SA sites, and/or one or more additional transgenes. The sequence of interest in the template polynucleotide may comprise one or more sequences encoding a functional polypeptide (e.g., a cDNA), with or without a promoter.

In some embodiments, nuclease-induced HDR results in an insertion of a transgene (also called "exogenous sequence" or "transgene sequence") for expression of a transgene for targeted insertion. The template polynucleotide sequence is typically not identical to the genomic sequence where it is placed. A template polynucleotide sequence can contain a non-homologous sequence flanked by two regions of homology to allow for efficient HDR at the location of interest. Additionally, template polynucleotide sequence can comprise a vector molecule containing sequences that are not homologous to the region of interest in cellular chromatin. A template polynucleotide sequence can contain several, discontinuous regions of homology to cellular chromatin. For example, for targeted insertion of sequences not normally present in a region of interest, said sequences can be present in a transgene and flanked by regions of homology to sequence in the region of interest.

Polynucleotides for insertion can also be referred to as "transgene" or "exogenous sequences" or "donor" polynucleotides or molecules. The template polynucleotide can be DNA, single-stranded and/or double-stranded and can be introduced into a cell in linear or circular form. See also, U.S. Patent Publication Nos. 20100047805 and 20110207221. The template polynucleotide can also be introduced in DNA form, which may be introduced into the cell in circular or linear form. If introduced in linear form, the ends of the template polynucleotide can be protected (e.g., from exonucleolytic degradation) by methods known. For example, one or more dideoxynucleotide residues are added to the 3' terminus of a linear molecule and/or self-complementary oligonucleotides are ligated to one or both ends. See, for example, Chang et al. (1987) Proc. Natl. Acad. Sci. USA 84:4959-4963; Nehls et al. (1996) Science 272: 886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. If introduced in double-stranded form, the template polynucleotide may include one or more nuclease target site(s), for example, nuclease target sites flanking the transgene to be integrated into the cell's genome. See, e.g., U.S. Patent Publication No. 20130326645.

In some embodiments, the template polynucleotide is double stranded. In some embodiments, the template polynucleotide is single stranded. In some embodiments, the template polynucleotide comprises a single stranded portion and a double stranded portion.

In some embodiments, the template polynucleotide contains the transgene, e.g., reporter molecule-encoding nucleic acid sequences, flanked by homology sequences (also called "homology arms") on the 5' and 3' ends, to allow the DNA repair machinery, e.g., homologous recombination machinery, to use the template polynucleotide as a template for repair, effectively inserting the transgene into the target site of integration in the genome. The homology arm should extend at least as far as the region in which end resection may occur, e.g., in order to allow the resected single stranded overhang to find a complementary region within the template polynucleotide. The overall length could be limited by parameters such as plasmid size or viral packaging limits. In some embodiments, a homology arm does not extend into repeated elements, e.g., ALU repeats or LINE repeats.

Exemplary homology arm lengths include at least or at least about 50, 100, 200, 250, 300, 400, 500, 600, 700, 750, 800, 900, 1000, 2000, 3000, 4000, or 5000 nucleotides. In some embodiments, the homology arm length is 50-100, 100-250, 250-500, 500-750, 750-1000, 1000-2000, 2000-3000, 3000-4000, or 4000-5000 nucleotides.

Target site (also known as "target position," "target DNA sequence" or "target location"), in some embodiments, refers to a site on a target DNA (e.g., the chromosome) that is modified by the one or more agent(s) capable of inducing a genetic disruption, e.g., a Cas9 molecule. For example, the target site can be a modified Cas9 molecule cleavage of the DNA at the target site and template polynucleotide directed modification, e.g., targeted insertion of the transgene, at the target site. In some embodiments, a target site can be a site between two nucleotides, e.g., adjacent nucleotides, on the DNA into which one or more nucleotides is added. The target site may comprise one or more nucleotides that are altered by a template polynucleotide. In some embodiments, the target site is within a target sequence (e.g., the sequence to which the gRNA binds). In some embodiments, a target site is upstream or downstream of a target sequence (e.g., the sequence to which the gRNA binds).

In some embodiments, the template polynucleotide comprises about 500 to 1000, e.g., 600 to 900 or 700 to 800, base pairs of homology on either side of the target site at the endogenous gene. In some embodiments, the template polynucleotide comprises about 500, 600, 700, 800, 900 or 1000 base pairs homology 5' of the target site, 3' of the target site, or both 5' and 3' of the target site.

In some embodiments, a template polynucleotide is to a nucleic acid sequence which can be used in conjunction with a nuclease, e.g., Cas9 molecule, and/or a gRNA molecule to alter the structure of a target site. In some embodiments, the target site is modified to have some or all of the sequence of the template polynucleotide, typically at or near cleavage site(s). In some embodiments, the template polynucleotide is single stranded. In some embodiments, the template polynucleotide is double stranded. In some embodiments, the template polynucleotide is DNA, e.g., double stranded DNA In some embodiments, the template polynucleotide is single stranded DNA. In some embodiments, the template polynucleotide is encoded on the same vector backbone, e.g. AAV genome, plasmid DNA, as the Cas9 and gRNA. In some embodiments, the template polynucleotide is excised from a vector backbone in vivo, e.g., it is flanked by gRNA recognition sequences. In some embodiments, the template polynucleotide is on a separate polynucleotide molecule as the Cas9 and gRNA. In some embodiments, the Cas9 and the gRNA are introduced in the form of a ribonucleoprotein (RNP) complex, and the template polynucleotide is introduced as a polynucleotide molecule, e.g., in a vector.

In some embodiments, the template polynucleotide alters the structure of the target site, e.g., insertion of transgene, by participating in a homology directed repair event. In some embodiments, the template polynucleotide alters the sequence of the target site.

In some embodiments, the template polynucleotide includes sequence that corresponds to a site on the target sequence that is cleaved by a Cas9-mediated cleavage event. In some embodiments, the template polynucleotide includes sequence that corresponds to both, a first site on the target sequence that is cleaved in a first Cas9 mediated event, and a second site on the target sequence that is cleaved in a second Cas9 mediated event.

A template polynucleotide typically comprises the following components: [5' homology arm]-[transgene]-[3' homology arm]. The homology arms provide for recombination into the chromosome, thus insertion of the transgene into the DNA at or near the cleavage site e.g., target site(s). In some embodiments, the homology arms flank the most distal cleavage sites.

In some embodiments, the template polynucleotide comprises the structure [5' homology arm]-[nucleic acid sequence encoding the reporter molecule]-[3' homology arm]. In some embodiments, the 5' homology arm and/or 3' homology arm comprises nucleic acid sequences homologous to nucleic acid sequences present at and/or surrounding the one or more target site(s).

In some embodiments, the 5' homology arm comprises nucleic acid sequences that are homologous to nucleic acid sequences 5' of the one or more target site(s). In some embodiments, the 3' homology arm comprises nucleic acid sequences that are homologous to nucleic acid sequences 3' of the one or more target site(s). In some embodiments, the 5' homology arm and 3' homology arm independently is between about 50 and 100, 100 and 250, 250 and 500, 500 and 750, 750 and 1000, 1000 and 2000 base pairs in length.

In some embodiments, the 3' end of the 5' homology arm is the position next to the 5' end of the transgene. In some embodiments, the 5' homology arm can extend at least 10, 20, 30, 40, 50, 100, 200, 300, 400, 500, 600, 700, 800, 900, 1000, 1500, 2000, 3000, 4000, or 5000 nucleotides 5' from the 5' end of the transgene. In some embodiments, the 5' end of the 3' homology arm is the position next to the 3' end of the transgene. In some embodiments, the 3' homology arm can extend at least 10, 20, 30, 40, 50, 100, 200, 300, 400, 500, 600, 700, 800, 900, 1000, 1500, 2000, 3000, 4000, or 5000 nucleotides 3' from the 3' end of the transgene.

Similarly, in some embodiments, the template polynucleotide has a 5' homology arm, a transgene, and a 3' homology arm, such that the template polynucleotide extends substantially the same distance on either side of the target site. For example, the homology arms may have different lengths, but the transgene may be selected to compensate for this. For example, the transgene may extend further 5' from the target site than it does 3' of the target site, but the homology arm 5' of the target site is shorter than the homology arm 3' of the target site, to compensate. The converse is also possible, e.g., that the transgene may extend further 3' from the target site than it does 5' of the target site, but the homology arm 3' of the target site is shorter than the homology arm 5' of the target site, to compensate. In some embodiments, for targeted insertion, the homology arms, e.g., the 5' and 3' homology arms, may each comprise about 1000 base pairs (bp) of sequence flanking the most distal gRNAs (e.g., 1000 bp of sequence on either side of the genetic disruption or target site).

In some embodiments, the template polynucleotide contains homology arms for targeting the endogenous Nur77 locus (exemplary nucleotide sequence of an endogenous human Nur77 set forth in SEQ ID NO:1; NCBI Reference Sequence: NM_001202233.1, encoding the amino acid sequence set forth in SEQ ID NO:2). In some embodiments, the genetic disruption of the Nur77 locus is introduced at or near the 3' end of the coding region, e.g., at or near the final exon of the coding region the gene, including sequence immediately before a stop codon, e.g., within the final exon of the coding sequence, or within 500 bp of the stop codon (e.g., less than 500, 450, 400, 350, 300, 250, 200, 150, 100 or 50 bp). In some embodiments, the genetic disruption of the Nur77 locus is introduced at an early coding region in the gene, including sequence immediately following a transcription start site, within a first exon of the coding sequence, or within 500 bp of the transcription start site (e.g., less than 500, 450, 400, 350, 300, 250, 200, 150, 100 or 50 bp), or within 500 bp of the start codon (e.g., less than 500, 450, 400, 350, 300, 250, 200, 150, 100 or 50 bp).

In some embodiments, the template polynucleotide comprises about 500 to 1000, e.g., 600 to 900 or 700 to 800, base pairs of homology on either side of the genetic disruption introduced by the targeted nucleases and/or gRNAs. In some embodiments, the template polynucleotide comprises about 500, 600, 700, 800, 900 or 1000 base pairs of 5' homology arm sequence, which is homologous to 500, 600, 700, 800, 900 or 1000 base pairs of sequence 5' of the genetic disruption (e.g., at the Nur77 locus), the transgene, and about 500, 600, 700, 800, 900 or 1000 base pairs of 3' homology arm sequence, which is homologous to 500, 600, 700, 800, 900 or 1000 base pairs of sequence 3' of the genetic disruption (e.g., at the Nur77 locus).

In some embodiments, the location of the genetic disruption (e.g., target site) and the design of the template polynucleotide are selected such that upon introduction of the genetic disruption and targeted integration of the transgene, e.g., nucleic acid sequences encoding a reporter molecule, is in-frame with the endogenous gene, e.g., endogenous Nur77 gene. In some embodiments, the transgene, e.g., nucleic acid sequences encoding a reporter molecule, is integrated or is targeted for integration, in-frame, near the end of the final exon of the endogenous Nur77 gene, such that expression of the transgene is under operable control of the endogenous Nur77 transcriptional regulatory elements, while permitting the expression of the endogenous Nur77 polypeptide (in some cases, except for the final several amino acids at the C-terminal). In some embodiments, a ribosome skipping element/self-cleavage element, such as a 2A element, is placed upstream of the transgene coding sequence, such that the ribosome skipping element/self-cleavage element is placed in-frame with the endogenous gene. In some embodiments, the transgene, e.g., nucleic acid sequences encoding a reporter molecule, is integrated or is targeted for integration such that the endogenous Nur77 transcriptional regulatory elements control the expression of the endogenous Nur77 polypeptide-T2A-reporter molecule.

In some exemplary embodiments, the encoded reporter molecule is or comprises a fluorescent protein, a luciferase, a β-galactosidase, a chloramphenicol acetyltransferase (CAT), a 0-glucuronidase (GUS), or a modified form thereof. In some embodiments, the fluorescent protein is or comprises a green fluorescent protein (GFP), enhanced green fluorescent protein (EGFP), a super-fold GFP (sfGFP; set forth in SEQ ID NO:36, encoded by nucleic acid sequence set forth in SEQ ID NO:35), red fluorescent protein (RFP), cyan fluorescent protein (CFP), blue green fluorescent protein (BFP), enhanced blue fluorescent protein (EBFP), and yellow fluorescent protein (YFP), or a variant thereof, including species variants, monomeric variants, and codon-optimized and/or enhanced variants of the fluorescent proteins. In some embodiments, the encoded reporter molecule is a red fluorescent protein (RFP), such as tdTomato, mCherry, mStrawberry, AsRed2, DsRed or DsRed2. In some embodiments, the encoded reporter molecule is tdTomato. For example, in some embodiments, the nucleic acid sequence encoding the reporter molecule comprises the sequence of nucleic acids set forth in SEQ ID NO: 7 or 53 or a sequence of nucleic acids that exhibits at least 85%, 86%, 87%, 88%, 89%, 90%, 91%, 92%, 93%, 94%, 95%, 96%, 97%, 98%, 99% or more sequence identity to any of SEQ ID NO: 7 or 53. In some embodiments, the encoded reporter molecule comprises the sequence of amino acids set forth in SEQ ID NO:8 or 54, or a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NO: 8 or 54.

In some cases, the ribosome skipping element/self-cleavage element, such as a T2A, can cause the ribosome to skip (ribosome skipping) synthesis of a peptide bond at the C-terminus of a 2A element, leading to separation between the end of the 2A sequence and the next peptide downstream (see, for example, de Felipe, *Genetic Vaccines and Ther.* 2:13 (2004) and de Felipe et al. *Traffic* 5:616-626 (2004)). This allows the inserted transgene to be controlled by the transcription of the endogenous promoter at the integration site, e.g., Nur77 promoter. Exemplary ribosome skipping element/self-cleavage element include 2A sequences from the foot-and-mouth disease virus (F2A, e.g., SEQ ID NO: 45), equine rhinitis A virus (E2A, e.g., SEQ ID NO: 44), *Thosea asigna* virus (T2A, e.g., SEQ ID NO: 6 or 56), and porcine teschovirus-1 (P2A, e.g., SEQ ID NO: 42 or 43) as described in U.S. Patent Publication No. 20070116690. In some embodiments, exemplary ribosome skipping element/self-cleavage element includes a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NO: 6, 42-45 or 56. In some embodiments, the template polynucleotide includes a T2A ribosome skipping element (sequence set forth in SEQ ID NO: 6 or 56) upstream of the transgene, e.g., nucleic acid sequences encoding a reporter molecule.

In some embodiments, the template polynucleotide comprises one or more mutations, e.g., silent mutations, that prevent the RNA-guided nuclease or DNA-binding nuclease fusion protein from recognizing and cleaving the template polynucleotide. The template polynucleotide may comprise, e.g., at least 1, 2, 3, 4, 5, 10, 20, or 30 silent mutations relative to the corresponding sequence in the genome of the cell to be altered. In some embodiments, the template polynucleotide comprises at most 2, 3, 4, 5, 10, 20, 30, or 50 silent mutations relative to the corresponding sequence in the genome of the cell to be altered. In some embodiments, the transgene contains one or more mutations, e.g., silent mutations that prevent Cas9 from recognizing and cleaving the template polynucleotide. The template polynucleotide may comprise, e.g., at least 1, 2, 3, 4, 5, 10, 20, or 30 silent mutations relative to the corresponding sequence in the genome of the cell to be altered. In some embodiments, the template polynucleotide comprises at most 2, 3, 4, 5, 10, 20, 30, or 50 silent mutations relative to the corresponding sequence in the genome of the cell to be altered. In some embodiments, homology arm contained in the template polynucleotide includes silent mutations, to prevent the RNA-guided nuclease or DNA-binding nuclease fusion protein from recognizing and cleaving the template polynucleotide.

In some embodiments, an exemplary template polynucleotide contains a polynucleotides encoding a T2A ribosomal skip element (sequence set forth in SEQ ID NO:5 or 55, encoding polypeptide sequence set forth in SEQ ID NO: 6 or 56), and the tdTomato fluorescent protein (sequence set forth in SEQ ID NO:7 or 53; encoding polypeptide sequence set forth in SEQ ID NO:8 or 54), flanked on either side of the T2A and tdTomato coding sequences by the 5' homology arm (set forth in SEQ ID NO:49, containing 2 silent mutations compared to the corresponding Nur77 genomic sequence set forth in SEQ ID NO:47) and the 3' homology arm (set forth in SEQ ID NO:50), homologous to sequences surrounding the stop codon of the endogenous Nur77 gene. In some embodiments, the transgene, e.g., T2A-tdTomato encoding sequences, can be targeted to be inserted in-frame with the endogenous Nur77 gene and prior to the stop codon. In some embodiments, an exemplary template polynucleotide for HDR includes a nucleic acid sequence set forth in SEQ ID:51. In some embodiments, an exemplary target site sequence for introduction of the genetic disruption or cleavage comprises the nucleic acid sequence TCATTGACAAGATCTTCATG (SEQ ID NO:65) and/or GCCTGGGAACACGTGTGCA (SEQ ID NO:66).

C. Plurality of Cells and Cell Library

In some aspects, also provided are methods of generating one or more T cells, e.g., a plurality of T cells, such as plurality of T cells that each contain a reporter molecule and a recombinant receptor, e.g., CAR. In some aspects, also provided are a plurality of T cells generated using such methods. In some aspects, also provided are one or more T cell, e.g. a plurality of T cells, such as any reporter T cells or T cell lines described herein, that contain a polynucleotide encoding a recombinant receptor, e.g., CAR or a recombinant receptor, e.g., CAR. In some embodiments, the recombinant receptor, e.g., CAR present in a T cell in the plurality is distinct from the recombinant receptor, e.g., CAR present in at least one of the other T cells in the plurality. Also provided are compositions containing any of the cells or plurality of cells described, and methods for assessing any of the plurality of cells described, including any screening methods.

In some embodiments, the plurality of cells, such as reporter T cells, is a library of cells, containing cells that contain various polynucleotides encoding candidate recombinant receptors, e.g., CARs. In some embodiments, the library of cells contain more than one cells that each contain a candidate recombinant receptor or a candidate recombinant receptor, e.g., CAR, that is distinct from other candidate recombinant receptors, e.g., CARs present in at least one of the other T cells in the library. In some embodiments, the library of cells together contain many distinct candidate recombinant receptors, e.g., CARs. In some embodiments, the plurality of T cells or library of T cells include at least or at least about 2, 5, 10, 25, 50, 100, 500 or $10^3$ cells expressing distinct candidate recombinant receptors, e.g., CARs. In some embodiments, the plurality of T cells or library of T cells include cells that together express at least or at least about 2, 5, 10, 25, 50, 100, 500, $10^3$ or $10^4$ or more distinct candidate recombinant receptors, e.g., CARs.

In some embodiments, the method involves producing a plurality of polynucleotides each encoding a recombinant receptor, wherein each polynucleotide comprises i) a vector backbone comprising a nucleic acid sequence encoding an intracellular signaling region and ii) a nucleic acid sequence encoding a binding domain; and introducing one of the plurality of polynucleotides encoding a recombinant receptor into a reporter T cell comprising a reporter molecule, wherein the expression of said reporter molecule is responsive to a signal through the intracellular signaling region, and the encoded recombinant receptor present in the reporter T cell is distinct from the encoded recombinant receptor present in at least one of the other reporter T cells in the plurality. Also provided are any of the resulting plurality of cells, e.g., reporter T cells, expressing a recombinant receptor, e.g., CAR, and compositions containing such plurality of cells, and methods for assessing the activity of such plurality of cells, including screening methods.

In some embodiments, the plurality of cells or library of cells encoding various candidate recombinant receptors, e.g., CARs, are assessed for expression and/or activity of the encoded recombinant receptor. In some embodiments, the plurality of cells or library of cells are screened and/or identified for having particular properties, e.g., expression and/or activity. Any assessment methods or screening methods described herein, such as those described in Sections II.B and IV below, can be employed to screen and/or identify cells and/or recombinant receptors that possess particular properties. In some embodiments, the provided methods involve incubating one or more reporter T cells from the plurality of reporter T cells described herein, in the presence or absence of an agent that binds to the binding domain of the recombinant receptor and/or an agent that induces or is capable of inducing a signal through an intracellular signaling region of the recombinant receptor; and assessing the one or more reporter T cells for expression of the reporter molecule. In some aspects, provided are methods of assessing antigen-dependent and antigen-independent signaling via the recombinant receptors.

III. POLYNUCLEOTIDES ENCODING CANDIDATE RECOMBINANT RECEPTORS, VECTORS AND LIBRARIES

Provided herein are polynucleotides encoding candidate recombinant receptors, vectors, and plurality of polynucleotides and/or vectors. In some embodiments, the provided polynucleotides can be used in the assessment and/or screening methods provided herein, for engineering cells, such as reporter T cells, to express the candidate recombinant receptors, e.g., CARs. In some embodiments, the provided polynucleotides can be used to generate a plurality or library of polynucleotides encoding a plurality of different recombinant receptors, e.g., CARs. In some embodiments, the polynucleotide includes a vector backbone. In some embodiments, the vector backbone includes common sequences, such as sequences encoding signaling and/or other components of the recombinant receptors, leader sequences and/or markers. In some embodiments, the vector backbones include one or more sites, such as restriction sites, to facilitate cloning, insertion and/or addition of various binding domains and/or other components of the recombinant receptor, to facilitate the generation, assessment and/or screening of various recombinant receptors.

In some embodiments, the polynucleotides and/or vector backboness described are included in the kits and/or articles of manufacture provided herein. Also provided are vectors, e.g., vector backbones, that can be used in the methods described herein. In some embodiments, provided are a plurality of vector backbones, e.g., a plurality of barcoded vector backbones. In some embodiments, the provided vector backbones can be employed to generate a plurality of a plurality or library of polynucleotides encoding a plurality of different recombinant receptors, e.g., CARs. Also provided are a plurality and/or library of such polynucleotides. In some embodiments, the polynucleotides encoding recombinant receptors, e.g., CARs, can be used to generate a plurality of reporter T cells, e.g., plurality of reporter T cells that express candidate recombinant receptors.

A. Encoded Recombinant Receptors

In some embodiments, the provided methods and vector backbones can be used to express, assess the activity of, screen and/or identify recombinant receptors, e.g., chimeric antigen receptors (CARs). In some embodiments, the provided methods and vector backbones are used to assess activity, expression and/or function of the encoded recombinant receptors, or screen and/or identify one or more recombinant receptors and/or recombinant receptor expressing cells from a plurality and/or library of polynucleotides encoding recombinant receptors. In some embodiments, the plurality of polynucleotides encode candidate recombinant receptors, e.g., generated from a plurality or library of polynucleotides and/or a plurality or library of candidate binding domains. In some embodiments, the provided reporter T cells, e.g., T cells that contain a reporter molecule, are engineered to express a recombinant receptor containing a recombinant receptor. In any of such embodiments, the encoded recombinant receptors can be any of the recombinant receptors described herein.

Among the recombinant receptors are antigen receptors that contain a binding domain and an intracellular signaling region. In some embodiments, the intracellular signaling region comprises an intracellular signaling domain. In some embodiments, the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM). In some embodiments, the intracellular signaling domain is or comprises an intracellular signaling domain of a CD3 chain, optionally a CD3-zeta (CD3ζ) chain, or a signaling portion thereof.

In some embodiments, the recombinant receptors include chimeric receptors, such as those containing binding domains or binding fragments thereof and intracellular signaling domains, functional non-TCR antigen receptors, chimeric antigen receptors (CARs), and T cell receptors (TCRs), such as recombinant TCRs, and components of any of the foregoing. In some embodiments, the recombinant receptors include chimeric autoantibody receptors (CAARs), such as any described in U.S. Patent Application Pub. No. US 2017/0051035.

In some embodiments, the recombinant receptor, such as a CAR, generally includes the extracellular antigen (or ligand) binding domain linked to one or more intracellular signaling components, e.g., a signaling region comprising an immunoreceptor tyrosine-based activation motif (ITAM), in some aspects via linkers and/or transmembrane domain(s).

In some embodiments, the intracellular signaling region comprises an intracellular signaling domain. In some embodiments, the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM). In some embodiments, the intracellular signaling domain is or comprises an intracellular signaling domain of a CD3 chain, optionally a CD3-zeta (CD3ζ) chain, or a signaling portion thereof.

1. Chimeric Antigen Receptors

In some embodiments, the recombinant receptor includes a chimeric antigen receptor (CAR). In some embodiments, the CAR is specific for a particular antigen (or marker or ligand), such as an antigen expressed on the surface of a particular cell type. In some embodiments, the antigen is a polypeptide. In some embodiments, it is a carbohydrate or other molecule. In some embodiments, the antigen is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

In particular embodiments, the recombinant receptor, such as a chimeric receptor, contains an intracellular signaling region, which includes a cytoplasmic signaling domain (also interchangeably called an intracellular signaling domain), such as a cytoplasmic (intracellular) region capable of inducing a primary activation signal in a T cell, for example, a cytoplasmic signaling domain of a T cell receptor (TCR) component (e.g. a cytoplasmic signaling domain of a zeta chain of a CD3-zeta (CD3ζ) chain or a functional variant or signaling portion thereof) and/or that comprises an immunoreceptor tyrosine-based activation motif (ITAM).

In some embodiments, the chimeric receptor further contains an extracellular binding domain that specifically binds to an antigen (or a ligand). In some embodiments, the chimeric receptor is a CAR that contains an extracellular antigen-recognition domain that specifically binds to an antigen. In some embodiments, the antigen(or a ligand), is a protein expressed on the surface of cells. In some embodiments, the CAR is a TCR-like CAR and the antigen is a processed peptide antigen, such as a peptide antigen of an intracellular protein, which, like a TCR, is recognized on the cell surface in the context of a major histocompatibility complex (MHC) molecule.

Exemplary antigen receptors, including CARs, and methods for engineering and introducing such receptors into cells, include those described, for example, in international patent application publication numbers WO200014257, WO2013126726, WO2012/129514, WO2014031687, WO2013/166321, WO2013/071154, WO2013/123061, U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) PLoS ONE 8(4): e61338; Turtle et al., Curr. Opin. Immunol., 2012 October; 24(5): 633-39; Wu et al., Cancer, 2012 Mar. 18(2): 160-75. In some aspects, the antigen receptors include a CAR as described in U.S. Pat. No. 7,446,190, and those described in International Patent Application Publication No.: WO/2014055668 A1. Examples of the CARs include CARs as disclosed in any of the aforementioned publications, such as WO2014031687, U.S. Pat. Nos. 8,339,645, 7,446,179, US 2013/0149337, U.S. Pat. Nos. 7,446,190, 8,389,282, Kochenderfer et al., 2013, Nature Reviews Clinical Oncology, 10, 267-276 (2013); Wang et al. (2012) J. Immunother. 35(9): 689-701; and Brentjens et al., Sci Transl Med. 2013 5(177). See also WO2014031687, U.S. Pat. Nos. 8,339,645, 7,446,179, US 2013/0149337, U.S. Pat. Nos. 7,446,190, and 8,389,282.

In some embodiments, the CAR is constructed with a specificity for a particular antigen (or marker or ligand), such as an antigen expressed in a particular cell type to be targeted by adoptive therapy, e.g., a cancer marker, and/or an antigen intended to induce a dampening response, such as an antigen expressed on a normal or non-diseased cell type. Thus, the CAR typically includes in its extracellular portion one or more antigen binding domains, such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy ($V_H$) and variable light ($V_L$) chains of a monoclonal antibody (mAb).

In some embodiments, the antibody or antigen-binding portion thereof is expressed on cells as part of a recombinant receptor, such as an antigen receptor. In some embodiments, the vector backbone contains one or more site(s) for introduction of a nucleic acid sequence encoding a binding domain, such as one of a plurality of candidate binding domains.

Among the antigen receptors are functional non-TCR antigen receptors, such as chimeric antigen receptors (CARs). Generally, a CAR containing an antibody or antigen-binding fragment that exhibits TCR-like specificity directed against peptide-MHC complexes also may be referred to as a TCR-like CAR. In some embodiments, the extracellular antigen binding domain specific for an MHC-peptide complex of a TCR-like CAR is linked to one or more intracellular signaling components, in some aspects via linkers and/or transmembrane domain(s). In some embodiments, such molecules can typically mimic or approximate a signal through a natural antigen receptor, such as a TCR, and, optionally, a signal through such a receptor in combination with a costimulatory receptor.

In some embodiments, the recombinant receptor, such as a chimeric receptor (e.g. CAR), includes a binding domain that binds, such as specifically binds, to an antigen (or a ligand). Among the antigens targeted by the chimeric receptors are those expressed in the context of a disease, condition, or cell type to be targeted via the adoptive cell therapy. Among the diseases and conditions are proliferative, neoplastic, and malignant diseases and disorders, including cancers and tumors, including hematologic cancers, cancers of the immune system, such as lymphomas, leukemias, and/or myelomas, such as B, T, and myeloid leukemias, lymphomas, and multiple myelomas.

In some embodiments, the antigen (or a ligand) is a polypeptide. In some embodiments, it is a carbohydrate or other molecule. In some embodiments, the antigen (or a ligand) is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

In some embodiments, the CAR contains an antibody or an antigen-binding fragment (e.g. scFv) that specifically recognizes or specifically binds an antigen, such as an intact antigen, expressed on the surface of a cell.

In some embodiments, the CAR contains a TCR-like antibody, such as an antibody or an antigen-binding fragment (e.g. scFv) that specifically recognizes or specifically binds an intracellular antigen, such as a tumor-associated antigen, presented on the cell surface as a MHC-peptide complex. In some embodiments, an antibody or antigen-binding portion thereof that recognizes an MHC-peptide complex can be expressed on cells as part of a recombinant receptor, such as an antigen receptor. Among the antigen receptors are functional non-TCR antigen receptors, such as chimeric antigen receptors (CARs). Generally, a CAR containing an antibody or antigen-binding fragment that exhibits TCR-like specificity directed against peptide-MHC complexes also may be referred to as a TCR-like CAR.

Reference to "Major histocompatibility complex" (MHC) refers to a protein, generally a glycoprotein, that contains a polymorphic peptide binding site or binding groove that can, in some cases, complex with peptide antigens of polypeptides, including peptide antigens processed by the cell machinery. In some cases, MHC molecules can be displayed or expressed on the cell surface, including as a complex with peptide, i.e. MHC-peptide complex, for presentation of an antigen in a conformation recognizable by an antigen receptor on T cells, such as a TCRs or TCR-like antibody. Generally, MHC class I molecules are heterodimers having a membrane spanning α chain, in some cases with three a domains, and a non-covalently associated β2 microglobulin. Generally, MHC class II molecules are composed of two transmembrane glycoproteins, a and J, both of which typically span the membrane. An MHC molecule can include an effective portion of an MHC that contains an antigen binding site or sites for binding a peptide and the sequences necessary for recognition by the appropriate antigen receptor. In some embodiments, MHC class I molecules deliver peptides originating in the cytosol to the cell surface, where a MHC-peptide complex is recognized by T cells, such as generally $CD8^+$ T cells, but in some cases CD4+ T cells. In some embodiments, MHC class II molecules deliver peptides originating in the vesicular system to the cell surface, where they are typically recognized by $CD4^+$ T cells. Generally, MHC molecules are encoded by a group of linked loci, which are collectively termed H-2 in the mouse and human leukocyte antigen (HLA) in humans. Hence, typically human MHC can also be referred to as human leukocyte antigen (HLA).

The term "MHC-peptide complex" or "peptide-MHC complex" or variations thereof, refers to a complex or association of a peptide antigen and an MHC molecule, such as, generally, by non-covalent interactions of the peptide in the binding groove or cleft of the MHC molecule. In some embodiments, the MHC-peptide complex is present or displayed on the surface of cells. In some embodiments, the MHC-peptide complex can be specifically recognized by an antigen receptor, such as a TCR, TCR-like CAR or antigen-binding portions thereof.

In some embodiments, a peptide, such as a peptide antigen or epitope, of a polypeptide can associate with an MHC molecule, such as for recognition by an antigen receptor. Generally, the peptide is derived from or based on a fragment of a longer biological molecule, such as a polypeptide or protein. In some embodiments, the peptide typically is about 8 to about 24 amino acids in length. In some embodiments, a peptide has a length of from or from about 9 to 22 amino acids for recognition in the MHC Class II complex. In some embodiments, a peptide has a length of from or from about 8 to 13 amino acids for recognition in the MHC Class I complex. In some embodiments, upon recognition of the peptide in the context of an MHC molecule, such as MHC-peptide complex, the antigen receptor, such as TCR or TCR-like CAR, produces or triggers an activation signal to the T cell that induces a T cell response, such as T cell proliferation, cytokine production, a cytotoxic T cell response or other response.

In some embodiments, a TCR-like antibody or antigen-binding portion, are known or can be produced by methods known (see e.g. US Published Application Nos. US 2002/0150914; US 2003/0223994; US 2004/0191260; US 2006/0034850; US 2007/00992530; US20090226474; US20090304679; and International PCT Publication No. WO 03/068201).

In some embodiments, an antibody or antigen-binding portion thereof that specifically binds to a MHC-peptide complex, can be produced by immunizing a host with an effective amount of an immunogen containing a specific MHC-peptide complex. In some cases, the peptide of the MHC-peptide complex is an epitope of antigen capable of binding to the MHC, such as a tumor antigen, for example a universal tumor antigen, myeloma antigen or other antigen as described below. In some embodiments, an effective amount of the immunogen is then administered to a host for eliciting an immune response, wherein the immunogen retains a three-dimensional form thereof for a period of time sufficient to elicit an immune response against the three-dimensional presentation of the peptide in the binding groove of the MHC molecule. Serum collected from the host is then assayed to determine if desired antibodies that recognize a three-dimensional presentation of the peptide in the binding groove of the MHC molecule is being produced. In some embodiments, the produced antibodies can be assessed to confirm that the antibody can differentiate the MHC-peptide complex from the MHC molecule alone, the peptide of interest alone, and a complex of MHC and irrelevant peptide. The desired antibodies can then be isolated.

In some embodiments, an antibody or antigen-binding portion thereof that specifically binds to an MHC-peptide complex can be produced by employing antibody library display methods, such as phage antibody libraries. In some embodiments, phage display libraries of mutant Fab, scFv or other antibody forms can be generated, for example, in which members of the library are mutated at one or more residues of a CDR or CDRs. See e.g. US published application No. US20020150914, US2014/0294841; and Cohen C J. et al. (2003) *J Mol. Recogn.* 16:324-332.

2. T Cell Receptors

In some embodiments, the recombinant receptor is a T cell receptor (TCR) or antigen-binding portion thereof that recognizes an peptide epitope or T cell epitope of a target polypeptide, such as an antigen of a tumor, viral or autoimmune protein.

In some embodiments, a "T cell receptor" or "TCR" is a molecule that contains a variable α and β chains (also known as TCRα and TCRβ, respectively) or a variable γ and δ chains (also known as TCRα and TCRβ, respectively), or antigen-binding portions thereof, and which is capable of specifically binding to a peptide bound to an MHC molecule. In some embodiments, the TCR is in the αβ form. Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules.

Unless otherwise stated, the term "TCR" should be understood to encompass full TCRs as well as antigen-binding portions or antigen-binding fragments thereof. In some embodiments, the TCR is an intact or full-length TCR, including TCRs in the αβ form or γδ form. In some embodiments, the TCR is an antigen-binding portion that is less than a full-length TCR but that binds to a specific peptide bound in an MHC molecule, such as binds to an MHC-peptide complex. In some cases, an antigen-binding portion or fragment of a TCR can contain only a portion of the structural domains of a full-length or intact TCR, but yet is able to bind the peptide epitope, such as MHC-peptide complex, to which the full TCR binds. In some cases, an antigen-binding portion contains the variable domains of a TCR, such as variable α chain and variable f chain of a TCR, sufficient to form a binding site for binding to a specific MHC-peptide complex. Generally, the variable chains of a TCR contain complementarity determining regions involved in recognition of the peptide, MHC and/or MHC-peptide complex.

In some embodiments, the variable domains of the TCR contain hypervariable loops, or complementarity determining regions (CDRs), which generally are the primary contributors to antigen recognition and binding capabilities and specificity. In some embodiments, a CDR of a TCR or combination thereof forms all or substantially all of the antigen-binding site of a given TCR molecule. The various CDRs within a variable region of a TCR chain generally are separated by framework regions (FRs), which generally display less variability among TCR molecules as compared to the CDRs (see, e.g., Jores et al., Proc. Nat'l Acad. Sci. U.S.A. 87:9138, 1990; Chothia et al., EMBO J. 7:3745, 1988; see also Lefranc et al., Dev. Comp. Immunol. 27:55, 2003). In some embodiments, CDR3 is the main CDR responsible for antigen binding or specificity, or is the most important among the three CDRs on a given TCR variable region for antigen recognition, and/or for interaction with the processed peptide portion of the peptide-MHC complex. In some contexts, the CDR1 of the alpha chain can interact with the N-terminal part of certain antigenic peptides. In some contexts, CDR1 of the beta chain can interact with the C-terminal part of the peptide. In some contexts, CDR2 contributes most strongly to or is the primary CDR responsible for the interaction with or recognition of the MHC portion of the MHC-peptide complex. In some embodiments, the variable region of the β-chain can contain a further hypervariable region (CDR4 or HVR4), which generally is involved in superantigen binding and not antigen recognition (Kotb (1995) Clinical Microbiology Reviews, 8:411-426).

In some embodiments, a TCR also can contain a constant domain, a transmembrane domain and/or a short cytoplasmic tail (see, e.g., Janeway et al., Immunobiology: The Immune System in Health and Disease, 3rd Ed., Current Biology Publications, p. 4:33, 1997). In some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction.

In some embodiments, a TCR chain contains one or more constant domain. For example, the extracellular portion of a given TCR chain (e.g., α-chain or β-chain) can contain two immunoglobulin-like domains, such as a variable domain (e.g., Vα or Vβ; typically amino acids 1 to 116 based on Kabat numbering Kabat et al., "Sequences of Proteins of Immunological Interest, US Dept. Health and Human Services, Public Health Service National Institutes of Health, 1991, 5th ed.) and a constant domain (e.g., α-chain constant domain or Cα, typically positions 117 to 259 of the chain based on Kabat numbering or β chain constant domain or $C_\beta$, typically positions 117 to 295 of the chain based on Kabat) adjacent to the cell membrane. In some cases, the extracellular portion of the TCR formed by the two chains contains two membrane-proximal constant domains, and two membrane-distal variable domains, which variable domains each contain CDRs. The constant domain of the TCR may contain short connecting sequences in which a cysteine residue forms a disulfide bond, thereby linking the two chains of the TCR. In some embodiments, a TCR may have an additional cysteine residue in each of the α and β chains, such that the TCR contains two disulfide bonds in the constant domains.

In some embodiments, the TCR chains contain a transmembrane domain. In some embodiments, the transmembrane domain is positively charged. In some cases, the TCR chain contains a cytoplasmic tail. In some cases, the structure allows the TCR to associate with other molecules like CD3 and subunits thereof. For example, a TCR containing constant domains with a transmembrane region may anchor the protein in the cell membrane and associate with invariant subunits of the CD3 signaling apparatus or complex. The intracellular tails of CD3 signaling subunits (e.g. CD3γ, CD3δ, CD3ε and CD3ζ chains) contain one or more immunoreceptor tyrosine-based activation motif or ITAM that are involved in the signaling capacity of the TCR complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds.

In some embodiments, the TCR can be generated from a known TCR sequence(s), such as sequences of Vα,β chains, for which a substantially full-length coding sequence is readily available. Methods for obtaining full-length TCR sequences, including V chain sequences, from cell sources are well known. In some embodiments, nucleic acids encoding the TCR can be obtained from a variety of sources, such as by polymerase chain reaction (PCR) amplification of TCR-encoding nucleic acids within or isolated from a given cell or cells, or synthesis of publicly available TCR DNA sequences.

In some embodiments, the TCR is obtained from a biological source, such as from cells such as from a T cell (e.g. cytotoxic T cell), T-cell hybridomas or other publicly available source. In some embodiments, the T-cells can be obtained from in vivo isolated cells. In some embodiments, the TCR is a thymically selected TCR. In some embodiments, the TCR is a neoepitope-restricted TCR. In some embodiments, the T-cells can be a cultured T-cell hybridoma or clone. In some embodiments, the TCR or antigen-binding portion thereof or antigen-binding fragment thereof can be synthetically generated from knowledge of the sequence of the TCR.

In some embodiments, the TCR is generated from a TCR identified or selected from screening a library of candidate TCRs against a target polypeptide antigen, or target T cell epitope thereof. TCR libraries can be generated by amplification of the repertoire of Vα and Vβ from T cells isolated from a subject, including cells present in PBMCs, spleen or other lymphoid organ. In some cases, T cells can be amplified from tumor-infiltrating lymphocytes (TILs). In some embodiments, TCR libraries can be generated from CD4+ or CD8+ cells. In some embodiments, the TCRs can be amplified from a T cell source of a normal of healthy subject, i.e. normal TCR libraries. In some embodiments, the TCRs can be amplified from a T cell source of a diseased subject, i.e. diseased TCR libraries. In some embodiments, degenerate primers are used to amplify the gene repertoire of Vα and Vβ, such as by RT-PCR in samples, such as T cells, obtained from humans. In some embodiments, scTv libraries can be assembled from naïve Vα and Vβ libraries in which the amplified products are cloned or assembled to be separated by a linker. Depending on the source of the subject and cells, the libraries can be HLA allele-specific. Alternatively, in some embodiments, TCR libraries can be generated by mutagenesis or diversification of a parent or scaffold TCR molecule. In some aspects, the TCRs are subjected to directed evolution, such as by mutagenesis, e.g., of the α or β chain. In some aspects, particular residues within CDRs of the TCR are altered. In some embodiments, selected TCRs can be modified by affinity maturation. In some embodiments, antigen-specific T cells may be selected, such as by screening to assess CTL activity against the peptide. In some aspects, TCRs, e.g. present on the antigen-specific T cells, may be selected, such as by binding activity, e.g., particular affinity or avidity for the antigen.

In some embodiments, the TCR or antigen-binding portion thereof is one that has been modified or engineered. In some embodiments, directed evolution methods are used to generate TCRs with altered properties, such as with higher affinity for a specific MHC-peptide complex. In some embodiments, directed evolution is achieved by display methods including, but not limited to, yeast display (Holler et al. (2003) Nat Immunol, 4, 55-62; Holler et al. (2000) Proc Natl Acad Sci USA, 97, 5387-92), phage display (Li et al. (2005) Nat Biotechnol, 23, 349-54), or T cell display (Chervin et al. (2008) J Immunol Methods, 339, 175-84). In some embodiments, display approaches involve engineering, or modifying, a known, parent or reference TCR. In some cases, a wild-type TCR can be used as a template for producing mutagenized TCRs in which in one or more residues of the CDRs are mutated, and mutants with an desired altered property, such as higher affinity for a desired target antigen, are selected.

In some embodiments, peptides of a target polypeptide for use in producing or generating a TCR of interest are known or can be readily identified. In some embodiments, peptides suitable for use in generating TCRs or antigen-binding portions can be determined based on the presence of an HLA-restricted motif in a target polypeptide of interest, such as a target polypeptide described below. In some embodiments, peptides are identified using available computer prediction models. In some embodiments, for predicting MHC class I binding sites, such models include, but are not limited to, ProPred1 (Singh and Raghava (2001) Bioinformatics 17(12):1236-1237, and SYFPEITHI (see Schuler et al. (2007) Immunoinformatics Methods in Molecular Biology, 409(1): 75-93 2007). In some embodiments, the MHC-restricted epitope is HLA-A0201, which is expressed in approximately 39-46% of all Caucasians and therefore, represents a suitable choice of MHC antigen for use preparing a TCR or other MHC-peptide binding molecule.

HLA-A0201-binding motifs and the cleavage sites for proteasomes and immune-proteasomes using computer prediction models are known. For predicting MHC class I binding sites, such models include, but are not limited to, ProPred1 (described in more detail in Singh and Raghava, ProPred: prediction of HLA-DR binding sites. BIOINFORMATICS 17(12):1236-1237 2001), and SYFPEITHI (see Schuler et al. SYFPEITHI, Database for Searching and T-Cell Epitope Prediction. in Immunoinformatics Methods in Molecular Biology, vol 409(1): 75-93 2007).

In some embodiments, the TCR or antigen binding portion thereof may be a recombinantly produced natural protein or mutated form thereof in which one or more property, such as binding characteristic, has been altered. In some embodiments, a TCR may be derived from one of various animal species, such as human, mouse, rat, or other mammal. A TCR may be cell-bound or in soluble form. In some embodiments, for purposes of the provided methods, the TCR is in cell-bound form expressed on the surface of a cell.

In some embodiments, the TCR is a full-length TCR. In some embodiments, the TCR is an antigen-binding portion. In some embodiments, the TCR is a dimeric TCR (dTCR). In some embodiments, the TCR is a single-chain TCR (sc-TCR). In some embodiments, a dTCR or scTCR have the structures as described in WO 03/020763, WO 04/033685, WO2011/044186.

In some embodiments, the TCR contains a sequence corresponding to the transmembrane sequence. In some embodiments, the TCR does contain a sequence corresponding to cytoplasmic sequences. In some embodiments, the TCR is capable of forming a TCR complex with CD3. In some embodiments, any of the TCRs, including a dTCR or scTCR, can be linked to signaling domains that yield an active TCR on the surface of a T cell. In some embodiments, the TCR is expressed on the surface of cells.

In some embodiments a dTCR contains a first polypeptide wherein a sequence corresponding to a TCR α chain variable region sequence is fused to the N terminus of a sequence corresponding to a TCR α chain constant region extracellular sequence, and a second polypeptide wherein a sequence corresponding to a TCR β chain variable region sequence is fused to the N terminus a sequence corresponding to a TCR β chain constant region extracellular sequence, the first and second polypeptides being linked by a disulfide bond. In some embodiments, the bond can correspond to the native interchain disulfide bond present in native dimeric αβ TCRs. In some embodiments, the interchain disulfide bonds are not present in a native TCR. In some embodiments, one or more cysteines can be incorporated into the constant region extracellular sequences of dTCR polypeptide pair. In some cases, both a native and a non-native disulfide bond may be desirable. In some embodiments, the TCR contains a transmembrane sequence to anchor to the membrane.

In some embodiments, a dTCR contains a TCR α chain containing a variable α domain, a constant α domain and a first dimerization motif attached to the C-terminus of the constant α domain, and a TCR β chain comprising a variable β domain, a constant β domain and a first dimerization motif attached to the C-terminus of the constant β domain, wherein the first and second dimerization motifs easily interact to form a covalent bond between an amino acid in the first dimerization motif and an amino acid in the second dimerization motif linking the TCR α chain and TCR β chain together.

In some embodiments, the TCR is a scTCR. Typically, a scTCR can be generated using known methods, See e.g., Soo Hoo, W. F. et al. PNAS (USA) 89, 4759 (1992); Wtilfing, C. and Plickthun, A., J. Mol. Biol. 242, 655 (1994); Kurucz, I. et al. PNAS (USA) 90 3830 (1993); International published PCT Nos. WO 96/13593, WO 96/18105, WO99/60120, WO99/18129, WO 03/020763, WO2011/044186; and Schlueter, C. J. et al. J. Mol. Biol. 256, 859 (1996). In some embodiments, a scTCR contains an introduced non-native disulfide interchain bond to facilitate the association of the TCR chains (see e.g. International published PCT No. WO 03/020763). In some embodiments, a scTCR is a non-disulfide linked truncated TCR in which heterologous leucine zippers fused to the C-termini thereof facilitate chain association (see e.g. International published PCT No. WO99/60120). In some embodiments, a scTCR contain a TCRα variable domain covalently linked to a TCRβ variable domain via a peptide linker (see e.g., International published PCT No. WO99/18129).

In some embodiments, a scTCR contains a first segment constituted by an amino acid sequence corresponding to a TCR α chain variable region, a second segment constituted by an amino acid sequence corresponding to a TCR β chain variable region sequence fused to the N terminus of an amino acid sequence corresponding to a TCR β chain constant domain extracellular sequence, and a linker sequence linking the C terminus of the first segment to the N terminus of the second segment.

In some embodiments, a scTCR contains a first segment constituted by an α chain variable region sequence fused to the N terminus of an α chain extracellular constant domain sequence, and a second segment constituted by a β chain variable region sequence fused to the N terminus of a sequence β chain extracellular constant and transmembrane sequence, and, optionally, a linker sequence linking the C terminus of the first segment to the N terminus of the second segment.

In some embodiments, a scTCR contains a first segment constituted by a TCR β chain variable region sequence fused to the N terminus of a β chain extracellular constant domain sequence, and a second segment constituted by an α chain variable region sequence fused to the N terminus of a sequence α chain extracellular constant and transmembrane sequence, and, optionally, a linker sequence linking the C terminus of the first segment to the N terminus of the second segment.

In some embodiments, the linker of a scTCRs that links the first and second TCR segments can be any linker capable of forming a single polypeptide strand, while retaining TCR binding specificity. In some embodiments, the linker sequence may, for example, have the formula -P-AA-P- wherein P is proline and AA represents an amino acid sequence wherein the amino acids are glycine and serine. In some embodiments, the first and second segments are paired so that the variable region sequences thereof are orientated for such binding. Hence, in some cases, the linker has a sufficient length to span the distance between the C terminus of the first segment and the N terminus of the second segment, or vice versa, but is not too long to block or reduces bonding of the scTCR to the target ligand. In some embodiments, the linker can contain from or from about 10 to 45 amino acids, such as 10 to 30 amino acids or 26 to 41 amino acids residues, for example 29, 30, 31 or 32 amino acids. In some embodiments, the linker has the formula -PGGG-(SGGGG)5-P- wherein P is proline, G is glycine and S is serine (SEQ ID NO:67). In some embodiments, the linker has the sequence GSADDAKKDAAKKDGKS (SEQ ID NO:68).

In some embodiments, the scTCR contains a covalent disulfide bond linking a residue of the immunoglobulin region of the constant domain of the α chain to a residue of the immunoglobulin region of the constant domain of the β chain. In some embodiments, the interchain disulfide bond in a native TCR is not present. In some embodiments, one or more cysteines can be incorporated into the constant region extracellular sequences of the first and second segments of the scTCR polypeptide. In some cases, both a native and a non-native disulfide bond may be desirable.

In some embodiments of a dTCR or scTCR containing introduced interchain disulfide bonds, the native disulfide bonds are not present. In some embodiments, the one or more of the native cysteines forming a native interchain disulfide bonds are substituted to another residue, such as to a serine or alanine. In some embodiments, an introduced disulfide bond can be formed by mutating non-cysteine residues on the first and second segments to cysteine. Exemplary non-native disulfide bonds of a TCR are described in published International PCT No. WO2006/000830.

In some embodiments, the TCR or antigen-binding fragment thereof exhibits an affinity with an equilibrium binding constant for a target antigen of between or between about 10-5 and 10-12 M and all individual values and ranges therein. In some embodiments, the target antigen is an MHC-peptide complex or ligand.

In some embodiments, nucleic acid or nucleic acids encoding a TCR, such as α and β chains, can be amplified by PCR, cloning or other suitable means and cloned into a suitable expression vector or vectors. The expression vector can be any suitable recombinant expression vector, and can be used to transform or transfect any suitable host. Suitable vectors include those designed for propagation and expansion or for expression or both, such as plasmids and viruses.

In some embodiments, the vector can be a vector of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), or the pEX series (Clontech, Palo Alto, Calif.). In some cases, bacteriophage vectors, such as λG10, λGT11, λZapII (Stratagene), λEMBL4, and λNM1149, also can be used. In some embodiments, plant expression vectors can be used and include pBI01, pBI101.2, pBI101.3, pBI121 and pBIN19 (Clontech). In some embodiments, animal expression vectors include pEUK-Cl, pMAM and pMAM-neo (Clontech). In some embodiments, a viral vector is used, such as a retroviral vector.

In some embodiments, the recombinant expression vectors can be prepared using standard recombinant DNA techniques. In some embodiments, vectors can contain regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based. In some embodiments, the vector can contain a nonnative promoter operably linked to the nucleotide sequence encoding the TCR or antigen-binding portion (or other MHC-peptide binding domain). In some embodiments, the promoter can be a non-viral promoter or a viral promoter, such as a cytomegalovirus (CMV) promoter, an SV40 promoter, an RSV promoter, and a promoter found in the long-terminal repeat of the murine stem cell virus. Other known promoters also are contemplated.

In some embodiments, to generate a vector encoding a TCR, the α and β chains are PCR amplified from total cDNA isolated from a T cell clone expressing the TCR of interest and cloned into one or more vectors. In some embodiments, the α and β chains are cloned into the same vector. In some embodiments, the α and β chains are cloned into different vectors. In some embodiments, the generated α and β chains are incorporated into a retroviral, e.g. lentiviral, vector.

3. Chimeric Auto-Antibody Receptor (CAAR)

In some embodiments, the recombinant receptor is a chimeric autoantibody receptor (CAAR). In some embodiments, the CAAR is specific for an autoantibody. In some embodiments, a cell expressing the CAAR, such as a T cell engineered to express a CAAR, can be used to specifically bind to and kill autoantibody-expressing cells, but not normal antibody expressing cells. In some embodiments, CAAR-expressing cells can be used to treat an autoimmune disease associated with expression of self-antigens, such as autoimmune diseases. In some embodiments, CAAR-expressing cells can target B cells that ultimately produce the autoantibodies and display the autoantibodies on their cell surfaces, mark these B cells as disease-specific targets for therapeutic intervention. In some embodiments, CAAR-expressing cells can be used to efficiently targeting and killing the pathogenic B cells in autoimmune diseases by targeting the disease-causing B cells using an antigen-specific chimeric autoantibody receptor. In some embodiments, the recombinant receptor is a CAAR, such as any described in U.S. Patent Application Pub. No. US 2017/0051035.

In some embodiments, the CAAR comprises an autoantibody binding domain, a transmembrane domain, and an intracellular signaling region. In some embodiments, the intracellular signaling region comprises an intracellular signaling domain. In some embodiments, the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM). In some embodiments, the intracellular signaling region comprises a secondary or costimulatory signaling region (secondary intracellular signaling regions).

In some embodiments, the autoantibody binding domain comprises an autoantigen or a fragment thereof. The choice of autoantigen can depend upon the type of autoantibody being targeted. For example, the autoantigen may be chosen because it recognizes an autoantibody on a target cell, such as a B cell, associated with a particular disease state, e.g. an autoimmune disease, such as an autoantibody-mediated autoimmune disease. In some embodiments, the autoimmune disease includes pemphigus vulgaris (PV). Exemplary autoantigens include desmoglein 1 (Dsg1) and Dsg3.

B. Vector Backbones

Provided are vectors, e.g., vector backbones, that can be used in the methods described herein, to facilitate assessment of activity, e.g., functional activity, of a recombinant receptor, e.g., CAR. Also provided are a plurality of such vector backbones, that can be used in the methods described herein, to facilitate assessment of activity, e.g., functional activity, of a variety of different candidate recombinant receptors, e.g., candidate recombinant receptors containing different binding domains and/or different components, such as different signaling components or different spacers. In some embodiments, the provided vector backbones and/or plurality of vector backbones can facilitate the generation, expression, engineering, assessment and/or identification of candidate recombinant receptors in the methods described herein. In some embodiments, the vector backbones and/or plurality of vector backbones can facilitate the expression of a plurality of candidate binding domains in the format of a recombinant receptor, e.g., CAR, and generation of a plurality of cells, e.g., reporter T cells, to rapidly and easily assess and/or screen to identify cells expressing recombinant receptors with desired characteristics. In some embodiments, the vector backbones and/or plurality of vector backbones can be used to engineer other cells, e.g., primary cells, to express the identified recombinant receptor. In some embodiments, the vector backbones and/or plurality of vector backbones can be employed in any of the methods of assessment, screening, engineering and/or generation provided herein.

In some embodiments, the vector backbone includes common sequences, such as sequences encoding signaling and/or other components of the recombinant receptors, leader sequences and/or markers. In some embodiments, the vector backbones include one or more sites, such as restriction sites, to facilitate cloning, insertion and/or addition of particular components, such as various binding domains and/or other components of the recombinant receptor, to facilitate the generation, assessment and/or screening of various recombinant receptors. In some embodiments, the vector comprises common sequences that are shared between different recombinant receptors to be assessed and/or screened, and contain one or more sites for introducing sequences encoding components that are not common or not shared between different recombinant receptors to be assessed/or screened. Such sites allow rapid generation of numerous polynucleotides encoding numerous different recombinant receptors that contain different components, e.g., binding domains, to permit small-, medium- or high-throughput screening methods to determine the activity, e.g., signaling activity and/or functional activity of the recombinant receptors.

1. Exemplary Vector Backbone

In some embodiments, an exemplary vector backbone contains common sequences, such as sequences encoding signaling and/or other components of the recombinant receptors, leader sequences and/or markers. In some embodiments, an exemplary vector backbone contains regulatory elements for expression of components of a recombinant receptor; a nucleic acid sequence encoding a leader sequence comprising a molecular barcode; one or more site(s) for introduction of a nucleic acid sequence encoding a binding domain; a nucleic acid sequence encoding a spacer; a nucleic acid sequence encoding an intracellular signaling region; and/or a nucleic acid sequence encoding one or more marker(s). In some embodiments, the vector backbone also contains sequences required for maintenance, replication, expression, transfer, transduction, integration and/or generation of the vector, e.g., viral vector sequence or plasmid sequence.

a. Regulatory Elements

In some embodiments, the vector backbone contains regulatory elements, e.g., transcriptional regulatory elements, for expression of the encoded recombinant receptor in a cell, e.g., reporter T cell. In some embodiments, the regulatory element is a promoter, enhancer or response element or elements. In some embodiments, the promoter is a constitutive promoter. In some embodiments, the promoter is a regulatable promoter.

One or more regulatory/control elements, e.g., a promoter, an enhancer, an intron, a polyadenylation signal, a Kozak consensus sequence, internal ribosome entry sites (IRES), a 2A sequence, and splice acceptor or donor can be included in the vectors. In some embodiments, the promoter is selected from among an RNA pol I, pol II or pol III promoter. In some embodiments, the promoter is recognized by RNA polymerase II (e.g., a CMV, SV40 early region or adenovirus major late promoter). In another embodiment, the promoter is recognized by RNA polymerase III (e.g., a U6 or H1 promoter). In some embodiments, the promoter can be a non-viral promoter or a viral promoter, such as a cytomegalovirus (CMV) promoter, an SV40 promoter, an RSV promoter, and a promoter found in the long-terminal repeat of the murine stem cell virus. Other promoters known also are contemplated.

In some embodiments, the regulatory element is a conditional promoter or enhancer or transactivator, such as an inducible promoter, enhancer, or transactivator or a repressible promoter, enhancer, or transactivator. In some embodiments, the promoter is a regulated promoter (e.g., inducible promoter). In some embodiments, the promoter is an inducible promoter or a repressible promoter. In some embodiments, the promoter comprises a Lac operator sequence, a tetracycline operator sequence, a galactose operator sequence or a doxycycline operator sequence, or is an analog thereof or is capable of being bound by or recognized by a Lac repressor or a tetracycline repressor, or an analog thereof.

In some embodiments, the promoter is or comprises a constitutive promoter. Exemplary constitutive promoters include, e.g., simian virus 40 early promoter (SV40), cytomegalovirus immediate-early promoter (CMV), human Ubiquitin C promoter (UBC), human elongation factor 1α promoter (EF1a), mouse phosphoglycerate kinase 1 promoter (PGK), and chicken β-Actin promoter coupled with CMV early enhancer (CAGG). In some embodiments, the constitutive promoter is a synthetic or modified promoter. In some embodiments, suitable promoters include, for example, RNA polymerase (pol) III promoters including, but not limited to, the (human and murine) U6 promoters, the (human and murine) H1 promoters, and the (human and murine) 7SK promoters. In some embodiments, a hybrid promoter also can be prepared that contains elements derived from, for example, distinct types of RNA polymerase (pol) III promoters. In some embodiments, the promoter is or comprises an MND promoter, a synthetic promoter that contains the U3 region of a modified MoMuLV LTR with myeloproliferative sarcoma virus enhancer (sequence set forth in SEQ ID NO:41 or 71; see Challita et al. (1995) J. Virol. 69(2):748-755). In some embodiments, the promoter is a tissue-specific promoter. In another embodiment, the promoter is a viral promoter. In another embodiment, the promoter is a non-viral promoter. In some embodiments, exemplary promoters can include, but are not limited to, human elongation factor 1 alpha (EF1α) promoter (sequence set forth in SEQ ID NO:69 or 70) or a modified form thereof (EF1α promoter with HTLV1 enhancer; sequence set forth in SEQ ID NO: 40) or the MND promoter (sequence set forth in SEQ ID NO:41 or 71). In some embodiments, the polynucleotide and/or vector does not include a regulatory element, e.g. promoter.

In some embodiments, modified promoters that contain sequence elements derived from two or more naturally occurring promoter sequences can be combined by the skilled person to effect transcription under a desired set of conditions or in a specific context. For example, the human and murine U6 RNA polymerase (pol) III and H1 RNA pol III promoters are well characterized. A promoter that is most effective for the desired application and cell type can be selected or modified so as to optimize modulation of the expression of one or more genes. In some embodiments, the promoter sequence can be one that does not occur in nature, so long as it functions in a eukaryotic cell, such as, for example, a mammalian T cell such as the reporter T cells described herein.

b. Leader Sequence and Barcodes

In some embodiments, the vector backbone contains nucleic acid sequences encoding a leader sequence (also known as signal peptide, signal sequence, targeting signal, localization signal, localization sequence, transit peptide or leader peptide). Leader sequences are typically short peptides present at the N-terminus of a protein that facilitates secretion or targeting of particular polypeptides. In some embodiments, exemplary leader sequence encoded by the vector backbones include the GMCSFR alpha chain leader sequence set forth in SEQ ID NO: 73 and encoded by the nucleotide sequence set forth in SEQ ID NO:72, CD8 alpha chain leader sequence set forth in SEQ ID NO: 74 or 75, or the human CD33 leader sequence set forth in SEQ ID NO:13, encoded by the nucleotide sequence set forth in SEQ ID NO: 12.

In some embodiments, the vector backbone can include molecular barcode sequences. Molecular barcodes are molecular identifiers contained or embedded among nucleic acid sequences, that can be used to identify particular nucleic acid molecules, e.g., a polynucleotide encoding a recombinant receptor, and/or particular cells that contain the nucleic acid molecule. In some embodiments, sequencing methods, such as high-throughput sequencing methods, can be used to evaluate and/or identify the molecular barcodes present in one or more of the polynucleotides. In some aspects, the barcode sequences can be used to facilitate assessment by medium- or high-throughput sequencing, deconvolution of data and/or assess specificity and biases in library screening and sequencing, and to allow a more rigorous statistical assessment for medium- or high-throughput sequencing. In some embodiments, the nucleic acid sequences encoding the leader sequences also contains and/or functions as a molecular barcode. In some embodiments, degeneracy of codons allows modification of several nucleotide positions without altering the amino acid sequence. In some embodiments, the nucleic acid sequences encoding the leader sequences that contain and/or function as a molecular barcode permits generation of a variety of molecular barcodes to identify or tag different polynucleotides without using additional nucleotide sequence space.

In an exemplary embodiment, a human CD33 leader sequence (nucleotide sequence set forth in SEQ ID NO: 12) can be incorporate a molecular barcode. In some embodiments, the nucleic acid sequence encoding the human CD33 leader peptide is modified to contain a 15-nucleotide molecular barcode region GCTBTGGGCHGGNGC (set forth in SEQ ID NO:14). In some embodiments, a representative modified CD33 leader peptide sequence is set forth in SEQ ID NO:15. In some embodiments, the positions B, H and N correspond to B=C or G or T; H=A or C or T and N=A or C or G or T, to generate 36 different molecular barcodes. In some embodiments, the molecular barcode region is placed within the 3' end of leader sequence to avoid altering nucleotides in or around the Kozak sequence or translation start site.

c. Site for Introduction of Sequences Encoding Binding Domain

In some embodiments, the vector backbone contains one or more site(s) for introduction of a nucleic acid sequence encoding a binding domain. In some embodiments, the one or more site(s) for introduction of a nucleic acid sequence encoding a binding domain comprises a restriction site. In some embodiments, the restriction site is a restriction site that does not occur or occurs 1, 2 or 3 or fewer within an endogenous human $V_H$ or $V_L$ gene. In some embodiments, the restriction sites is or comprises restriction sites selected from among NheI, XbaI, BsmBI, RsrII and/or CpoI sites. In some embodiments, the vector backbone comprises a non-specific "stuffer" sequences for replacement with candidate binding domain-encoding sequences. In some embodiments, the stuffer sequence is placed between two restriction sites. In some embodiments, restriction enzyme digestion of the vector backbone permits insertion of nucleic acid sequences encoding candidate binding domains that are flanked by restriction enzyme sites and digested using the restriction enzymes. In some embodiments, the restriction sites flanking the nucleic acid sequences encoding the candidate binding domains are digested with the same enzymes as the vector backbone and/or enzymes that result in compatible cohesive ends. Any known restriction site is contemplated.

In an exemplary embodiment, the vector backbone contains nucleic acid sequences encoding the wild-type human CD33 leader peptide is modified to include an XbaI site at the 3' end. In some cases, the XbaI site can be used to clone inserts digested with NheI (e.g., candidate binding domain sequence library amplified with primers containing an NheI restriction site), as XbaI site and NheI site have compatible cohesive ends. In some embodiment, the digested vector backbone and amplified binding domain-encoding sequences are ligated. In some embodiments, the ligated product after digestion of the vector with XbaI and the insert with NheI re-generates CD33 leader peptide sequence, to have a sequence of MPLLLLLPLLWAGALA (SEQ ID NO:48). In some embodiments, the XbaI overhang can also be generated by digesting the vector with BsmBI (an asymmetric cutting restriction enzyme).

In some embodiments, the vector backbone is capable of accepting an insert comprising nucleic acid sequences encoding one of a plurality of binding domains or a portion thereof. In some embodiments, the insert comprises a nucleic acid sequence encoding a $V_H$ region of the binding domain. In some embodiments, the insert comprises a nucleic acid sequence encoding a $V_L$ region of the binding domain. In some embodiments, the insert comprises a nucleic acid sequence encoding a $V_H$ region and a $V_L$ region of the binding domain.

In some embodiments, the vector backbone contains site(s) for introduction of a nucleic acid sequence encoding one or both of $V_H$ and $V_L$ of a binding domain. In some embodiments, In some embodiments, the vector backbone contains site(s) for introduction of a nucleic acid sequence encoding a $V_H$ and a $V_L$ of a binding domain in various different orientations, for example, such that the encoded binding domain contains, from its N to C terminus in order: VH-VL, VH-linker-VL, VL-$V_H$ or VL-linker-$V_H$.

d. Spacer

In some embodiments, the vector backbone contains a nucleic acid sequence encoding a spacer. In some embodiments, the spacer sequence can be of various lengths. In some embodiments, the encoded spacer may be or include at least a portion of an immunoglobulin constant region or variant or modified version thereof, such as a hinge region, e.g., an IgG4 hinge region, and/or a $C_H1/C_L$ and/or Fc region. In some embodiments, the vector backbone further comprises a spacer and/or a hinge region. In some embodiments, the constant region or portion is of a human IgG, such as IgG4 or IgG1. In some aspects, the portion of the constant region serves as a spacer region between the binding domain, e.g., scFv, and transmembrane domain. The spacer can be of a length that provides for increased responsiveness of the cell following antigen binding, as compared to in the absence of the spacer. In some examples, the spacer is at or about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. In some embodiments, the spacer is at least 100 amino acids in length, such as at least 110, 125, 130, 135, 140, 145, 150, 160, 170, 180, 190, 200, 210, 220, 230, 240, or 250 amino acids in length. In some embodiments, a spacer is at least about 12 amino acids, at least about 119 amino acids or less, at least about 125 amino acids, at least about 200 amino acids, or at least about 220 amino acids, or at least about 225 amino acids.

Exemplary spacers include an IgG hinge alone, an IgG hinge linked to one or more of a $C_H2$ and $C_H3$ domain, or IgG hinge linked to the $C_H3$ domain. In some embodiments, the IgG hinge, $C_H2$ and/or $C_H3$ can be derived all or in part from IgG4 or IgG2. In some embodiments, the spacer can be a chimeric polypeptide containing one or more of a hinge, $C_H2$ and/or $C_H3$ sequence(s) derived from IgG4, IgG2, and/or IgG2 and IgG4. In some embodiments, the spacer can be derived all or in part from IgG4 and/or IgG2 and can contain mutations, such as one or more single amino acid mutations in one or more domains. In some examples, the amino acid modification is a substitution of a proline (P) for a serine (S) in the hinge region of an IgG4. In some embodiments, the amino acid modification is a substitution of a glutamine (Q) for an asparagine (N) to reduce glycosylation heterogeneity, such as an N177Q mutation at position 177, in the $C_H2$ region, of the full-length IgG4 Fc sequence or an N176Q, at position 176, in the $C_H2$ region, of the full-length IgG2 Fc. In some embodiments, the spacer is or comprises an IgG4/2 chimeric hinge or a modified IgG4 hinge; an IgG2/4 chimeric $C_H2$ region; and an IgG4 $C_H3$ region and optionally is about 228 amino acids in length. In some embodiments, the spacer is a modified IgG4 hinge spacer, IgG4 hinge-$C_H3$ spacer, or a modified IgG4 hinge-IgG2/IgG4 $C_H2$-IgG4 $C_H3$ spacer. In some embodiments, the spacer is an IgG4 hinge spacer, IgG4 hinge-$C_H3$ spacer, or IgG4/IgG2 hinge-IgG2/IgG4 $C_H2$-IgG4 $C_H3$ spacer.

In some aspects, the spacer contains only a hinge region of an IgG, such as only a hinge of IgG4 or IgG1, such as the hinge only spacer set forth in SEQ ID NO:20. In other embodiments, the spacer is an Ig hinge, e.g., and IgG4 hinge, linked to a $C_H2$ and/or $C_H3$ domains. In some embodiments, the spacer is an Ig hinge, e.g., an IgG4 hinge, linked to a $C_H3$ domain only, such as set forth in SEQ ID NO:22. In some embodiments, the spacer is an Ig hinge, e.g., an IgG4 hinge, linked to $C_H2$ and $C_H3$ domains, such as set forth in SEQ ID NO:24. In some embodiments, the spacer is or comprises a glycine-serine rich sequence or other flexible linker such as known flexible linkers. Exemplary spacers include IgG4 hinge alone (short spacer), IgG4 hinge linked to the $C_H3$ domain (medium spacer) or IgG4 hinge linked to $C_H2$ and $C_H3$ domains (long spacer). Exemplary spacers include, but are not limited to, those described in Hudecek et al. (2013) *Clin. Cancer Res.,* 19:3153, Hudecek et al. (2015) *Cancer Immunol Res.* 3(2): 125-135 or international patent application publication number WO2014031687. In some embodiments, the vector backbone includes nucleic acid sequence encoding a long spacer derived from a modified IgG4 hinge-$C_H2$-$C_H3$ (SEQ ID NO: 24; encoded by nucleic acid sequence set forth in SEQ ID NO:25); a medium spacer derived from a modified IgG4 hinge-$C_H3$ (SEQ ID NO:22; encoded by nucleic acid sequence set forth in SEQ ID NO:23); or a short spacer derived from an IgG4 hinge region (SEQ ID NO: 20; encoded by nucleic acid sequence set forth in SEQ ID NO:21). In some embodiments, the IgG hinge, $C_H2$ and/or $C_H3$ can be derived all or in part from IgG4 or IgG2.

In some embodiments, the constant region or portion is of IgD. In some embodiments, the spacer has the sequence set forth in SEQ ID NO: 26. In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 20, 22, 24 or 26.

e. Intracellular Signaling Regions

In some embodiments, the vector backbone contains a nucleic acid sequence encoding an intracellular signaling region. Among the intracellular signaling region are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

In some embodiments, the vector backbone includes sequences encoding at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the backbone plasmid contains sequences encoding one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25, or CD16. For example, in some aspects, the CAR includes a chimeric molecule between CD3-zeta (CD3-ζ) or Fc receptor γ and CD8, CD4, CD25 or CD16.

In some embodiments, upon ligation of the recombinant receptor, such as a CAR, the cytoplasmic domain or intracellular signaling region of the CAR activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling region of an antigen receptor component or costimulatory molecule is used in place of an intact immunostimulatory chain, for example, if it transduces the effector function signal. In some embodiments, the intracellular signaling regions, e.g., comprising intracellular domain or domains, include the cytoplasmic sequences of the T cell receptor (TCR), and in some aspects also those of co-receptors that in the natural context act in concert with such receptor to initiate signal transduction following antigen receptor engagement, and/or any derivative or variant of such molecules, and/or any synthetic sequence that has the same functional capability.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the vector backbone does not include a component for generating a costimulatory signal. In some aspects, an additional CAR is expressed in the same cell and provides the component for generating the secondary or costimulatory signal.

T cell activation is in some aspects described as being mediated by two classes of cytoplasmic signaling sequences: those that initiate primary activation through the TCR (primary cytoplasmic signaling sequences), and those that act to provide a secondary or co-stimulatory signal (secondary cytoplasmic signaling sequences). In some aspects, the vector backbone includes one or both of such signaling components.

In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR or CD3 zeta, FcR gamma or FcR beta. In some embodiments, cytoplasmic signaling molecule(s) in the CAR contain(s) a cytoplasmic signaling domain, portion thereof, or sequence derived from CD3 zeta.

In some embodiments, the CAR includes a signaling region and/or transmembrane portion of a costimulatory receptor, such as CD28, 4-1BB, OX40, DAP10, and ICOS. In some aspects, the same CAR includes both the signaling region and costimulatory components. In some embodiments, the intracellular signaling region further comprises a costimulatory signaling region. In some embodiments, the costimulatory signaling region comprises an intracellular signaling domain of a T cell costimulatory molecule or a signaling portion thereof. In some embodiments, the costimulatory signaling region comprises an intracellular signaling domain of a CD28, a 4-1BB or an ICOS or a signaling portion thereof.

In some embodiments, the signaling region is included within one CAR, whereas the costimulatory component is provided by another CAR recognizing another antigen. In some embodiments, the CARs include activating or stimulatory CARs, and costimulatory CARs, both expressed on the same cell (see WO2014/055668).

In certain embodiments, the intracellular signaling region comprises a CD28 transmembrane and signaling domain linked to a CD3 (e.g., CD3-zeta) intracellular domain. In some embodiments, the intracellular signaling region comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR in some aspects is one that includes multiple costimulatory domains of different costimulatory receptors.

In some embodiments, the chimeric antigen receptor contains an intracellular domain of a T cell costimulatory molecule. In some aspects, the T cell costimulatory molecule is CD28 or 4-1BB.

In some embodiments, the intracellular signaling region comprises an intracellular costimulatory signaling domain of human CD28 or functional variant or portion thereof, such as a 41 amino acid domain thereof and/or such $\alpha$ domain with an LL to GG substitution at positions 186-187 of a native CD28 protein. In some embodiments, the intracellular signaling domain can comprise the sequence of amino acids set forth in SEQ ID NO: 29 or 30 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 29 or 30. In some embodiments, the intracellular region comprises an intracellular costimulatory signaling domain of 4-1BB or functional variant or portion thereof, such as a 42-amino acid cytoplasmic domain of a human 4-1BB (also known as CD137, Accession No. Q07011.1) or functional variant or portion thereof, such as the sequence of amino acids set forth in SEQ ID NO: 31 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 31.

In some embodiments, the intracellular signaling region comprises a human CD3 chain, optionally a CD3 zeta stimulatory signaling domain or functional variant thereof, such as an 112 AA cytoplasmic domain of isoform 3 of human CD3ζ (Accession No.: P20963.2) or a CD3 zeta signaling domain as described in U.S. Pat. No. 7,446,190 or U.S. Pat. No. 8,911,993. In some embodiments, the intracellular signaling region comprises the sequence of amino acids set forth in SEQ ID NO: 32, 33 or 34 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 32, 33 or 34.

f. Markers

In some embodiments, the vector backbone contains a nucleic acid sequence encoding one or more marker(s). In some embodiments, the one or more marker(s) is a transduction marker, surrogate marker and/or a selection marker.

In some embodiments, the marker is a transduction marker or a surrogate marker. A transduction marker or a surrogate marker can be used to detect cells that have been introduced with the polynucleotide, e.g., a polynucleotide encoding a recombinant receptor. In some embodiments, the transduction marker can indicate or confirm modification of a cell. In some embodiments, the surrogate marker is a protein that is made to be co-expressed on the cell surface with the recombinant receptor, e.g. CAR. In particular embodiments, such a surrogate marker is a surface protein that has been modified to have little or no activity. In certain embodiments, the surrogate marker is encoded on the same polynucleotide that encodes the recombinant receptor. In some embodiments, the nucleic acid sequence encoding the recombinant receptor is operably linked to a nucleic acid sequence encoding a marker, optionally separated by an internal ribosome entry site (IRES), or a nucleic acid encoding a self-cleaving peptide or a peptide that causes ribosome skipping, such as a 2A sequence, such as a T2A, a P2A, a E2A or a F2A. Extrinsic marker genes may in some cases be utilized in connection with engineered cell to permit detection or selection of cells and, in some cases, also to promote cell suicide.

Exemplary surrogate markers can include truncated cell surface polypeptides, such as a truncated human epidermal growth factor receptor 2 (tHER2), a truncated epidermal growth factor receptor (EGFRt, exemplary EGFRt sequence set forth in SEQ ID NO:11 or 76) or a prostate-specific membrane antigen (PSMA) or modified form thereof. EGFRt may contain an epitope recognized by the antibody cetuximab (Erbitux®) or other therapeutic anti-EGFR antibody or binding molecule, which can be used to identify or select cells that have been engineered with the EGFRt construct and a recombinant receptor, such as a chimeric antigen receptor (CAR), and/or to eliminate or separate cells expressing the receptor. See U.S. Pat. No. 8,802,374 and Liu et al., Nature Biotech. 2016 April; 34(4): 430-434). In some aspects, the marker, e.g. surrogate marker, includes all or part (e.g., truncated form) of CD34, a NGFR, or epidermal growth factor receptor (e.g., tEGFR). In some embodiments, the nucleic acid encoding the marker is operably linked to a polynucleotide encoding for a linker sequence, such as a cleavable linker sequence, e.g., T2A. For example, a marker, and optionally a linker sequence, can be any as disclosed in PCT Pub. No. WO2014031687. For example, the marker can be a truncated EGFR (tEGFR) that is, optionally, linked to a linker sequence, such as a T2A cleavable linker sequence. An exemplary polypeptide for a truncated EGFR (e.g. tEGFR) comprises the sequence of amino acids set forth in SEQ ID NO: 11 or 76 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 11 or 76.

In some embodiments, the marker is or comprises a fluorescent protein, such as green fluorescent protein (GFP), enhanced green fluorescent protein (EGFP), such as superfold GFP (sfGFP; set forth in SEQ ID NO:36, encoded by nucleic acid sequence set forth in SEQ ID NO:35), red fluorescent protein (RFP), such as tdTomato, mCherry, mStrawberry, AsRed2, DsRed or DsRed2, cyan fluorescent protein (CFP), blue green fluorescent protein (BFP), enhanced blue fluorescent protein (EBFP), and yellow fluorescent protein (YFP), and variants thereof, including species variants, monomeric variants, and codon-optimized and/or enhanced variants of the fluorescent proteins. In some embodiments, the marker is or comprises an enzyme, such as a luciferase, the lacZ gene from *E. coli*, alkaline phosphatase, secreted embryonic alkaline phosphatase (SEAP), chloramphenicol acetyl transferase (CAT). Exemplary light-emitting reporter genes include luciferase (luc), β-galactosidase, chloramphenicol acetyltransferase (CAT), β-glucuronidase (GUS) or variants thereof.

In some embodiments, the marker is a selection marker. In some embodiments, the selection marker is or comprises a polypeptide that confers resistance to exogenous agents or drugs. In some embodiments, the selection marker is an antibiotic resistance gene. In some embodiments, the selection marker is an antibiotic resistance gene confers antibiotic resistance to a mammalian cell. In some embodiments, the selection marker is or comprises a Puromycin resistance gene, a Hygromycin resistance gene, a Blasticidin resistance gene, a Neomycin resistance gene, a Geneticin resistance gene or a Zeocin resistance gene or a modified form thereof.

g. Transmembrane Domains, Linkers and Other Sequences

In some embodiments, the vector backbone also includes sequences encoding various other components, including transmembrane domains, linkers and other sequences. In some embodiments, the sequences encoding these components are placed between or adjacent to components such as regulatory elements for expression of components of a recombinant receptor; the nucleic acid sequence encoding a leader sequence comprising a molecular barcode; one or more site(s) for introduction of a nucleic acid sequence encoding a binding domain; the nucleic acid sequence encoding a spacer; the nucleic acid sequence encoding an intracellular signaling region; and/or the nucleic acid sequence encoding one or more marker(s). In some embodiments, the vector backbone also contains sequences required for maintenance, replication, expression, transfer, transduction, integration and/or generation of the vector, e.g., viral vector sequence or plasmid sequence.

In the vector backbones provided herein for use in generating polynucleotides encoding a recombinant receptor, the binding domain generally is linked to one or more intracellular signaling components, such as signaling components that mimic activation through an antigen receptor complex, such as a TCR complex, in the case of a CAR, and/or signal via another cell surface receptor. Thus, in some embodiments, the binding domain is linked to one or more transmembrane and intracellular signaling regions. In some embodiments, the transmembrane domain is fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

In some embodiments, the vector backbone includes sequences encoding a transmembrane domain disposed between the extracellular domain and the intracellular signaling region. In some aspects, the transmembrane domain contains a transmembrane portion of CD28. In some embodiments, the transmembrane domain is or comprises a transmembrane domain derived from human CD28 or variant thereof, e.g., a 27-amino acid transmembrane domain of a human CD28 (Accession No.: P10747.1), or is a transmembrane domain that comprises the sequence of amino acids set forth in SEQ ID NO: 27 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO:27; in some embodiments, the transmembrane-domain containing portion of the recombinant receptor comprises the sequence of amino acids set forth in SEQ ID NO: 28 or a sequence of amino acids having at least at or about 85%, 86%, 87%, 88%, 89%, 90%, 91%, 92%, 93%, 94%, 95%, 96%, 97%, 98%, 99% or more sequence identity thereto.

In some embodiments, the vector backbone comprises sequences encoding a linker. In some embodiments, the linker is or comprises a glycine-serine rich sequence or other flexible linker such as known flexible linkers. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the intracellular signaling regions.

In some embodiments, the vector backbone can include sequences encoding a ribosome skipping element/self-cleavage element. In some embodiments, the ribosome skipping element/self-cleavage element links or is placed between sequences encoding any of the other components described herein. In some cases, the ribosome skipping element/self-cleavage element, such as a T2A, can cause the ribosome to skip (ribosome skipping) synthesis of a peptide bond at the C-terminus of a 2A element, leading to separation between the end of the 2A sequence and the next peptide downstream (see, for example, de Felipe, *Genetic Vaccines and Ther.* 2:13 (2004) and de Felipe et al. *Traffic* 5:616-626 (2004)). This allows the inserted transgene to be controlled by the transcription of the endogenous promoter at the integration site, e.g., Nur77 promoter. Exemplary ribosome skipping element/self-cleavage element include 2A sequences from the foot-and-mouth disease virus (F2A, e.g., SEQ ID NO: 45), equine rhinitis A virus (E2A, e.g., SEQ ID NO: 44), *Thosea asigna* virus (T2A, e.g., SEQ ID NO: 6 or 56), and porcine teschovirus-1 (P2A, e.g., SEQ ID NO: 42 or 43) as described in U.S. Patent Publication No. 20070116690. In some embodiments, exemplary ribosome skipping element/self-cleavage element includes a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NO: 6, 42-45 or 56.

In some embodiments, the vector backbone comprises viral sequences. In some embodiments, the vector backbone contains sequences required for maintenance, replication, expression, transfer, transduction, integration and/or generation of the vector, e.g., viral vector sequence or plasmid sequence. In some embodiments, the vector backbone contains sequences required for a viral vector delivery system. Viral vector delivery systems include DNA and RNA viruses, which have either episomal or integrated genomes after delivery to the cell. For a review of gene therapy procedures, see Anderson, Science 256:808-813 (1992); Nabel & Felgner, TIBTECH 11:211-217 (1993); Mitani & Caskey, TIBTECH 11:162-166 (1993); Dillon. TIBTECH 11:167-175 (1993); Miller, Nature 357:455-460 (1992); Van Brunt, Biotechnology 6(10): 1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Bohm (eds) (1995); and Yu et al., Gene Therapy 1:13-26 (1994). Viral-based systems in some embodiments include retroviral, lentivirus, adenoviral, adeno-associated and herpes simplex virus vectors for gene transfer. In some embodiments, the vector backbone is or comprises an expression vector, such as a viral expression vector. In some aspects, the expression vector is a retroviral expression vector, an adenoviral expression vector, a DNA plasmid expression vector, or an AAV expression vector, or for other delivery methods described herein.

2. Exemplary Lentiviral Vector Backbone

In some embodiments, provided are exemplary lentiviral vector backbones for use in connection with the methods provided herein. In some embodiments, the lentiviral vectors include a human elongation factor 1 alpha (EF1a) promoter with HTLV1 enhancer sequence set forth in SEQ ID NO: 40, 69 or 70) or an MND promoter, a synthetic promoter that contains the U3 region of a modified MoMuLV LTR with myeloproliferative sarcoma virus enhancer (sequence set forth in SEQ ID NO:41 or 71; see Challita et al. (1995) J. Virol. 69(2):748-755); a human CD33 leader sequence containing a plasmid barcode (SEQ ID NO:15); a non-specific "stuffer" sequences for replacement with candidate binding domain-encoding sequences; a short, medium or long spacer derived from immunoglobulin sequences (SEQ ID NO:20, 22 or 24, respectively); a CD28 transmembrane domain (SEQ ID NO: 46); a 4-1BB-derived intracellular domain (SEQ ID NO: 31) or a CD28-derived intracellular domain (SEQ ID NO: 29); a CD3-zeta derived intracellular signaling region (SEQ ID NO: 32, 33 or 34), and lentiviral backbone sequences. The long spacer is derived from a modified IgG4 hinge-$C_H2$-$C_H3$ (SEQ ID NO: 24; encoded by nucleic acid sequence set forth in SEQ ID NO:25); the medium spacer is derived from a modified IgG4 hinge-$C_H3$ (SEQ ID NO:22; encoded by nucleic acid sequence set forth in SEQ ID NO:23); and the short spacer is derived from an IgG4 hinge region (SEQ ID NO: 20; encoded by nucleic acid sequence set forth in SEQ ID NO:21). The vectors also encoded downstream T2A ribosomal skip elements (SEQ ID NO: 5) between coding sequences and a super-fold green fluorescent protein (sfGFP, set forth in SEQ ID NO:35, encoding SEQ ID NO: 36) or an enhanced blue fluorescent protein (EBFP), for use as a transduction marker, and a Puromycin resistance gene (PuroR) for selection.

In some embodiments, the viral vectors contains NheI, XbaI, BsmBI and RsrII restriction enzyme sites for cloning the amplified candidate binding domain-encoding sequences. Nucleic acid sequences encoding the wild-type human CD33 leader peptide is modified to include an XbaI site at the 3' end. In some cases, the XbaI site can be used to clone inserts digested with NheI (e.g., candidate binding domain-encoding sequence library amplified with primers containing an NheI restriction site), as XbaI site and NheI site have compatible cohesive ends. The ligated product after digestion of the vector with XbaI and the insert with NheI re-generates CD33 leader peptide sequence, to have a sequence of MPLLLLLPLLWAGALA (SEQ ID NO:48). The XbaI overhang can also be generated by digesting the vector with BsmBI (an asymmetric cutting restriction enzyme). The CD33 leader peptide-encoding sequences are also modified to incorporate a plasmid barcode. Degeneracy of codons allows modification of several nucleotide positions without altering the amino acid sequence. Nucleotide sequences are modified (at positions indicated with B, H and N; B=C or G or T; H=A or C or T and N=A or C or G or T) to generate 36 different plasmid barcodes. The barcode is placed within the 3' end of leader sequence to avoid altering nucleotides in or around the Kozak sequence or translation start site. The barcode sequences can be used to facilitate assessment by medium- or high-throughput sequencing, to assess specificity and biases in library screening and sequencing, and to allow a more rigorous statistical assessment for medium- or high-throughput sequencing, without using additional nucleotide sequence space.

C. Candidate Binding Domains and Library

In some embodiments, sequences encoding a binding domain, such as one of a plurality of candidate binding domains, is inserted into the vector backbone, in connection with the methods provided herein. In some embodiments, methods provided herein are used to generate candidate recombinant receptors, e.g., CARs, using sequences encoding candidate binding domains and one or more of the vector backbones described herein. In some embodiments, the methods and the vector backbones are employed to assess the expression and/or activity of a recombinant receptor containing such binding domains. In some embodiments, the methods provided herein include introducing sequences encoding a plurality or library of binding domains into the vector backbone containing components of a recombinant receptor, thereby allowing expression of the binding domain in the context of a recombinant receptor. In some embodiments, the generated polynucleotide can be introduced into a T cell, e.g., a reporter T cell. In some embodiments, a plurality of such polynucleotides are introduced, generating a plurality of reporter T cells. In some embodiments, the vector backbones can be employed to assess and screen numerous candidate binding domains expressed in a format of a recombinant receptor, in a low-, medium- or high-throughput screening methods.

In some embodiments, the binding domain is or comprises an antibody or functional antigen-binding fragments. In some embodiments, the binding domains include those that are single domain antibodies, containing a heavy chain variable ($V_H$) region that, without pairing with a light chain antigen-binding site (e.g., light chain variable ($V_L$) region) and/or without any additional antibody domain or binding site, are capable of specifically binding to a target antigen. Also among the binding domains are multi-domain antibodies, such as those containing $V_H$ and $V_L$ domains, comprised of the $V_H$ domain or antigen-binding site thereof of the single-domain antibody. In some embodiments, the binding domains include a heavy chain variable region and a light chain variable region, such as scFvs. The binding domains include antibodies that specifically bind to a specific target antigen. Among the binding domains are human antibodies. In some embodiments, the binding domains containing such antibodies, e.g., single-chain proteins, fusion proteins, and/or recombinant receptors such as chimeric receptors, include antigen receptors. In some embodiments, the binding domain is or comprises Ig heavy chain, VHH antibodies (also known as Nanobodies), engineered fibronectin domains or an autoantigen or a fragment thereof. In some embodiments, the binding domain is an autoantigen or a fragment thereof, that can bind an autoantibody.

Among the binding domains are monoclonal antibodies, including monoclonal antibody fragments. The term "monoclonal antibody" as used herein refers to an antibody obtained from or within a population of substantially homogeneous antibodies, i.e., the individual antibodies comprising the population are identical, except for possible variants containing naturally occurring mutations or arising during production of a monoclonal antibody preparation, such variants generally being present in minor amounts. In contrast to polyclonal antibody preparations, which typically include different antibodies directed against different epitopes, each monoclonal antibody of a monoclonal antibody preparation is directed against a single epitope on an antigen. The term is not to be construed as requiring production of the antibody by any particular method. A monoclonal antibody may be made by a variety of techniques, including but not limited to generation from a hybridoma, recombinant DNA methods, phage-display and other antibody display methods.

The terms "polypeptide" and "protein" are used interchangeably to refer to a polymer of amino acid residues, and are not limited to a minimum length. Polypeptides, including the binding domains and antibody chains and other peptides, e.g., linkers and binding peptides, may include amino acid residues including natural and/or non-natural amino acid residues. The terms also include post-expression modifications of the polypeptide, for example, glycosylation, sialylation, acetylation, phosphorylation, and the like. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

The term "antibody" herein is used in the broadest sense and includes polyclonal and monoclonal antibodies, including intact antibodies and functional (antigen-binding) antibody fragments, including fragment antigen binding (Fab) fragments, $F(ab')_2$ fragments, Fab' fragments, Fv fragments, recombinant IgG (rIgG) fragments, variable heavy chain ($V_H$) regions capable of specifically binding the antigen, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and subclasses thereof, IgM, IgE, IgA, and IgD.

In some embodiments, the binding domains, e.g., antibody or fragments thereof, specifically recognize or specifically bind an antigen is a full-length antibody. In some embodiments, the heavy and light chains of an antibody can be full-length or can be an antigen-binding portion (a Fab, F(ab')2, Fv or a single chain Fv fragment (scFv)). In other embodiments, the antibody heavy chain constant region is chosen from, e.g., IgG1, IgG2, IgG3, IgG4, IgM, IgA1, IgA2, IgD, and IgE, particularly chosen from, e.g., IgG1, IgG2, IgG3, and IgG4, more particularly, IgG1 (e.g., human IgG1). In another embodiment, the antibody light chain constant region is chosen from, e.g., kappa or lambda, particularly kappa.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., J. Immunol. 150: 880-887 (1993); Clarkson et al., Nature 352:624-628 (1991).

Single-domain antibodies are antibody fragments comprising all or a portion of the heavy chain variable domain or all or a portion of the light chain variable domain of an antibody. In certain embodiments, a single-domain antibody is a human single-domain antibody. In some embodiments, the CAR comprises an antibody heavy chain domain that specifically binds the antigen, such as a cancer marker or cell surface antigen of a cell or disease to be targeted, such as a tumor cell or a cancer cell, such as any of the target antigens described herein or known.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

In some embodiments, a library of binding domains, e.g., an antibody or antigen binding fragment library is generated. In some aspects, the library contains a diverse pool of polypeptides, each of which includes an immunoglobulin domain, e.g., an immunoglobulin variable domain.

In some embodiments, the library of binding domains contains polypeptides that include a $V_H$ domain and a $V_L$ domain. The library can include the antibody as a Fab fragment (e.g., using two polypeptide chains) or a single chain Fv (e.g., using a single polypeptide chain). Other formats can also be used.

As in the case of the Fab and other formats, the antibody can include a constant region as part of a light or heavy chain. In one embodiment, each chain includes one constant region, e.g., as in the case of a Fab. In other embodiments, additional constant regions are included.

In some embodiments, the candidate binding domains are expressed and assessed in a recombinant receptor, e.g., CAR, as an extracellular portion containing an antibody or antibody fragment. In some embodiments, the antibody or fragment includes an scFv.

In some embodiments, the antigen (or a ligand) is a polypeptide. In some embodiments, it is a carbohydrate or other molecule. In some embodiments, the antigen (or a ligand) is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells. In some embodiments, the recombinant receptor contains an antibody or an antigen-binding fragment (e.g. scFv) that specifically recognizes or specifically binds an antigen, such as an intact antigen, expressed on the surface of a cell.

In some embodiments, the antigen is or includes $\alpha v\beta 6$ integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrin receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, β-acetylated GD2 (OGD2), ganglioside GD3, glycoprotein 100 (gp100), glypican-3 (GPC3), G Protein Coupled Receptor 5D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22Rα), IL-13 receptor alpha 2 (IL-13Rα2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen is or includes CD20, CD19, CD22, ROR1, CD45, CD21, CD5, CD33, Igkappa, Iglambda, CD79a, CD79b or CD30.

In some embodiments, the antigen is or includes a pathogen-specific or pathogen-expressed antigen. In some embodiments, the antigen is a viral antigen (such as a viral antigen from HIV, HCV, HBV, etc.), bacterial antigens, and/or parasitic antigens.

1. Source of Candidate Binding Domains

In some embodiments, nucleic acids encoding the candidate binding domain can be obtained from a variety of sources, such as by polymerase chain reaction (PCR) amplification of candidate binding domain-encoding nucleic acids within or isolated from a given cell or cells, or synthesis of publicly available candidate binding domain DNA sequences. In some embodiments, a candidate binding domain may be one identified from an initial or first screen of a library of library of candidate binding domains. In some embodiments, candidate binding domains can be generated by synthesis of publicly available candidate binding domain DNA sequences. In some embodiments, the candidate binding domains can be generated by methods of mutagenesis and/or chain swapping. In some embodiments, the plurality or library of sequences encoding candidate binding domains can include at least or at least about 2, 5, 10, 100, $10^3$, $10^4$, $10^5$, $10^6$, $10^7$, $10^8$, $10^9$, $10^{10}$ or more distinct sequences encoding candidate binding domains. In some embodiments, the plurality of nucleic acid sequences encoding a binding domain includes at least 2, 5, 10, 25, 50, 100, 500, $10^3$, $10^4$, $10^5$, $10^6$ or more different nucleic acid sequences. In some embodiments, the plurality of polynucleotides encoding a recombinant receptor includes at least 2, 5, 10, 25, 50, 100, 500, $10^3$, $10^4$, $10^5$, $10^6$ or more different polynucleotides. In some embodiments, the plurality of reporter T cells for screening comprises at least 2, 5, 10, 25, 50, 100, 500, $10^3$, $10^4$, $10^5$, $10^6$ or more different reporter T cells.

In some embodiments, a plurality, e.g., library, of binding domains, e.g., antibodies or antigen-binding fragments can be generated or obtained. In some embodiments, such methods have been used to produce a TCR-like antibody or antigen-binding portion (see e.g. US Published Application Nos. US 2002/0150914; US 2003/0223994; US 2004/0191260; US 2006/0034850; US 2007/00992530; US20090226474; US20090304679; and International PCT Publication No. WO 03/068201).

In some embodiments, the sequence of candidate binding domains can be obtained from candidate binding domains that are obtained and/or selected from a biological source, such as from a sample containing immune cells known to produce or express the candidate binding domain, such as B cells, B-cell hybridomas or other publicly available source. In some embodiments, the B-cells can be obtained from in vivo isolated cells, e.g., cells isolated from a subject, such as a human. Nucleic acid encoding candidate binding domains can be obtained from the immune cells of, e.g., a human, a primate, mouse, rabbit, camel, or rodent. Any cells may be used as a source for a library. In some cases, immunoglobulin genes can be obtained from blood lymphocytes, bone marrow, spleen or other immunoglobulin-containing source. In some embodiments the source of cells for the library may be PBMCs, splenocytes, or bone marrow cells. In some cases, immunoglobulin genes are obtained from B cells. In one example, the cells are selected for a particular property. B cells at various stages of maturity can be selected. In another example, the B cells are naïve. In some embodiments, B cells from a human donor may be used.

In some embodiments, candidate binding domain-producing immune cells can be isolated from the blood or other biological samples of a subject or host, such as a human or other animal, such as a human or other animal that has been immunized or that is suffering from an infection, cancer, an autoimmune condition, or any other diseases to identify a pathogen-, tumor- and/or disease-specific candidate binding domains, e.g., for therapeutic use. In some embodiments, the human may be diagnosed with a disease, be exhibiting symptoms of a disease, not be diagnosed with a disease, or not be exhibiting symptoms of a disease.

In some embodiments, the subject or host, e.g., a human subject, may be one that was exposed to and/or who can produce candidate binding domains against an infectious agent (e.g., viruses, bacteria, parasites, prions, etc), antigen, disease or an antigen associated with a disease or condition, e.g., a tumor-associated antigen. In some cases, the subject or host, e.g., a non-human animal subject, may be one that was exposed to and/or who can produce candidate binding domains against an infectious agent (e.g., viruses, bacteria, parasites, prions, etc), antigen, disease or an antigen associated with a disease or condition, e.g., a tumor-associated antigen. Certain immune cells from immunized hosts produce candidate binding domains that recognize or bind one or more target antigens and/or one or more unknown antigens.

In some embodiments, the biological source, e.g. B cells or sample containing B cells, is one that provides the naïve candidate binding domain repertoire of a normal donor who does not have a disease or condition, or was not previously exposed or immunized with the antigen of interest. In some embodiments, immune cells from non-immunized human or non-human donors are utilized. The naïve repertoire of an animal (the repertoire before antigen challenge) provides the animal with candidate binding domains that can bind with moderate affinity (KA of about $1\times10^{-6}$ to $1\times10^{-7}$ M) to essentially any non-self molecule. The sequence diversity of candidate binding domain binding sites is not encoded directly in the germline but is assembled in a combinatorial manner from V gene segments. Immunizations trigger any immune cell making a $V_H$-$V_L$ combination that binds the immunogen to proliferate (clonal expansion) and to produce the candidate binding domain against the immunogen. The use of spleen cells and/or immune cells or other peripheral blood lymphocytes (PBLs) from an unimmunized subject can provide a better representation of the possible candidate binding domain repertoire, and also permits the construction of a subsequent candidate binding domain library, such as a candidate binding domain library.

In some embodiments, to generate and select candidate binding domains for screening, immune cells from the subject or host can be enriched for cells that produce candidate binding domains that recognize or bind the target antigen of interest, e.g., an antigen associated with a disease or disorder, by any suitable method, such as screening and sorting the cells using fluorescence-activated cell sorting (FACS), magnetic activated cell sorting (MACS), panning or other screening method to generate a plurality of immune cells from a sample, such as an immune cell library, before the candidate binding domains are identified and/or sequenced. In some aspects, candidate binding domains may be selected, such as by binding activity, e.g., particular affinity or avidity for the antigen.

In some embodiments, the antibody libraries can include IgM-derived antibody genes, which generally represent non-immune or naïve antibody genes, i.e. sometimes called a naive antibody library. For example, in some embodiments, naïve libraries of antibody fragments have been constructed, for example, by cloning of the rearranged V-genes from the IgM RNA of B cells of un-immunized donors isolated from peripheral blood lymphocytes, bone marrow or spleen cells (see, for example, Griffiths et al, EMBO Journal, 12(2), 725-734, 1993, Marks et al, J. Mol. Biol., 222, 581-597, 1991). In some embodiments, the antibody libraries can include IgG-derived antibody genes, although IgG-based libraries are typically biased to particular antigen(s).

In one embodiment, fluorescent-activated cell sorting (FACS) is used to sort B cells that express surface-bound IgM, IgD, or IgG molecules. Further, B cells expressing different isotypes of IgG can be isolated. In another embodiment, the B or T cell is cultured in vitro. The cells can be stimulated in vitro, e.g., by culturing with feeder cells or by adding mitogens or other modulatory reagents, such as antibodies to CD40, CD40 ligand or CD20, phorbol myristate acetate, bacterial lipopolysaccharide, concanavalin A, phytohemagglutinin or pokeweed mitogen.

In some embodiments, the cells are isolated from a subject that has a disease or disorder, e.g., cancer or an immunological disorder. The subject can be a human, or a non-human animal, e.g., an animal model for the human disease, or an animal having an analogous disorder. In some embodiments, the antibody library is an immune library, such as constructed from antibodies obtained from infected or diseased subjects. In some embodiments, an immune library may contain antibody members that have higher affinity binding than can be obtained using naïve antibody libraries or antibody libraries derived from normal or healthy subjects.

In some embodiments, the cells have activated a program of somatic hypermutation. Cells can be stimulated to undergo somatic mutagenesis of immunoglobulin genes, for example, by treatment with anti-immunoglobulin, anti-CD40, and anti-CD38 antibodies (see, e.g., Bergthorsdottir et al. (2001) J. Immunol. 166:2228). In another embodiment, the cells are naïve.

The nucleic acid encoding an immunoglobulin variable domain can be isolated from a natural repertoire by the following exemplary method. First, RNA is isolated from the immune cell. Full length (i.e., capped) mRNAs are separated (e.g. by degrading uncapped RNAs with calf intestinal phosphatase). The cap is then removed with tobacco acid pyrophosphatase and reverse transcription is used to produce the cDNAs.

The reverse transcription of the first (antisense) strand can be done in any manner with any suitable primer. See, e.g., de Haard et al. (1999) J. Biol. Chem. 274:18218-30. The primer binding region can be constant among different immunoglobulins, e.g., in order to reverse transcribe different isotypes of immunoglobulin. The primer binding region can also be specific to a particular isotype of immunoglobulin. Typically, the primer is specific for a region that is 3' to a sequence encoding at least one CDR. In another embodiment, poly-dT primers may be used (e.g., for the heavy-chain genes).

A synthetic sequence can be ligated to the 3' end of the reverse transcribed strand. The synthetic sequence can be used as a primer binding site for binding of the forward primer during PCR amplification after reverse transcription. The use of the synthetic sequence can obviate the need to use a pool of different forward primers to fully capture the available diversity.

The variable domain-encoding gene is then amplified, e.g., using one or more rounds. If multiple rounds are used, nested primers can be used for increased fidelity. The amplified nucleic acid is then cloned into a library vector.

Any method for amplifying nucleic acid sequences may be used for amplification. Methods that maximize, and do not bias, diversity may be used. A variety of techniques can be used for nucleic acid amplification. The polymerase chain reaction (PCR; U.S. Pat. Nos. 4,683,195 and 4,683,202, Saiki, et al. (1985) Science 230, 1350-1354) utilizes cycles of varying temperature to drive rounds of nucleic acid synthesis. Transcription-based methods utilize RNA synthesis by RNA polymerases to amplify nucleic acid (U.S. Pat. Nos. 6,066,457; 6,132,997; 5,716,785; Sarkar et. al., Science (1989) 244: 331-34; Stofler et al., Science (1988) 239: 491). NASBA (U.S. Pat. Nos. 5,130,238; 5,409,818; and 5,554,517) utilizes cycles of transcription, reverse-transcription, and RnaseH-based degradation to amplify a DNA sample. Still other amplification methods include rolling circle amplification (RCA; U.S. Pat. Nos. 5,854,033 and 6,143,495) and strand displacement amplification (SDA; U.S. Pat. Nos. 5,455,166 and 5,624,825).

Antibody libraries can be constructed by a number of processes (see, e.g., WO 00/70023). Further, elements of each process can be combined with those of other processes. The processes can be used such that variation is introduced into a single immunoglobulin domain (e.g., $V_H$ or $V_L$) or into multiple immunoglobulin domains (e.g., $V_H$ and $V_L$). The variation can be introduced into an immunoglobulin variable domain, e.g., in the region of one or more of CDR1, CDR2, CDR3, FR1, FR2, FR3, and FR4, referring to such regions of either and both of heavy and light chain variable domains. In one embodiment, variation is introduced into all three CDRs of a given variable domain. In another embodiment, the variation is introduced into CDR1 and CDR2, e.g., of a heavy chain variable domain. Any combination is feasible. In one process, antibody libraries are constructed by inserting diverse oligonucleotides that encode CDRs into the corresponding regions of the nucleic acid. The oligonucleotides can be synthesized using monomeric nucleotides or trinucleotides. For example, Knappik et al. (2000) J. Mol. Biol. 296:57-86 describes a method for constructing CDR encoding oligonucleotides using trinucleotide synthesis and a template with engineered restriction sites for accepting the oligonucleotides.

In some embodiments, the binding domain library contains nucleic acids that encode antibodies or antibody fragments. The nucleic acid molecules can be generated separately, such that upon expression an antibody is formed. For example, nucleic molecules can be generated encoding a $V_H$ chain of an antibody and/or nucleic acid molecules can be generated encoding a $V_L$ chain of an antibody. In some aspects, upon co-expression of the nucleic acid molecules in a cell, an antibody is generated. Alternatively, an scFv library can be generated in which a single nucleic acid molecule can be generated that encodes both the variant $V_H$ and $V_L$ chains of an antibody, generally separated by a linker.

In some embodiments, the binding domain library can be generated and/or placed into the vector backbone (e.g., cloned) in one or more different orientations. In some embodiments, the binding domain is generated and/or placed into the vector backbone (e.g., cloned) in such that the binding domain can comprise, from its N to C terminus in order: VH-$V_L$. In some embodiments, the binding domain is generated and/or placed into the vector backbone (e.g., cloned) in such that the binding domain can comprise, from its N to C terminus in order: VL-$V_H$. In some embodiments, the $V_H$ and $V_L$ are separated by a linker. In some embodiments, the binding domain is generated and/or placed into the vector backbone (e.g., cloned) in such that the binding domain can comprise, from its N to C terminus in order: VH-VL, VH-linker-VL, VL-$V_H$ or VL-linker-$V_H$. In some embodiments, the encoded $V_H$ region is amino-terminal to the $V_L$ region. In some embodiments, the encoded $V_H$ region is carboxy-terminal to the $V_L$ region. In any of the binding domain libraries herein, the nucleic acid molecules also can further contain nucleotides for the hinge region and/or constant regions (e.g. $C_L$ or $C_H1$, $C_H2$ and/or $C_H3$) of the antibody. Further, the nucleic acid molecules optionally can include nucleotides encoding peptide linkers. Methods to generate and express antibodies can be adapted for use in generating any antibody library. Hence, the antibody libraries can include members that are full-length antibodies, or that are antibody fragments thereof. In some embodiments, antibody libraries are scFv libraries. In some embodiments, antibody libraries are Fab libraries. Further, it is understood that upon screening and selection of an antibody from the library, the selected member can be generated in any form, such as a full-length antibody or as an antibody fragment.

In some embodiments, the sequence of candidate binding domains can be obtained from artificial or synthetic sources, such as an artificial library, or can be obtained by varying or introducing mutations into known candidate binding domain sequences, or can be obtained by combinatorially joining known candidate binding domain sequences or known candidate binding domain chains, e.g., known $V_H$ or $V_L$ chains. In some embodiments, chain swapping can be used to generate candidate binding domain libraries. In some embodiments, the $V_H$ domain is α domain that is common among all the binding domains in the library, and the $V_L$ domain is swapped in, from a library of different $V_L$ sequences. In some embodiments, the $V_L$ domain is α domain that is common among all the binding domains in the library, and the $V_H$ domain is swapped in, from a library of different $V_H$ sequences. In some embodiments, the library is a light chain swap library (with $V_H$ domain shared between all the binding domains in the library). In some embodiments, the library is a heavy chain swap library (with $V_L$ domain shared between all the binding domains in the library).

In some embodiments, the sequence of candidate binding domains can be generated employing antibody library display methods, such as phage antibody libraries, cell surface display libraries, ribosome display libraries, mRNA display libraries, and dsDNA display libraries. In some embodiments, phage display libraries of mutant Fab, scFv or other antibody forms can be generated, for example, in which members of the library are mutated at one or more residues of a CDR or CDRs. See e.g. US published application No. US20020150914, US2014/0294841; and Cohen C J. et al. (2003) *J Mol. Recogn.* 16:324-332.

In some embodiments, candidate binding domain libraries can be generated by mutagenesis or diversification of a parent or scaffold candidate binding domain molecule. In some aspects, the candidate binding domains are subjected to directed evolution, such as by mutagenesis, e.g., of the $V_H$ or $V_L$ chain. In some aspects, particular residues within CDRs of the candidate binding domain are altered. In some embodiments, selected candidate binding domains can be modified by affinity maturation.

In some embodiments, candidate binding domain libraries, e.g., scFv libraries, can be generated or modified by changing the order or orientation of the domains or regions of the antigen-binding domain, or other components. In some embodiments, the vector backbone can be used to generate a plurality of receptors, such as chimeric antigen receptor (CARs), wherein the $V_H$ and the $V_L$ domains are linked in different order or orientation. In some embodiments, a library can be generated in which the antigen-binding domain contains a $V_H$ and a $V_L$ in which the $V_H$ is encoded upstream of the $V_L$ (e.g., the antigen-binding domain having a $V_H$-$V_L$ orientation). In some embodiments, a library can be generated in which the antigen-binding domain contains a $V_H$ and a $V_L$ in which the $V_L$ is encoded upstream of the $V_H$ (e.g., the antigen-binding domain having a $V_L$-$V_H$ orientation). In some embodiments, the order of the $V_H$ and the $V_L$ can be reversed to generate a different binding domain or different plurality of binding domains.

In certain embodiments, the candidate binding domains can include one or more amino acid substitutions, e.g., as compared to a candidate binding domain from a natural repertoire, e.g., human repertoire. Sites of interest for substitutional mutagenesis include the CDRs and FRs. Amino acid substitutions may be introduced into the candidate binding domain of interest and can be screened for a desired activity.

In some embodiments, one or more residues within a CDR of a candidate binding domain, such as a candidate binding domain identified from a natural human repertoire is/are substituted. In some embodiments, the substitution is made to revert a sequence or position in the sequence to a germline sequence, such as a candidate binding domain sequence found in the germline (e.g., human germline), for example, to reduce the likelihood of immunogenicity, e.g., upon administration to a human subject.

Some exemplary mutagenesis techniques include: error-prone PCR (Leung et al. (1989) Technique 1:11-15), recombination, DNA shuffling using random cleavage (Stemmer (1994) Nature 389-391; termed "nucleic acid shuffling"), RACHITT™ (Coco et al. (2001) Nature Biotech. 19:354), site-directed mutagenesis (Zooler et al. (1987) Nucl Acids Res 10:6487-6504), cassette mutagenesis (Reidhaar-Olson (1991) Methods Enzymol. 208:564-586) and incorporation of degenerate oligonucleotides (Griffiths et al. (1994) EMBO J. 13:3245).

In an exemplary embodiment, lentiviral vector backbones described herein are used to generate a library of nucleic acid molecules encoding candidate CARs by mutagenesis and/or chain swapping. In some embodiments, a nucleic acid sequence encoding a binding domain is used as template to generate mutagenized scFv sequences by error-prone PCR, with primers containing restriction sites for cloning into a vector backbone, e.g., NheI or XbaI and RsrII restriction sites. Error-prone polymerase and increased $Mn^{2+}$ concentration in the reaction can be used to increase error rate in the amplification, thereby generating randomly mutated binding domain sequences. In an exemplary embodiment, the amplified products are cloned into the vector after restriction enzyme digestion with NheI or XbaI and RsrII.

In some cases, the heavy chain variable domain ($V_H$) or light chain variable domain ($V_L$) can be replaced with a $V_H$ or a $V_L$ from a different binding domain, e.g., scFv, using chain swapping. In an exemplary embodiment, nucleic acid sequences encoding a binding domain, e.g., scFv, is altered to contain an asymmetric BsmBI restriction site in the nucleic acid sequences encoding the linker between the $V_H$ and the $V_L$ domains. In an exemplary embodiment, nucleic acid sequences encoding a $V_H$ or a $V_L$ domain are amplified from an scFv library, a heavy chain variable domain library or a light chain variable domain library by PCR using primers containing compatible restriction ends. In an exemplary embodiment, the amplified products are cloned into vectors digested with NheI/BsmBI for heavy chain swapping or BsmBI/RsrII for light chain swapping. In some embodiments, upon ligation of the amplified $V_H$ or a $V_L$-encoding nucleic acid, the BsmBI site is lost and parental linker sequence is restored. In some embodiments, the order of the $V_H$ and the $V_L$ can be reversed, to generate a different binding domain or different plurality of binding domains.

D. Cloning and/or Assembly and Generation of Vector Library

In some embodiments, the sequences encoding a candidate binding domain can be introduced or inserted into any of the vector backbones described herein. Any known methods, such as molecular cloning, assembly of amplified or synthesized fragments, overlap PCR and other methods can be used to introduce or insert the sequences encoding a candidate binding domain into any the vector backbone for generation of a plurality of polynucleotides encoding recombinant receptors. In some embodiments, any of the provided vector backbones can be employed to generate a plurality of a plurality or library of polynucleotides encoding a plurality of different recombinant receptors, e.g., CARs. Also provided are a plurality and/or library of such polynucleotides, e.g., vector libraries. In some embodiments, the vector libraries can be used to generate virus libraries used to transduce a plurality of cells, e.g., reporter T cells. In some embodiments, the plurality of polynucleotides, e.g., vector library, and/or the plurality of viruses, e.g., virus library, can include at least or at least about 2, 5, 10, 100, $10^3$, $10^4$, $10^5$, $10^6$, $10^7$, $10^1$, $10^9$, $10^{10}$ or more distinct polynucleotides and/or viruses encoding candidate recombinant receptors.

In some embodiments, nucleic acid sequences encoding candidate binding molecules can be amplified and cloned into the vector backbone by employing restriction enzymes. Exemplary methods that utilize the vector backbones permit efficient cloning of sequences encoding candidate binding domains, e.g., scFv, with or without peptide leader sequences. In an exemplary embodiment, NheI and RsrII are selected as restriction enzymes for digestion of the candidate binding domain insert sequences, as NheI does not cut within human $V_H$ or $V_L$ genes and RsrII only cuts 2 germline $V_H$ sequences, thereby allowing preservation of the candidate binding domain, e.g., scFv, sequence library. In an exemplary embodiment, polymerase chain reaction (PCR) primers containing NheI and RsrII restriction enzyme sites and degenerate primer sequences for amplifying human $V_H$ and $V_L$, are used to amplify candidate binding domain sequences from a sequence library that did not contain peptide leader sequences. Once amplified, the PCR products are digested with NheI and RsrII restriction enzymes, and ligated to the lentiviral vector described above containing the CD33 leader peptide-encoding sequence, digested with XbaI or BsmBI and RsrII restriction enzyme. For a binding domain sequence library that contained leader sequences, the candidate binding domain sequences are amplified using primers containing NheI and RsrII restriction enzyme sites and degenerate primer sequences for amplifying human $V_H$ and $V_L$. In an exemplary embodiment, PCR products are digested with NheI and RsrII restriction enzymes, and ligated to the lentiviral vector digested with NheI and RsrII restriction enzymes.

In some cases, candidate binding domain sequences can be assembled or inserted into the vector using ligation independent methods, such as Gibson Assembly® methods.

E. Introduction of Polynucleotides and Generation of Cell Library

In some aspects, the provided polynucleotides, e.g., encoding the recombinant receptor, are introduced to the cell, e.g., reporter T cell. In some embodiments, such nucleic acid molecule or complex thereof can be introduced into cells, such as T cells, by known methods. Such methods include, but are not limited to, introduction in the form of recombinant viral vectors (e.g. retroviruses, lentiviruses, adenoviruses), liposomes or nanoparticles. In some embodiments, methods can include microinjection, electroporation, particle bombardment, Calcium Phosphate transfection, cell compression, squeezing. In some embodiments, the polynucleotides may be included in vectors, e.g., any of the vector backbones described herein.

In some embodiments, the polynucleotides encoding recombinant receptors, e.g., CARs, can be used to generate a plurality of reporter T cells, e.g., plurality of reporter T cells that express candidate recombinant receptors. In some embodiments, the plurality of T cells or library of T cells include cells that together express at least or at least about 2, 5, 10, 25, 50, 100, 500 or $10^3$ distinct candidate recombinant receptors, e.g., CARs.

Introduction of the polynucleotide encoding the recombinant receptor may be carried out using any of a number of known methods. In some embodiments, the provided vector backbone comprises vector sequences, e.g., vector sequences for introducing or transferring nucleic acid sequences into a cell. Such vectors include viral and non-viral systems, including lentiviral and gammaretroviral systems, as well as transposon-based systems such as PiggyBac or Sleeping Beauty-based gene transfer systems. Exemplary methods include those for transfer of nucleic acids encoding the receptors, including via viral, e.g., retroviral or lentiviral, transduction, transposons, and electroporation.

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 Nov. 29(11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) *J. Immunother.* 35(9): 689-701; Cooper et al. (2003) *Blood.* 101: 1637-1644; Verhoeyen et al. (2009) *Methods Mol Biol.* 506: 97-114; and Cavalieri et al. (2003) Blood. 102(2): 497-505.

In some embodiments, recombinant nucleic acids are transferred into T cells via electroporation (see, e.g., Chicaybam et al, (2013) *PLoS ONE* 8(3): e60298 and Van Tedeloo et al. (2000) *Gene Therapy* 7(16): 1431-1437). In some embodiments, recombinant nucleic acids are transferred into T cells via transposition (see, e.g., Manuri et al. (2010) Hum Gene Ther 21(4): 427-437; Sharma et al. (2013) *Molec Ther Nucl* Acids 2, e74; and Huang et al. (2009) *Methods Mol Biol* 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

In some embodiments, viral and non-viral based gene transfer methods can be used to introduce nucleic acids into cells, such as T cells. Such methods can be used to administer nucleic acids encoding components to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Methods of non-viral delivery of nucleic acids include lipofection, nucleofection, microinjection, biolistics, virosomes, liposomes, immunoliposomes, polycation or lipid: nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™) Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration). Other delivery vehicles include polymeric carriers, chemical carriers, lipoplexes, polyplexes, dendrimers, nanoparticles, emulsion and/or agents that trigger natural endocytosis or phagocytosis pathways. Other approaches and vectors for transfer of the nucleic acids encoding the recombinant products are those described, e.g., in international patent application, Publication No.: WO2014055668, and U.S. Pat. No. 7,446,190.

IV. METHODS OF ASSESSING, SCREENING AND/OR IDENTIFICATION

Also provided herein are methods of assessing, screening and/or identifying particular cells, e.g., a T cell that express a particular recombinant receptor. Also provided are screening platforms that include such methods. In some embodiments, also provided are methods of assessment and identification of a recombinant receptor that has desired characteristics and/or properties, among a plurality of recombinant receptors. In some embodiments, one or more of the reporter T cells provided herein that are engineered to express one of a plurality of candidate recombinant receptors, can be screened and identified. In some embodiments, the provided methods involve identifying one or more reporter T cells among the plurality that express the recombinant receptor on the surface of the cell, express the reporter molecule in the presence of the agent and/or do not express the reporter molecule in the absence of the agent. In some embodiments, the methods for assessing, screening and/or identification involve enrichment or selection steps. In some embodiments, the methods can be used in low-, medium- or high-throughput screening methods to determine the activity, e.g., signaling activity and/or functional activity of the exogenous recombinant receptor, e.g., CAR, introduced into the T cells or plurality of T cells.

A. Enrichment/Selection

In some embodiments, the method can include a step of enrichment or selection. In some embodiments, the enrichment or selection step can facilitate the screening and identification by enriching for and/or selecting for cells that contain recombinant receptors that exhibit desired characteristics, such that the cells expressing recombinant receptors that exhibit some undesired characteristics, such as low expression, unstable expression and/or high antigen-independent activity and/or tonic signaling, is easily screened out. In large-scale screening, such methods can be used to narrow desired candidates rapidly and easily, to achieve efficient screening and identification without waste of resources.

In some embodiments, a selection marker, e.g., selection marker contained in the vector backbone, can be used to enrich and/or select cells. In some embodiments, a selection marker such as a Puromycin resistance gene, can be used to select cells that have been transduced or transfected, and/or enrich for infected cells and eliminate cells containing CARs that are expressed at a very low level or exhibit poor stability.

In some embodiments, affinity based methods can be used to enrich and/or select cells. Affinity based methods can be used to separate, isolate or select different cells based on the expression of the recombinant receptor and/or antigen binding or recognition by the recombinant receptor. In some embodiments, the separation is affinity- or immunoaffinity-based separation. In some embodiments, the separation of cells based on the cells' expression or expression level of the recombinant receptor can be carried out by incubation with a binding partner that specifically binds to such receptor, e.g., purified or recombinant antigen, followed generally by washing steps and separation of cells having bound the purified or recombinant antigen, from those cells having not bound. In some embodiments, cells expressing candidate recombinant receptors can be selected using biotinylated antigen and immobilized streptavidin or anti-biotin magnetic columns.

In some embodiments, cells expressing candidate recombinant receptors can also be labeled with a fluorescently labeled antigen conjugate and sorted by fluorescence activated cell sorting (FACS), selecting for cells expressing recombinant receptors that bind to the antigen. In some embodiments, the cells can be subject to enrichment by magnetic selection for binding to specific antigens and/or FACS to isolate a particular population. In some embodiments, the cells can be subject to enrichment by magnetic selection for binding to specific antigens, followed by co-culture with antigen expressing target cells to assess reporter expression and/or other activity, such as antigen binding. In some embodiments, cells can be enriched by co-culture with antigen-expressing cells and sorted based on reporter expression, using FACS.

In some embodiments, the library of candidate recombinant receptor-expressing cells is selected or screened to identify and select out cells that exhibit high levels of antigen-independent activity and/or tonic signaling. In some embodiments, certain recombinant receptors can exhibit high tonic signaling, which can lead to loss of cells over time, by cell death or slowed growth. Candidate recombinant receptors that exhibit high antigen-independent activity and/or tonic signaling can be selected out using methods such as puromycin selection, fluorescence based cell sorting (FACS)-based selection, growth selection or bioinformatics analysis. Selection marker can also be used to select for recombinant receptors with higher expression and can favor recombinant receptors with low to no antigen-independent activity and/or tonic signaling, as poor recombinant receptor expression are observed to be associated with high antigen-independent activity and/or tonic signaling in some embodiments. Cells expressing high levels of recombinant receptor can also be selected using FACS, based on high recombinant receptor expression or high surrogate marker expression.

In some embodiments, the enrichment or selection step can include a growth selection. In some embodiments, cells exhibiting high antigen-independent activity and/or tonic signaling can be selected out by subjecting cells to a growth selection. In some embodiments, cells that express a candidate recombinant receptor that exhibits high antigen-independent activity and/or tonic signaling can grow more slowly or die during prolonged culture. The library of cells can be subject to expansion and extended growth, whereby the cells in the library that have high antigen-independent activity and/or tonic signaling are outcompeted. In some embodiments, a library of candidate recombinant receptor-expressing reporter cells can also be sorted by FACS based on expression of the reporter without incubation with antigen to isolate cells with high and low antigen-independent activity and/or tonic signaling; and after incubation with antigen or antigen-expressing target cells to isolate cells with high and low antigen-specific signaling. In some embodiments, the enrichment/selection may be performed multiple times to identify cells that express the recombinant receptor at a higher level and/or exhibit higher activity.

B. Assessment of Activity and/or Expression

In some embodiments, the methods include assessing activity and/or expression of the recombinant receptor, e.g., in some cases, based on expression of the reporter. In some embodiments, any of the provided cells and/or cell lines, e.g., reporter T cells, can be used in connection with any of the methods provided herein, e.g., to assess activity of a recombinant receptor, e.g., CAR. In some embodiments, a polynucleotide encoding a recombinant receptor, e.g., CAR, can be introduced into any of the provided cells and/or cell lines, e.g., reporter T cell lines, to be expressed and assessed for expression and/or activity, e.g., functional activity, including signaling through signaling regions contained in the recombinant receptor. In some embodiments, any of the provided cells and/or cell lines can also be used to assess other activities, such as antigen binding, antigen-specific activity, antigen-independent (tonic) signaling and/or stability of recombinant receptor expression. In some embodiments, the provided plurality of reporter cells, e.g., library of reporter cells, can be assessed for expression and/or activity. In some embodiments, expression of the reporter molecule, e.g., a Nur77 reporter, can provide a reliable, rapid, dose-dependent and cell intrinsic readout of activity of the recombinant receptor. Thus such methods can be used for screening cells in low-, medium- or high-throughput screening methods.

In some embodiments of the methods involve incubating one or more of the plurality of reporter T cells, each comprising i) a recombinant receptor, e.g., CAR, that contains an intracellular signaling region and ii) a reporter molecule, wherein the expression of said reporter molecule is responsive to a signal through the intracellular signaling region of the recombinant receptor, wherein the incubating is carried out in the presence and/or absence of an agent that binds to the binding domain of the recombinant receptor and/or an agent that induces or is capable of inducing a signal through the intracellular signaling region of the recombinant receptor; and assessing the one or more reporter T cells for expression of the reporter molecule. In some embodiments, the methods involve assessing expression of the reporter molecule, separately, in the presence of the agent, and in the absence of the agent.

In some embodiments, the methods also involve identifying one or more reporter T cells among the plurality that express the recombinant receptor on the surface of the cell, express the reporter molecule in the presence of the agent and/or do not express the reporter molecule in the absence of the agent.

In some embodiments, the expression of the recombinant receptor on the surface of the cell can be assessed. Approaches for determining expression of the recombinant receptor on the surface of the cell may include use of chimeric antigen receptor (CAR)-specific antibodies (e.g., Brentjens et al., Sci. Transl. Med. 2013 March; 5(177): 177ra38), Protein L (Zheng et al., J. Transl. Med. 2012 February; 10:29), epitope tags, and monoclonal antibodies that specifically bind to a CAR polypeptide (see international patent application Pub. No. WO2014190273). In some embodiments, the expression of the recombinant receptor on the surface of the cell, e.g., reporter T cell, can be assessed, for example, by flow cytometry, using binding molecules that can bind to the recombinant receptor or a portion thereof that can be detected. In some embodiments, the binding molecules used for detecting expression of the recombinant receptor an anti-idiotypic antibody, e.g., an anti-idiotypic agonist antibody specific for a binding domain, e.g., scFv, or a portion thereof. In some embodiments, the binding molecule is or comprises an isolated or purified antigen, e.g., recombinantly expressed antigen. In some embodiments, the binding molecule is or comprises an isolated or purified antigen that is detectable, e.g., conjugated to a detectable moiety. In some embodiments, the binding molecule is or comprises an antigen that is complexed with another molecule. In some embodiment, the binding molecule is or comprises an MHC-peptide complex, e.g., a peptide-MHC tetramer or a modified form thereof. In some embodiments, the recombinant receptor is a recombinant T cell receptor (TCR), and the binding domain is or comprises an epitope, such as a polypeptide or a peptide epitope thereof, in complex with one or more MHC molecules or complexes. In some embodiments, the recombinant receptors is a chimeric autoantibody receptor (CAAR) and the agent is an autoantibody or a fragment thereof.

In some embodiments, expression of the recombinant receptor can be assessed by detecting the expression of a surrogate marker, e.g., a marker that indicate or confirms modification of a cell. In some embodiments, the surrogate marker is a protein that is made to be co-expressed on the cell surface with the recombinant receptor, e.g. CAR. In particular embodiments, such a surrogate marker is a surface protein that has been modified to have little or no activity. In certain embodiments, the surrogate marker is encoded on the same polynucleotide that encodes the recombinant receptor. In some embodiments, the nucleic acid sequence encoding the recombinant receptor is operably linked to a nucleic acid sequence encoding a marker, optionally separated by an internal ribosome entry site (IRES), or a nucleic acid encoding a self-cleaving peptide or a peptide that causes ribosome skipping, such as a 2A sequence, such as a T2A, a P2A, a E2A or a F2A.

One or more extrinsic marker genes may in some cases be utilized in connection with engineered cell to permit detection or selection of cells and, in some cases, also to promote cell suicide. Exemplary surrogate markers can include truncated cell surface polypeptides, such as a truncated human epidermal growth factor receptor 2 (tHER2), a truncated epidermal growth factor receptor (EGFRt, exemplar EGFRt sequence set forth in SEQ ID NO:11 or 76) or a prostate-specific membrane antigen (PSMA) or modified form thereof. EGFRt may contain an epitope recognized by the antibody cetuximab (Erbitux®) or other therapeutic anti-EGFR antibody or binding molecule, which can be used to identify or select cells that have been engineered with the EGFRt construct and a recombinant receptor, such as a chimeric antigen receptor (CAR), and/or to eliminate or separate cells expressing the receptor. See U.S. Pat. No. 8,802,374 and Liu et al., Nature Biotech. 2016 April; 34(4): 430-434). In some embodiments, the marker is or comprises a fluorescent protein, such as green fluorescent protein (GFP), enhanced green fluorescent protein (EGFP), such as super-fold GFP (sfGFP; set forth in SEQ ID NO:36, encoded by nucleic acid sequence set forth in SEQ ID NO:35), red fluorescent protein (RFP), such as tdTomato, mCherry, mStrawberry, AsRed2, DsRed or DsRed2, cyan fluorescent protein (CFP), blue green fluorescent protein (BFP), enhanced blue fluorescent protein (EBFP), and yellow fluorescent protein (YFP), and variants thereof, including species variants, monomeric variants, and codon-optimized and/or enhanced variants of the fluorescent proteins. In some embodiments, the marker is or comprises an enzyme, such as a luciferase, the lacZ gene from *E. coli*, alkaline phosphatase, secreted embryonic alkaline phosphatase (SEAP), chloramphenicol acetyl transferase (CAT). Exemplary light-emitting reporter genes include luciferase (luc), β-galactosidase, chloramphenicol acetyltransferase (CAT), β-glucuronidase (GUS) or variants thereof. In some embodiments, the marker gene is different from the reporter molecule or the detectable signal generated by the reporter.

In some embodiments, the binding of a binding molecule, e.g, an antibody or antigen-binding fragment thereof or a purified antigen, and/or expression of a molecule can be detected with a detectable label. In some embodiments, the binding and/or expression is detected by any suitable method or means, such as but not limited to flow cytometry, immunocytochemistry, immunohistochemistry, western blot analysis, and ELISA. Other exemplary methods of detection include EIA, immunofluorescence, polymerase chain reaction (PCR), reverse transcriptase PCR (RT-PCR), in situ PCR, quantitative PCR, fluorescence-activated cell sorting (FACS), enzymatic activity assays, gas chromatography/mass spectroscopy (GC/MS), high performance liquid chromatography (HPLC), liquid chromatography-dual mass spectrometry (LC-MS/MS), liquid chromatography-electrospray ionization-tandem mass spectrometry (LC-ESI-MS), nuclear magnetic resonance (NMR), in situ hybridization, Western blot, Northern blot, Southern blot, in vivo imaging, microarrays, transcriptome sequencing, and/or any known high throughput methods.

In some embodiments, the stability of the expression of the recombinant receptor is assessed. In some embodiments, stability of expression is assessed by determining the expression level of the recombinant receptor, after incubation and/or culture of the cells over various length of time after introduction of the polynucleotide encoding the recombinant receptor into the cells, e.g., reporter T cells. In some embodiments, the stability of expression is assessed after 1, 2, 3, 4, 5, 6, 7, 8, 9, 10, 11, 12, 13, 14, 21 or 28 days or more after introduction of the polynucleotide encoding the recombinant receptor into the cells, e.g., reporter T cells.

In some embodiments, the expression of the reporter is responsive to and/or indicative of the quality and/or strength of the signal through the intracellular signaling region and/or binding and/or recognition of the recombinant receptor to a target antigen or epitope. In some embodiments, the expression of the reporter is activated upon signal through the intracellular signaling region and/or binding and/or recognition of the recombinant receptor to a target antigen or epitope. In some embodiments, the intracellular signaling region comprises a signaling domain, such as a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM). Thus, in some embodiments, the expression for the reporter can be indicative of signals, e.g., cellular signals, through the primary signaling domain, signaling domain that is capable of inducing primary activation signal in T cell, signaling domain of T cell receptor (TCR) component, and/or signaling domain comprising an immunoreceptor tyrosine-based activation motif (ITAM).

In some embodiments, the reporter cells or cell lines or one or more of the plurality of reporter T cells can be assessed for expression of the reporter molecule after incubating the reporter cells that is engineered to express a recombinant receptor, e.g., CAR, in the presence of an agent that binds the binding domain of the recombinant receptor.

In some embodiments, the agent is or comprises an antigen or an epitope thereof, e.g., an antigen that specifically binds and/or is recognized by the binding domain of the recombinant receptor. In some embodiments, the antigen can include purified or isolated antigen, recombinantly expressed antigen or antigen-expressing target cells, e.g., cells that are engineered to express the antigen or epitope that specifically binds to and/or is recognized by the binding domain of the recombinant receptor or target cells that endogenously express the antigen or epitope. In some embodiments, the antigen is a purified or isolated antigen. In some embodiments, the purified or isolated antigen is immobilized on a support, e.g., on a surface, such as a plate, a bead or a column. In some embodiments, the agent is or comprises a tumor cell that is engineered to express the target antigen or epitope. In some embodiments, the tumor cell is engineered so that the target antigen is conditionally expressed, e.g., induced or repressed upon specific conditions. In some embodiments, the target antigen can be expressed under the operable control of an inducible or repressible promoter, e.g., Lac operator sequence, a tetracycline operator sequence, a galactose operator sequence or a doxycycline operator sequence, or an analog thereof. In some embodiments, the agent is or comprises an anti-idiotypic antibody, e.g., an anti-idiotypic agonist antibody specific for a binding domain, e.g, scFv, or a portion thereof.

In some embodiments, the agent is or comprises antigen that is complexed with another molecule. In some embodiment, the agent is or comprises an MHC-peptide complex, e.g., a peptide-MHC tetramer or a modified form thereof. In some embodiments, the recombinant receptor is a recombinant T cell receptor (TCR), and the agent is or comprises an epitope, such as a polypeptide or a peptide epitope thereof, in complex with one or more MHC molecules or complexes. In some embodiments, the expression of the reporter molecule assessed in the presence of the agent is indicative of antigen-specific activity of the recombinant receptor.

In some embodiments, the reporter cells or cell lines or one or more of the plurality of reporter T cells can be assessed after incubation with one or more different agents, e.g., related antigens or antigens from different species. In some embodiments, the one or more different agents can include corresponding antigen from different species, e.g., to assess species cross reactivity. In some embodiments, the agent can be one or more different purified or isolated antigen. In some embodiments, the agent can be one or more different target cells, each expressing a different antigen, e.g., related antigens or corresponding antigen from different species. For example, the agent can be a particular antigen that is specifically recognized by or specifically bound by the recombinant receptor, but from different species such as human, cynomolgus monkey or mouse. In some embodiments, the degree of species cross-reactivity can be determined using the expression of the reporter in the presence of different antigens from different species.

In some embodiments, the reporter cells or cell lines or one or more of the plurality of reporter T cells can be assessed for expression of the reporter molecule after incubating the reporter cells that is engineered to express a recombinant receptor, e.g., CAR, in the absence of an agent that binds the binding domain of the recombinant receptor. In some embodiments, the expression of the reporter molecule assessed in the absence of the agent is indicative of antigen-independent activity or signaling (also known as "tonic signaling") through the recombinant receptor, e.g., CAR. Antigen-independent activity and/or tonic signaling through a recombinant receptor can lead to increased differentiation and exhaustion of T cells that express the recombinant receptor, thus can limit the T cell's activity, effect or potency. For CAR-expressing T cells, tonic or constitutive phosphorylation of CD3-ζ, triggered by antigen-independent clustering of the scFvs in the CARs, can induce early exhaustion of the CAR-expressing T cells and limit their expansion and/or persistence (see, e.g., Long et al. (2015) Nat Med. 21(6):581-90; Mamonkin et al., J Immunol May 1, 2016, 196 (1 Supplement) 143.7; Gomes-Silva et al. (2017) Cell Reports 21:17-26). In some cases, during engineering and ex vivo expansion of the cells for CAR expression, the cells may exhibit phenotypes indicative of exhaustion, due to antigen-independent activity and/or tonic signaling through the CAR. Exhausted T cells also show reduced proliferative potential and cytokine production, and higher apoptosis and expression of inhibitory receptors (see, e.g., Long et al. (2015) Nat Med. 21(6):581-90) Thus, a recombinant receptor that exhibits low or no antigen-independent activity and/or tonic signaling, can be desired.

In some embodiments, the provided reporter T cells and methods can be employed to assess antigen-independent activity and/or tonic signaling through a particular recombinant receptor and/or to screen a plurality of recombinant receptor-expressing cells to identify cells expressing recombinant receptors that exhibit low or no tonic signaling. In some embodiments, the reporter cell contains a reporter molecule, such as a fluorescent protein or other detectable molecule, such as a red fluorescent protein, e.g., a tdTomato reporter molecule, expressed under the control of the endogenous Nur77 transcriptional regulatory elements. In some embodiments, the Nur77 reporter expression is cell intrinsic. As described herein, the Nur77 reporter expression is cell intrinsic and dependent upon signaling through a recombinant reporter containing a primary activation signal in a T cell, a signaling domain of a T cell receptor (TCR) component, and/or a signaling domain comprising an immunoreceptor tyrosine-based activation motif (ITAM), such as a CD3ζ chain. Nur77 expression is generally not affected or influenced by other signaling pathways such as cytokine signaling or toll-like receptor (TLR) signaling (see, e.g., Ashouri et al., (2017) J. Immunol. 198:657-668), which may act in a cell extrinsic manner and may not depend on signaling through the recombinant receptor. Thus, only cells that express the exogenous recombinant receptor containing the appropriate signaling regions is capable of expressing Nur77 upon stimulation (e.g., binding of the specific antigen). As described herein, Nur77 expression also can show a dose-dependent response to the amount of stimulation (e.g., antigen). In some embodiments, assessing the one or more reporter T cells, e.g., from a plurality of reporter T cells, for expression of the reporter molecule after incubation without or in the absence of an agent that binds to the binding domain of the recombinant receptor (e.g., specific antigen) and/or an agent that induces or is capable of inducing a signal through an intracellular signaling region of the recombinant receptor (e.g., specific antigen), can indicate the level of tonic signaling through the recombinant receptor. In some embodiments, the expression the Nur77 reporter in the presence of a particular recombinant receptor, can be assessed in the presence of the specific antigen (e.g., in the presence of or co-culture with antigen-expressing cells, or in the presence of recombinant and/or purified antigen) and the absence of the specific antigen, to compare antigen-dependent signaling and antigen-independent signaling via the recombinant receptor.

In some embodiments, the methods also involve identifying one or more reporter T cells among the plurality that express the reporter molecule in the presence of the agent, indicating high antigen-specific activity, and/or that do not express the reporter molecule in the absence of the agent, indicating low tonic signaling.

In some embodiments, the reporter cells or cell lines or one or more of the plurality of reporter T cells can be assessed for the activity, phenotypes and/or function of the T cells, e.g., reporter T cells expressing recombinant receptors. In some embodiments, the methods further include assessing aspects of T cell activation, such as assessing release of cytokines and/or assessing functional activity of the T cell, e.g., cytolytic activity and/or helper T cell activity.

In some embodiments, the one or more reporter T cells can be assessed for cell phenotypes, e.g., expression of particular cell surface markers. In some embodiments, the T cells, e.g., reporter T cells expressing recombinant receptors, are assessed for expression of T cell activation markers, T cell exhaustion markers, and/or T cell differentiation markers. In some embodiments, the cell phenotype is assessed before administration. In some embodiments, the cell phenotype is assessed after administration. T cell activation markers, T cell exhaustion markers, and/or T cell differentiation markers for assessment include any markers known in the art for particular subsets of T cells, e.g., CD25, CD38, human leukocyte antigen-DR (HLA-DR), CD69, CD44, CD137, KLRG1, $CD62L^{low}$, $CCR7^{low}$, CD71, CD2, CD54, CD58, CD244, CD160, programmed cell death protein 1 (PD-1), lymphocyte activation gene 3 protein (LAG-3), T-cell immunoglobulin domain and mucin domain protein 3 (TIM-3), cytotoxic T lymphocyte antigen-4 (CTLA-4), band T lymphocyte attenuator (BTLA) and/or T-cell immunoglobulin and immunoreceptor tyrosine-based inhibitory motif domain (TIGIT) (see, e.g., Liu et al., Cell Death and Disease (2015) 6, e1792). In some embodiments, the assessed cell surface marker is CD25, PD-1 and/or TIM-3. In some embodiments, the assessed cell surface marker is CD25.

In some embodiments, the one or more reporter T cells can be assessed for cytokine production. In some cases, such measured cytokines can include, without limitation, interleukin-2 (IL-2), interferon-gamma (IFNγ), interleukin-4 (IL-4), TNF-alpha (TNFα), interleukin-6 (IL-6), interleukin-10 (IL-10), interleukin-12 (IL-12), granulocyte-macrophage colony-stimulating factor (GM-CSF), CD107a, and/or TGF-beta (TGFβ). Assays to measure cytokines are well known in the art, and include but are not limited to, ELISA, intracellular cytokine staining, cytometric bead array, RT-PCR, ELISPOT, flow cytometry and bio-assays in which cells responsive to the relevant cytokine are tested for responsiveness (e.g. proliferation) in the presence of a test sample.

C. Identification of Cells and/or Recombinant Receptors

In some embodiments, the methods involve identifying one or more reporter T cells among the plurality that express the recombinant receptor on the surface of the cell, that possess desired properties or characteristics. In some embodiments, cells expressing candidate recombinant receptors that exhibit one or more desired characteristics, such as high and stable recombinant receptor, e.g., CAR, expression, strong on-target activity (e.g., antigen-specific activity) and/or low antigen-independent activity and/or tonic signaling, are identified. In some embodiments, the methods also include determining the sequence of the encoded recombinant receptor or portion thereof, e.g., the binding domain, of recombinant receptors that possess or exhibit desired properties or characteristics.

In some embodiments, candidate recombinant receptors that exhibit high and stable recombinant receptor, e.g., CAR surface expression, high antigen-specific activity, low tonic signaling and/or high antigen affinity, can be selected or identified. Any of the assessment and/or selection steps can be used alone or in combination, depending on the desired properties and/or specific characteristics of the expressed recombinant receptor, e.g., CARs. Cells may also be assessed after incubation with a different and/or related antigen, e.g., antigen from a different species, to assess potential off-target effects and potential cross-reactivity.

In some embodiments, cells expressing candidate recombinant receptors that exhibit low tonic signaling is identified. In some embodiments, high levels of antigen-independent activity and/or tonic signaling can be associated with loss of cells over time, by cell death or slowed growth. In some embodiments, high tonic signaling can lead to increased differentiation and exhaustion of T cells that express the recombinant receptor, thus can limit the T cell's activity, effect, persistence or potency. In some embodiments, candidate recombinant receptors are identified, based on assessment of expression of the reporter molecule after incubation in the absence of an agent that binds to the binding domain of the recombinant receptor and/or an agent that induces or is capable of inducing a signal through the intracellular signaling region of the recombinant receptor, e.g., specific target antigen. In some embodiments, cells that express low or no tonic signaling after incubation in the absence of specific target antigen, is identified and/or isolated.

In some embodiments, cells expressing candidate recombinant receptors that exhibit high antigen-specific activity is identified. In some embodiments, candidate recombinant receptors are identified, based on assessment of expression of the reporter molecule after incubation in the presence of an agent that binds to the binding domain of the recombinant receptor and/or an agent that induces or is capable of inducing a signal through the intracellular signaling region of the recombinant receptor, e.g., specific target antigen. In some embodiments, cells that express high levels of reporter molecule expression after incubation in the presence of the agent, e.g., specific target antigen, is identified. In some embodiments, high level of reporter molecule expression in the presence of a target antigen indicates high antigen-specific activity, and thus potentially high functional activity of T cells expressing the recombinant receptor, e.g., CAR. In some embodiments, high level of reporter molecule expression in the presence a target antigen indicates potentially high efficacy of T cells expressing the recombinant receptor, e.g., CAR, when used in therapy, e.g., adoptive T cell therapy.

In some embodiments, cells expressing candidate recombinant receptors that exhibit other desired properties and/or characteristics, e.g., high or low recombinant receptor expression, stable expression, low or high species cross reactivity, and/or low or high cytokine production, can be identified.

At any or all of the steps of in the screening process, such as the binding domain (e.g., scFv) library, vector library, viral library, cell library stage and/or in particular selected and/or isolated populations or individual binding domains, vectors, recombinant receptors, viruses and/or cells, the nucleic acid sequences, e.g., nucleic acid sequences encoding the scFv, of the library and/or population of cells can be determined by high-throughput sequencing, to determine clonal diversity, library representation and clone enrichment. In some embodiments, the nucleic acid sequence and/or the amino acid sequence of one or more of the recombinant receptors or a portion thereof, e.g., the binding domain, can be determined at any stage of the methods provided herein. In some embodiments, the complexity and diversity of the sequences present at any or all steps of the methods provided herein, can be assessed.

In some embodiments, the sequence can be determined on a population level, e.g., among the plurality and/or library of binding domains, polynucleotides, vectors, viruses and/or cells. In some embodiments, the sequence can be determined in individual binding domains, polynucleotides, vectors, viruses and/or cells. In some embodiments, the sequence can be determined before or after identification of cells expressing candidate recombinant receptors that exhibit desired properties and/or characteristics. In some embodiments, the sequence can be determined after identification of cells expressing candidate recombinant receptors that exhibit desired properties and/or characteristics, e.g., to determine the sequences of the recombinant receptor exhibiting the desired properties and/or characteristics.

The nucleic acid sequence encoding the recombinant receptor, e.g., CAR or a binding domain, e.g., antigen-binding scFv portion of the recombinant receptor, can be determined using traditional nucleic acid sequencing methods (e.g., Sanger sequencing) or high-throughput sequencing. Any known high-throughput sequencing methods can be employed to assess the sequences present in the plurality or individual binding domains, polynucleotides, vectors, viruses and/or cells, including, e.g., 454 Sequencing, Sanger sequencing, sequencing by synthesis, Illumina's reversible terminator method, Roche's pyrosequencing method (454), Life Technologies' sequencing by ligation (the SOLiD platform) or Life Technologies' Ion Torrent platform, or any methods described in U.S. Pat. Nos. 5,547,835; 5,171,534; 5,622,824; 5,674,743; 4,811,218; 5,846,727; 5,075,216; 5,405,746; 5,858,671; 5,374,527; 5,409,811; 5,707,804; 5,821,058; 6,087,095; 5,876,934; 6,258,533; 5,149,625; Margulies et al., Nature 2005 437: 376-80; Ronaghi et al., Analytical Biochemistry 1996 242: 84-9; Shendure et al., Science 2005 309: 1728-32; Imelfort et al., Brief Bioinform. 2009 10:609-18; Fox et al., Methods Mol Biol. 2009; 553:79-108; Appleby et al., Methods Mol Biol. 2009; 513: 19-39 and Morozova et al., Genomics. 2008 92:255-64.

D. Assessment in Primary Cells

In some embodiments, the methods further include assessing aspects of T cell activation, such as assessing release of cytokines and/or assessing functional activity of the T cell, e.g., cytolytic activity and/or helper T cell activity, in other cells, such as primary T cells. In some embodiments, after screening for and identifying candidate recombinant receptors, e.g. CARs, having particular properties, polynucleotides encoding the identified recombinant receptors, e.g., CARs, can be introduced into other types of cells, e.g., primary cells isolated from subjects, to assess T cell activation by the identified TCR and T cell functionality.

In some embodiments, at least some of the functional assays are performed in primary T cells, such as those isolated directly from a subject and/or isolated from a subject and frozen, such as primary CD4+ and/or CD8+ T cells. In some embodiments, the polynucleotides encoding some the plurality of recombinant receptor, e.g., CARs, e.g., such as those that are identified to have particular properties, e.g., high antigen-specific activity and low tonic signaling, are introduced into primary T cells, such as CD4+ cells or CD8+ cells, and are assessed for expression and functional activity. For example, in some embodiments, lentiviruses containing polynucleotides encoding the recombinant receptors, e.g., CARs, are packaged and transduced into primary T cells. In some embodiments, function of the primary T cells is assessed after expression of the recombinant receptor, e.g., CAR, and binding of the antigen or epitope.

In some embodiments, the methods include performing functional assays or detecting function of the recombinant receptor, e.g., CAR, or the T cell. For example, functional assays for determining recombinant receptor, e.g., CAR, activity or T cell activity include detection of cytokine secretion, cytolytic activity and/or helper T cell activity. For example, assessment of T cell activation includes assessing release of cytokines, and/or assessing functional activity of the T cell. In some embodiments, upon binding of the recombinant receptor, e.g., CAR, to an antigen or an epitope, the cytoplasmic domain or intracellular signaling domain of the recombinant receptor, e.g., CAR, activates at least one of the normal effector functions or responses of an immune cell, e.g., T cell engineered to express the recombinant receptor, e.g., CAR. For example, in some contexts, the recombinant receptor, e.g., CAR, induces a function of a T cell such as cytolytic activity and/or helper T cell activity, such as secretion of cytokines or other factors. In some embodiments, the intracellular signaling regions include the cytoplasmic sequences of the recombinant receptor, e.g., CAR, and in some aspects also those of co-receptors that in the natural context act in concert with such receptor to initiate signal transduction following antigen receptor engagement, and/or any derivative or variant of such molecules, and/or any synthetic sequence that has the same functional capability.

In some embodiments, T cells or T cell compositions, e.g., primary T cells, containing the recombinant receptor, e.g., CAR, are assessed for an immunological readout, such as using a T cell assay. In some embodiments, the recombinant receptor (e.g., CAR)-expressing cells can activate a CD8+ T cell response. In some embodiments, CD8+ T cell responses can be assessed by monitoring CTL reactivity using assays that include, but are not limited to, target cell lysis via $^{51}Cr$ release, target cell lysis assays using real-time imaging reagents, target cell lysis assays using apoptosis detection reagent (e.g., Caspase 3/7 reagent), or detection of interferon gamma release, such as by enzyme-linked immunosorbent spot assay (ELISA), intracellular cytokine staining or ELISPOT. In some embodiments, the recombinant receptor (e.g., CAR)-expressing cells can activate a CD4+ T cell response. In some aspects, CD4+ T cell responses can be assessed by assays that measure proliferation, such as by incorporation of [$^{3}H$]-thymidine into cellular DNA and/or by the production of cytokines, such as by ELISA, intracellular cytokine staining or ELISPOT. In some cases, the cytokine can include, for example, interleukin-2 (IL-2), interferon-gamma (IFN-gamma), interleukin-4 (IL-4), TNF-α, interleukin-6 (IL-6), interleukin-10 (IL-10), interleukin-12 (IL-12) or TGF β.

In some embodiments, the activity of the identified recombinant receptors, such as any expression and/or functional activity described above, can be assessed in primary cells, after incubation in the presence or absence of an agent that binds to the binding domain of the recombinant receptor and/or an agent that induces or is capable of inducing a signal through the intracellular signaling region of the recombinant receptor. In some embodiments, the agent comprises a target antigen or epitope specifically recognized by or specifically bound by the recombinant receptor. For recombinant receptors that are recombinant TCRs, recognition or binding of the peptide epitope, such as a MHC class I or class II epitope, by the recombinant receptor, e.g., CAR can elicit or activate a CD8+ T cell response and/or a CD4+ T cell response.

In some embodiments, polynucleotide encoding the binding domain of the identified recombinant receptor can be cloned into an exemplary vector backbone such as any described herein, or into other vectors or delivery vehicles, such as retroviral vectors or transposons, for delivering the sequences encoding the candidate recombinant receptors into primary cells.

In some embodiments, primary human T cell populations expressing the identified recombinant receptors, e.g., CARs, can be generated and tested. Vectors or other delivery vehicles containing the nucleic acid sequences encoding the recombinant receptor can be used to introduce the recombinant receptor-encoding sequences to CD4+ and CD8+ T cells in populations isolated from human PBMC samples obtained from healthy donors. In some embodiments, the genetically engineered human CD4+ and CD8+ T cells expressing various candidate CARs identified can be assessed for binding of a recombinant or purified target antigen and/or various responses following co-culture with target antigen expressing cells.

In some embodiments, after transduction and expansion, the cells can be assessed for surrogate transduction marker expression, and an anti-idiotypic antibody or detectably labeled recombinant or purified target antigen to verify expression and antigen binding of the CAR.

In some embodiments, cytolytic activity of the recombinant receptor-expressing cells can be assessed by incubation with target antigen-expressing cells. For example, the cells can be incubated un the presence of NucRed dye, and lysis of target cells can be measured by assessing the staining intensity of cells for the NucRed dye. Cells in which lysis occurred exhibit reduced staining intensity for the dye. Other known cytolytic assays can be used.

In some embodiments, cytokine release can be assessed following incubation of the recombinant receptor-expressing cells with antigen-expressing and control target cells. CD4+ and CD8+ recombinant receptor expressing T cells are co-cultured with target antigen-expressing cells. The supernatants from the co-cultured cells can be collected for measurement of IFN-γ, TNF-α, or IL-2 using a cytokine immunoassay. Other cytokine assays that can be used include intracellular cytokine signaling and flow cytometry.

In some embodiments, proliferation of the candidate CAR-expressing T cells can be assessed by flow cytometry following incubation with target antigen-expressing cells. CD8+ or CD4+ recombinant receptor-expressing T cells are labeled with a cell proliferation assay dye, such as CellTrace™ violet. Cells are co-cultured with target antigen-expressing cells. Division of the recombinant receptor-expressing T cells is indicated by dye dilution, as assessed by flow cytometry. Other known proliferation assay methods can also be used to assess the proliferative capacity of the candidate recombinant receptor-expressing T cells.

E. High-Throughput or Large-Scale Methods

Any of the steps of the methods provided herein, including inserting the nucleic acid sequence encoding binding domains into the vector backbones, introducing the polynucleotides into the T cells or plurality of T cells, assessing the T cells or plurality of T cells for particular properties and identifying the T cells or plurality of T cells with particular properties, can be performed in high-throughput, large-scale, multiplexed and/or high-efficiency systems, e.g., with the assistance of automated systems, disposable systems, addressable arrays and/or robotic methods, thereby reducing the time and resources required to screen the plurality of candidate recombinant receptors.

In some embodiments, the methods can be performed in a medium- or high-throughput or large-scale manner. In some embodiments, the screening can be performed by assessing numerous cells in the plurality or library at the same time. In some embodiments, one or more of the aspects, e.g., expression of the recombinant receptor, antigen binding, antigen-specific activity, antigen-independent activity and/or tonic signaling activity, and/or other phenotype or activity assays can be performed simultaneously, assessing several characteristics or parameters at once. In some embodiments, tens to hundreds to thousands to hundreds of thousands to millions or more cells can be tested. High-throughput methods can be performed manually or can be automated, such as using robotics or software.

In some embodiments, each reporter T cell expressing a candidate recombinant receptor in a library of reporter T cells can be screened individually and separately for expression and/or activity. In some embodiments, screening can be performed in an addressable library. Any addressable array technology known in the art can be employed for screening of library members, including cells, recombinant receptors or binding domains. For example, cells, e.g., reporter T cells, expressing a candidate receptor, can be physically separated from each other, such as by formatting in a spatial array, such as a multiwell plate or plates, such that each individual locus of the plate corresponds to one individual reporter T cell expressing a candidate receptor. Multiwell plates can include, but are not limited to, 12-well, 24-well, 48-well, 96-well plates, 384-well plates, and 1536-well plates. In some instances, the identity of each member in a position of the array, e.g. each well of the array, is known. In some embodiments, an isolated or purified antigen or cells expressing such antigen, can be present, e.g. added, to each position of the array, to permit contacting of members of the library with the target antigen or ligand.

In some embodiments, the reporter T cells expressing candidate recombinant receptors can be pooled and screened, such as in a non-addressable format. Examples of such other non-addressable formats include by display, in particular, any display format that facilitates screening of the members of the libraries for an activity or activities. In some embodiments, libraries are screened using a display technique in which there is a physical link between individual molecules of the library (phenotype) and the genetic information encoding them (genotype).

F. Exemplary Screening Platform

Figure 11A:
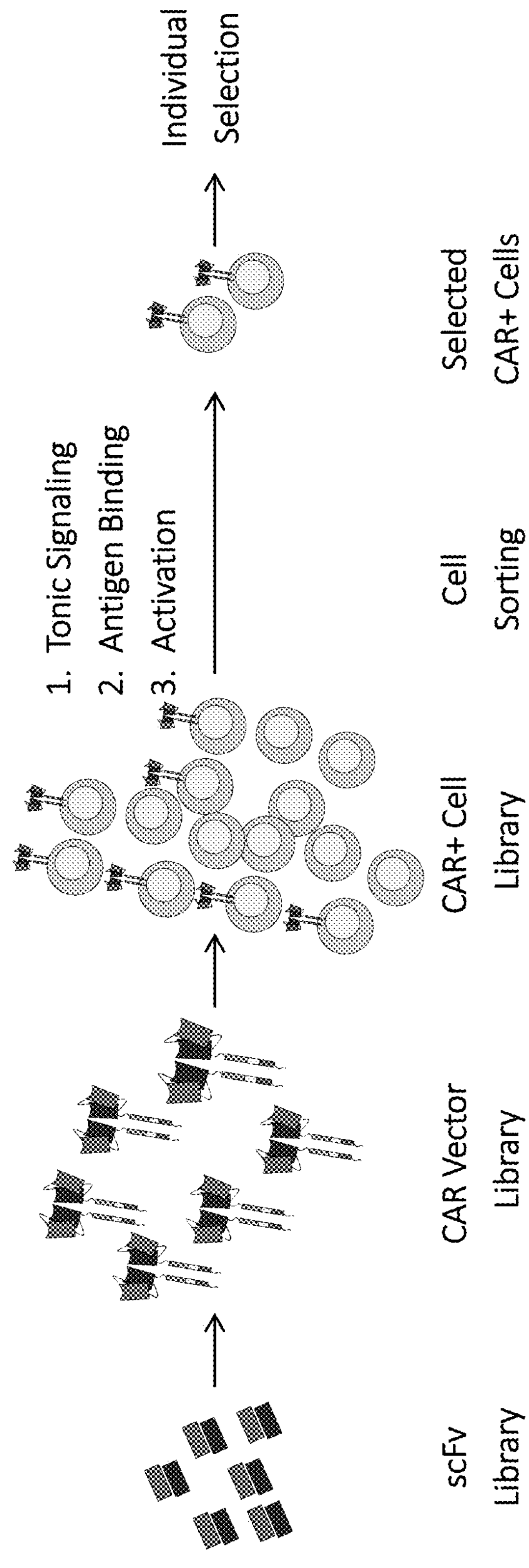
FIGS. 11A and 11B depict schematic representation of exemplary embodiments of methods described herein, e.g., for screening CAR candidate libraries.
Figure 11B:
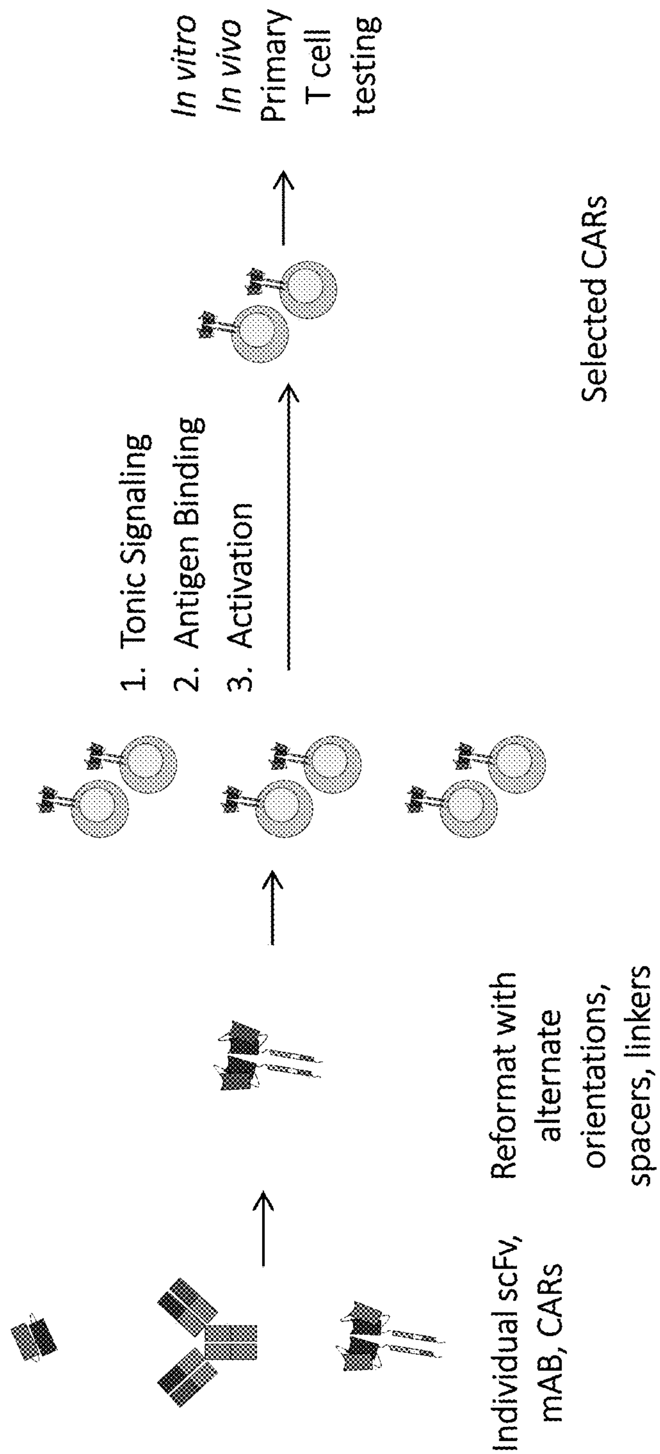

In some embodiments, the screening platform described herein can be used to assess, screen and/or identify recombinant receptors and/or cells expressing recombinant receptors, with desired characteristics. Schematic representation of an exemplary embodiment of such methods, e.g., for screening CAR candidate libraries, is shown in FIGS. 11A and 11B. The screening platform and methods can be used to screen a vector library containing a plurality of nucleic acid molecules encoding candidate recombinant receptors, e.g., CARs, containing different binding domains, spacers and/or intracellular signaling domains. In some embodiments, the methods can be used to assess antigen-specific activity and/or antigen-independent activity and/or tonic signaling. In some embodiments, the methods can be used to identify one or more reporter T cells among the plurality that express the recombinant receptor on the surface of the cell, express the reporter molecule in the presence of the agent and/or do not express the reporter molecule in the absence of the agent.

In an exemplary embodiment, nucleic acid sequences encoding various binding domains, such as scFv sequences obtained from scFv libraries, selected candidate scFvs, or mutagenized or chain-swapped scFv libraries, are amplified and cloned into the lentiviral vectors containing a short, medium or long spacer, to generate a vector library that encodes candidate CARs. For example, in some embodiments, a plurality of polynucleotides encoding scFvs that bind to CD19 are obtained from human donors or sequences of anti-CD19 monoclonal antibodies. In some embodiments, the scFv libraries can contain more than $1\times10^3$, $1\times10^4$, $1\times10^5$, $1\times10^6$, $1\times10^7$, $1\times10^8$, $1\times10^9$, $1\times10^{10}$ or more different scFvs. In some embodiments, other types of binding domains such as Ig heavy chain only, VHH antibodies (also known as Nanobodies), or engineered fibronectin domains can be used to generate the vector library. The vector can include plasmid barcodes for use in tracking individual clones. The vector library is used to make lentiviral preparations for transduction, generating a viral library. In some embodiments, other vectors, such as retroviral vector or transposons can be used to generate a vector library.

In an exemplary embodiment, the lentiviral preparation (e.g., viral library) is used to infect the Nur77-tdTomato Jurkat reporter cells at a low multiplicity of infection (MOI) to ensure single copy transduction, to generate a plurality of cells, e.g., a library of cells, each expressing a candidate CAR. In some embodiments, the vector library can be introduced into the reporter cells by electroporation. High throughput sequencing can be utilized to determine the diversity and frequency of scFv sequences that are represented at each step. The number of individual clones is adjusted at both the vector library generation and the cell library generation steps to ensure complete library representation and to avoid loss of clones.

In an exemplary embodiment, cells in the cell library can be subject to selection at a low concentration of puromycin to enrich for infected cells and eliminate cells containing CARs that are expressed at a very low level or exhibit poor stability. For CARs recognizing a soluble protein antigen, the library of candidate CAR-expressing cells can be selected using biotinylated antigen and immobilized streptavidin or anti-biotin magnetic columns. Candidate CAR-expressing cells can also be labeled with a fluorescent antigen conjugate and sorted by flow cytometry, selecting for CAR-expressing cells containing CARs that bind to the antigen.

In some embodiments, candidate CAR-expressing cells are assessed for expression and/or functional characteristics. In an exemplary embodiment, the cells can be assessed for expression of the CAR and antigen binding, e.g., using anti-idiotypic antibodies specific for a particular scFv or recombinant antigen that can be detected, e.g., fluorescently labeled CD19 or BCMA-Fc. The cells can be assessed for tdTomato expression from the Nur77-tdTomato reporter by flow cytometry in response to immobilized antigen or co-culture with antigen-expressing target cells, thereby selecting for functional CARs. In some embodiments, a library of anti-CD19 CAR-expressing cells can be co-cultured with target cells expressing the CD19 antigen and tdTomato expression can be detected by flow cytometry. In some embodiments, other cell phenotypes can be determined, such as expression of the T-cell activation marker CD69, using anti-CD69 antibodies by flow cytometry. In some embodiments, the cell library can be screened for properties, including CAR surface expression, antigen-specific activation, stability of CAR expression, antigen-independent activity and/or tonic signaling and binding affinity.

In some embodiments, the cells can be subject to enrichment by magnetic selection for binding to specific antigens, followed by fluorescence activated cell sorting (FACS) to isolate a particular population. In some embodiments, the cells can be subject to enrichment by magnetic selection for binding to specific antigens, followed by co-culture with antigen expressing target cells to assess Nur77 -tdTomato reporter expression. In some embodiments, cells can be enriched by co-culture with antigen-expressing cells and sorted based on tdTomato expression, using FACS.

In some embodiments, the library of candidate CAR-expressing cells is selected or screened to identify and select out cells that exhibit high levels of antigen-independent activity and/or tonic signaling. In some embodiments, certain CARs can exhibit high tonic signaling, which can lead to loss of cells over time, by cell death or slowed growth. Candidate CARs that exhibit high tonic signaling can be selected out using methods such as puromycin selection, fluorescence based cell sorting (FACS)-based selection, growth selection or bioinformatics analysis. Puromycin treatment can be used to select for CARs with higher expression and can favor CARs with low to no tonic signaling, as poor CAR expression are observed to be associated with high tonic signaling in some embodiments. Cells expressing high levels of CAR can also be selected using FACS, based on high CAR expression or high surrogate marker expression.

In an exemplary embodiment, cells exhibiting high tonic signaling can also be selected out by subjecting cells to a growth selection. Cells that express a candidate CAR that exhibits high tonic signaling can grow more slowly or die during prolonged culture. The library of cells can be subject to expansion and extended growth (e.g., 7 to 10 days), whereby the cells in the library that have high tonic signaling are outcompeted. The library of candidate CAR-expressing reporter cells can also be sorted by FACS based on expression of the Nur77-tdTomato reporter without incubation with antigen to isolate cells with high and low tonic signaling; and after incubation with antigen or antigen-expressing target cells to isolate cells with high and low antigen-specific signaling.

In some embodiments, the library of transduced cells are screened for properties, including CAR surface expression, antigen-specific activation, stability of CAR expression, tonic signaling and antigen affinity. In some embodiments, cells expressing candidate CARs that exhibit one or more desired characteristics, such as high and stable CAR expression, strong on-target activity and/or low antigen-independent activity and/or tonic signaling, are identified. In an exemplary embodiment, the scFv sequence can be determined using traditional sequencing or high-throughput sequencing. In some embodiments, candidate CARs that exhibit high and stable CAR surface expression, high antigen-specific activation, low tonic signaling and/or high antigen affinity, can be selected or identified. Any of the assessment and/or selection steps can be used alone or in combination, depending on the desired properties and/or specific characteristics of the expressed CARs. Cells may also be assessed after incubation with a different and/or related antigen, e.g., antigen from a different species, to assess potential off-target effects and potential cross-reactivity.

In an exemplary embodiment, high throughput sequencing can be utilized to determine scFv sequence diversity and frequency at each step. In some embodiments, using the sequence information and bioinformatics analysis, CARs that exhibit antigen-specific signaling without substantial tonic signaling can be identified. At any or all of the steps of in the screening process, such as the binding domain (e.g., scFv) library, vector library, viral library, cell library stage and/or in particular selected and/or isolated populations, the nucleic acid sequences, e.g., nucleic acid sequences encoding the scFv, of the library and/or population of cells can be determined by high-throughput sequencing, to determine clonal diversity, library representation and clone enrichment. In some embodiments, a large library can be screened using the methods described to identify a smaller subset or a number of individual clones that exhibit desired expression and/or functional properties (FIG. 11A). In some embodiments, the smaller subset or individual clones can be assessed, for example, after changing the order of the chains and/or using different spacer lengths, by employing the methods described, e.g., using the vectors, reporter cells, assessment and/or selection steps (FIG. 11B).

In some cases, the identified candidate CARs can be introduced into primary T cells isolated from a human donor and tested for surface expression and/or one or more functional activities of the T cells expressing the CAR, such as antigen binding, cytolytic activity, cytokine production and cell proliferation.

V. ARTICLES OF MANUFACTURE AND KITS

Also provided are articles of manufacture, systems, apparatuses, and kits useful in performing the provided methods. Also provided are articles of articles of manufacture, systems, apparatuses, and kits that contain the provided reporter T cells and/or vector backbones. In some embodiments, the provided articles of manufacture or kits contain reporter T cells and/or vector backbones for insertion of the nucleic acid sequences encoding candidate binding domains, e.g., to generate recombinant receptors. In some embodiments, the articles of manufacture or kits can be used in methods of generating a plurality of polynucleotides and/or reporter T cells, e.g., encoding a plurality of candidate recombinant receptors. In some embodiments, the articles of manufacture or kits provided herein contain T cells, T cell lines and/or a plurality of T cells, such as reporter T cells, described herein.

In some embodiments, the articles of manufacture or kits provided herein contain T cells, T cell lines and/or plurality of T cells, such as any reporter T cells, reporter T cell lines and/or a plurality of reporter T cells described herein. In some embodiments, the T cells, reporter T cell lines and/or a plurality of reporter T cells or any of the modified T cells provided in the articles and/or kits can be used in accordance with used the screening methods described herein. In some embodiments, the articles of manufacture or kits provided herein contain control T cells, reporter T cell lines and/or a plurality of reporter T cells. In some embodiments, the articles of manufacture or kits include one or more reporter T cells, e.g., reporter T cells that contain a reporter molecule, wherein the expression of said reporter molecule is responsive to a signal through the intracellular signaling region. In some embodiments, the articles of manufacture or kits include one or a plurality of reporter T cells, e.g., reporter T cells that contain a reporter molecule and a recombinant receptor, e.g., one of a plurality of recombinant receptors.

In some embodiments, the articles of manufacture or kits include vector backbones useful in performing the provided methods, such as any of the vector backbones described herein. In some embodiments, the vector backbones include nucleic acid sequences encoding binding domains as part of the plasmid or backbone in the articles of manufacture provided herein. In some embodiments, the articles of manufacture or kits provided herein contain control vector backbones.

In some embodiments, the articles of manufacture or kits include one or more components for insertion of nucleic acid sequences encoding the candidate binding domains and/or recombinant receptors into the vector backbone, such as those components for molecular cloning, e.g., restriction enzymes, and/or an in vitro nucleic acid assembly. In some embodiments, the in vitro nucleic acid assembly is Gibson Assembly®. In some embodiments, the articles or manufacture or kits include restriction enzymes, an exonuclease, a polymerase and a ligase, e.g., a DNA exonuclease, a DNA polymerase and/or a DNA ligase.

In some embodiments, the articles of manufacture or kits include one or more components used to assess the properties of the cells expressing the recombinant receptors and/or the recombinant receptors. For example, the articles of manufacture or kits can include binding reagents, e.g., antibodies, antigen-binding fragments thereof, purified or isolated antigen or fragments thereof and/or probes, used to assess particular properties of the introduced candidate recombinant receptors, e.g., cell surface expression of the candidate recombinant receptors, and/or detectable signal produced by the reporter molecule in the reporter T cell, e.g., a Nur77 reporter. In some embodiments, the articles of manufacture or kits can include components that are used for detection of particular properties, such as labeled components, e.g., fluorescently labeled components and/or components that can produce a detectable signal, e.g., substrates that can produce fluorescence or luminescence.

In some embodiments, the articles of manufacture or kits include one or more containers, typically a plurality of containers, packaging material, and a label or package insert on or associated with the container or containers and/or packaging, generally including instructions for use, e.g., instructions for nucleic acid assembly and/or introduction of the assembled nucleic acid molecules or sets of nucleic acid molecules into of cells, such as transfection or transduction of cells used in the provided methods, such as T cells, T cell lines and/or plurality of T cells. In some embodiments, the articles of manufacture and kits include components and/or containers that facilitate high-throughput or large-scale assembly and/or screening. In some embodiments, the articles of manufacture and kits can include high-throughput or large-scale format containers, e.g., multi-well specimen plates, such as a 96-well plate or a 384-well plate.

The articles of manufacture provided herein contain packaging materials. Packaging materials for use in packaging the provided materials are well known to those of skill in the art. See, for example, U.S. Pat. Nos. 5,323,907, 5,052,558 and 5,033,252, each of which is incorporated herein in its entirety. Examples of packaging materials include, but are not limited to, blister packs, bottles, tubes, inhalers, pumps, bags, vials, containers, syringes, disposable laboratory supplies, e.g., pipette tips and/or plastic plates, or bottles. The articles of manufacture or kits can include a device so as to facilitate dispensing of the materials or to facilitate use in a high-throughput or large-scale manner, e.g., to facilitate use in robotic equipment. Typically, the packaging is non-reactive with the compositions contained therein.

In some embodiments, the T cells, T cell lines and/or plurality of T cells, the vector backbone and/or the one or more components for generation of polynucleotides and/or cells or plurality of polynucleotides and/or cells are packaged separately. In some embodiments, each container can have a single compartment. In some embodiments, other components of the articles of manufacture or kits are packaged separately, or together in a single compartment.

VI. DEFINITIONS

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

The terms "polypeptide" and "protein" are used interchangeably to refer to a polymer of amino acid residues, and are not limited to a minimum length. Polypeptides, including the provided antibodies and antibody chains and other peptides, e.g., linkers, may include amino acid residues including natural and/or non-natural amino acid residues. The terms also include post-expression modifications of the polypeptide, for example, glycosylation, sialylation, acetylation, phosphorylation, and the like. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As used herein, "percent (%) amino acid sequence identity" and "percent identity" when used with respect to an amino acid sequence (reference polypeptide sequence) is defined as the percentage of amino acid residues in a candidate sequence (e.g., the subject antibody or fragment) that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

An amino acid substitution may include replacement of one amino acid in a polypeptide with another amino acid. The substitution may be a conservative amino acid substitution or a non-conservative amino acid substitution. Amino acid substitutions may be introduced into a binding molecule, e.g., antibody, of interest and the products screened for a desired activity, e.g., retained/improved antigen binding, decreased immunogenicity, or improved ADCC or CDC.

Amino acids generally can be grouped according to the following common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

In some embodiments, conservative substitutions can involve the exchange of a member of one of these classes for another member of the same class. In some embodiments, non-conservative amino acid substitutions can involve exchanging a member of one of these classes for another class.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

As used herein, a composition refers to any mixture of two or more products, substances, or compounds, including cells. It may be a solution, a suspension, liquid, powder, a paste, aqueous, non-aqueous or any combination thereof.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

VII. EXEMPLARY EMBODIMENTS

Among the provided embodiments are:

1. A reporter T cell, comprising a nucleic acid sequence encoding a reporter molecule operably linked to a transcriptional regulatory element of the endogenous locus encoding Nur77.

2. The reporter T cell of embodiment 1, further comprising a recombinant receptor, optionally a chimeric antigen receptor (CAR).

3. The reporter T cell of any of embodiments 1-2, wherein the transcriptional regulatory element is a promoter, an enhancer or a response element or a portion thereof.

4. The reporter T cell of any of embodiments 1-3, wherein the nucleic acid sequence encoding the reporter molecule is integrated at or near the endogenous locus encoding Nur77.

5. The reporter T cell of any of embodiments 1-4, wherein the nucleic acid sequence encoding the reporter molecule is targeted for integration by
   a) inducing a genetic disruption at one or more target site(s) at or near the endogenous locus encoding Nur77; and
   b) introducing a template polynucleotide for homology directed repair (HDR).

6. The reporter T cell of embodiment 5, wherein the genetic disruption is induced by a DNA binding protein or DNA-binding nucleic acid that specifically binds to or hybridizes to the target site, optionally a fusion protein comprising a DNA-targeting protein and a nuclease or an RNA-guided nuclease.

7. The reporter T cell of embodiment 6, wherein the fusion protein comprising a DNA-targeting protein and a nuclease or the RNA-guided nuclease is or comprises a zinc finger nuclease (ZFN), a TAL-effector nuclease (TALEN), or a CRISPR-Cas9 combination that specifically binds to, recognizes, or hybridizes to the target site.

8. The reporter T cell of embodiment 6 or embodiment 7, wherein the RNA-guided nuclease comprises a guide RNA (gRNA) having a targeting domain that is complementary to the target site.

9. The reporter T cell of any of embodiments 5-8, wherein the target site is at or near the final exon of the endogenous locus encoding Nur77.

10. The reporter T cell of any of embodiments 5-9, wherein the one or more target site(s) comprise the nucleic acid sequence TCATTGACAAGATCTTCATG (SEQ ID NO:65) and/or GCCTGGGAACACGTGTGCA (SEQ ID NO:66).

11. The reporter T cell of any of embodiments 5-10, wherein the template polynucleotide comprises the structure [5' homology arm]-[nucleic acid sequence encoding the reporter molecule]-[3' homology arm].

12. The reporter T cell of embodiment 11, wherein the 5' homology arm and/or 3' homology arm comprises nucleic acid sequences homologous to nucleic acid sequences present at and/or surrounding the one or more target site(s).

13. The reporter T cell of embodiment 11 or embodiment 12, wherein the 5' homology arm comprises nucleic acid sequences that are homologous to nucleic acid sequences 5' of the one or more target site(s).

14. The reporter T cell of any of embodiments 11-13, wherein the 3' homology arm comprises nucleic acid sequences that are homologous to nucleic acid sequences 3' of the one or more target site(s).

15. The reporter T cell of any of embodiments 11-14, wherein the 5' homology arm and 3' homology arm independently is between about 50 and 100, 100 and 250, 250 and 500, 500 and 750, 750 and 1000, 1000 and 2000 base pairs in length.

16. The reporter T cell of any of embodiments 11-15, wherein the nucleic acid sequence encoding the reporter molecule is targeted for integration in-frame with the endogenous Nur77 coding sequence, optionally separated by a nucleic acid sequence encoding a ribosome skip element selected from among a T2A, a P2A, a E2A or a F2A.

17. The reporter T cell of any of embodiments 1-16, wherein the reporter molecule is or comprises a fluorescent protein, a luciferase, a β-galactosidase, a chloramphenicol acetyltransferase (CAT), a β-glucuronidase (GUS), or a modified form thereof.

18. The reporter T cell of any of embodiments 1-17, wherein the reporter molecule comprises a fluorescent protein, optionally a red fluorescent protein, optionally tdTomato.

19. The reporter T cell of any of embodiments 1-18, wherein the reporter molecule comprises the sequence of amino acids set forth in SEQ ID NO:8 or 54, or a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NO: 8 or 54.

20. The reporter T cell of any of embodiments 1-19, wherein the T cell is an immortalized cell line.

21. The reporter T cell of any of embodiments 1-20, wherein the T cell line is a Jurkat cell line or a derivative thereof, optionally Jurkat T cell clone E6-1.

22. A plurality of reporter T cells, comprising one or more of the reporter T cells of any of embodiments 1-21.

23. A method for assessing activity of a recombinant receptor, comprising:

a) incubating one or more of the reporter T cells of any of embodiments 2-21 or the plurality of reporter T cells of embodiment 22, each of said reporter T cells comprising a recombinant receptor, wherein the incubating is carried out in the presence or absence of an agent that binds to the binding domain of the recombinant receptor and/or an agent that induces or is capable of inducing a signal through the intracellular signaling region of the recombinant receptor; and b) assessing the one or more reporter T cells for expression of the reporter molecule.

24. The method of embodiment 19, wherein the recombinant receptor is a chimeric antigen receptor (CAR).

25. A method for assessing activity of a recombinant receptor that is a chimeric antigen receptor (CAR), comprising a) incubating one or more reporter T cells each comprising i) a recombinant receptor that is a CAR comprising an intracellular signaling region and ii) a reporter molecule, wherein the expression of said reporter molecule is responsive to a signal through the intracellular signaling region of the recombinant receptor, wherein the incubating is carried out in the presence or absence of an agent that binds to the binding domain of the recombinant receptor and/or an agent that induces or is capable of inducing a signal through the intracellular signaling region of the recombinant receptor; and b) assessing the one or more reporter T cells for expression of the reporter molecule.

26. The method of any of embodiments 23-25, wherein the one or more reporter T cells comprises a plurality of reporter T cells.

27. The method of embodiment 26, wherein the recombinant receptor present in the one or more reporter T cell is distinct from the recombinant receptor present in at least one of the other reporter T cells in the plurality.

28. A method of generating a plurality of reporter T cells, comprising:

a) producing a plurality of polynucleotides each encoding a recombinant receptor, wherein each polynucleotide comprises i) a vector backbone comprising a nucleic acid sequence encoding an intracellular signaling region and ii) a nucleic acid sequence encoding a binding domain; and b) introducing one of the plurality of polynucleotides encoding a recombinant receptor into a reporter T cell comprising a reporter molecule, wherein the expression of said reporter molecule is responsive to a signal through the intracellular signaling region, and the encoded recombinant receptor present in the reporter T cell is distinct from the encoded recombinant receptor present in at least one of the other reporter T cells in the plurality.

29. A method for assessing activity of a recombinant receptor, comprising a) incubating one or more reporter T cells from the plurality of reporter T cells of embodiment 28 in the presence or absence of an agent that binds to the binding domain of the recombinant receptor and/or an agent that induces or is capable of inducing a signal through an intracellular signaling region of the recombinant receptor; and b) assessing the one or more reporter T cells for expression of the reporter molecule.

30. The method of any of embodiments 23-29, wherein the agent comprises a target antigen or epitope specifically recognized by the recombinant receptor.

31. The method of any of embodiments 23-30, wherein incubating is carried out in the absence of the agent, thereby assessing tonic signaling and/or antigen independent activity of the recombinant receptor.

32. The method of any of embodiments 23-31, wherein incubating is carried out in the presence of the agent, thereby assessing antigen-specific activity of the recombinant receptor.

33. The method of any of embodiments 23-32, further comprising assessing expression of the recombinant receptor on the surface of the cell.

34. The method of any of embodiments 23-33, further comprising identifying one or more reporter T cells among the plurality that express the recombinant receptor on the surface of the cell, express the reporter molecule in the presence of the agent and/or do not express the reporter molecule in the absence of the agent.

35. A method for screening recombinant receptors, comprising:

a) producing a plurality of polynucleotides each encoding a recombinant receptor that is a chimeric antigen receptor (CAR), wherein each polynucleotide comprises i) a vector backbone comprising a nucleic acid sequence encoding an intracellular signaling region and ii) a nucleic acid sequence encoding a binding domain;

b) introducing one of the plurality of polynucleotides encoding a recombinant receptor into a reporter T cell comprising a reporter molecule, wherein the expression of said reporter molecule is responsive to a signal through the intracellular signaling region, and the encoded recombinant receptor present in the reporter T cell is distinct from the encoded recombinant receptor present in at least one of the other reporter T cells in the plurality;

c) incubating one or more reporter T cells from the plurality of reporter T cells in the presence or absence of an agent that binds to the binding domain of the recombinant receptor and/or an agent that induces or is capable of inducing a signal through an intracellular signaling region of the recombinant receptor;

d) assessing the one or more reporter T cells for expression of the reporter molecule and/or expression of the recombinant receptor on the surface of the cell; and e) identifying one or more reporter T cells among the plurality that express the recombinant receptor on the surface of the cell, express the reporter molecule in the presence of the agent and/or do not express the reporter molecule in the absence of the agent.

36. The method of embodiment 35, wherein the agent comprises a target antigen or epitope specifically recognized by the recombinant receptor.

37. The method of embodiment 35 or embodiment 36, wherein incubating is carried out in the absence of the agent, thereby assessing tonic signaling and/or antigen independent activity of the recombinant receptor.

38. The method of any of embodiments 35-37, wherein incubating is carried out in the presence of the agent, thereby assessing antigen-specific activity of the recombinant receptor.

39. The method of any of embodiments 25-38, wherein the intracellular signaling region comprises an intracellular signaling domain.

40. The method cell of embodiment 39, wherein the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM).

41. The method of embodiment 40, wherein the intracellular signaling domain is or comprises an intracellular signaling domain of a CD3 chain, optionally a CD3-zeta (CD3ζ) chain, or a signaling portion thereof.

42. The method of any of embodiments 25-41, wherein the intracellular signaling region further comprises a costimulatory signaling region.

43. The method of embodiment 42, wherein the costimulatory signaling region comprises an intracellular signaling domain of a T cell costimulatory molecule or a signaling portion thereof.

44. The method of embodiment 42 or embodiment 43, wherein the costimulatory signaling region comprises an intracellular signaling domain of a CD28, a 4-1BB or an ICOS or a signaling portion thereof.

45. The method of any of embodiments 25-44, wherein the reporter molecule is encoded by a nucleic acid sequence under the operable control of a regulatory element that is responsive to the quality and/or strength of the signal through the intracellular signaling region and/or binding and/or recognition of the recombinant receptor to a target antigen or epitope.

46. The method of embodiment 45, wherein the regulatory element is or comprises a transcriptional regulatory element, optionally promoter, an enhancer or a response element or a portion thereof.

47. The method of embodiment 45 or embodiment 46, wherein the regulatory element is or comprises a transcriptional regulatory element of a gene whose expression is induced and/or is upregulated upon signal through the intracellular signaling region of the recombinant receptor and/or binding and/or recognition of the recombinant receptor to a target antigen or epitope.

48. The method of embodiment 47, wherein the gene is Nur77 and the regulatory element is or comprises a transcriptional regulatory element of the Nur77 gene.

49. The method of embodiment 48, wherein the transcriptional regulatory element comprises the Nur77 promoter or portion thereof containing a response element or elements recognized by a transcription factor.

50. The method of any of embodiments 45-49, wherein the regulatory element comprises a response element or elements recognized by a transcription factor that is activated upon signal through the intracellular signaling region and/or binding and/or recognition of the recombinant receptor to a target antigen or epitope, optionally comprising an immunoreceptor tyrosine-based activation motif (ITAM).

51. The method of embodiment 50, wherein the transcription factor is selected from among NFAT family transcription factors or NFκB family of transcription factors.

52. The method of embodiment 50 or embodiment 51, wherein the transcription factor is NFAT or NFκB.

53. The method of any of embodiments 25-52, wherein the regulatory element is a transcriptional regulatory element of the endogenous locus encoding Nur77, optionally a promoter, an enhancer or a response element of the endogenous locus encoding Nur77.

54. The method of any of embodiments 25-53, wherein the nucleic acid sequence encoding the reporter molecule is integrated at or near the endogenous locus encoding Nur77.

55. The method of any of embodiments 1-54, wherein the nucleic acid sequence encoding the reporter molecule is targeted for integration by a) inducing a genetic disruption at one or more target site(s) at or near the endogenous locus encoding Nur77; and b) introducing a template polynucleotide for homology directed repair (HDR).

56. The method of embodiment 55, wherein the genetic disruption is induced by a DNA binding protein or DNA-binding nucleic acid that specifically binds to or hybridizes to the target site, optionally a fusion protein comprising a DNA-targeting protein and a nuclease or an RNA-guided nuclease.

57. The method of embodiment 56, wherein the fusion protein comprising a DNA-targeting protein and a nuclease or the RNA-guided nuclease is or comprises a zinc finger nuclease (ZFN), a TAL-effector nuclease (TALEN), or a CRISPR-Cas9 combination that specifically binds to, recognizes, or hybridizes to the target site.

58. The method of embodiment 56 or embodiment 57, wherein the RNA-guided nuclease comprises a guide RNA (gRNA) having a targeting domain that is complementary to the target site.

59. The method of any of embodiments 55-58, wherein the target site is at or near the final exon of the endogenous locus encoding Nur77.

60. The method of any of embodiments 55-59, wherein the one or more target site(s) comprise the nucleic acid sequence TCATTGACAAGATCTTCATG (SEQ ID NO:65) and/or GCCTGGGAACACGTGTGCA (SEQ ID NO:66).

61. The method of any of embodiments 55-60, wherein the template polynucleotide comprises the structure [5' homology arm]-[nucleic acid sequence encoding the reporter molecule]-[3' homology arm].

62. The method of embodiment 61, wherein the 5' homology arm and/or 3' homology arm comprises nucleic acid sequences homologous to nucleic acid sequences present at and/or surrounding the one or more target site(s).

63. The method of embodiment 61 or embodiment 62, wherein the 5' homology arm comprises nucleic acid sequences that are homologous to nucleic acid sequences 5' of the one or more target site(s).

64. The method of any of embodiments 61-63, wherein the 3' homology arm comprises nucleic acid sequences that are homologous to nucleic acid sequences 3' of the one or more target site(s).

65. The method of any of embodiments 61-64, wherein the 5' homology arm and 3' homology arm independently is between about 50 and 100, 100 and 250, 250 and 500, 500 and 750, 750 and 1000, 1000 and 2000 base pairs in length.

66. The method of any of embodiments 61-65, wherein the nucleic acid sequence encoding the reporter molecule is targeted for integration in-frame with the endogenous Nur77 coding sequence, optionally separated by a nucleic acid sequence encoding a ribosome skip element selected from among a T2A, a P2A, a E2A or a F2A.

67. The method of any of embodiments 1-66, wherein the reporter molecule is or comprises a fluorescent protein, a luciferase, a β-galactosidase, a chloramphenicol acetyltransferase (CAT), a (3-glucuronidase (GUS), or a modified form thereof.

68. The method of any of embodiments 1-67, wherein the reporter molecule comprises a fluorescent protein, optionally a red fluorescent protein, optionally tdTomato.

69. The method of any of embodiments 1-68, wherein the reporter molecule comprises the sequence of amino acids set forth in SEQ ID NO:8 or 54, or a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NO: 8 or 54.

70. The method of any of embodiments 28-69, wherein the polynucleotide encoding the recombinant receptor comprises a vector backbone.

71. The method of embodiment 70, wherein the vector backbone comprises a nucleic acid sequence encoding the intracellular signaling region.

72. The method of embodiment 71, wherein the encoded intracellular signaling region comprises an intracellular signaling domain.

73. The method cell of embodiment 72, wherein the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM).

74. The method of embodiment 73, wherein the intracellular signaling domain is or comprises an intracellular signaling domain of a CD3 chain, optionally a CD3-zeta (CD3ζ) chain, or a signaling portion thereof.

75. The method of any of embodiments 70-74, wherein the vector backbone further comprises one or more site(s) for introduction of a nucleic acid sequence encoding a binding domain.

76. The method of embodiment 75, wherein the one or more site(s) for introduction of a nucleic acid sequence encoding a binding domain comprises a restriction site.

77. The method of embodiment 76, wherein the restriction site is a restriction site that does not occur or occurs 1, 2 or 3 or fewer times within an endogenous human $V_H$ or $V_L$ gene.

78. The method of any of embodiments 70-77, wherein the vector backbone further comprises a nucleic acid sequence encoding a transmembrane domain disposed between the one or more site(s) for introduction of a nucleic acid sequence encoding a binding domain and the nucleic acid sequence encoding the intracellular signaling region.

79. The method of any of embodiments 70-78, wherein the encoded intracellular signaling region further comprises a costimulatory signaling region.

80. The method of embodiment 79, wherein the costimulatory signaling region comprises an intracellular signaling domain of a T cell costimulatory molecule or a signaling portion thereof.

81. The method of embodiment 79 or embodiment 80, wherein the costimulatory signaling region comprises an intracellular signaling domain of a CD28, a 4-1BB or an ICOS or a signaling portion thereof.

82. The method of any of embodiments 79-81, wherein the costimulatory signaling region is between the transmembrane domain and the intracellular signaling region.

83. The method of any of embodiments 70-82, wherein the vector backbone further comprises a nucleic acid sequence encoding a leader sequence.

84. The method of embodiment 83, wherein the leader sequence is derived from the leader sequence of human CD33.

85. The method of embodiment 83 or embodiment 84, wherein the nucleic acid sequences encoding the leader sequence comprises a molecular barcode.

86. The method of embodiment 85, wherein each molecular barcode is distinct from at least one of the molecular barcodes present in the plurality of polynucleotides.

87. The method of embodiment 85 or embodiment 86, wherein the molecular barcode comprises the sequence GCTBTGGGCHGGNGC (SEQ ID NO:14), wherein B=C or G or T; H=A or C or T; and N=A or C or G or T.

88. The method of any of embodiments 70-87, wherein the vector backbone further comprises regulatory elements for expression of components of the recombinant receptor.

89. The method of embodiment 88, wherein the regulatory element for expression is a promoter.

90. The method of embodiment 89, wherein the promoter is selected from among an RNA pol I, pol II or pol III promoter.

91. The method of embodiment 89 or 90, wherein the promoter is selected from:

a pol III promoter that is a U6 or H1 promoter; or a pol II promoter that is a CMV, SV40 early region or adenovirus major late promoter.

92. The method of any of embodiments 89-91, wherein the promoter is or comprises a human elongation factor 1 alpha (EF1a) promoter or an MND promoter or a modified form thereof.

93. The method of any of embodiments 89-91, wherein the promoter is an inducible promoter or a repressible promoter.

94. The method of embodiment 93, wherein the promoter comprises a Lac operator sequence, a tetracycline operator sequence, a galactose operator sequence or a doxycycline operator sequence, or is an analog thereof or is capable of being bound by or recognized by a Lac repressor or a tetracycline repressor, or an analog thereof.

95. The method of embodiment 94, wherein the promoter comprises a Lac operator sequence, a tetracycline operator sequence, a galactose operator sequence or a doxycycline operator sequence.

96. The method of any of embodiments 70-95, wherein the vector backbone further comprises a nucleic acid sequence encoding a spacer and/or a hinge region.

97. The method of embodiment 96, wherein the encoded spacer is derived from an immunoglobulin or a portion thereof.

98. The method of embodiment 96 or embodiment 90, wherein the encoded spacer is derived from a hinge of IgG4 or IgG1, a hinge of IgG4 linked to a $C_H3$ domain, or a hinge of IgG4 linked to a $C_H2$ and $C_H3$ domains.

99. The method of any of embodiments 96-98, wherein the encoded spacer comprises the sequence of amino acids set forth in SEQ ID NO: 20, 22 or 24, or a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NO: 20, 22 or 24.

100. The method of any of embodiments 70-99, wherein the vector further comprises a nucleic acid sequence encoding one or more marker(s), that optionally is or comprises a transduction marker and/or a selection marker.

101. The method of embodiment 100, wherein the transduction marker comprises a fluorescent protein, a cell surface protein or a modified form thereof.

102. The method of embodiment 101, wherein the selection marker comprises a Puromycin resistance gene, a Hygromycin resistance gene, a Blasticidin resistance gene, a Neomycin resistance gene, a Geneticin resistance gene or a Zeocin resistance gene or a modified form thereof.

103. The method of any of embodiments 70-102, wherein the vector backbone further comprises a nucleic acid sequence encoding an internal ribosome entry site (IRES) or a ribosome skip element selected from among a T2A, a P2A, a E2A or a F2A separating the nucleic acid sequences encoding one or more components of the recombinant receptor and/or markers.

104. The method of any of embodiments 70-103, wherein the vector backbone is capable of accepting an insert comprising nucleic acid sequences encoding one of a plurality of binding domains.

105. The method of embodiment 104, wherein the binding domain is or comprises an antibody or an antibody fragment thereof, which optionally is a single chain fragment.

106. The method of embodiment 105, wherein the fragment comprises antibody variable regions joined by a flexible linker.

107. The method of embodiment 105 or embodiment 106, wherein the fragment comprises an scFv.

108. The method of any of embodiments 70-107, wherein the vector backbone is a viral vector.

109. The method of embodiment 108, wherein the viral vector is a retroviral vector.

110. The method of embodiments 108 or embodiment 109, wherein the viral vector is a lentiviral vector.

111. The method of embodiment 110, wherein the lentiviral vector is derived from HIV-1.

112. The method of any of embodiments 28-111, wherein the plurality of nucleic acid sequences encoding a binding domain comprises at least 2, 5, 10, 25, 50, 100, 500, $10^3$, $10^4$, $10^5$, $10^6$ or more different nucleic acid sequences.

113. The method of any of embodiments 28-112, wherein the plurality of polynucleotides encoding a recombinant receptor comprises at least 2, 5, 10, 25, 50, 100, 500, $10^3$, $10^4$, $10^5$, $10^6$ or more different polynucleotides.

114. The method of any of embodiments 25-113, wherein the T cell is an immortalized cell line.

115. The method of any of embodiments 25-114, wherein the T cell line is a Jurkat cell line or a derivative thereof, optionally Jurkat T cell clone E6-1.

116. A plurality of reporter T cells, comprising one or more of the reporter T cells generated by the method of any of embodiments 28-115.

117. A plurality of polynucleotides encoding a recombinant receptor, comprising one or more of the polynucleotides encoding a recombinant receptor assessed in the method of any of embodiments 25-115.

118. A reporter T cell, identified by the method of any of embodiments 34-115.

119. A polynucleotide encoding a recombinant receptor present in the reporter T cell identified by the method of any of embodiments 34-115.

120. A binding domain, encoded by the polynucleotide encoding the recombinant receptor present in the reporter T cell identified by the method of any of embodiments 34-115.

121. A recombinant receptor, encoded by the polynucleotide encoding the recombinant receptor present in the reporter T cell identified by the method of any of embodiments 34-115. 122.

A vector backbone, comprising a) regulatory elements for expression of components of a recombinant receptor, b) a nucleic acid sequence encoding a leader sequence comprising a molecular barcode, c) one or more site(s) for introduction of a nucleic acid sequence encoding a binding domain; d) a nucleic acid sequence encoding a spacer, e) a nucleic acid sequence encoding an intracellular signaling region, and optionally f) a nucleic acid sequence encoding one or more marker(s).

123. The vector backbone of embodiment 122 that is capable of accepting an insert comprising nucleic acid sequences encoding one of a plurality of binding domains.

124. The vector backbone of embodiment 122 or embodiment 123, wherein the binding domain is or comprises an antibody or an antibody fragment thereof, which optionally is a single chain fragment.

125. The vector backbone of embodiment 124, wherein the fragment comprises antibody variable regions joined by a flexible linker.

126. The vector backbone of embodiment 124 or embodiment 125, wherein the fragment comprises an scFv.

127. The vector backbone of any one of embodiments 122-126, wherein the regulatory element for expression is a promoter.

128. The vector backbone of embodiment 127, wherein the promoter is selected from among an RNA pol I, pol II or pol III promoter.

129. The vector backbone of embodiment 127 or 128, wherein the promoter is selected from:

a pol III promoter that is a U6 or H1 promoter; or a pol II promoter that is a CMV, SV40 early region or adenovirus major late promoter.

130. The vector backbone of any of embodiments 127-129, wherein the promoter is or comprises a human elongation factor 1 alpha (EF1α) promoter or an MND promoter or a modified form thereof.

131. The vector backbone of any of embodiments 127-129, wherein the promoter is an inducible promoter or a repressible promoter.

132. The vector backbone of embodiment 131, wherein the promoter comprises a Lac operator sequence, a tetracycline operator sequence, a galactose operator sequence or a doxycycline operator sequence, or is an analog thereof or is capable of being bound by or recognized by a Lac repressor or a tetracycline repressor, or an analog thereof.

133. The vector backbone of embodiment 132, wherein the promoter comprises a Lac operator sequence, a tetracycline operator sequence, a galactose operator sequence or a doxycycline operator sequence.

134. The vector backbone of any of embodiments 122-133, wherein the leader sequence is derived from the leader sequence of human CD33.

135. The vector backbone of any of embodiments 122-134, wherein the nucleic acid sequences encoding the leader sequence comprises a molecular barcode.

136. The vector backbone of embodiment 135, wherein each molecular barcode is distinct from at least one of the molecular barcodes present in the plurality of polynucleotides.

137. The vector backbone of embodiment 135 or embodiment 136, wherein the molecular barcode comprises the sequence GCTBTGGGCHGGNGC (SEQ ID NO:14), wherein B=C or G or T; H=A or C or T; and N=A or C or G or T.

138. The vector backbone of any of embodiments 122-137, wherein the one or more site(s) for introduction of a nucleic acid sequence encoding a binding domain comprises a restriction site.

139. The vector backbone of embodiment 138, wherein the restriction site is a restriction site that does not occur or occurs 1, 2 or 3 or fewer times within an endogenous human $V_H$ or $V_L$ gene.

140. The vector backbone of any of embodiments 122-139, wherein the encoded spacer is derived from an immunoglobulin or a portion thereof.

141. The vector backbone of any of embodiments 122-140, wherein the encoded spacer is derived from a hinge of IgG4 or IgG1, a hinge of IgG4 linked to a $C_H3$ domain, or a hinge of IgG4 linked to a $C_H2$ and $C_H3$ domains.

142. The vector backbone of any of embodiments 122-141, wherein the encoded spacer comprises the sequence of amino acids set forth in SEQ ID NO: 20, 22 or 24, or a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NO: 20, 22 or 24.

143. The vector backbone of any of embodiments 122-142, wherein the encoded intracellular signaling region comprises an intracellular signaling domain.

144. The vector backbone of any of embodiments 122-143, wherein the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM).

145. The vector backbone of embodiment 144, wherein the intracellular signaling domain is or comprises an intracellular signaling domain of a CD3 chain, optionally a CD3-zeta (CD3ζ) chain, or a signaling portion thereof.

146. The vector backbone of any of embodiments 122-145, further comprising a nucleic acid sequence encoding a transmembrane domain disposed between the one or more site(s) for introduction of a nucleic acid sequence encoding a binding domain and the nucleic acid sequence encoding the intracellular signaling region.

147. The vector backbone of any of embodiments 122-146, wherein the encoded intracellular signaling region further comprises a costimulatory signaling region.

148. The vector backbone of embodiment 147, wherein the costimulatory signaling region comprises an intracellular signaling domain of a T cell costimulatory molecule or a signaling portion thereof.

149. The vector backbone of embodiment 147 or embodiment 148, wherein the costimulatory signaling region comprises an intracellular signaling domain of a CD28, a 4-1BB or an ICOS or a signaling portion thereof.

150. The vector backbone of any of embodiments 147-149, wherein the costimulatory signaling region is between the transmembrane domain and the intracellular signaling region.

151. The vector backbone of any of embodiments 122-150, wherein the one or more marker(s) is or comprises a transduction marker and/or a selection marker.

152. The vector backbone of embodiment 151, wherein the transduction marker comprises a fluorescent protein, a cell surface protein or a modified form thereof.

153. The vector backbone of embodiment 152, wherein the selection marker comprises a Puromycin resistance gene, a Hygromycin resistance gene, a Blasticidin resistance gene, a Neomycin resistance gene, a Geneticin resistance gene or a Zeocin resistance gene or a modified form thereof.

154. The vector backbone of any of embodiments 122-153, wherein the vector backbone further comprises a nucleic acid sequence encoding an internal ribosome entry site (IRES) or a ribosome skip element selected from among a T2A, a P2A, a E2A or a F2A separating the nucleic acid sequences encoding one or more components of the recombinant receptor and/or markers.

155. The vector backbone of any of embodiments 122-154, that is a viral vector.

156. The vector backbone of embodiment 155, wherein the viral vector is a retroviral vector.

157. The vector backbone of embodiments 155 or embodiment 156, wherein the viral vector is a lentiviral vector.

158. The vector backbone of embodiment 157, wherein the lentiviral vector is derived from HIV-1.

159. A kit, comprising:

the reporter T cell of any of embodiments 1-22; and optionally instructions for use.

160. A kit, comprising:

the vector backbone of any of embodiments 122-158; and optionally instructions for use.

161. A kit, comprising:

the reporter T cell of any of embodiments 1-22;

the vector backbone of any of embodiments 122-158; and optionally instructions for use.

VIII. EXAMPLES

The following examples are included for illustrative purposes only and are not intended to limit the scope of the invention.

Example 1: Generation of Nur77-tdTomato Reporter Cell Line

An exemplary reporter cell line was generated containing a Nur77-tdTomato knock-in reporter. Orphan nuclear hormone receptor Nur77 (also called Nr4a1; exemplary human Nur77 DNA sequence set forth in SEQ ID NO:1, encoding the polypeptide set forth in SEQ ID NO:2) is an immediate-early response gene induced by activation of signal from the T cell receptor and/or via molecules containing immunoreceptor tyrosine-based activation motif (ITAM). A Jurkat T cell clone E6-1 (ATCC® TIB-152™) was engineered by co-transfection of a vector encoding a Nur77-targeting guide RNA (gRNA)/CRISPR-Cas9 (gRNA targeting domain sequences set forth in SEQ ID NOS: 3 and 4), and exemplary template DNA for knock-in of the tdTomato reporter by homology directed repair (HDR; template DNA sequence set forth in SEQ ID NO:51). The template DNA contained polynucleotides encoding a T2A ribosomal skip element (sequence set forth in SEQ ID NO:5, encoding polypeptide sequence set forth in SEQ ID NO: 6), and the tdTomato fluorescent protein (sequence set forth in SEQ ID NO:7; encoding polypeptide sequence set forth in SEQ ID NO:8), flanked on either side of the T2A and tdTomato coding sequences by the 5' homology arm (set forth in SEQ ID NO:49, containing 2 silent mutations to reduce cleavage of the template DNA by CRISPR/Cas9) and the 3' homology arm (set forth in SEQ ID NO:50), homologous to sequences surrounding the stop codon of the endogenous Nur77 gene. The T2A-tdTomato encoding sequences were targeted to be inserted in-frame with the endogenous Nur77 gene, prior to the stop codon.

Transfected cells were expanded, and then incubated with phorbol 12-myristate 13-acetate (PMA) and ionomycin for 6 hours and assessed for tdTomato expression, and cells that expressed tdTomato were sorted using flow cytometry. Knock-in at the Nur77 locus was confirmed by DNA sequencing. A schematic of an exemplary Nur77 reporter line and signaling components is shown in FIG. 12.

Isolated tdTomato$^+$ cells were assessed for response to PMA/ionomycin stimulation. Two exemplary clones were incubated with a three-fold serial dilution of PMA/ionomycin, at 80 nM PMA and 1.34 μM ionomycin (1× stim), and 3-fold (⅓× stim), 9-fold (1/9× stim) and 27-fold dilution (1/27× stim), compared to resting (no stimulation). As shown in FIG. 1, a dose-dependent increase in expression of tdTomato was observed with increasing PMA/ionomycin concentration. The results are consistent with the utility of the Nur77-tdTomato reporter in assessing dose-dependent stimulation of the reporter cells using PMA/ionomycin.

Example 2: Assessment of Nur77-tdTomato Reporter Signal in Reporter Cell Lines Expressing a Chimeric Antigen Receptor (CAR)

The exemplary Nur77-tdTomato reporter cell line was engineered to express various exemplary chimeric antigen receptors, and reporter expression was assessed.

A. Anti-CD19 CAR

A viral vector containing polynucleotides encoding exemplary anti-CD19 chimeric antigen receptors (CARs) were introduced into the Nur77-tdTomato reporter cell line generated as described in Example 1. The exemplary CARs included an anti-CD19 CARs specific to human CD19, containing either an FMC63-derived scFv (designated as anti-CD19 CAR #1; set forth in SEQ ID NO:61) or an SJ25C1-derived scFv (designated as anti-CD19 CAR #2; set forth in SEQ ID NO:64). Each CAR further contained a spacer, a CD28 transmembrane region, a 4-1BB-derived (anti-CD19 CAR #1) or CD28-derived (anti-CD19 CAR #2) intracellular domain and a CD3-zeta derived intracellular signaling region, separated by polynucleotides encoding a T2A ribosomal skip element, and a truncated receptor, which served as a surrogate marker for CAR expression.

1. Response to Anti-Idiotypic Antibody Stimulation

Reporter cells transduced with viral vector encoding anti-CD19 CAR #1 were incubated for 6 hours in 96-well cell culture plates coated overnight with increasing concentrations (0.008 μg/mL, 0.04 μg/mL, 0.2 μg/mL, 1 μg/mL and 5 μg/mL) of anti-idiotypic antibody agonist antibody specific for the FMC63-derived scFv antigen binding domain in the anti-CD19 CAR #1. Cells transduced to express anti-CD19 CAR #2, which contains a distinct SJ25C1-derived scFv, was used as control (Control). Reporter activation was assessed by detecting tdTomato expression by flow cytometry, and CAR expression was assessed by staining with an antibody specific to the truncated receptor to detect surrogate marker expression.

Figure 2A:
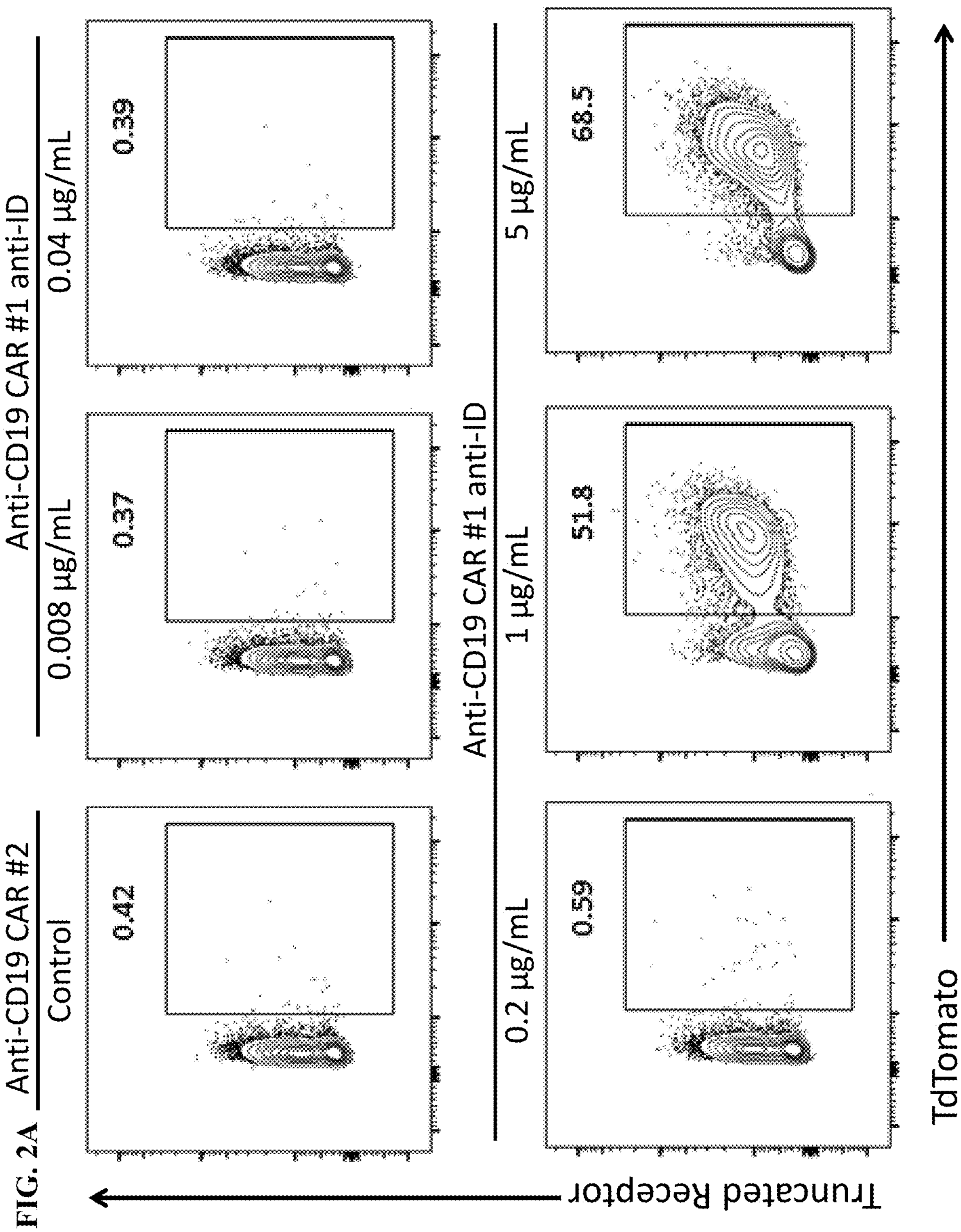
FIG. 2A depicts the expression level of tdTomato and a truncated receptor (surrogate marker for chimeric antigen receptor (CAR) expression), as detected by flow cytometry, in anti-CD19 CAR #1-expressing cells, incubated for 6 hours in 96-well cell culture plates coated overnight with increasing concentrations (0.008 μg/mL, 0.04 μg/mL, 0.2 μg/mL, 1 μg/mL and 5 μg/mL) of anti-idiotypic antibody agonist antibody specific for the FMC63-derived scFv antigen binding domain in the anti-CD19 CAR #1. Anti-CD19 CAR #2, which contains a distinct SJ25C1-derived scFv, was used as control (Control).

As shown in FIG. 2A, only reporter cells expressing the CAR (as determined by staining of the truncated receptor) exhibited tdTomato expression, indicating that the Nur77 reporter was cell intrinsic, induced only upon stimulation of an appropriate signal via the signaling regions of the CAR expressed in the cell. The results indicate that Nur77 reporter expression was induced in an antigen-specific manner via the CAR, as opposed to a non-specific signal, such as in response to a factor produced in response to CAR signaling and acting in trans in a non-specific manner. A dose-dependent increase in tdTomato expression was observed upon incubation with increasing concentrations of anti-idiotypic antibody.

2. Co-Culture with Target Cells

Figure 2B:
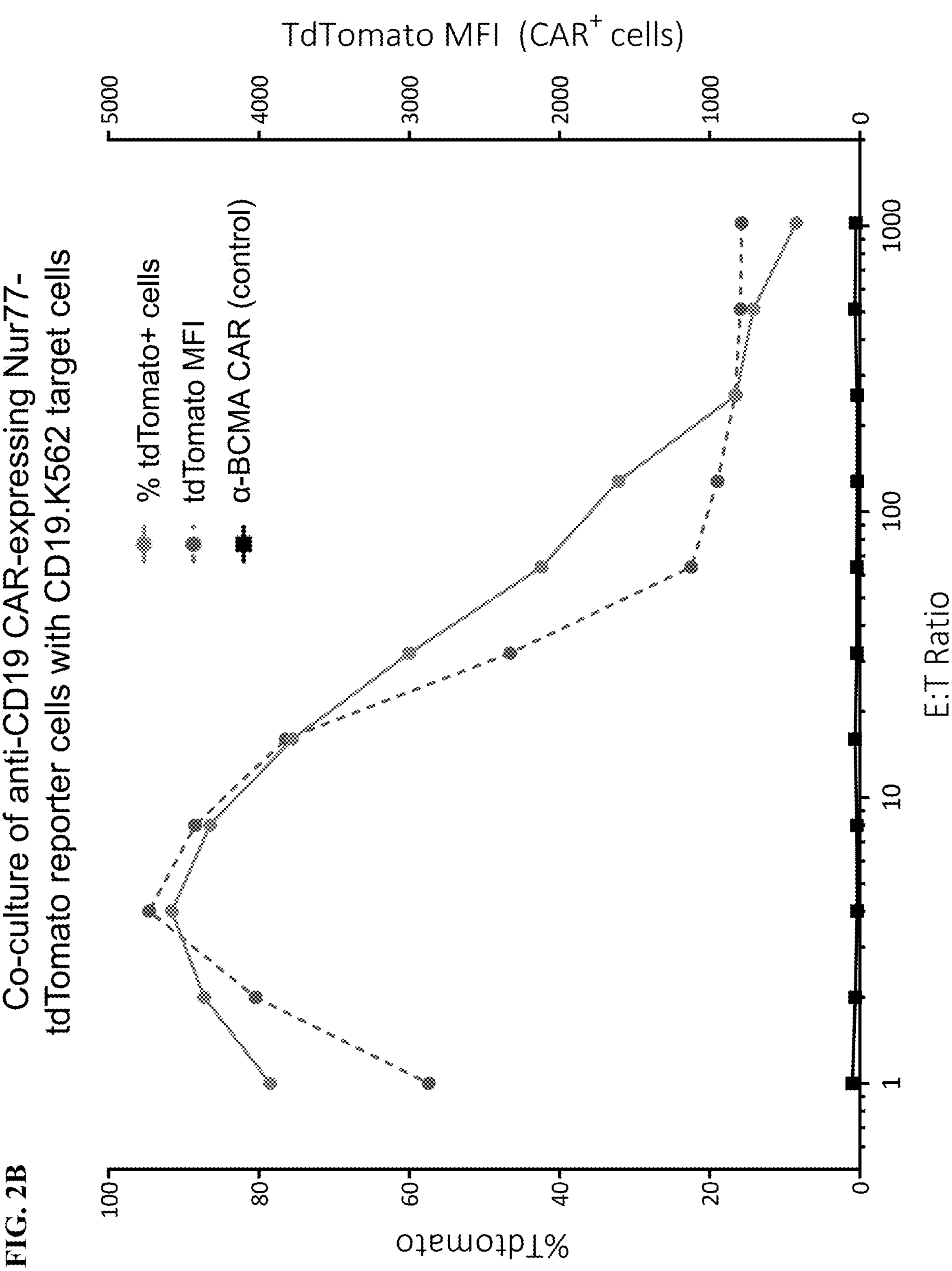
FIG. 2B depicts the percentage of tdTomato+ cells and mean fluorescence intensity (MFI) of tdTomato expression in reporter cells expressing anti-CD19 CAR #1, co-cultured with CD19-expressing K562 human myelogenous leukemia target cells (CD19.K562), at various effector:target (E:T) ratios. Cells expressing a CAR specific for a different antigen (anti-BCMA CAR) was used as control.

Reporter cells expressing anti-CD19 CAR #1 were co-cultured with CD19-expressing K562 human myelogenous leukemia target cells (CD19.K562), at various effector:target (E:T) ratios. Reporter cells engineered to express a CAR targeting a different antigen, an anti-BCMA CAR, were used as control. The mean fluorescence intensity (MFI) of tdTomato expression, and expression of the surrogate marker, were determined using flow cytometry. As shown in FIG. 2B, Nur77-tdTomato reporter cells exhibited a dose-dependent response to stimulation with target cells expressing the antigen recognized by the CAR. No response to stimulation with CD19-expressing target cells was observed by the control reporter cells expressing a CAR against a non-target antigen.

B. Anti-BCMA

A viral vector containing polynucleotides encoding exemplary anti-BCMA chimeric antigen receptors (CARs) were introduced into the exemplary Nur77-tdTomato reporter cell line generated as described in Example 1. Each exemplary CAR contained a different scFv antigen-binding domain specific for human BCMA (designated as anti-BCMA CAR #1, anti-BCMA CAR #2, anti-BCMA CAR #3, and anti-BCMA CAR #4). Each CAR further contained sequences encoding a spacer, a CD28 transmembrane region, a 4-1BB-derived intracellular domain and a CD3-zeta derived intracellular signaling region, separated by polynucleotides encoding a T2A ribosomal skip element, and a truncated receptor, which served as a surrogate marker for CAR expression.

1. Response to Stimulation with BCMA-Fc

Figure 2C:
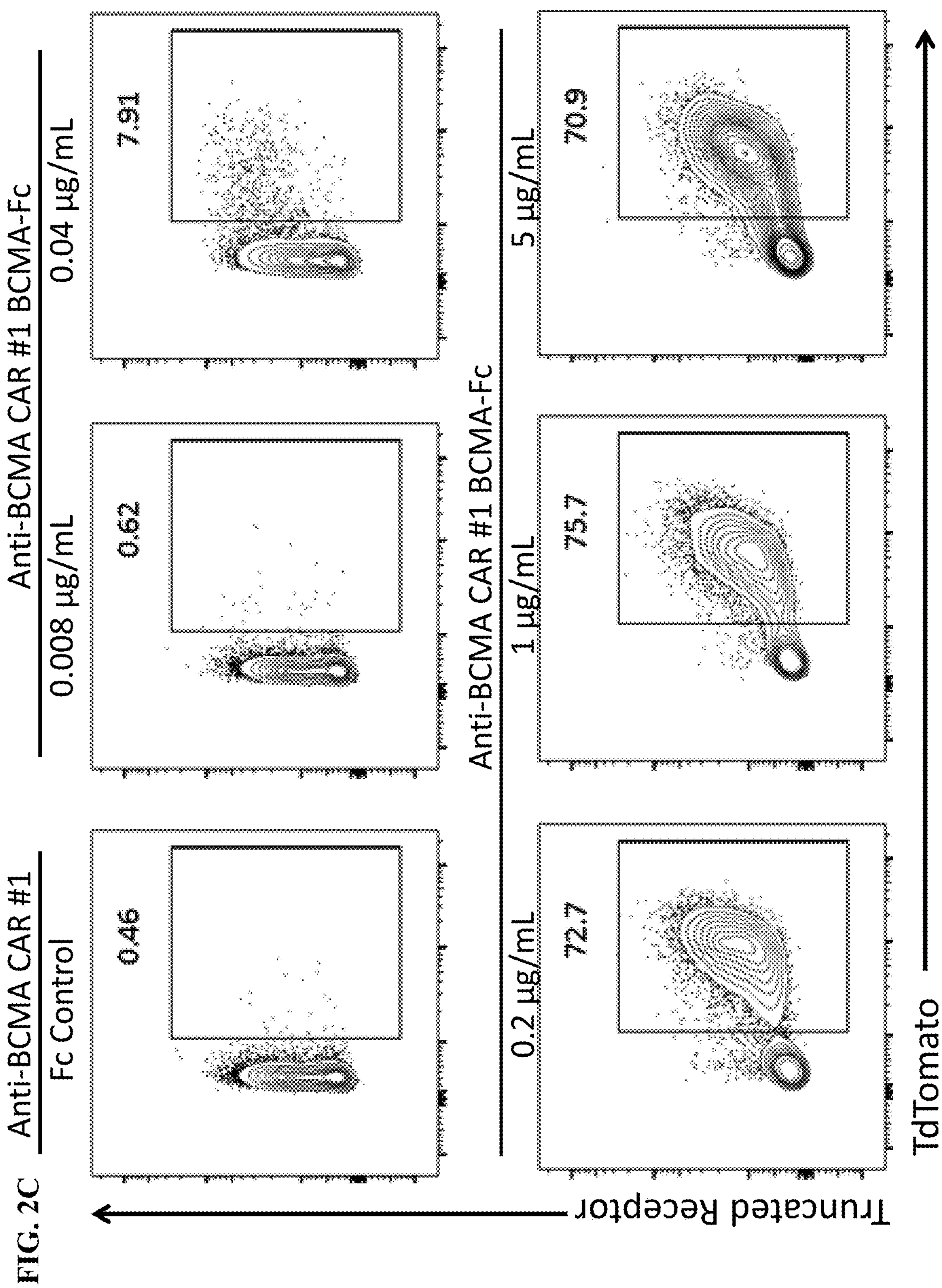
FIG. 2C depicts the expression level of tdTomato and a truncated receptor (surrogate marker for CAR expression), as detected by flow cytometry, in anti-BCMA CAR #1-expressing cells, incubated for 6 hours in 96-well cell culture plates coated overnight with (0.008 μg/mL, 0.04 μg/mL, 0.2 μg/mL, 1 μg/mL and 5 μg/mL) of BCMA-Fc (soluble human BCMA fused at its C-terminus to an Fc region of IgG) fusion polypeptide. A recombinant Fc polypeptide was used as a control (Fc Control).

Reporter cells transduced with a viral vector encoding anti-BCMA CAR #1 were incubated for 6 hours in 96-well cell culture plates that had been coated overnight with increasing concentrations (0.008 μg/mL, 0.04 μg/mL, 0.2 μg/mL, 1 μg/mL and 5 μg/mL) of BCMA-Fc (soluble human BCMA fused at its C-terminus to an Fc region of IgG) fusion polypeptide. A recombinant Fc polypeptide was used as a control (Fc Control). As shown in FIG. 2C, a dose-dependent increase in tdTomato expression was observed upon stimulation of anti-BCMA CAR-expressing reporter cells with recombinant antigen.

Figure 2D:
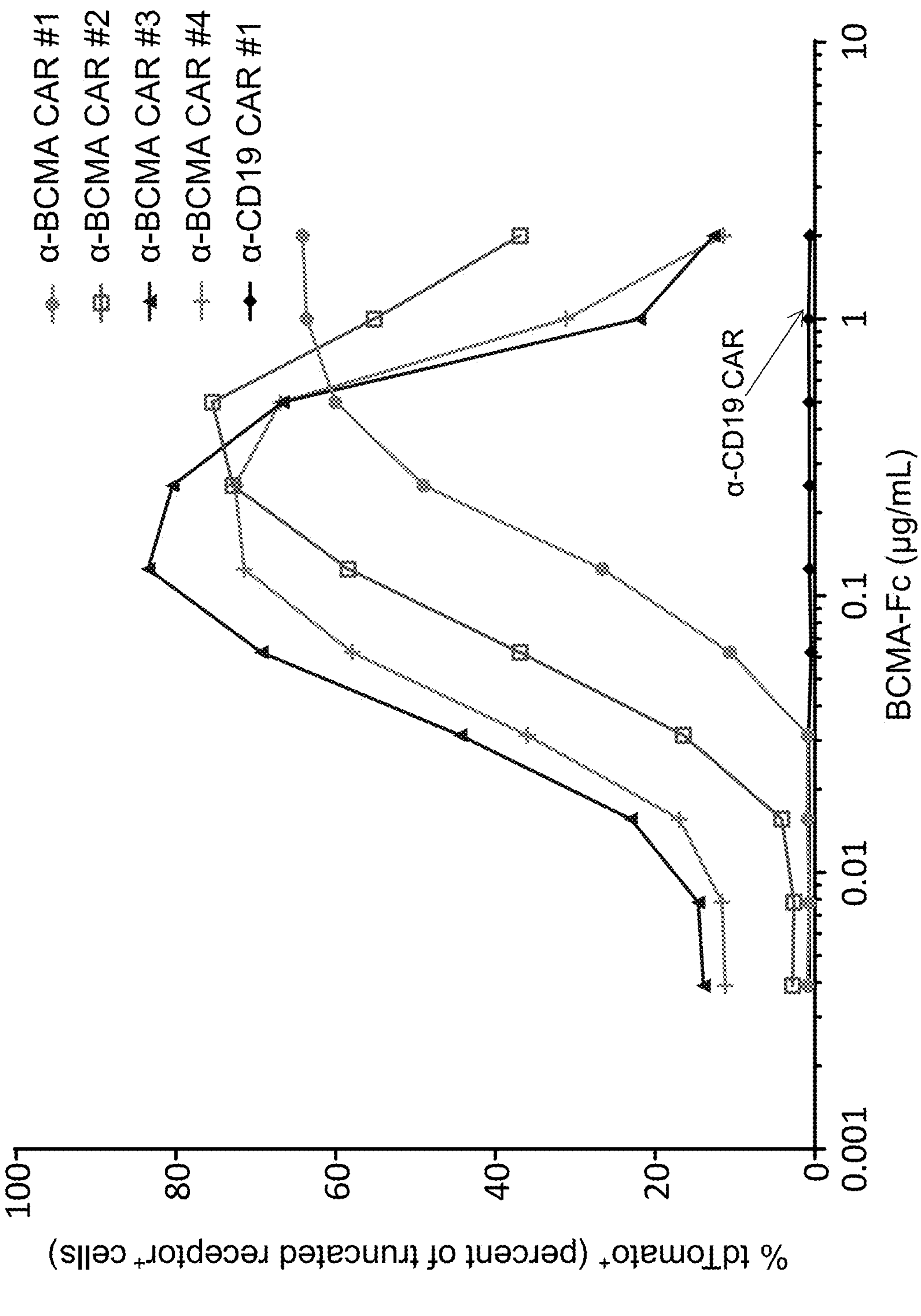
FIG. 2D depicts the percentage of tdTomato+ cells among cells expressing the truncated receptor, in reporter cells expressing anti-BCMA CAR #1, anti-BCMA CAR #2, anti-BCMA CAR #3, and anti-BCMA CAR #4, incubated with ten (10) 2-fold serial dilution of BCMA-Fc. Cells expressing a CAR specific for a different antigen (anti-CD19 CAR) was used as control.

In another study, reporter cells engineered to express anti-BCMA CAR #1, anti-BCMA CAR #2, anti-BCMA CAR #3, and anti-BCMA CAR #4 were incubated with ten (10) 2-fold serial dilution of BCMA-Fc. Reporter cells expressing anti-CD19 CAR #1, described above in Example 2, was used as a non-target control. The percentage of tdTomato-expressing cells within the population of cells expressing the CAR (as determined based on expression of the surrogate marker) was determined. As shown in FIG. 2D, a dose-dependent increase in tdTomato expression was observed upon stimulation of with recombinant antigen. No response to stimulation with BCMA-Fc was observed by the control reporter cells expressing a CAR against a non-target antigen.

The results were consistent with the utility of the exemplary Nur77-tdTomato reporter in assessing dose-dependent signals through various exemplary CARs, using various methods of stimulation.

2. Response to Stimulation with Antigen-Expressing Cells

Nur77 reporter cells substantially as described above with a red fluorescent protein (RFP) (e.g. tdTomato) were engineered to express anti-BCMA CAR #1. Antigen specificity of the reporter cells was assessed by comparing the activation of the reporter cells in response to BCMA-expressing MM1S target cells, with K562 target cells engineered to express a non-BCMA (non-target) protein, and parental K562 cells. The anti-BCMA CAR #1-expressing cells were incubated 24 hours with the target cells listed above, at 5:1, 1:1, and 1:5 effector:target cell ratios, and activation was determined by measuring the percentage of cells expressing RFP by flow cytometry. The results demonstrated that anti-BCMA CAR-expressing cells were activated by BCMA-expressing MM1S target cells, but not BCMA-negative target cells (parental or cells expressing the non-BCMA protein).

3. Response to Stimulation with Multiple Myeloma Cell Lines

Nur77 reporter cells substantially as described above with a RFP (e.g. tdTomato) were transduced with a viral vector encoding anti-BCMA CAR #1 and were incubated for 20 hours with NALM6, Daudi, RPMI-8226, MM1S, OPM2, and H929 cells. Different levels of RFP expression were observed depending on the cell line which conferred stimulation of the anti-BCMA CAR-expressing reporter cells.

To assess the amounts of BCMA expression on the surface of the multiple myeloma cell lines used to stimulate the anti-BCMA CAR-expressing reporter cells, the cells were stained with anti-human BCMA antibody (BioLegend, San Diego, CA), flow cytometry events were collected on an LSRFortessa™ flow cytometer (BD Biosciences, San Jose, CA) and data were analyzed with FlowJo software (Treestar Inc., Ashland, OR). BCMA antigen density (AD) was determined by using Quantum™ Simply Cellular® anti-Mouse IgG microsphere beads coated with the same anti-human BCMA antibody. Microspheres were labeled and BCMA antibody binding capacity was calculated. The results confirmed the detection of a parameter (detectable levels of the reporter) indicative of specific CAR activity in CAR-expressing reporter cells, when incubated with each of the various different BCMA-expressing cells, exhibiting a range of different antigen densities, and not when incubated target-negative cells. Degree of the RFP generally was increased in which lower levels of surface BCMA expression was observed exhibited lower levels of the reporter indicative of activity. Likewise, CAR-expressing reporter cells incubated with cell lines in which higher levels of surface BCMA expression was observed exhibited lower levels of the reporter indicative of activity. Thus, the density of BCMA expression on the surface of the various multiple myeloma cell lines was observed to correlate with the level of a parameter indicative of antigen-specific activity of reporter cells expressing anti-BCMA CAR #1, indicating that cells expressing the CAR can exhibit activity over a range of antigen densities, and in some aspects can exhibit increased activity with increased antigen levels. The results were consistent with the utility of the exemplary RFP reporter in assessing dose-dependent signals.

C. Exemplary Anti-Tumor Target CAR

To test reactivity of a CAR against tumor cells, a viral vector containing polynucleotides encoding a chimeric antigen receptors (CARs) against an exemplary target antigen were introduced into the exemplary Nur77-tdTomato reporter cell line generated as described in Example 1. Six formats of CARs were generated, including two orientations of the $V_H$ and $V_L$ chains with an IgG4 hinge spacer, IgG4 hinge-$C_H3$ spacer, or IgG4/IgG2 hinge-IgG2/IgG4 $C_H2$-IgG4 $C_H3$ spacer. Each CAR further contained sequences encoding a CD28 transmembrane region, a 4-1BB-derived intracellular domain and a CD3-zeta derived intracellular signaling region, separated by polynucleotides encoding a T2A ribosomal skip element, and a coding sequence for green fluorescent protein reporter for use as a transduction marker.

1. Sensitivity of CAR Screening Assay

The reporter T cells were transduced with lentiviral constructs encoding the exemplary CAR with IgG4 hinge, IgG4 hinge-$C_H3$, or IgG4/IgG2 hinge-IgG2/IgG4 $C_H2$-IgG4 $C_H3$ spacers. As a control, reporter cells also were transduced with a CAR against a known tumor antigen target, with a IgG4/IgG2 hinge-IgG2/IgG4 $C_H2$-IgG4 $C_H3$ spacer.

Expression of all constructs was under an EF1α promoter. The CAR-expressing reporter cells were co-cultured with a tumor cell line.

The CAR-expressing Jurkat T cells were observed to exhibit increased levels of activation (as indicated by reporter and CD69 levels) in response to increased numbers of target cells. The anti-tumor target CAR-expressing Jurkat cells exhibited maximum activation at about 20,000 target cells per well, when the well reached confluency. Reporter cells expressing the exemplary CAR with the IgG4 hinge spacer exhibited the highest level of activation. The control CAR-expressing cells achieved 100% activation at 2,500 target cells per well. Reporter cells expressing the control CAR with an IgG4 hinge spacer approached 100% activation at approximately 750 target cells/well.

2. Activity of CAR-Expressing T-Cells in the Presence of Cancer Cell Lines

CAR positive cells were determined by flow cytometry based on GFP expression and/or anti-IgG staining. The CAR-positive cells were then incubated for 2 days in 96-well cell culture plates with exemplary human tumor cell lines: breast cancer (SK-BR-3, MCF7, and MDA-MB-231), pancreatic cancer (MIA PaCa-2, PANC-1, BxPC-3, SU86.86, and Panc10.05), ovarian cancer (OVCAR-8, Caov-3, ES-2, NIH:OVCAR-3, and OVCAR-4), lung cancer (A549 and NCI-H1975), head and neck squamous cell carcinoma (HNSCC; UPCI:SCC152), cervical cancer (CaSki), dermal cancer (SV-80), acute myeloid leukemia (AML; Kasumi-1, SH-2, HT-93, HL60, ML-2, BDCM, KG-1, SKM-1, THP-1, and OCI-M1) or chronic myeloid leukemia (CML; K-562). Expression of the reporter and CD69 were determined using flow cytometry. Percentage of CAR-expressing cells detected as positive for both surface CD69 expression and the reporter signal (and the difference of this percentage above signal observed for cells cultured in media alone (i.e., in the absence of target cells)), was calculated for each condition as an indicator of activation. The exemplary CAR-expressing reporter cells exhibited response to stimulation with at least one cell line representing each indication.

3. Activity of CAR-Expressing T-Cells on Normal Cells

The exemplary CAR-expressing reporter cells described above were also tested for reactivity to normal human cells. The exemplary CAR-expressing reporter cells were incubated with CD4+ T cells, CD8+ T cells, and the negative blood fraction (e.g. CD4− and CD8− T cells) from a healthy donor, peripheral blood mononuclear cells (PBMCs), fresh apheresis sample from a healthy donor, primary dermal fibroblasts, human umbilical vein cells (HUVEC), and a panel of epithelial cell samples, including those generated from renal, mammary, and prostate epithelial cells and tested for activation as described above. The exemplary CAR expressing cells did not exhibit CD69 (above levels observed for cultures of the cells with media alone) following incubation with most normal human cells, except for a subset of primary epithelial cell samples. In this experiment, the exemplary CAR-expressing reporter cells exhibited an increase in CD69/reporter levels when incubated with two out of three human primary epithelial samples tested (mammary and prostate epithelial cells) in this specific assay.

4. Assessment of Target Specificity CAR-Expressing T-Cells

Activation of CAR-expressing T cells against an exemplary target antigen was tested in response to other non-target antigens. The exemplary CAR-expressing reporter T cells were plated in uncoated wells or in wells containing different immobilized recombinant non-target proteins and the exemplary target antigen of the CAR. Activation of the CAR-expressing reporter cells was determined by expression of the reporter. Only incubation with the recombinant target antigen yielded activation of the exemplary CAR-expressing reporter T cells above baseline.

Figure 3:
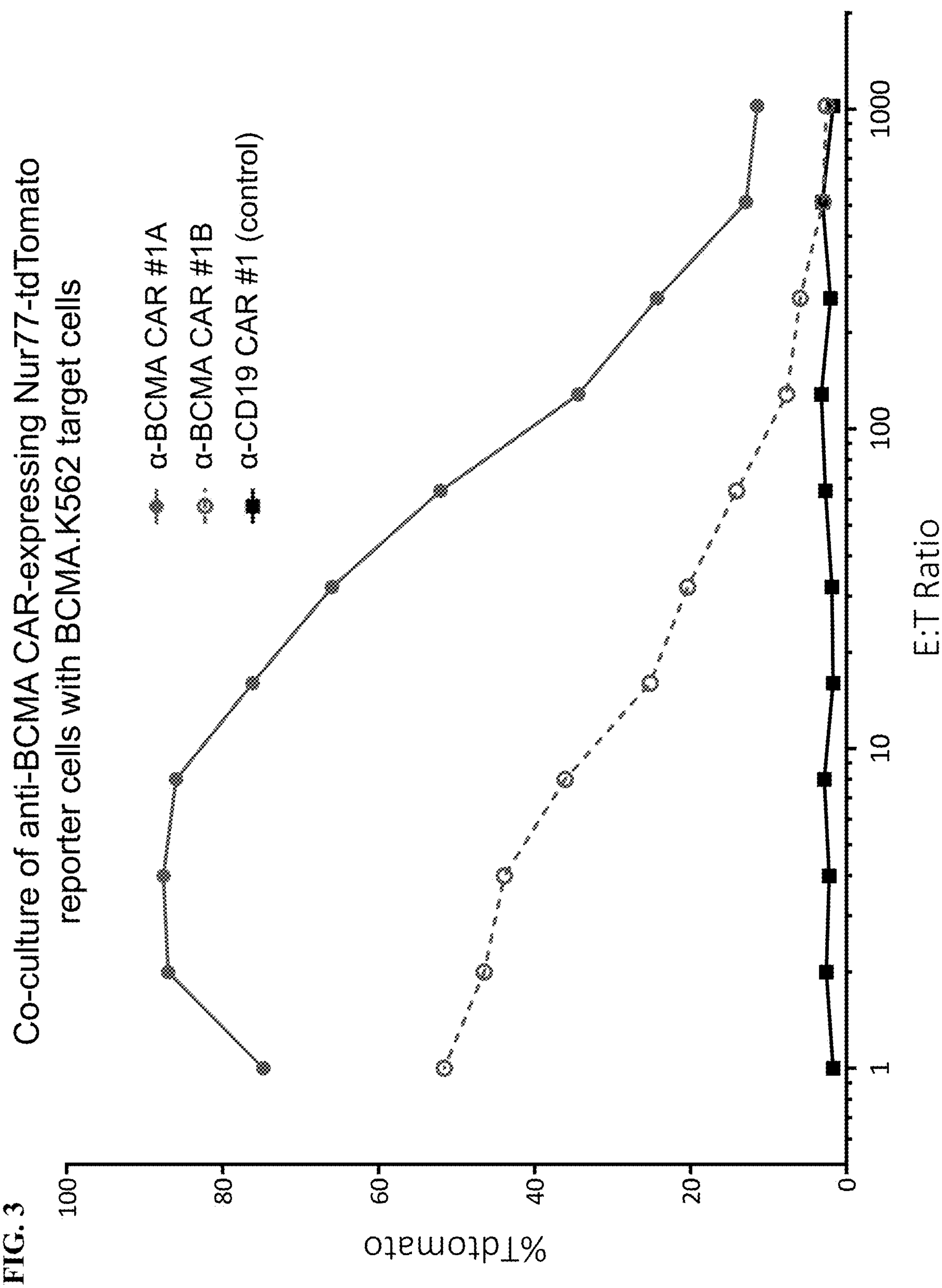
FIG. 3 depicts the percentage of tdTomato+ cells among reporter cells expressing anti-BCMA CAR #1A (containing a longer spacer derived from a modified IgG4 Hinge-$C_H2$-$C_H3$) or anti-BCMA CAR #1B (containing a shorter spacer derived from IgG4 hinge), following co-cultured with human BCMA-expressing K562 target cells (BCMA.K562) target cells at various E:T ratios.

Example 3: Assessment of Nur77-tdTomato Reporter Signal in Reporter Cell Lines Expressing Chimeric Antigen Receptors (CARs) Containing Spacers of Different Length Expression of the reporter in cells engineered to express anti-BCMA CARs containing the same antigen-binding domain but spacers of different length, was determined after co-culture with target cells. The exemplary Nur77-tdTomato cells, generated as described in Example 1, were engineered to express anti-BCMA CAR #1A (containing a longer spacer derived from a modified IgG4 Hinge-$C_H2$-$C_H3$, set forth in SEQ ID NO:24) or anti-BCMA CAR #1B (containing a shorter spacer derived from IgG4 hinge, set forth in SEQ ID NO:20). Each contained the same anti-BCMA scFv. The cells were co-cultured with human BCMA-expressing K562 target cells (BCMA.K562) target cells at various E:T ratios. Reporter cells expressing a CAR targeting a different antigen, the anti-CD19 CAR #1 described in Example 2, were used as control. As shown in FIG. 3, the Nur77-tdTomato expression level was observed to be different in the anti-BCMA CARs containing different spacer lengths, and a dose-dependent response to stimulation with target cells expressing BCMA was observed. The results were consistent with the utility of the exemplary Nur77-tdTomato reporter for assessing functional activity differences among different CARs, including CARs containing different spacer lengths.

Example 4: Assessment of Antigen-Independent (Tonic) Signaling from Different Chimeric Antigen Receptors (CARs)

The exemplary Nur77-tdTomato reporter cells were transduced with a viral vector encoding anti-CD19 CAR #1, anti-BCMA CAR #1, anti-BCMA CAR #2, anti-BCMA CAR #3, or anti-BCMA CAR #4, generated generally as described in Example 2, with the exception that the surrogate marker for transduction was super-fold green fluorescent protein, sfGFP, set forth in SEQ ID NO:35, encoding SEQ ID NO: 36). A viral vector encoding an anti-BCMA CAR containing a different anti-BCMA scFv, designated as anti-BCMA CAR #5, also was generated and transduced into the reporter cell. The various CAR-expressing cells were incubated without antigen stimulation to assess the degree of antigen-independent (tonic) signaling for 3 days and evaluated for the expression of tdTomato by flow cytometry.

Figure 4:
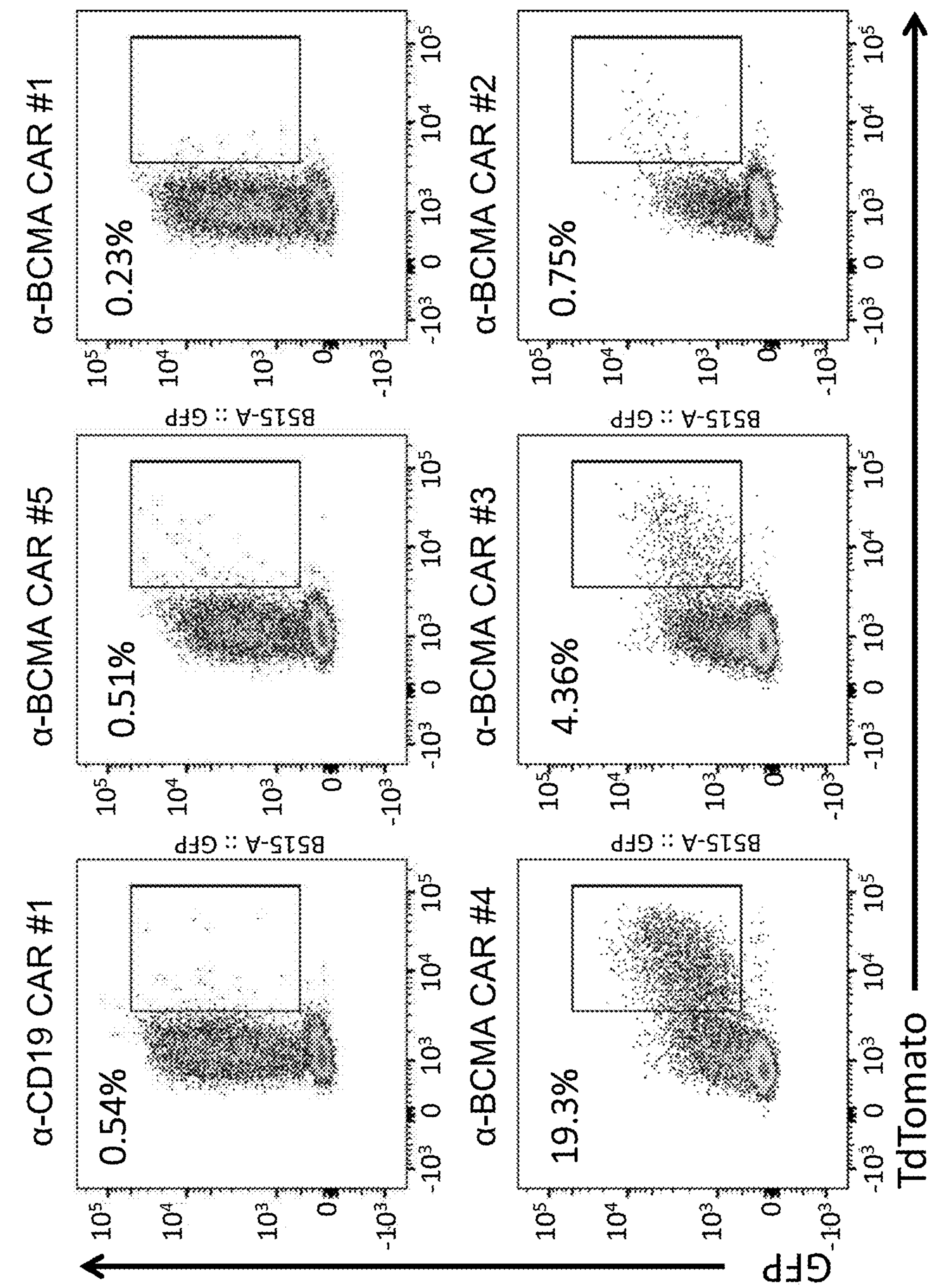
FIG. 4 depicts the expression level of tdTomato and GFP (surrogate marker for CAR expression), as detected by flow cytometry, in reporter cells expressing anti-CD19 CAR #1, anti-BCMA CAR #1, anti-BCMA CAR #2, anti-BCMA CAR #3, or anti-BCMA CAR #5, incubated without antigen stimulation to assess the degree of antigen-independent (tonic) signaling for 3 days.

As shown in FIG. 4, various CAR-expressing cell lines exhibited a varying degree of tdTomato expression in the absence of antigen stimulation. The percentage of tdTomato+ cells (indicative of tonic reporter activation) among CAR-expressing cells (indicated by GFP+ cells) varied from 0.23% to 19.3%, in cells expressing different CARs. This result indicated that the Nur77-tdTomato reporter cells can be used to assess tonic signaling of CAR-expressing cells.

Example 5: Assessment of Antigen-Independent (Tonic) Signaling from Chimeric Antigen Receptors (CARs) Containing Different Intracellular Domains Antigen-independent (tonic) signaling was assessed in reporter cells expressing various CARs containing different intracellular signaling regions. The exemplary Nur77-tdTomato reporter cells were transduced with a viral vector encoding anti-CD19 CAR #1, anti-BCMA CAR #1, anti-BCMA CAR #2, anti-BCMA CAR #3, or anti-BCMA CAR #5, generated generally as described in Examples 2 and 4, with the exception that the CARs contained intracellular domains derived from 4-1BB or CD28, and the surrogate marker for transduction was a truncated receptor. The various CAR-expressing cells were incubated without antigen stimulation to assess the degree of antigen-independent (tonic) signaling and evaluated for the expression of tdTomato by flow cytometry.

Figure 5A:
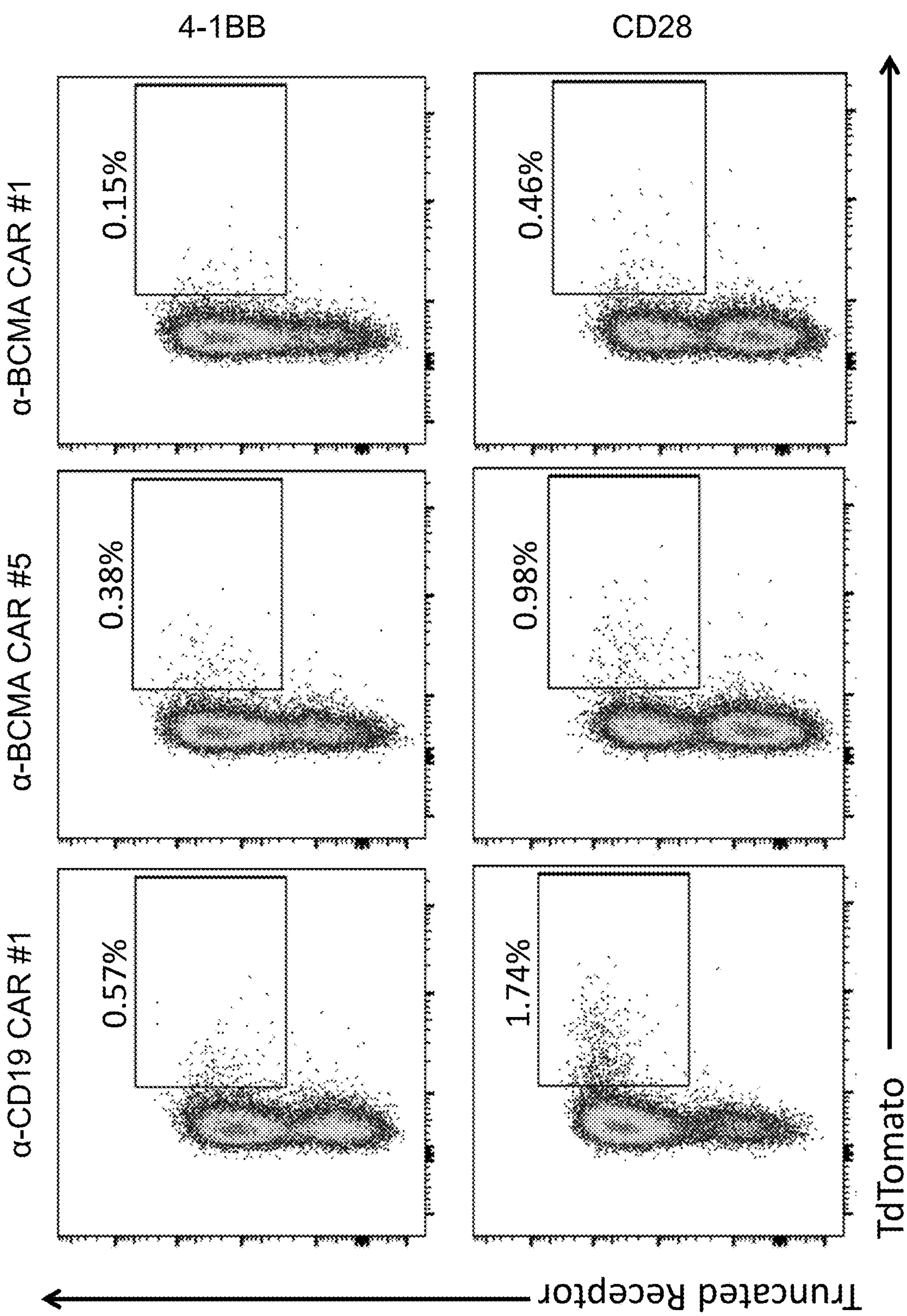
FIGS. 5A and 5B depict the expression level of tdTomato and truncated receptor (surrogate marker for CAR expression), as detected by flow cytometry, in reporter cells expressing anti-CD19 CAR #1, anti-BCMA CAR #1, anti-BCMA CAR #2, anti-BCMA CAR #3, or anti-BCMA CAR #5 that contain intracellular domains derived from 4-1BB or CD28 incubated without antigen stimulation to assess the degree of antigen-independent (tonic) signaling.
Figure 5B:
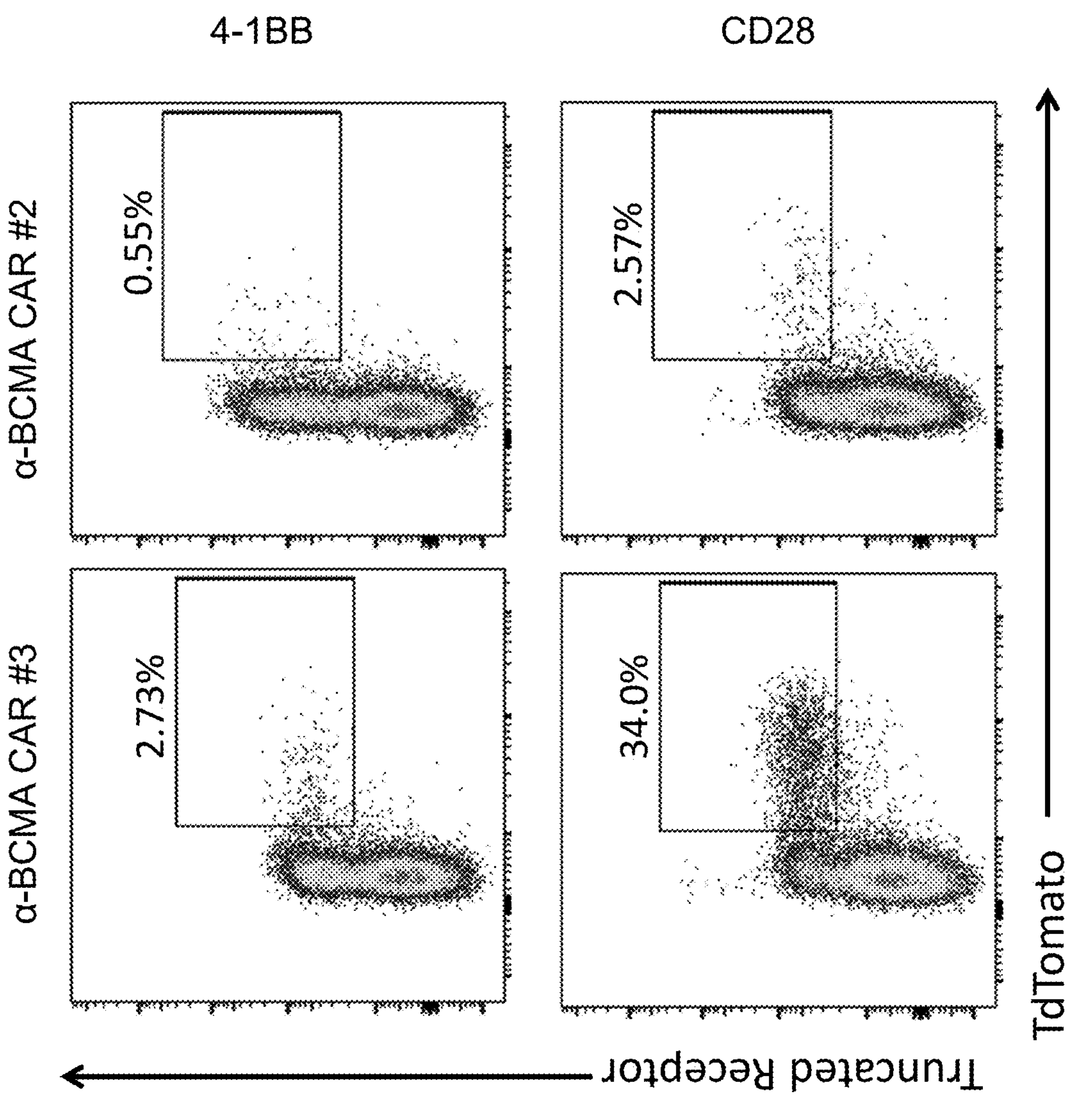

As shown in FIGS. 5A and 5B, the 4-1BB- and CD28-derived intracellular domains in various CARs resulted in different levels of tonic signaling, as indicated by the percentage of tdTomato+ cells among the CAR+ cells (as determined based on expression of the surrogate marker). The results further support that the exemplary Nur77-tdTomato reporter cell line can be used to assess functional activity differences, such as those associated with antigen-independent tonic signaling, among different CARs, including CARs containing different intracellular domains (e.g., 4-1BB- or CD28-derived intracellular signaling domains).

Example 6: Assessment of Effect of Viral Dose on Antigen-Independent (Tonic) Signaling Tonic signaling was assessed in cells transduced with varying doses of CAR-encoding viral preparations. Nur77-tdTomato reporter cells were transduced with 10 μL, 50 μL, 100 μL and 400 μL of viral preparations containing a viral vector encoding an anti-BCMA CAR. On days 3 and 11 after transduction, CAR expression and reporter expression were assessed by flow cytometry.

Figure 6:
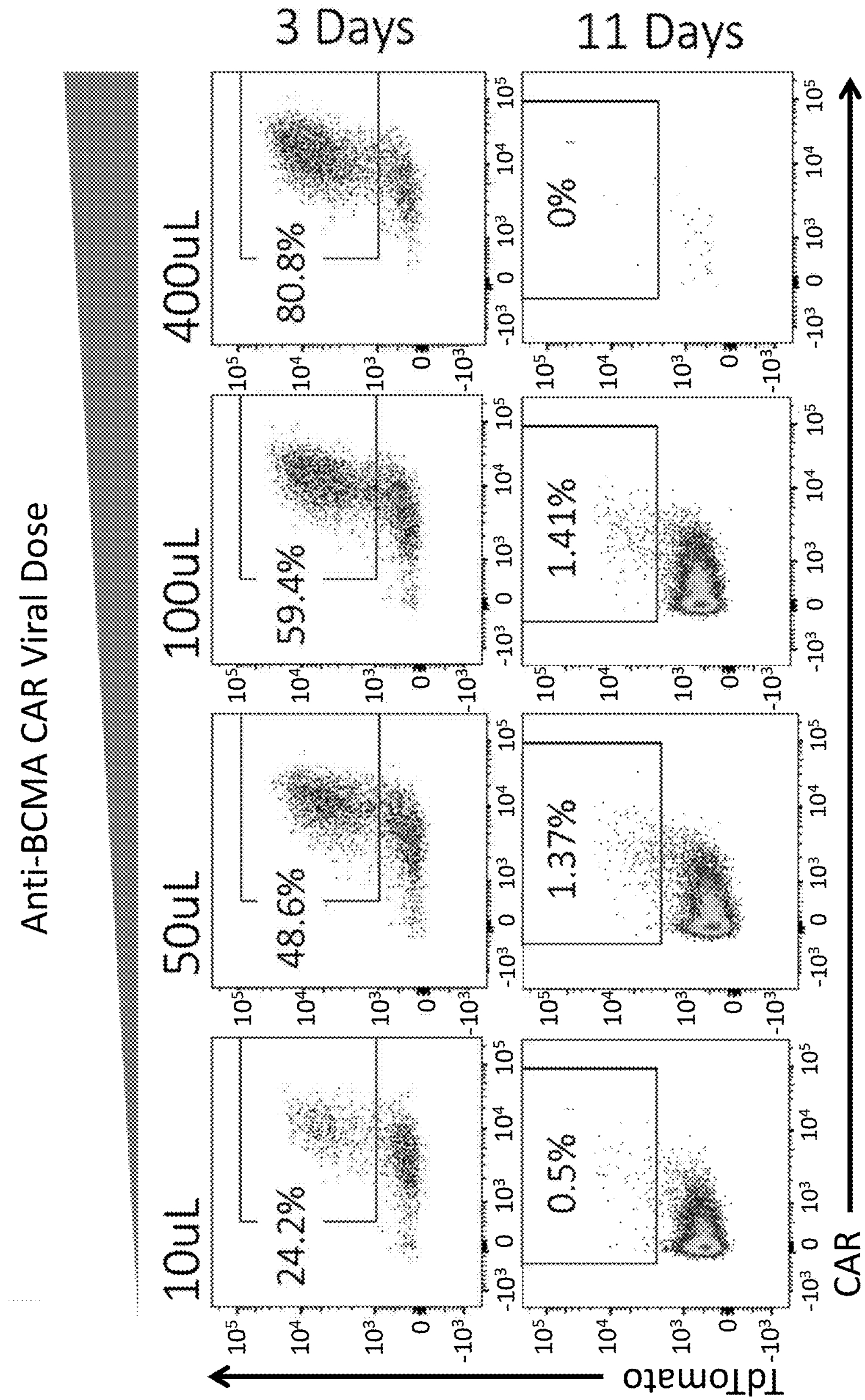
FIG. 6 depicts the expression level of tdTomato and CAR expression, as detected by flow cytometry, in reporter cells transduced with 10 μL, 50 μL, 100 μL and 400 μL of viral preparations containing a viral vector encoding an anti-BCMA CAR, on day 3 and day 11 after transduction.

As shown in FIG. 6, on day 3, increasing viral dose was observed to be associated with higher reporter activation, indicating higher tonic signaling. On day 11, very few live cells were observed in the sample transduced with the highest viral dose. The results showed that transduction with a higher viral dose can lead to higher tonic signaling in the absence of antigen stimulation. Similar results were observed in transduced primary T cells.

Example 7: Assessment of Antigen Cross-Reactivity of Chimeric Antigen Receptors (CARs) Using Reporter Cell Line The exemplary Nur77-tdTomato cell line engineered to express anti-BCMA CAR #1, specific for human BCMA and generated as generally described in Example 2, was employed to assess species cross reactivity of the antigen-binding domains of CARs. The reporter cell line expressing anti-BCMA CAR #1 was co-cultured with K562 human myelogenous leukemia cells expressing human BCMA (huBCMA), murine BCMA (muBCMA) or cynomolgus monkey BCMA (cynoBCMA), at an E:T ratio of 2:1 or 5:1. The percentage of tdTomato+ cells were determined by flow cytometry.

Figure 7A:
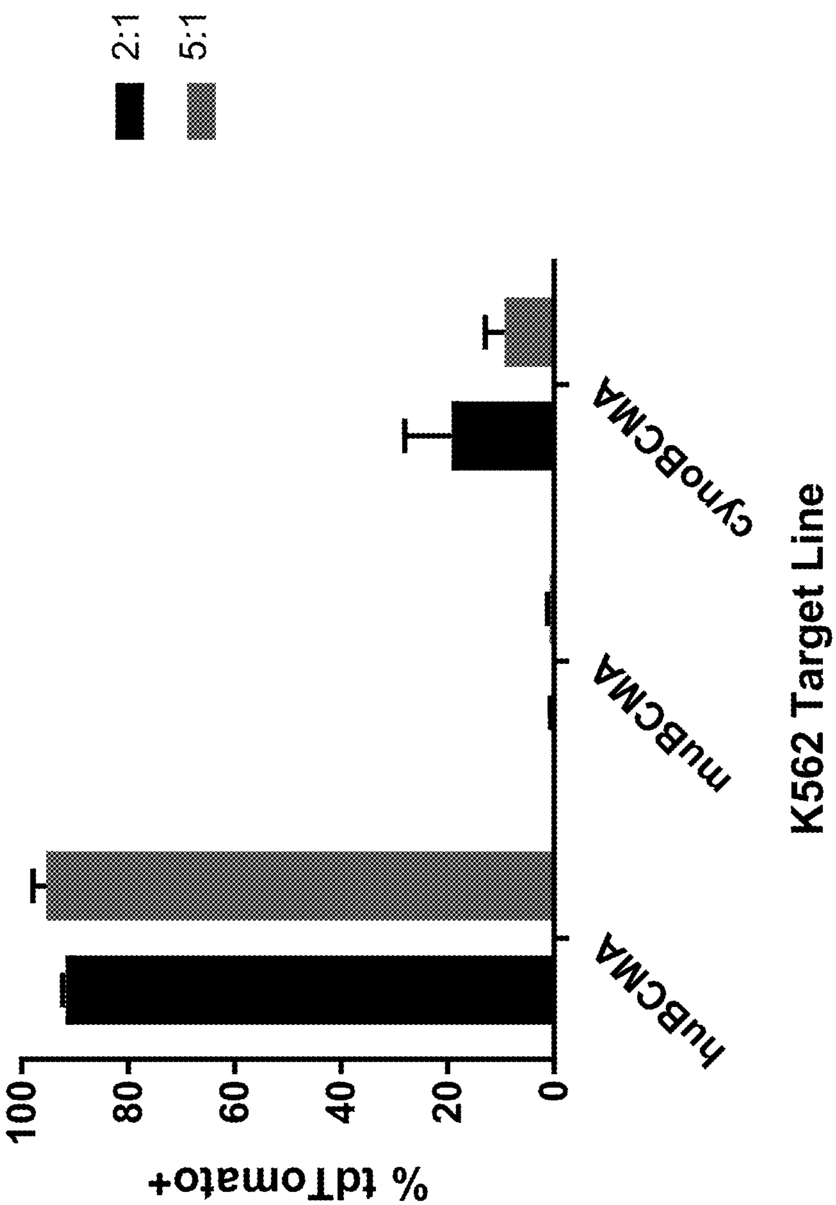
FIG. 7A depicts the percentage of tdTomato+ cells, as assessed by flow cytometry, among the Nur77-tdTomato reporter cells engineered to express anti-BCMA CAR #1, specific for human BCMA, co-cultured with K562 human myelogenous leukemia cells expressing human BCMA (huBCMA), murine BCMA (muBCMA) or cynomolgus monkey BCMA (cynoBCMA), at an E:T ratio of 2:1 or 5:1.

As shown in FIG. 7A, more than 90% of the anti-BCMA CAR #1-expressing cells were observed to be tdTomato+ when cultured with target cells expressing huBCMA, at both E:T ratios tested. In comparison, when cultured with target cells expressing muBCMA, very few cells were tdTomato+, indicating very low cross-reactivity. When cultured with target cells expressing cynoBCMA, approximately 10 to 20% of the cells were tdTomato+, indicating some cross-reactivity by cynoBCMA.

The reporter cell line expressing anti-BCMA CAR #1 was incubated with increasing concentrations (0, 0.1, 0.25, 1, 2.5, 10, 25 and 100 μg/mL) of huBCMA and cynoBCMA coated on 96-well flat-bottom plates. The percentage of tdTomato+ cells and the mean fluorescence intensity (MFI) of the tdTomato signal in CAR+ cells were determined.

Figure 7B:
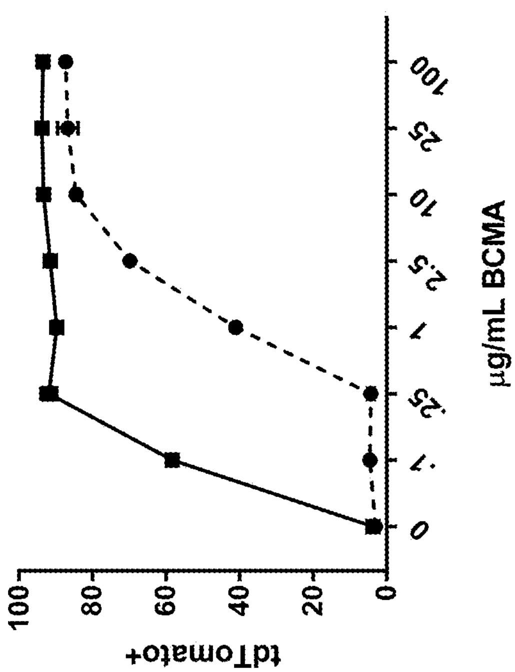
FIGS. 7B and 7C depict the percentage (FIG. 7B) and mean fluorescence intensity (MFI.
Figure 7C:
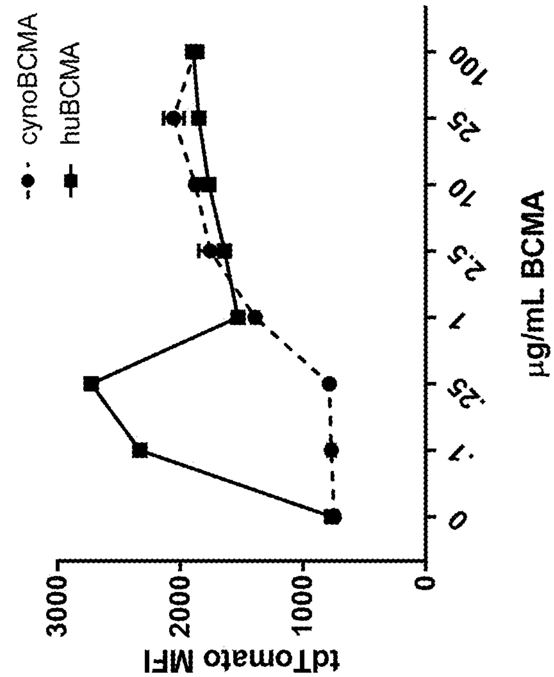

As shown in FIGS. 7B and 7C, cynoBCMA did not cross-react with anti-BCMA CAR #1 at low concentrations, but did at high concentrations. The results support that the reporter cell line can be used to assess antigen cross-reactivity, such as species cross-reactivity, of an antigen-binding domain of a CAR.

Example 8: Assessment of Signaling Activity of Engineered T Cell Receptors (TCRs) in Reporter Cell Line Nur77-tdTomato reporter cells, generated as described in Example 1, were transduced with a viral vector encoding a recombinant T cell receptor (TCR) specific for a human papillomavirus (HPV) 16 E6(29-38) peptide (designated TCR #1). Jurkat cells without the reporter were transduced with a viral vector encoding TCR #1 or a recombinant TCR specific for HPV 16 E7(11-19) peptide (designated TCR #2). $1\times10^5$ transduced cells were incubated for 44 hours with a mixture of K562 target cells that were CD86 IL-2KO HLA-KO HLA-A2 (knocked out for endogeous IL-2 and HLA, and engineered to express exogenous CD86 and HLA-A2) and engineered to stably express a PEST sequence (a string of amino acids enriched in prolines (P), glutamates (E), serines (S) and threonines (T)) from HPV E6(1-51) or E7(1-36). Cells expressing each TCR were incubated with a total of $1\times10^5$ K562 target cells, expressing an antigen specifically recognized by the TCR (specific antigen) or an antigen that is not specifically recognized by the particular TCR (non-specific antigen) in the following proportions: 100% specific; 50% specific, 50% non-specific; 20% specific, 80% non-specific; 10% specific, 90% non-specific; 1% specific, 99% non-specific; 0.1% specific, 99.9% non-specific; 100% non-specific. Cells were assessed for tdTomato and CD69 expression, to determine the activation state of the cells.

Figure 8A:
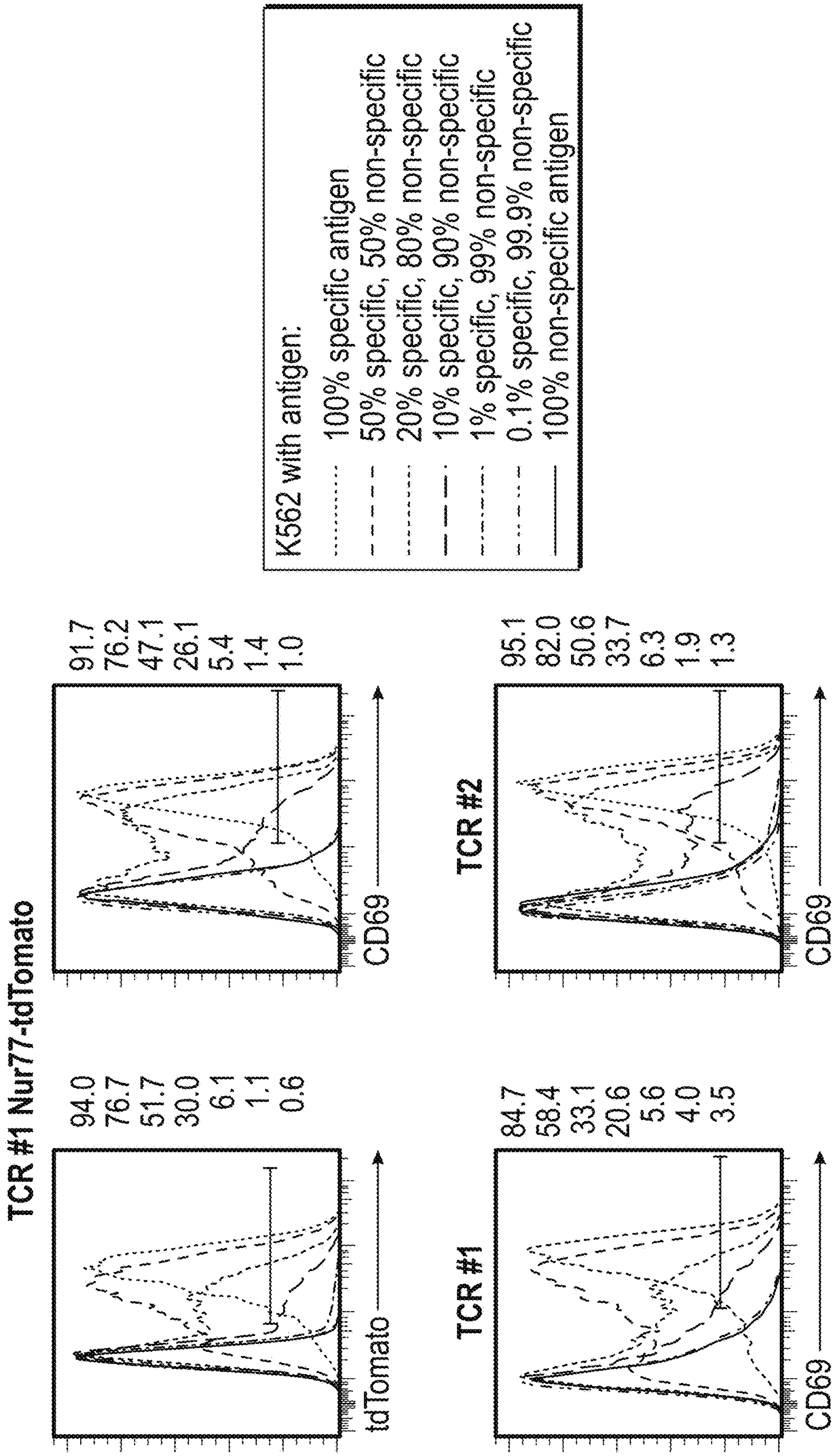
FIG. 8A depicts the expression level of tdTomato and CD69 in reporter cells expressing recombinant T cell receptor (TCR) specific for a human papillomavirus (HPV) 16 E6(29-38) peptide (designated TCR #1), and in Jurkat cells without the reporter expressing TCR #1 or a recombinant TCR specific for HPV 16 E7(11-19) peptide (designated TCR #2). Cells were incubated for 44 hours with a mixture of K562 target cells that were CD86 IL-2KO HLA-KO HLA-A2 (knocked out for endogeous IL- 2 and HLA, and engineered to express exogenous CD86 and HLA-A2) and engineered to stably express a PEST sequence (a string of amino acids enriched in prolines (P), glutamates (E), serines (S) and threonines (T)) from HPV E6(1-51) or E7(1-36). Cells expressing each TCR were incubated with a total of $1\times10^5$ K562 target cells, expressing an antigen specifically recognized by the TCR (specific antigen) or an antigen that is not specifically recognized by the particular TCR (non-specific antigen) in the following proportions: 100% specific; 50% specific, 50% non-specific; 20% specific, 80% non-specific; 10% specific, 90% non-specific; 1% specific, 99% non-specific; 0.1% specific, 99.9% non-specific; 100% non-specific.

As shown in FIG. 8A, expression of tdTomato was sensitive to the number of target cells expressing specific antigen, demonstrating the sensitivity of the reporter cells for monitoring stimulation to varying numbers of specific antigen-expressing cells in the culture. Expression of the tdTomato reporter was observed to be similar to that of the activation marker CD69.

In another study, Nur77-tdTomato expression was determined in TCR-expressing reporter cells cultured with target cells that had been incubated with antigen peptides or target cells engineered to stably express antigens. Approximately $1\times10^5$ reporter cells expressing anti-HPV 16 E6 TCR #1 specific to E6(29-38) were cultured for 41 hours with a total of $1\times10^5$ of CD86 IL-2KO HLA-KO HLA-A2 K562 target cells that were incubated with 10 μM E6(29-38) peptide, 10 μM E7(11-19) peptide, 10 μM MART1(26-35) (also known as Melan-A) peptide or without antigen; or K562 target cells that were transfected with a cDNA expression vector for stable expression of PEST E6(1-51), PEST E6(37-87), PEST E6(73-123), PEST E6(109-156), PEST E7(1-36), PEST E7(22-57), PEST E7(43-78), PEST E7(64-98), PEST MART1, E6(1-38), E7 or MART1. Cells were incubated with or without interferon gamma (IFNγ).

Figure 8B:
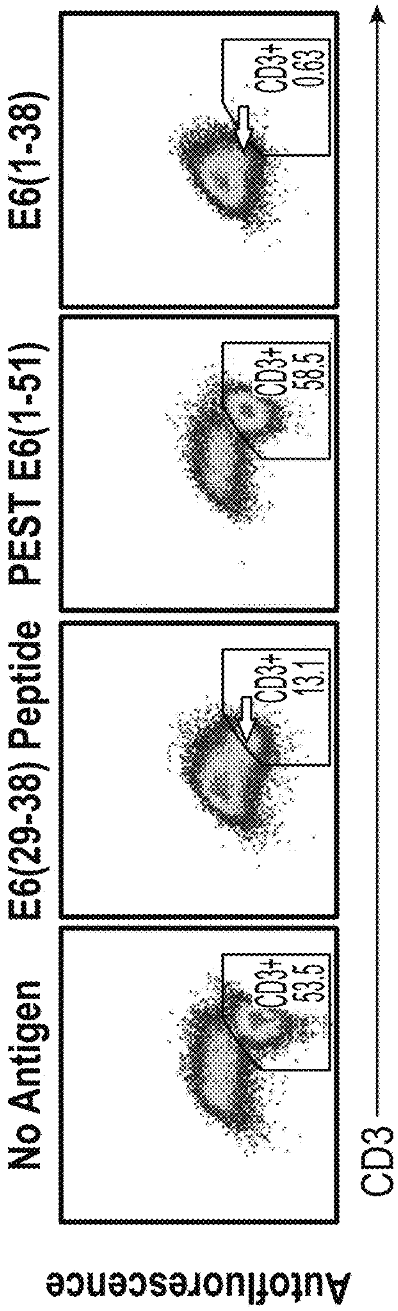
FIG. 8B depicts CD3 and autofluorescence levels in reporter cells expressing TCR #1, incubated without antigen, cells incubated with E6(29-38) peptide, and target cells transfected to stably express PEST E6(1-51) or E6(1-38).
Figure 8C:
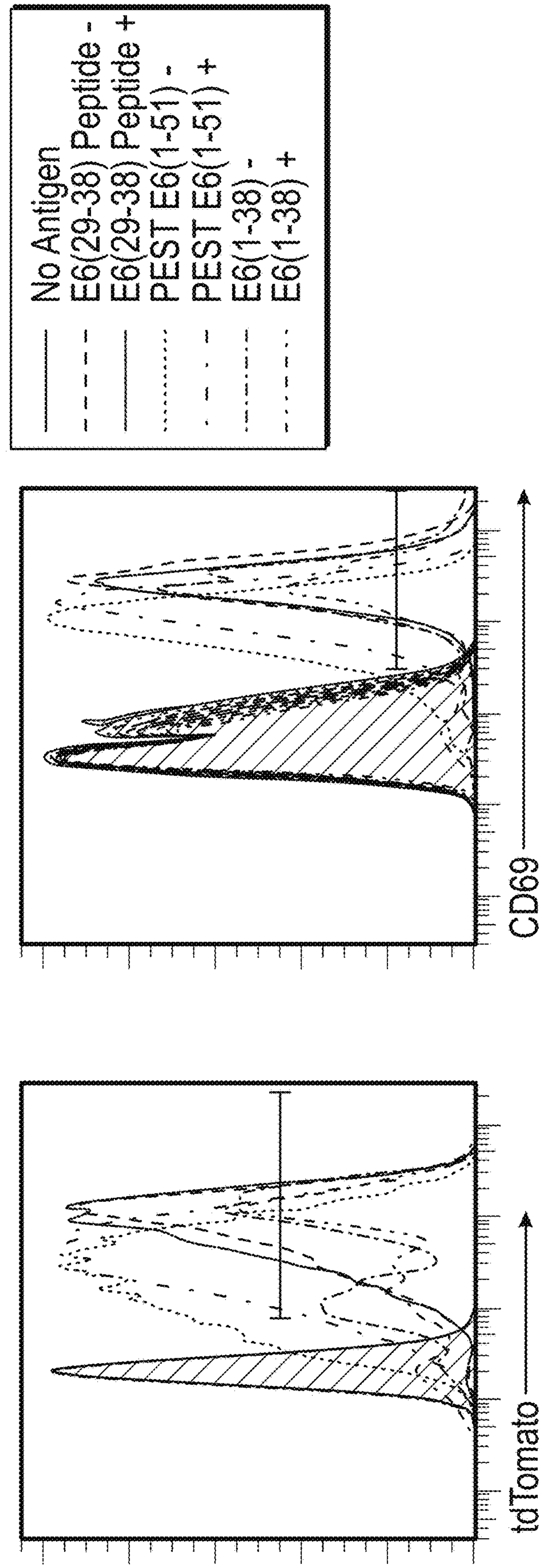
FIG. 8C depicts tdTomato and CD69 expression levels, as detected by flow cytometry, among live CD3+ TCR-expressing cells, upon culturing with target cells incubated with antigen peptides or target cells stably expressing antigen, both with (+) or without (−) IFNγ.

FIGS. 8B and 8C show exemplary results from culture with target cells incubated without antigen, cells incubated with E6(29-38) peptide, and target cells transfected to stably express PEST E6(1-51) or E6(1-38). Incubation with E6(29-38) peptide or stable expression of E6(1-38) resulted in a reduction of surface expression of TCR, which is consistent with ligation of the TCR by the MHC:peptide complex (FIG. 8B). Among live CD3+ TCR-expressing cells, tdTomato was expressed upon culturing with target cells incubated with antigen peptides or target cells stably expressing antigen, both with (dashed line) or without (solid line) IFNγ. The degree of expression correlated to the specificity of peptide stimulation, as greater reporter expression was observed following culture with target cells incubated with E6(29-38) peptide or having stable expression of E6(1-38). Expression of the tdTomato reporter was observed to be similar to that of the activation marker CD69 (FIG. 8C).

The results are consistent with the utility of the Nur77-tdTomato reporter for detecting signals following ligation of recombinant T cell receptors (TCRs).

Example 9: Platform for Screening Candidate Chimeric Antigen Receptors (CARs)

A screening platform for small-, medium- or large-scale screening of candidate chimeric antigen receptors (CARs) was developed and tested. The platform allowed various antigen-binding domains, such as scFvs, to be expressed in the context of a CAR and screened, and allowed rapid determination of expression and functional activity, such as antigen-dependent and antigen-independent signals through the signaling domains of the CAR. The platform included employing vector backbones that contain restriction sites for cloning of antigen-binding domains, an exemplary leader sequence containing an exemplary plasmid barcode, polynucleotides encoding spacers of various lengths, transmembrane and signaling components of the CAR, and transduction and selection markers, and Nur77 reporter cells to facilitate rapid assessment of expression and activity. In an exemplary study, the vector backbones were used to clone various scFv sequences for expression in a CAR format, and transduced into the exemplary Nur77-tdTomato reporter cell described in Example 1.

A. Generation of Vector Backbones and Cloning of Candidate scFv-Encoding Nucleic Acids A plurality of backbone constructs were generated for efficient insertion of an antigen-binding domain of a CAR for expression and screening of different CARs using the Nur77 reporter cells. The plurality of backbone constructs were generated to each contain polynucleotides encoding one different component of the CAR while keeping in common other components of the CAR. In one example as described below, a plurality of backbone vector constructs were generated to contain spacers of different lengths (e.g., short, e.g., SEQ ID NO:20; medium, e.g., SEQ ID NO:22; and long, e.g., SEQ ID NO:24) and common sequences for other components of the CAR, such as a transmembrane domain (e.g., human CD28 transmembrane domain) and an intracellular signaling region containing a costimulatory signaling region (e.g., derived from human 4-1BB or human CD28) and a signaling domain (e.g. derived from human CD3zeta). A series of such backbone constructs were generated in which the costimulatory signaling region was derived from 4-1BB or from CD28, thereby generating 6 different backbone vector constructs containing one of the versions of the spacer matched with one of the costimulatory signaling regions. Various permutations of such backbone constructs can be generated. The backbone constructs also were generated to contain an upstream promoter, such as the MND promoter or the EF1α-HTLV1 promoter. The backbone constructs also contained exemplary plasmid barcodes for use in subsequent identification and sequencing of the expressed CAR. The backbone vector constructs also can contain components of viral vectors, such as lentiviral vectors, for lentiviral-based transduction of a cell line. The backbone vector constructs can be used for low-, medium- or high-throughput screening of candidate CARs.

Figure 9A:
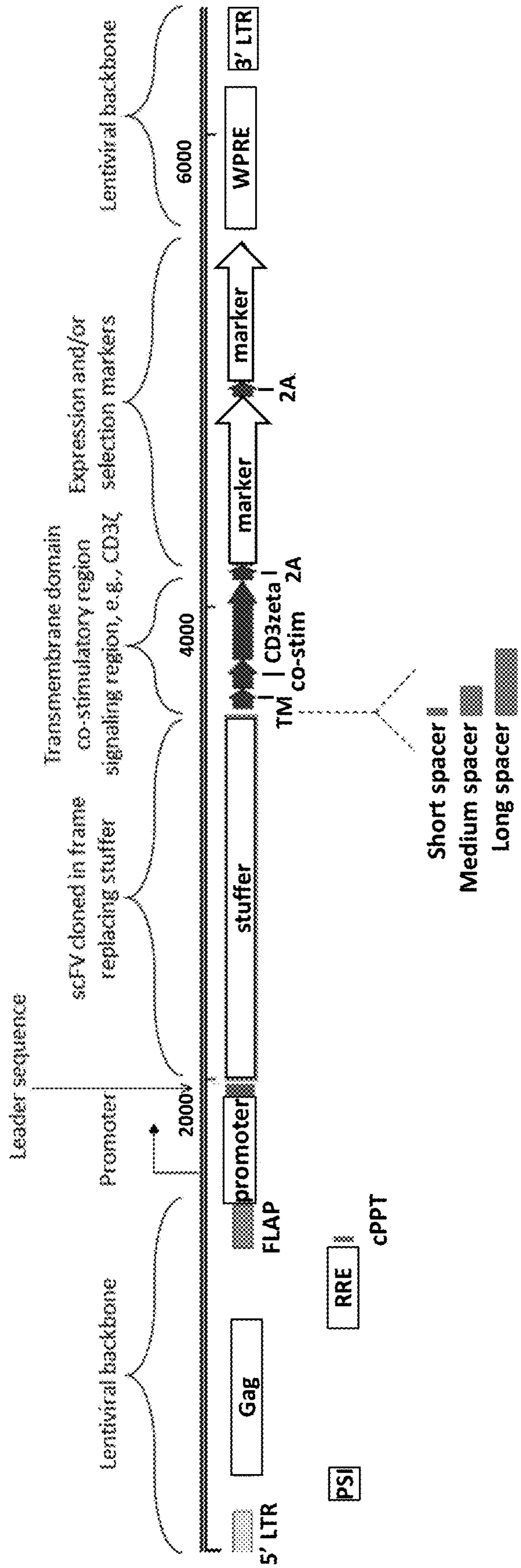
FIG. 9A depict a schematic representation of components of the exemplary lentiviral backbone vectors, including barcoded leader sequences.

Exemplary lentiviral backbone constructs were generated. Schematic representation of components of the exemplary lentiviral backbone vectors, including barcoded leader sequences, are shown in FIG. 9A. For cloning, restriction sites were chosen that did not occur or occurred very few times within an endogenous human $V_H$ or $V_L$ genes. Examples of such restriction sites include NheI or RsrII sites. As shown, the antigen-binding domain of an exemplary CAR or scFv of an scFv library can be inserted between restriction sites to replace the "stuffer" sequence. Prior to cloning, polymerase chain reaction (PCR) primers containing appropriate restriction enzyme sites (e.g., NheI or RsrII sites) and degenerate primer sequences for amplifying human $V_H$ and $V_L$, were used to amplify candidate scFv sequences from an scFv sequence library with or without a peptide leader sequence.

Figure 9B:
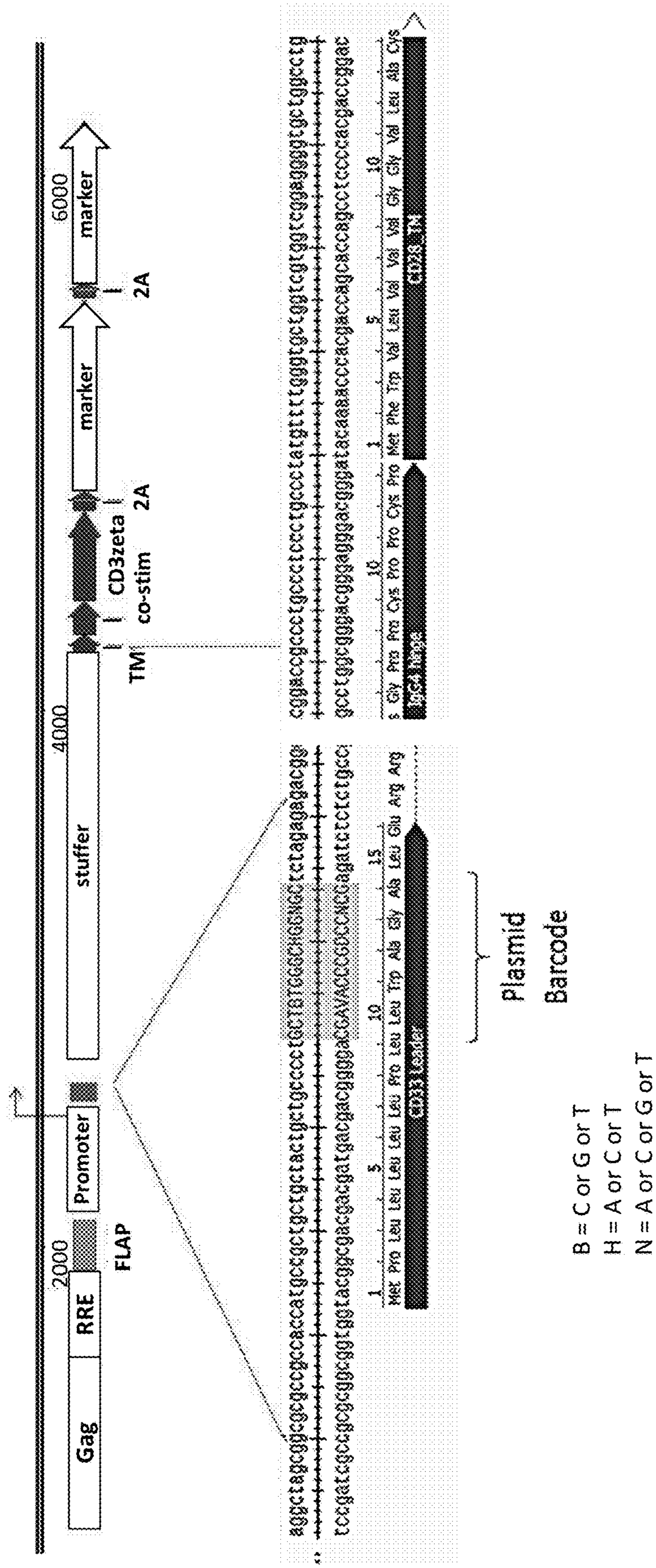
FIG. 9B depicts a schematic representation of an exemplary CD33 leader sequence containing a barcode and other components of an exemplary lentiviral backbone vector.

The inserted polynucleotide encoding the antigen-binding domain can include a peptide leader sequence or the peptide leader sequence can be contained as part of the backbone vector construct. The leader peptide-encoding sequences (e.g. CD33 leader peptide) were also modified using degenerate codons to incorporate a plasmid barcode (FIG. 9B). Nucleotide sequences were modified (at positions indicated with B, H and N in FIG. 9B; B=C or G or T; H=A or C or T and N=A or C or G or T) to generate 36 different plasmid barcodes. The barcode was placed within the 3' end of leader sequence to avoid altering nucleotides in or around the Kozak sequence or translation start site.

B. Expression of CARs Using Vector Backbone

A library of CAR lentiviral vectors was generated in which various scFvs were cloned into the lentiviral vector backbone generated as described above. scFv antigen-binding domain from anti-CD19 CAR #1, anti-BCMA CAR #1 and anti-BCMA CAR #5, described above in Examples 2 and 4, were amplified and cloned into an exemplary vector backbone containing the MND promoter and either a short spacer or a long spacer. The backbone vector also included a CD28 transmembrane domain, an intracellular signaling region containing the 4-1BB-derived intracellular domain and CD3zeta domain, and GFP as a surrogate marker separated from the encoded CAR by a T2A self-cleaving peptide.

Figure 10A:
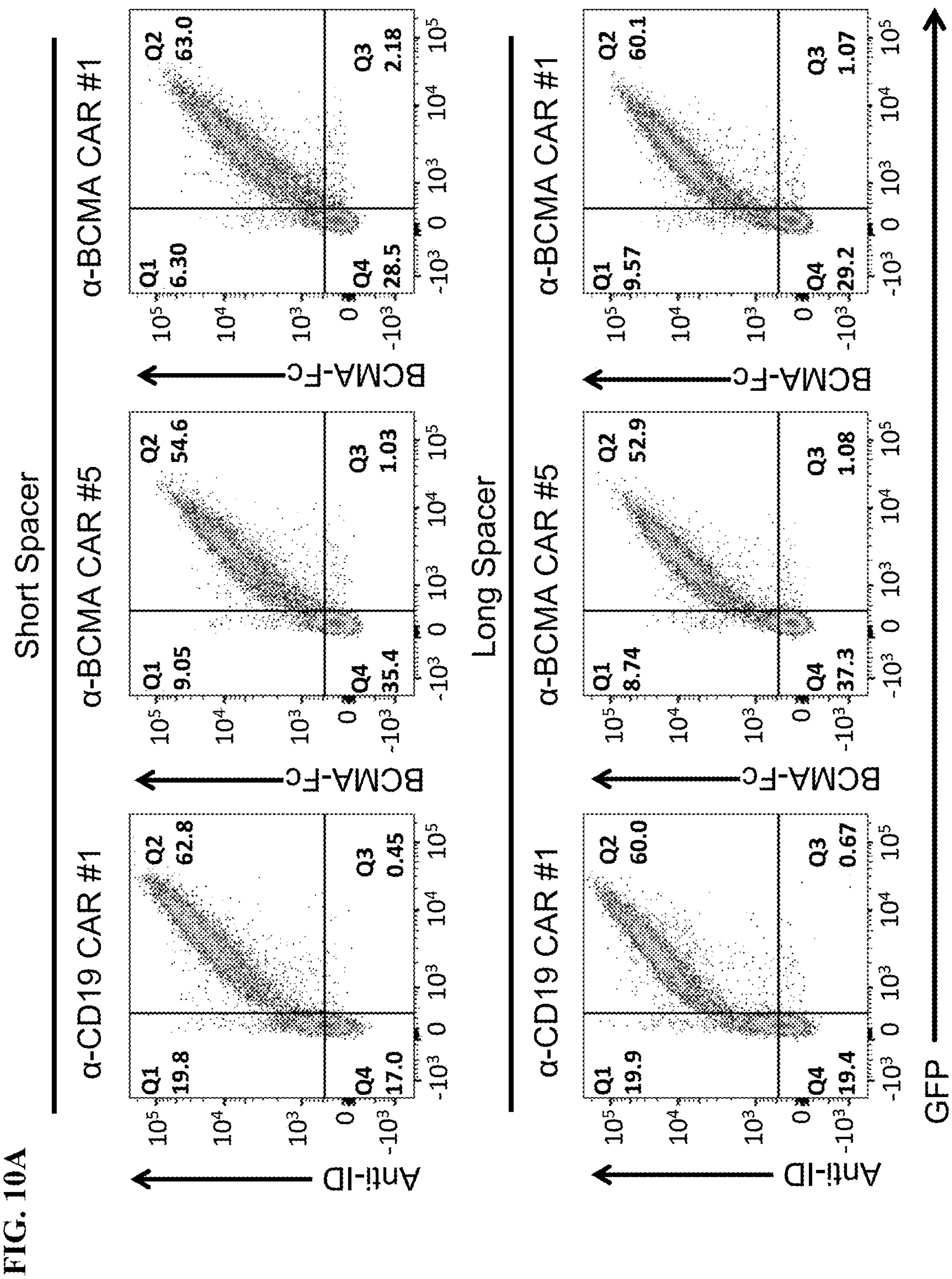
FIG. 10A depicts expression levels of CAR expression, as detected by staining with an anti-idiotypic antibody agonist antibody specific for the FMC63-derived scFv antigen binding domain in the anti-CD19 CAR #1 or BCMA-Fc and GFP (surrogate marker for CAR expression), as detected by flow cytometry, in cells transduced with CAR constructs generated using an exemplary lentiviral backbone containing a short spacer or a long spacer and scFv antigen-binding domains from anti-CD19 CAR #1, anti-BCMA CAR #1 and anti-BCMA CAR #5.

Jurkat cells were individually transduced with viral preparations generated from each vector of the library, and expression of each CAR (as assessed by staining with an anti-idiotypic antibody agonist antibody specific for the FMC63-derived scFv antigen binding domain in the anti-CD19 CAR #1 or BCMA-Fc) and GFP was assessed by flow cytometry. Untransduced Jurkat cells or cells subject to mock transduction (mock) were used as controls. As shown in FIG. 10A, CAR expression was observed to be high and correlated with GFP expression, in cells engineered to express CARs using the vector backbone. Similar results were observed using a backbone vector construct with the EF1α-HTLV1 promoter.

The library of CAR lentiviral vectors are individually transduced into the exemplary Nur77-tdTomato reporter cell line, generated as described in Example 1, and incubated in the presence and/or absence of target antigen or antigen-expressing target cells to assess antigen-specific and antigen-independent tonic signaling. Reporter activation is assessed by detecting reporter (e.g. tdTomato) expression by flow cytometry. Other phenotypes or functional activity can also be assessed. Cells expressing CARs from among the library that exhibit one or more desired characteristics can be selected or identified, and the sequence of the scFv antigen binding domain can be determined.

C. Library Enrichment

In another example, a library of cells transduced with a lentiviral vector CAR library were enriched by selection using a selection agent specific to a selection marker contained in the backbone vector construct, e.g. puromycin resistance gene (PuroR). A library of CAR lentiviral vectors was generated in which the scFv antigen-binding domains from anti-CD19 CAR #1, anti-BCMA CAR #1, anti-BCMA CAR #2, anti-BCMA CAR #3, anti-BCMA CAR #4 and anti-BCMA CAR #5, described above in Examples 2 and 4, were cloned into a vector backbone described above, containing the long spacer (LS) or the short spacer (SS). The vector backbone included puromycin resistance gene (PuroR) as a selection marker.

Jurkat cells were individually transduced with viral preparations generated from each vector of the library. Cells were assessed for CAR expression (as assessed by anti-idiotypic antibody specific for the scFv of anti-CD19 CAR #1 or BCMA-Fc) and GFP expression by flow cytometry. Transduced cells were also subject to puromycin selection in culture for 7 days, at concentrations ranging from 0.1 to 2 μg/mL, and assessed for viability.

Figure 10B:
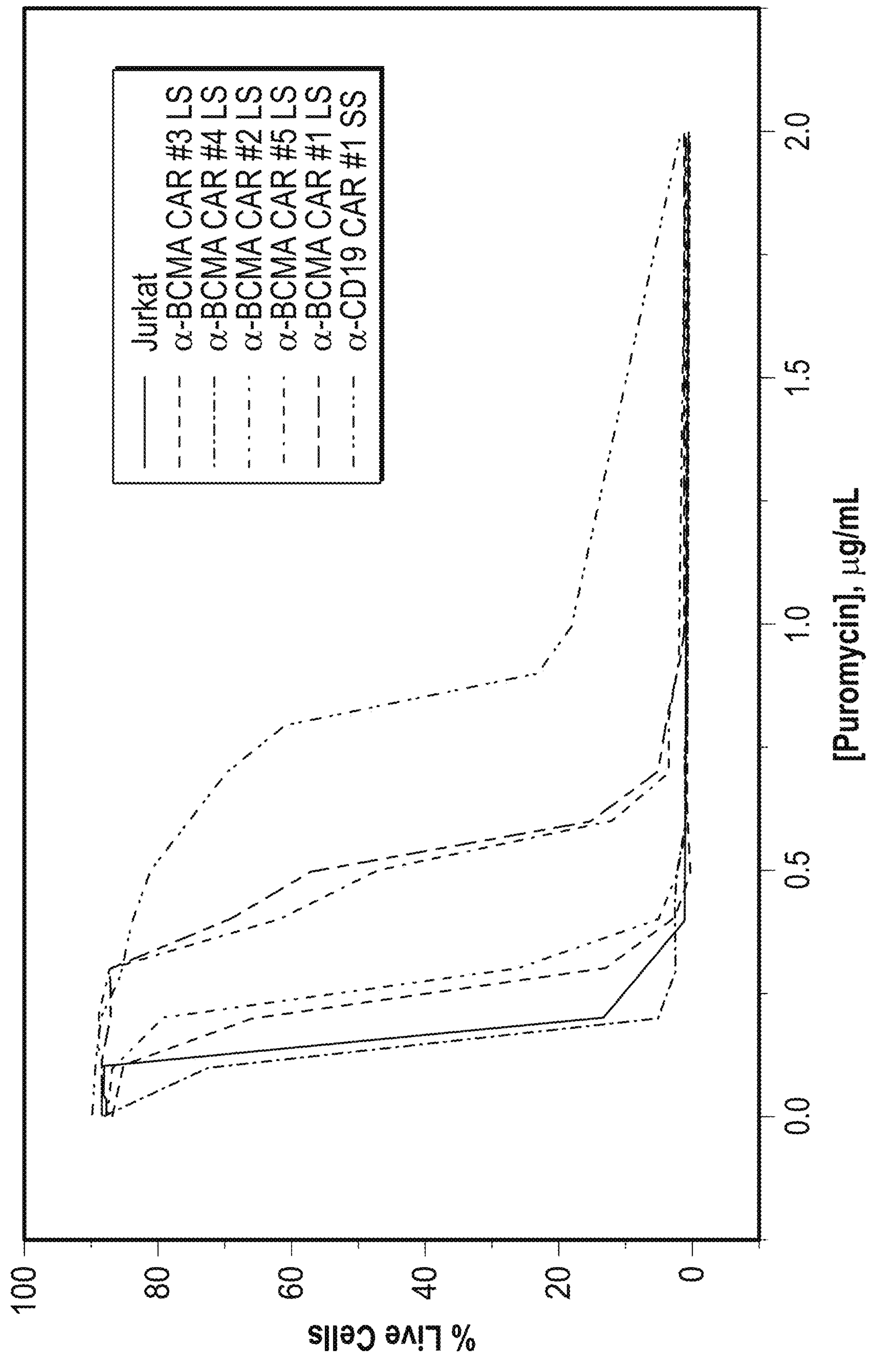
FIG. 10B depicts the percentage of live cells among cells transduced with lentiviral vectors containing a puromycin resistance gene and a long spacer (LS) or a short spacer (SS), into which the scFv antigen-binding domains from anti-CD19 CAR #1, anti-BCMA CAR #1, anti-BCMA CAR #2, anti-BCMA CAR #3, anti-BCMA CAR #4 and anti-BCMA CAR #5 are cloned, after incubation with puromycin concentrations ranging from 0.1 to 2 μg/mL for 7 days.
Figure 10C:
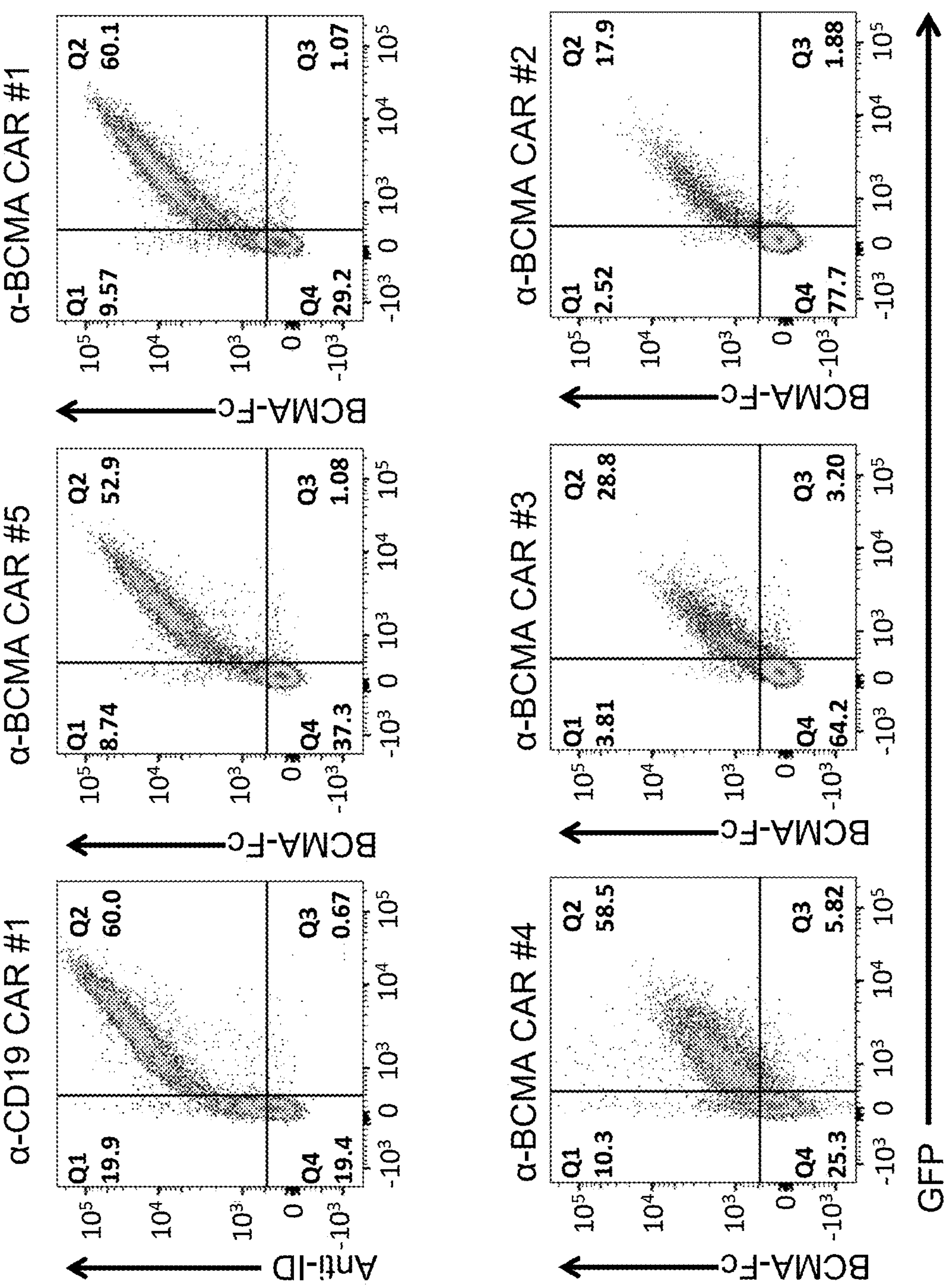
FIG. 10C depicts expression levels of CAR expression, as detected by staining with an anti-idiotypic antibody agonist antibody specific for the FMC63-derived scFv antigen binding domain in the anti-CD19 CAR #1 or BCMA-Fc) and GFP (surrogate marker for CAR expression), as detected by flow cytometry, in cells transduced with CAR constructs generated using an exemplary lentiviral backbone and scFv antigen-binding domains from anti-CD19 CAR #1, anti-BCMA CAR #1, anti-BCMA CAR #2, anti-BCMA CAR #3, anti-BCMA CAR #4 and anti-BCMA CAR #5.

As shown in FIGS. 10B and 10C, the percentage of live cells after puromycin selection generally corresponded to the level of CAR expression shown by flow cytometry. Cells expressing CARs that exhibited higher level of expression (FIG. 10C) survived better at high puromycin concentrations (FIG. 10B). The results showed that the presence of a selection marker can be used to select out CARs with poor/low expression, thereby allowing for enrichment of cells that express CARs at high levels.

Example 10: Screening Candidate Chimeric Antigen Receptors (CARs) after Selection An exemplary candidate chimeric antigen receptors (CARs) library was generated based on a large scFv library, and screened using the screening platform method generally as described in Example 9 above.

A large library of anti-BCMA scFv sequences, containing approximately $3\times10^6$ unique clones, were cloned into an exemplary vector backbone, generally described in Example 9 above, containing a promoter and either a short, a medium or a long spacer, to generate a plasmid library of CAR-encoding sequences. The backbone vector also included a transmembrane domain, an intracellular signaling region containing the 4-1BB-derived intracellular domain and CD3zeta domain, and GFP as a surrogate marker separated from the encoded CAR by a T2A self-cleaving peptide, and a puromycin resistance gene (PuroR) as a selection marker, separated from GFP by T2A.

Jurkat Nur77 reporter cells were transduced with viral preparations generated from the CAR-encoding plasmid library, to generate a library of cells. The library of cells transduced with a lentiviral vector CAR library were enriched by puromycin selection, to select for cells that contain and express the PuroR selection marker contained in the backbone vector construct. After puromycin selection, CAR-expressing cells were further selected by magnetic cell selection with a biotinylated recombinant BCMA antigen. The selected cells were further cultured, then sorted by flow cytometry after staining with fluorescently labeled BCMA. A lentiviral vector encoding anti-BCMA CAR #1, anti-BCMA CAR #3, anti-BCMA CAR #4 and anti-BCMA CAR #5, described in Example 9 above, were also generated for comparison.

Table 1 sets forth the percentage of clones before and after selection, and fold enrichment for 20 clones with the highest percentage in the pool after selection.

TABLE 1

Cell enrichment of exemplary clones.

| | Starting % | Selected % | Fold Change |
|---|---|---|---|
| A | 1.81E−02 | 22.43% | 1236.44 |
| B | 1.59E−02 | 11.76% | 741.37 |
| C | 2.37E−03 | 9.47% | 3993.79 |
| D | 2.05E−03 | 3.52% | 1718.05 |
| E | 1.95E−03 | 1.70% | 869.82 |
| F | 1.05E−02 | 1.32% | 126.36 |
| G | 1.49E−03 | 1.05% | 705.32 |
| H | 4.65E−04 | 1.04% | 2229.97 |
| I | 2.79E−04 | 0.96% | 3453.54 |
| J | 2.80E−02 | 0.79% | 28.28 |
| K | 2.33E−04 | 0.65% | 2807.02 |
| L | 9.30E−04 | 0.64% | 688.67 |
| M | 4.33E−03 | 0.55% | 127.88 |
| N | 6.51E−04 | 0.55% | 848.23 |
| O | 5.49E−03 | 0.48% | 88.02 |
| P | 1.86E−04 | 0.41% | 2226.05 |
| Q | 7.91E−04 | 0.36% | 458.45 |
| R | 8.84E−04 | 0.36% | 406.98 |
| S | 9.30E−05 | 0.34% | 3670.11 |
| T | 4.65E−05 | 0.31% | 6732.65 |

Approximately 80 of the top CAR clones present in the pool after puromycin selection, magnetic selection and flow cytometry-based sorting were isolated and individually assessed by flow cytometry for transduction (as assessed GFP expression), BCMA binding (as assessed by staining with BCMA-Fc). The cells were also assessed for Nur77-tdTomato expression after co-culturing with target cells expressing BCMA to assess antigen-dependent signaling, and without target cells to assess antigen-independent signaling.

Among the selected cells tested for BCMA binding and Nur77-tdTomato expression with or without antigen stimulation, a varying levels of binding and Nur77 expression levels were observed. The results were consistent with the utility of the screening method to generate, enrich and identify a plurality of CAR-expressing cells from a large library of binding domains, to rapidly identify CARs with desired properties (for example, high CAR expression, low antigen-independent signaling, and high antigen-dependent signaling).

Example 11: Screening a Candidate Chimeric Antigen Receptor (CAR) Library Generated by Chain Swapping An exemplary candidate chimeric antigen receptors (CARs) library was generated, containing a common variable heavy ($V_H$) domain of an scFv, and a plurality of variable light ($V_L$) domain swapped in, from a library of $V_L$ domain. The light chain swapped library was screened and assessed for various properties and CARs with particular properties were identified.

A backbone vector similar to those described in Example 9 and FIG. 9A were used to generate a light chain swapped library, based on a parental scFv sequence that binds a target antigen. The vector backbone contained NheI and RsrII restriction sites for cloning in scFv sequences. The vector also included nucleic acid sequences encoding a spacer, a transmembrane domain, a co-stimulatory domain and a CD3zeta, and GFP as a surrogate marker separated from the CAR-encoding sequences by a T2A self-cleaving peptide. A parental scFv-encoding sequence containing a $V_H$-encoding sequence, a linker and a $V_L$-encoding sequence was engineered to contain an asymmetric BsmBI restriction site within the sequences encoding the linker between the sequences encoding the $V_H$ and the $V_L$ domains, and was cloned into the backbone vector. Nucleic acid sequences encoding various $V_L$ domains were amplified by PCR from an scFv library obtained from naïve T cells, using primers containing compatible restriction ends. Amplified products were cloned into the vector digested with BsmBI/RsrII for light chain swapping. Upon ligation of the amplified $V_L$-encoding sequences, a library of plasmids encoding a plurality of scFvs, with a common $V_H$ sequence and different $V_L$ sequences, was generated.

Approximately 56 different light chain swapped CARs were selected for viral transduction into Jurkat Nur77 reporter cells. Viral preparations from the plasmid encoding a CAR containing the parental scFv, and various non-specific CAR-encoding plasmids were used as control. The transduced cells were assessed by flow cytometry for transduction (GFP expression) and antigen binding (as assessed by staining with a recombinant target antigen-Fc fusion protein). Nur77-tdTomato expression was assessed after an overnight co-culture of the transduced Jurkat Nur77 reporter cells at a 1:1 ratio with K562 human myelogenous leukemia target cells expressing a low level of the target antigen and a high level of the target antigen to assess antigen-dependent signaling, K562 cells expressing a related but distinct antigen to assess antigen selectivity, K562 cells without any antigen expression and without any target cells to assess antigen-independent signaling.

The results showed that many of the light chain swapped CARs exhibited improved binding to the target antigen, compared to the parental CAR. The results also showed that some of the light chain swapped CARs exhibited higher antigen-dependent signaling, lower antigen-independent signaling, and improved antigen selectivity. The results were consistent with the utility of the method to generate various libraries, including a chain-swapped library containing a common portion of the binding domain (e.g., $V_H$ region), to rapidly identify CARs with desired properties (for example, high CAR expression, low antigen-independent signaling, and high antigen-dependent signaling).

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

SEQUENCES

| SEQ ID NO: | Sequence | Description |
|---|---|---|
| 1 | ttcctggtgtaagctttggtatggatggtggccgtctccctacagactgggagctg<br>ttagagggcagggatcctagctgacacatctatgtcctcgccttggttggaggcct<br>ccaccatggacagaggccaggccctgcccctcccaggcagcctggctccttctgct<br>gggccctgaaggcagacgggataatgtggttggccaaggcctgttggtccatccag<br>agtgagatgccctgtatccaagcccaatatgggacaccagcaccgagtccgggacc<br>ccgtgaccacctggcaagcgacccctgaccctgagttcatcaagcccaccatgg<br>acctggccagccccgaggcagccccgctgcccccactgccctgcccagcttcagc<br>accttcatggacggctacacaggagagtttgacaccttcctctaccagctgccagg<br>aacagtccagccatgctcctcagcctcctcctcggcctcctccacatcctcgtcct<br>cagccacctcccctgcctctgcctccttcaagttcgaggacttccaggtgtacggc<br>tgctaccccggcccctgagcggcccagtggatgaggccctgtcctccagtggctc<br>tgactactatggcagcccctgctcggccccgtcgccctccacgcccagcttccagc<br>cgccccagctctctccctgggatggctccttcggccacttctcgcccagccagact<br>tacgaaggcctgcgggcatggacagagcagctgcccaaagcctctgggcccccaca<br>gcctccagccttcttttccttcagtcctcccaccggccccagccccagcctggccc<br>agagccccctgaagttgttcccctcacaggccacccaccagctgggggagggagag<br>agctattccatgcctacggccttcccaggtttggcacccacttctccacaccttga<br>gggctcggggatactggatacacccgtgacctcaaccaaggcccggagcggggccc<br>caggtggaagtgaaggccgctgtgctgtgtggggacaacgcttcatgccagcat<br>tatggtgtccgcacatgtgagggctgcaagggcttcttcaagcgcacagtgcagaa<br>aaacgccaagtacatctgcctggctaacaaggactgccctgtggacaagaggcggc<br>gaaaccgctgccagttctgccgcttccagaagtgcctggcggtgggcatggtgaag<br>gaagttgtccgaacagacagcctgaaggggcggcggggccggctaccttcaaaacc<br>caagcagcccccagatgcctcccctgccaatctcctcacttccctggtccgtgcac<br>acctggactcagggcccagcactgccaaactggactactccaagttccaggagctg<br>gtgctgccccactttgggaaggaagatgctggggatgtacagcagttctacgacct<br>gctctccggttctctggaggtcatccgcaagtgggcggagaagatccctggctttg<br>ctgagctgtcaccggctgaccaggacctgttgctggagtcggccttcctggagctc<br>ttcatcctccgcctggcgtacaggtctaagccaggcgagggcaagctcatcttctg<br>ctcaggcctggtgctacaccggctgcagtgtgcccgtggcttcggggactggattg<br>acagtatcctggccttctcaaggtccctgcacagcttgcttgtcgatgtccctgcc<br>ttcgcctgcctctctgcccttgtcctcatcaccgaccggcatgggctgcaggagcc<br>gcggcgggtggaggagctgcagaaccgcatcgccagctgcctgaaggagcacgtgg<br>cagctgtggcgggcgagccccagccagccagctgcctgtcacgtctgttgggcaaa<br>ctgcccgagctgcggaccctgtgcacccagggcctgcagcgcatcttctacctcaa<br>gctggaggacttggtgccccctccacccatcattgacaagatcttcatggacacgc | Human Nur77<br>DNA NCBI<br>Reference<br>Sequence: NM_001202233.1 |

-continued

| SEQ ID NO: | Sequence | Description |
|---|---|---|
| | tgcccttctgacccctgcctgggaacacgtgtgcacatgcgcactctcatatgcca ccccatgtgcctttagtccacggacccccagagcacccccaagcctgggcttgagc tgcagaatgactccaccttctcacctgctccaggaggtttgcagggagctcaagcc cttggggagggggatgccttcatgggggtgaccccacgatttgtcttatcccccccc agcctggccccggcctttatgttttttgtaagataaaccgtttttaacacatagcg ccgtgctgtaaataagcccagtgctgctgtaaatacaggaagaaagagcttgaggt gggagcggggctgggaggaagggatgggccccgccttcctgggcagcctttccagc ctcctgctggctctctcttcctaccctccttccacatgtacataaactgtcactct aggaagaagacaaatgacagattctgacatttatatttgtgtattttcctggattt atagtatgtgacttttctgattaatatatttaatatattgaataaaaaatagacat gtagttggaactgaaaaaaaaaaaaaa | |
| 2 | MWLAKACWSIQSEMPCIQAQYGTPAPSPGPRDHLASDPLTPEFIKPTMDLASPEAA PAAPTALPSFSTFMDGYTGEFDTFLYQLPGTVQPCSSASSSASSTSSSSATSPASA SFKFEDFQVYGCYPGPLSGPVDEALSSSGSDYYGSPCSAPSPSTPSFQPPQLSPWD GSFGHFSPSQTYEGLRAWTEQLPKASGPPQPPAFFSFSPPTGPSPSLAQSPLKLFP SQATHQLGEGESYSMPTAFPGLAPTSPHLEGSGILDTPVTSTKARSGAPGGSEGRC AVCGDNASCQHYGVRTCEGCKGFFKRTVQKNAKYICLANKDCPVDKRRRNRCQFCR FQKCLAVGMVKEVVRTDSLKGRRGRLPSKPKQPPDASPANLLTSLVRAHLDSGPST AKLDYSKFQELVLPHFGKEDAGDVQQFYDLLSGSLEVIRKWAEKIPGFAELSPADQ DLLLESAFLELFILRLAYRSKPGEGKLIFCSGLVLHRLQCARGEGDWIDSILAFSR SLHSLLVDVPAFACLSALVLITDRHGLQEPRRVEELQNRIASCLKEHVAAVAGEPQ PASCLSRLLGKLPELRTLCTQGLQRIFYLKLEDLVPPPPIIDKIFMDTLP | Human Nur77 NCBI Reference Sequence: NP_001189162.1 |
| 3 | CAUGAAGAUCUUGUCAAUGA | Human Nur77 gRNA 1 targeting domain |
| 4 | UGCACACGUGUUCCCAGGC | Human Nur77 gRNA 2 targeting domain |
| 5 | gaaggcagaggctctctcctcacatgtggggatgttgaagaaaatccaggtccc | T2A DNA |
| 6 | EGRGSLLTCGDVEENPGP | T2A protein |
| 7 | gtgagcaagggcgaggaggtgatcaaggagtttatgagattcaaagtccggatgga gggcagcatgaacggacatgagttcgaaattgagggagaaggcgagggacgacctt acgagggaacacagaccgccaaactgaaagtgacaaaaggcggacctctgccattt gcttgggacatcctgagtccacagttcatgtatggctctaaggcttacgtgaaaca ccctgccgatattcccgactacaaaaaactgagtttccctgaaggcttcaaatggg aacgagtgatgaactttgaggacggaggcctggtgacagtgacacaggactctagt ctccaggacggcacactcatctacaaagtgaaaatgagggggcaccaatttccctcc cgatggacctgtcatgcagaaaaaaacaatgggatgggaggcttctaccgaacgac tgtacccacgggatggagtgctgaaaggcgagatccatcaggcactgaaactgaag gatggcggccattacctggtcgagttcaaaaccatctatatggccaaaaaacccgt ccagctgcctggctactattacgtggataccaaactggacattacctctcacaatg aagactacacaatcgtcgagcagtacgagaggagtgagggccgacaccacctcttc ctcgggcatggcaccggcagcaccggcagcggcagctccggcaccgctagttccga ggacaacaacatggccgtcatcaaagagttcatgcgcttcaaggtgcgcatggagg gctccatgaacggccacgagttcgagatcgagggcgagggcgagggccgcccctac gagggcacccagaccgccaagctgaaggtgaccaagggcggccccctgcccttcgc ctgggacatcctgtcccccagttcatgtacggctccaaggcgtacgtgaagcacc ccgccgacatccccgattacaagaagctgtccttccccgagggcttcaagtgggag cgcgtgatgaacttcgaggacggcggtctggtgaccgtgacccaggactcctccct gcaggacggcacgctgatctacaaggtgaagatgcgcggcaccaacttccccccccg acggccccgtaatgcagaagaagaccatgggctgggaggcctccaccgagcgcctg taccccgcgacggcgtgctgaagggcgagatccaccaggccctgaagctgaagga cggcggccactacctggtggagttcaagaccatctacatggccaagaagcccgtgc aactgcccggctactactacgtggacaccaagctggacatcacctcccacaacgag gactacaccatcgtggaacagtacgagcgctccgagggccgccaccacctgttcct gtacggcatggacgagctgtac | tdTomato DNA |
| 8 | VSKGEEVIKEFMRFKVRMEGSMNGHEFEIEGEGEGRPYEGTQTAKLKVTKGGPLPF AWDILSPQFMYGSKAYVKHPADIPDYKKLSFPEGFKWERVMNFEDGGLVTVTQDSS LQDGTLIYKVKMRGTNFPPDGPVMQKKTMGWEASTERLYPRDGVLKGEIHQALKLK DGGHYLVEFKTIYMAKKPVQLPGYYYVDTKLDITSHNEDYTIVEQYERSEGRHHLF LGHGTGSTGSGSSGTASSEDNNMAVIKEFMRFKVRMEGSMNGHEFEIEGEGEGRPY EGTQTAKLKVTKGGPLPFAWDILSPQFMYGSKAYVKHPADIPDYKKLSFPEGFKWE RVMNFEDGGLVTVTQDSSLQDGTLIYKVKMRGTNFPPDGPVMQKKTMGWEASTERL YPRDGVLKGEIHQALKLKDGGHYLVEFKTIYMAKKPVQLPGYYYVDTKLDITSHNE DYTIVEQYERSEGRHHLFLYGMDELY | tdTomato protein |

-continued

SEQUENCES

| SEQ ID NO: | Sequence | Description |
|---|---|---|
| 9 | CTCAAGCTGGAGGACTTGGTGCCCCCTCCACCCATCATTGACAAGATCTTCATGGA CACGCTGCCCTTCTGACCCCTGCCTGGGAACACGTGTGCACATGCGCACTCTCATA TGCCACCCCATGTGCCTTTAGTCCACGG | Human Nur77 final exon and 3' UTR sequence |
| 10 | GAGTTCGACCTCCTGAACCACGGGGGAGGTGGGTAGTAACTGTTCTAGAAGTACCT GTGCGACGGGAAGACTGGGGACGGACCCTTGTGCACACGTGTACGCGTGAGAGTAT ACGGTGGGGTACACGGAAATCAGGTGCC | Human Nur77 final exon and 3' UTR sequence complement strand sequence |
| 11 | MLLLVTSLLLCELPHPAFLLIPRKVCNGIGIGEFKDSLSINATNIKHFKNCTSISG DLHILPVAFRGDSFTHTPPLDPQELDILKTVKEITGFLLIQAWPENRTDLHAFENL EIIRGRTKQHGQFSLAVVSLNITSLGLRSLKEISDGDVIISGNKNLCYANTINWKK LFGTSGQKTKIISNRGENSCKATGQVCHALCSPEGCWGPEPRDCVSCRNVSRGREC VDKCNLLEGEPREFVENSECIQCHPECLPQAMNITCTGRGPDNCIQCAHYIDGPHC VKTCPAGVMGENNTLVWKYADAGHVCHLCHPNCTYGCTGPGLEGCPTNGPKIPSIA TGMVGALLLLLVVALGIGLFM | EGFRt |
| 12 | atgccgctgctgctactgctgcccctGCTgTGGGCaGGgGCtctagag | CD33 leader sequence |
| 13 | MPLLLLLPLLWAGALE | CD33 leader sequence |
| 14 | GCTBTGGGCHGGNGC | CD33 barcode region |
| 15 | atgccgctgctgctactgctgcccctGCTBTGGGCHGGNGCtctagag | CD33 leader sequence |
| 16 | aggctagcggcgcgccgccaccatgccgctgctgctactgctgcccctGCTBTGGG CHGGNGCtctagagagacgg | CD33 barcode in vector containing NheI, XbaI and BsmBI sites |
| 17 | tccgatcgccgcgcggcggtggtacggcgacgacgatgacgacggggaCGAVACCC GDCCNCGagatctctctgcc | CD33 barcode in vector containing NheI, XbaI and BsmBI sites complement strand |
| 18 | cggaccgccctgccctccctgccctatgttttgggtgctggtcgtggtcggagggg tgctggcctg | Hinge-CD28 TM in vector containing RsrII site |
| 19 | gcctrggcgggacgggagggacgggatacaaaacccacgaccagcaccagcctccc cacgaccggac | Hinge-CD28 TM in vector containing RsrII site complement strand |
| 20 | ESKYGPPCPPCP | IgG4 hinge spacer (short spacer) |
| 21 | GAATCTAAGTACGGACCGCCTTGTCCTCCATGTCCT | IgG4 hinge spacer (short spacer) |
| 22 | ESKYGPPCPPCPGQPREPQVYTLPPSQEEMTKNQVSLTCLVKGFYPSDIAVEWESN GQPENNYKTTPPVLDSDGSFFLYSRLTVDKSRWQEGNVFSCSVMHEALHNHYTQKS LSLSLGK | Hinge-CH3 spacer (medium spacer) |
| 23 | GAATCTAAGTACGGACCGCCTTGTCCTCCATGTCCTGGCCAGCCAAGAGAACCCCA GGTGTACACACTGCCTCCAAGCCAAGAGGAAATGACCAAGAACCAGGTGTCCCTGA CCTGCCTGGTCAAGGGCTTCTACCCTTCCGATATCGCCGTGGAATGGGAGAGCAAT GGCCAGCCTGAGAACAACTACAAGACCACACCTCCTGTGCTGGACAGCGACGGCTC ATTCTTCCTGTACAGCCGGCTGACCGTGGACAAGAGCAGATGGCAAGAGGGCAACG TGTTCAGCTGCAGCGTGATGCACGAGGCCCTGCACAACCACTACACCCAGAAGTCT CTGAGCCTGAGCCTGGGCAAG | Hinge-CH3 spacer (medium spacer) |
| 24 | ESKYGPPCPPCPAPPVAGPSVFLFPPKPKDTLMISRTPEVTCVVVDVSQEDPEVQF NWYVDGVEVHNAKTKPREEQFQSTYRVVSVLTVLHQDWLNGKEYKCKVSNKGLPSS IEKTISKAKGQPREPQVYTLPPSQEEMTKNQVSLTCLVKGFYPSDIAVEWESNGQP ENNYKTTPPVLDSDGSFFLYSRLTVDKSRWQEGNVFSCSVMHEALHNHYTQKSLSL SLGK | Hinge-CH2-CH3 spacer |
| 25 | GAATCTAAGTACGGACCGCCTTGTCCTCCATGTCCTGCTCCTCCAGTTGCCGGACC TTCCGTGTTCCTGTTTCCTCCAAAGCCTAAGGACACCCTGATGATCAGCAGAACCC CTGAAGTGACCTGCGTGGTGGTGGACGTGTCCCAAGAGGATCCTGAGGTGCAGTTC AACTGGTATGTGGACGGCGTGGAAGTGCACAACGCCAAGACCAAGCCTAGAGAGGA ACAGTTCCAGAGCACCTACAGAGTGGTGTCCGTGCTGACAGTGCTGCACCAGGATT GGCTGAACGGCAAAGAGTACAAGTGCAAGGTGTCCAACAAGGGCCTGCCTAGCAGC ATCGAGAAAACCATCAGCAAGGCCAAGGGCCAGCCAAGAGAACCCCAGGTGTACAC ACTGCCTCCAAGCCAAGAGGAAATGACCAAGAACCAGGTGTCCCTGACCTGCCTGG TCAAGGGCTTCTACCCTTCCGATATCGCCGTGGAATGGGAGAGCAATGGCCAGCCT GAGAACAACTACAAGACCACACCTCCTGTGCTGGACAGCGACGGCTCATTCTTCCT | Hinge-CH2-CH3 spacer |

-continued

| SEQ ID NO: | Sequence | Description |
|---|---|---|
| | GTACAGCCGGCTGACCGTGGACAAGAGCAGATGGCAAGAGGGCAACGTGTTCAGCT GCAGCGTGATGCACGAGGCCCTGCACAACCACTACACCCAGAAGTCTCTGAGCCTG AGCCTGGGCAAG | |
| 26 | RWPESPKAQASSVPTAQPQAEGSLAKATTAPATTRNTGRGGEEKKKEKEKEEQEER ETKTPECPSHTQPLGVYLLTPAVQDLWLRDKATFTCFVVGSDLKDAHLTWEVAGKV PTGGVEEGLLERHSNGSQSQHSRLTLPRSLWNAGTSVTCTLNHPSLPPQRLMALRE PAAQAPVKLSLNLLASSDPPEAASWLLCEVSGFSPPNILLMWLEDQREVNTSGFAP ARPPPQPGSTTFWAWSVLRVPAPPSPQPATYTCVVSHEDSRTLLNASRSLEVSYVT DH | IgD-hinge-Fc |
| 27 | FWVLVVVGGVLACYSLLVTVAFIIFWV | CD28 (amino acids 153-179 of Accession No. P10747) |
| 28 | IEVMYPPPYLDNEKSNGTIIHVKGKHLCPSPLFPGPSKPFWVLVVVGGVLACYSLL VTVAFIIFWV | CD28 (amino acids 114-179 of Accession No. P10747) |
| 29 | RSKRSRLLHSDYMNMTPRRPGPTRKHYQPYAPPRDFAAYRS | CD28 (amino acids 180-220 of P10747) |
| 30 | RSKRSRGGHSDYMNMTPRRPGPTRKHYQPYAPPRDFAAYRS | CD28 (LL to GG) |
| 31 | KRGRKKLLYIFKQPFMRPVQTTQEEDGCSCRFPEEEEGGCEL | 4-1BB (amino acids 214-255 of Q07011.1) |
| 32 | RVKFSRSADAPAYQQGQNQLYNELNLGRREEYDVLDKRRGRDPEMGGKPRRKNPQE GLYNELQKDKMAEAYSEIGMKGERRRGKGHDGLYQGLSTATKDTYDALHMQALPPR | CD3 zeta |
| 33 | RVKFSRSAEPPAYQQGQNQLYNELNLGRREEYDVLDKRRGRDPEMGGKPRRKNPQE GLYNELQKDKMAEAYSEIGMKGERRRGKGHDGLYQGLSTATKDTYDALHMQALPPR | CD3 zeta |
| 34 | RVKFSRSADAPAYKQGQNQLYNELNLGRREEYDVLDKRRGRDPEMGGKPRRKNPQE GLYNELQKDKMAEAYSEIGMKGERRRGKGHDGLYQGLSTATKDTYDALHMQALPPR | CD3 zeta |
| 35 | ATGGTGTCCAAGGGCGAAGAACTGTTTACCGGCGTGGTGCCCATCCTGGTGGAACT GGATGGGGATGTGAACGGCCACAAGTTCAGCGTCAGAGGCGAAGGCGAAGGGGATG CCACAAACGGCAAGCTGACCCTGAAGTTCATCTGCACCACCGGAAAGCTGCCCGTG CCTTGGCCTACACTGGTCACCACACTGACATACGGCGTGCAGTGCTTTAGCAGATA CCCCGACCATATGAAGCAGCACGACTTCTTCAAGAGCGCCATGCCTGAGGGCTACG TGCAAGAGAGAACCATCACCTTCAAGGACGACGGCACCTACAAGACACGGGCCGAA GTGAAGTTTGAGGGCGACACCCTGGTCAACCGGATCGAGCTGAAGGGCATCGACTT CAAAGAGGACGGCAACATCCTGGGCCACAAGCTCGAGTACAACTTCAACAGCCACA ACGTGTACATCACCGCCGACAAGCAGAAGAACGGCATCAAGGCCAACTTCAAGATC CGGCACAACGTCGAGGATGGCTCTGTGCAGCTGGCCGATCACTACCAGCAGAACAC ACCCATCGGAGATGGCCCAGTGCTGCTGCCCGATAACCACTACCTGAGCACACAGA GCAAGCTGAGCAAGGACCCCAACGAGAAGCGGGACCACATGGTGCTGCTGGAATTT GTGACAGCCGCCGGAATCACCCACGGCATGGACGAGCTGTATAAGATAA | super-fold green fluorescent protein nucleic acid |
| 36 | MVSKGEELFTGVVPILVELDGDVNGHKFSVRGEGEGDATNGKLTLKFICTTGKLPV PWPTLVTTLTYGVQCFSRYPDHMKQHDFFKSAMPEGYVQERTITFKDDGTYKTRAE VKFEGDTLVNRIELKGIDFKEDGNILGHKLEYNFNSHNVYITADKQKNGIKANFKI RHNVEDGSVQLADHYQQNTPIGDGPVLLPDNHYLSTQSKLSKDPNEKRDHMVLLEF VTAAGITHGMDELYK | super-fold green fluorescent protein amino acid |
| 37 | MLQMAGQCSQNEYFDSLLHACIPCQLRCSSNTPPLTCQRYCNASVTNSVKGTNAIL WTCLGLSLIISLAVFVLMFLLRKISSEPLKDEFKNTGSGLLGMANIDLEKSRTGDE IILPRGLEYTVEECTCEDCIKSKPKVDSDHCFPLPAMEEGATILVTTKTNDYCKSL PAALSATEIEKSISAR | Human BCMA; GenBank No. BAB60895.1 |
| 38 | MAQQCFHSEYFDSLLHACKPCHLRCSNPPATCQPYCDPSVTSSVKGTYTVLWIFLG LTLVLSLALFTISFLLRKMNPEALKDEPQSPGQLDGSAQLDKADTELTRIRAGDDR IFPRSLEYTVEECTCEDCVKSKPKGDSDHFFPLPAMEEGATILVTTKTGDYGKSSV PTALQSVMGMEKPTHTR | Mouse BCMA; NCBI No. NP_035738.1 |
| 39 | MLQMARQCSQNEYFDSLLHDCKPCQLRCSSTPPLTCQRYCNASMTNSVKGMNAILW TCLGLSLIISLAVFVLTFLLRKMSSEPLKDEFKNTGSGLLGMANIDLEKGRTGDEI VLPRGLEYTVEECTCEDCIKNKPKVDSDHCFPLPAMEEGATILVTTKTNDYCNSLS AALSVTEIEKSISAR | Cynomolgus BCMA; GenBank No. EHH60172.1 |
| 40 | GGATCTGCGATCGCTCCGGTGCCCGTCAGTGGGCAGAGCGCACATCGCCCACAGTC CCCGAGAAGTTGGGGGGAGGGGTCGGCAATTGAACCGGTGCCTAGAGAAGGTGGCG CGGGGTAAACTGGGAAAGTGATGTCGTGTACTGGCTCCGCCTTTTTCCCGAGGGTG GGGGAGAACCGTATATAAGTGCAGTAGTCGCCGTGAACGTTCTTTTTCGCAACGGG | Ef1 alpha promoter with HTLV1 enhancer |

-continued

SEQUENCES

| SEQ ID NO: | Sequence | Description |
|---|---|---|
| | TTTGCCGCCAGAACACAGCTGAAGCTTCGAGGGGCTCGCATCTCTCCTTCACGCGC CCGCCGCCCTACCTGAGGCCGCCATCCACGCCGGTTGAGTCGCGTTCTGCCGCCTC CCGCCTGTGGTGCCTCCTGAACTGCGTCCGCCGTCTAGGTAAGTTTAAAGCTCAGG TCGAGACCGGGCCTTTGTCCGGCGCTCCCTTGGAGCCTACCTAGACTCAGCCGGCT CTCCACGCTTTGCCTGACCCTGCTTGCTCAACTCTACGTCTTTGTTTCGTTTTCTG TTCTGCGCCGTTACAGATCCAAGCTGTGACCGGCGCCTAC | |
| 41 | GAACAGAGAAACAGGAGAATATGGGCCAAACAGGATATCTGTGGTAAGCAGTTCCT GCCCCGGCTCAGGGCCAAGAACAGTTGGAACAGCAGAATATGGGCCAAACAGGATA TCTGTGGTAAGCAGTTCCTGCCCCGGCTCAGGGCCAAGAACAGATGGTCCCCAGAT GCGGTCCCGCCCTCAGCAGTTTCTAGAGAACCATCAGATGTTTCCAGGGTGCCCCA AGGACCTGAAATGACCCTGTGCCTTATTTGAACTAACCAATCAGTTCGCTTCTCGC TTCTGTTCGCGCGCTTCTGCTCCCCGAGCTCTATATAAGCAGAGCTCGTTTAGTGA ACCGTCAGATC | MND promoter |
| 42 | GSGATNFSLLKQAGDVEENPGP | P2A |
| 43 | ATNFSLLKQAGDVEENPGP | P2A |
| 44 | QCTNYALLKLAGDVESNPGP | E2A |
| 45 | VKQTLNFDLLKLAGDVESNPGP | F2A |
| 46 | MFWVLVVVGGVLACYSLLVTVAFIIFWV | CD28 TM |
| 47 | AATCTCACTATGTTGCCCGAGCTGGTCTCGAACTCCTGGGCTCAAATGATCCTCCT GTCTCAGCCTCCTAAAGTGCTGGGATTACAGGTGTGAGCCACCACGCCTAGCCCTT CACTGTGACTTCTGACAGTGCAGATCAGATTGGTTGTGCCTGTTTTGGACTTTATG TAAATGTAGTTCTGCAGGATGGAATCTGGTGTTGAATGCAGAGGTTTTCAGATTTC TCTGTTTTTTAAAGGAAAGAATCCACCCTCGTTCATTTTTTCACTTAAATTGCACA GGGGACCCAACGATATAGAACACAATCAGAGGTACTCTGGGCTGAGGGAGTGCTGA GTTCTGAGGCTGGGTTTCTCAGAACAGTCTAGATTTTAAAAACCCAATGATCTAGC CAGAAAACGTAGGTTAGGATTTTATTTCCCGTTTGTGACCCTGGGCAAGTCATTAG CCTCCTGGGCCTCGGGTTCTCACTTGGAGTATGAGGATAATGAGGGTTACTGCTTC TCAGACTTGTGACGATGCTTACTAATGGCCAACATGTGAATGCGCTTTTGTGAAGT GCCAGCAGAGCATGAGGGGTGGTCAGGGGCAGCAGTTTTAGGGGCCTGGGGGAGGC TGGGGCTTTGGGGGCCTGGTTCTCAGATGTACAGCTAATCCTGTACCCTTCCCGCA GACCGGCATGGGCTGCAGGAGCCGCGGCGGGTGGAGGAGCTGCAGAACCGCATCGC CAGCTGCCTGAAGGAGCACGTGGCAGCTGTGGCGGGCGAGCCCCAGCCAGCCAGCT GCCTGTCACGTCTGTTGGGCAAACTGCCCGAGCTGCGGACCCTGTGCACCCAGGGC CTGCAGCGTATCTTCTACCTCAAGCTGGAGGACTTGGTGCCCCCTCCACCCATCAT TGACAAGATCTTCATGGACACGCTGCCCTTC | Nur77 genomic sequence corresponding to left homology arm (chr12:52,058,015-52,058,941 hg38 assembly) |
| 48 | MPLLLLLPLLWAGALA | CD33 leader regenerated XbaI/NheI digested sequence |
| 49 | AATCTCACTATGTTGCCCGAGCTGGTCTCGAACTCCTGGGCTCAAATGATCCTCCT GTCTCAGCCTCCTAAAGTGCTGGGATTACAGGTGTGAGCCACCACGCCTAGCCCTT CACTGTGACTTCTGACAGTGCAGATCAGATTGGTTGTGCCTGTTTTGGACTTTATG TAAATGTAGTTCTGCAGGATGGAATCTGGTGTTGAATGCAGAGGTTTTCAGATTTC TCTGTTTTTTAAAGGAAAGAATCCACCCTCGTTCATTTTTTCACTTAAATTGCACA GGGGACCCAACGATATAGAACACAATCAGAGGTACTCTGGGCTGAGGGAGTGCTGA GTTCTGAGGCTGGGTTTCTCAGAACAGTCTAGATTTTAAAAACCCAATGATCTAGC CAGAAAACGTAGGTTAGGATTTTATTTCCCGTTTGTGACCCTGGGCAAGTCATTAG CCTCCTGGGCCTCGGGTTCTCACTTGGAGTATGAGGATAATGAGGGTTACTGCTTC TCAGACTTGTGACGATGCTTACTAATGGCCAACATGTGAATGCGCTTTTGTGAAGT GCCAGCAGAGCATGAGGGGTGGTCAGGGGCAGCAGTTTTAGGGGCCTGGGGGAGGC TGGGGCTTTGGGGGCCTGGTTCTCAGATGTACAGCTAATCCTGTACCCTTCCCGCA GACCGGCATGGGCTGCAGGAGCCGCGGCGGGTGGAGGAGCTGCAGAACCGCATCGC CAGCTGCCTGAAGGAGCACGTGGCAGCTGTGGCGGGCGAGCCCCAGCCAGCCAGCT GCCTGTCACGTCTGTTGGGCAAACTGCCCGAGCTGCGGACCCTGTGCACCCAGGGC CTGCAGCGTATCTTCTACCTCAAGCTGGAGGACTTGGTGCCCCCTCCACCtATCAT cGACAAGATCTTCATGGACACGCTGCCCTTC | Nur77 left homology arm (chr12:52,058,015-52,058,941 hg38 assembly), with silent mutations |
| 50 | GCCTGGGAACACGTGTGCACATGCGCACTCTCATATGCCACCCCATGTGCCTTTAG TCCACGGACCCCCAGAGCACCCCCAAGCCTGGGCTTGAGCTGCAGAATGACTCCAC CTTCTCACCTGCTCCAGGAGGTTTGCAGGGAGCTCAAGCCCTTGGGGAGGGGGATG CCTTCATGGGGGTGACCCCACGATTTGTCTTATCCCCCCCAGCCTGGCCCCGGCCT TTATGTTTTTTGTAAGATAAACCGTTTTTAACACATAGCGCCGTGCTGTAAATAAG CCCAGTGCTGCTGTAAATACAGGAAGAAAGAGCTTGAGGTGGGAGCGGGGCTGGGA GGAAGGGATGGGCCCCGCCTTCCTGGGCAGCCTTTCCAGCCTCCTGCTGGCTCTCT CTTCCTACCCTCCTTCCACATGTACATAAACTGTCACTCTAGGAAGAAGACAAATG | Nur77 right homology arm (chr12:52,058,950-52,059,924 hg38 assembly): |

-continued

SEQUENCES

| SEQ ID NO: | Sequence | Description |
| --- | --- | --- |
| | ACAGATTCTGACATTTATATTTGTGTATTTTCCTGGATTTATAGTATGTGACTTTT<br>CTGATTAATATATTTAATATATTGAATAAAAAATAGACATGTAGTTGGAACTGAGA<br>TTCAGTCTGTCTCTGATGCCCCCTCCCCACTCCCCCACCAGACACACCCCATCATT<br>ACATAAGAGATGGGCTGCTCAAGATGAAACTTGGATGTTACCAGCCTGAGCTGTCA<br>GGCCTCAGTGTACTCATTTGTAAAAGGCGGATAATAATGACACCTGCTTCACGAGG<br>TTGTTATGCAAAGCACTTAGACTAATTTCTAACACGTGGGAAGCCTGCATTAGCTG<br>TGCCTGGCTAGCTGTGCCTGGCTCATTGCTGGGGTCTGCAGTGGCTGACTAGCCCA<br>GGGGTCACTGCAGGGCCCTAGCAATAGACTTAGCCGCAGATCTCAGGGTTGTCATG<br>TTTCCTAAACTGGACATATATTCTCTGATTCTTGATTTCCACATCCATAAAACAAG<br>AATAGACCCAGCCTCACAGAGCT | |
| 51 | cagcctcctaaagtgctgggattacaggtgtgagccaccacgcctagcccttcact<br>gtgacttctgacagtgcagatcagattggttgtgcctgttttggactttatgtaaa<br>tgtagttctgcaggatggaatctggtgttgaatgcagaggttttcagatttctctg<br>tttttaaaggaaagaatccaccctcgttcatttttttcacttaaattgcacagggg<br>acccaacgatatagaacacaatcagaggtactctgggctgagggagtgctgagttc<br>tgaggctgggtttctcagaacagtctagattttaaaaacccaatgatctagccaga<br>aaacgtaggttaggattttatttcccgtttgtgaccctgggcaagtcattagcctc<br>ctgggcctcgggttctcacttggagtatgaggataatgagggttactgcttctcag<br>acttgtgacgatgcttactaatggccaacatgtgaatgcgcttttgtgaagtgcca<br>gcagagcatgaggggtggtcaggggcagcagttttaggggcctgggggaggctggg<br>gctttgggggcctggttctcagatgtacagctaatcctgtacccttcccgcagacc<br>ggcatgggctgcaggagccgcggcgggtggaggagctgcagaaccgcatcgccagc<br>tgcctgaaggagcacgtggcagctgtggcgggcgagccccagccagccagctgcct<br>gtcacgtctgttgggcaaactgcccgagctgcggaccctgtgcacccagggcctgc<br>agcgtatcttctacctcaagctggaggacttggtgccccctccacctatcatcgac<br>aagatcttcatggacacgctgcccttcggatccggagaaggcagaggctctctcct<br>cacatgtggggatgttgaagaaaatccaggtcccggtgtgagcaagggcgaggagg<br>tgatcaaggagtttatgagattcaaagtccggatggagggcagcatgaacggacat<br>gagttcgaaattgagggagaaggcgagggacgaccttacgagggaacacagaccgc<br>caaactgaaagtgacaaaaggcggacctctgccatttgcttgggacatcctgagtc<br>cacagttcatgtatggctctaaggcttacgtgaaacaccctgccgatattcccgac<br>tacaaaaaactgagtttccctgaaggcttcaaatgggaacgagtgatgaactttga<br>ggacggaggcctggtgacagtgacacaggactctagtctccaggacggcacactca<br>tctacaaagtgaaaatgaggggcaccaatttccctcccgatggacctgtcatgcag<br>aaaaaaacaatgggatgggaggcttctaccgaacgactgtacccacgggatggagt<br>gctgaaaggcgagatccatcaggcactgaaactgaaggatggcggccattacctgg<br>tcgagttcaaaaccatctatatggccaaaaaacccgtccagctgcctggctactat<br>tacgtggataccaaactggacattacctctcacaatgaagactacacaatcgtcga<br>gcagtacgagaggagtgagggccgacaccacctcttcctcgggcatggcaccggca<br>gcaccggcagcggcagctccggcaccgctagttccgaggacaacaacatggccgtc<br>atcaaagagttcatgcgcttcaaggtgcgcatggagggctccatgaacggccacga<br>gttcgagatcgagggcgagggcgagggccgcccctacgagggcacccagaccgcca<br>agctgaaggtgaccaagggcggccccctgcccttcgcctgggacatcctgtccccc<br>cagttcatgtacggctccaaggcgtacgtgaagcaccccgccgacatccccgatta<br>caagaagctgtccttccccgagggcttcaagtgggagcgcgtgatgaacttcgagg<br>acggcggtctggtgaccgtgacccaggactcctccctgcaggacggcacgctgatc<br>tacaaggtgaagatgcgcggcaccaacttcccccccgacggccccgtaatgcagaa<br>gaagaccatgggctgggaggcctccaccgagcgcctgtaccccgcgacggcgtgc<br>tgaagggcgagatccaccaggccctgaagctgaaggacggcggccactacctggtg<br>gagttcaagaccatctacatggccaagaagcccgtgcaactgcccggctactacta<br>cgtggacaccaagctggacatcacctcccacaacgaggactacaccatcgtggaac<br>agtacgagcgctccgagggccgccaccacctgttcctgtacggcatggacgagctg<br>tacaaatgactcgagcctgggaacacgtgtgcacatgcgcactctcatatgccacc<br>ccatgtgcctttagtccacggacccccagagcacccccaagcctgggcttgagctg<br>cagaatgactccaccttctcacctgctccaggaggtttgcagggagctcaagccct<br>tggggaggggggatgccttcatgggggtgaccccacgatttgtcttatcccccccag<br>cctggccccggcctttatgtttttgtaagataaaccgtttttaacacatagcgcc<br>gtgctgtaaataagcccagtgctgctgtaaatacaggaagaaagagcttgaggtgg<br>gagcggggctgggaggaagggatgggccccgccttcctgggcagcctttccagcct<br>cctgctggctctctcttcctaccctccttccacatgtacataaactgtcactctag<br>gaagaagacaaatgacagattctgacatttatatttgtgtattttcctggatttat<br>agtatgtgacttttctgattaatatatttaatatattgaataaaaaatagacatgt<br>agttggaactgagattcagtctgtctctgatgccccctccccactcccccaccaga<br>cacaccccatcattacataagagatgggctgctcaagatgaaacttggatgttacc<br>agcctgagctgtcaggcctcagtgtactcatttgtaaaaggcggataataatgaca<br>cctgcttcacgaggttgttatgcaaagcacttagactaatttctaacacgtgggaa<br>gcctgcattagctgtgcctggctagctgtgcctggctcattgctggggtctgcagt<br>ggctgactagcccaggggtcactgcagggccctagcaatagacttagccgcagatc<br>tcagggttgtcatgtttcctaaactggacatatattctctgattcttgatttccac<br>atccataaaacaagaatagacccagcctcacagagct | Nur77 knock-in construct sequence |

-continued

SEQUENCES

| SEQ ID NO: | Sequence | Description |
|---|---|---|
| 52 | RHGLQEPRRVEELQNRIASCLKEHVAAVAGEPQPASCLSRLLGKLPELRTLCTQGL QRIFYLKLEDLVPPPPIIDKIFMDTLPF | Nur77 final exon |
| 53 | atggtgagcaagggcgaggaggtcatcaaagagttcatgcgcttcaaggtgcgcat ggagggctccatgaacggccacgagttcgagatcgagggcgagggcgagggccgcc cctacgagggcacccagaccgccaagctgaaggtgaccaagggcggccccctgccc ttcgcctgggacatcctgtccccccagttcatgtacggctccaaggcgtacgtgaa gcaccccgccgacatccccgattacaagaagctgtccttccccgagggcttcaagt gggagcgcgtgatgaacttcgaggacggcggtctggtgaccgtgacccaggactcc tccctgcaggacggcacgctgatctacaaggtgaagatgcgcggcaccaacttccc ccccgacggccccgtaatgcagaagaagaccatgggctgggaggcctccaccgagc gcctgtaccccccgcgacggcgtgctgaagggcgagatccaccaggccctgaagctg aaggacggcggccactacctggtggagttcaagaccatctacatggccaagaagcc cgtgcaactgcccggctactactacgtggacaccaagctggacatcacctcccaca acgaggactacaccatcgtggaacagtacgagcgctccgagggccgccaccacctg ttcctggggcatggcaccggcagcaccggcagcggcagctccggcaccgcctcctc cgaggacaacaacatggccgtcatcaaagagttcatgcgcttcaaggtgcgcatgg agggctccatgaacggccacgagttcgagatcgagggcgagggcgagggccgcccc tacgagggcacccagaccgccaagctgaaggtgaccaagggcggcccctgccctt cgcctgggacatcctgtccccccagttcatgtacggctccaaggcgtacgtgaagc accccgccgacatccccgattacaagaagctgtccttccccgagggcttcaagtgg gagcgcgtgatgaacttcgaggacggcggtctggtgaccgtgacccaggactcctc cctgcaggacggcacgctgatctacaaggtgaagatgcgcggcaccaacttccccc ccgacggccccgtaatgcagaagaagaccatgggctgggaggcctccaccgagcgc ctgtaccccccgcgacggcgtgctgaagggcgagatccaccaggccctgaagctgaa ggacggcggccactacctggtggagttcaagaccatctacatggccaagaagcccg tgcaactgcccggctactactacgtggacaccaagctggacatcacctcccacaac gaggactacaccatcgtggaacagtacgagcgctccgagggccgccaccacctgtt cctgtacggcatggacgagctgtacaagtaa | tdTomato DNA sequence (GenBank: AY678269.1) |
| 54 | MVSKGEEVIKEFMRFKVRMEGSMNGHEFEIEGEGEGRPYEGTQTAKLKVTKGGPLP FAWDILSPQFMYGSKAYVKHPADIPDYKKLSFPEGFKWERVMNFEDGGLVTVTQDS SLQDGTLIYKVKMRGTNFPPDGPVMQKKTMGWEASTERLYPRDGVLKGEIHQALKL KDGGHYLVEFKTIYMAKKPVQLPGYYYVDTKLDITSHNEDYTIVEQYERSEGRHHL FLGHGTGSTGSGSSGTASSEDNNMAVIKEFMRFKVRMEGSMNGHEFEIEGEGEGRP YEGTQTAKLKVTKGGPLPFAWDILSPQFMYGSKAYVKHPADIPDYKKLSFPEGFKW ERVMNFEDGGLVTVTQDSSLQDGTLIYKVKMRGTNFPPDGPVMQKKTMGWEASTER LYPRDGVLKGEIHQALKLKDGGHYLVEFKTIYMAKKPVQLPGYYYVDTKLDITSHN EDYTIVEQYERSEGRHHLFLYGMDELYK | tdTomato protein sequence (GenBank: AAV52169.1) |
| 55 | ctcgagggcggcggagagggcagaggaagtcttctaacatgcggtgacgtggagga gaatcccggccctagg | T2A DNA |
| 56 | LEGGGEGRGSLLTCGDVEENPGPR | T2A protein |
| 57 | CGGGTGAAGTTCAGCAGAAGCGCCGACGCCCCTGCCTACCAGCAGGGCCAGAATCA GCTGTACAACGAGCTGAACCTGGGCAGAAGGGAAGAGTACGACGTCCTGGATAAGC GGAGAGGCCGGGACCCTGAGATGGGCGGCAAGCCTCGGCGGAAGAACCCCCAGGAA GGCCTGTATAACGAACTGCAGAAAGACAAGATGGCCGAGGCCTACAGCGAGATCGG CATGAAGGGCGAGCGGAGGCGGGGCAAGGGCCACGACGGCCTGTATCAGGGCCTGT CCACCGCCACCAAGGATACCTACGACGCCCTGCACATGCAGGCCCTGCCCCCAAGG | CD3 zeta DNA |
| 58 | ESKYGPPCPPCPAPEFLGGPSVFLFPPKPKDTLMISRTPEVTCVVVDVSQEDPEVQ FNWYVDGVEVHNAKTKPREEQFNSTYRVVSVLTVLHQDWLNGKEYKCKVSNKGLPS SIEKTISKAKGQPREPQVYTLPPSQEEMTKNQVSLTCLVKGFYPSDIAVEWESNGQ PENNYKTTPPVLDSDGSFFLYSRLTVDKSRWQEGNVFSCSVMHEALHNHYTQKSLS LSLGK | Hinge-CH2-CH3 spacer(long spacer) |
| 59 | EVKLQQSGAELVRPGSSVKISCKASGYAFSSYWMNWVKQRPGQGLEWIGQIYPGDG DTNYNGKFKGQATLTADKSSSTAYMQLSGLTSEDSAVYFCARKTISSVVDFYFDYW GQGTTVTVSS | SJ25C1 VH |
| 60 | DIELTQSPKFMSTSVGDRVSVTCKASQNVGTNVAWYQQKPGQSPKPLIYSATYRNS GVPDRFTGSGSGTDFTLTITNVQSKDLADYFCQQYNRYPYTSGGGTKLEIKR EVKLQQSGAELVRPGSSVKISCKASGYAFSSYWMNWVKQRPGQGLEWIGQIYPGDG | SJ25C1 VL |
| 61 | DTNYNGKFKGQATLTADKSSSTAYMQLSGLTSEDSAVYFCARKTISSVVDFYFDYW GQGTTVTVSSGGGGSGGGGSGGGGSDIELTQSPKFMSTSVGDRVSVTCKASQNVGT NVAWYQQKPGQSPKPLIYSATYRNSGVPDRFTGSGSGTDFTLTITNVQSKDLADYF CQQYNRYPYTSGGGTKLEIKR | SJ25C1 scFv |

-continued

SEQUENCES

| SEQ ID NO: | Sequence | Description |
|---|---|---|
| 62 | EVKLQESGPGLVAPSQSLSVTCTVSGVSLPDYGVSWIRQPPRKGLEWLGVIWGSET<br>TYYNSALKSRLTIIKDNSKSQVFLKMNSLQTDDTAIYYCAKHYYYGGSYAMDYWGQ<br>GTSVTVSS | FMC63 VH |
| 63 | DIQMTQTTSSLSASLGDRVTISCRASQDISKYLNWYQQKPDGTVKLLIYHTSRLHS<br>GVPSRFSGSGSGTDYSLTISNLEQEDIATYFCQQGNTLPYTFGGGTKLEIT | FMC63 VL |
| 64 | DIQMTQTTSSLSASLGDRVTISCRASQDISKYLNWYQQKPDGTVKLLIYHTSRLHS<br>GVPSRFSGSGSGTDYSLTISNLEQEDIATYFCQQGNTLPYTFGGGTKLEITGSTSG<br>SGKPGSGEGSTKGEVKLQESGPGLVAPSQSLSVTCTVSGVSLPDYGVSWIRQPPRK<br>GLEWLGVIWGSETTYYNSALKSRLTIIKDNSKSQVFLKMNSLQTDDTAIYYCAKHY<br>YYGGSYAMDYWGQGTSVTVSS | FMC63 scFv |
| 65 | TCATTGACAAGATCTTCATG | HumanNur77<br>gRNAtarget1 |
| 66 | GCCTGGGAACACGTGTGCA | HumanNur77<br>gRNA target 2 |
| 67 | -PGGG-$(SGGGG)_5$-P- wherein P is proline, G is glycine and<br>S is serine | linker |
| 68 | GSADDAKKDAAKKDGKS | linker |
| 69 | cgtgaggctccggtgcccgtcagtgggcagagcgcacatcgcccacagtccccgag<br>aagttggggggaggggtcggcaattgaaccggtgcctagagaaggtggcgcggggt<br>aaactgggaaagtgatgtcgtgtactggctccgocttttttcccgagggtgggggag<br>aaccgtatataagtgcagtagtcgccgtgaacgttctttttcgcaacgggtttgcc<br>gccagaacacaggtaagtgccgtgtgtggttcccgcgggcctggcctctttacggg<br>ttatggcccttgcgtgccttgaattacttccacgcccctggctgcagtacgtgatt<br>cttgatcccgagcttcgggttggaagtgggtgggagagttcgaggccttgcgctta<br>aggagccccttcgcctcgtgcttgagttgaggcctggcctgggcgctggggccgcc<br>gcgtgcgaatctggtggcaccttcgcgcctgtctcgctgctttcgataagtctcta<br>gccatttaaaatttttgatgacctgctgcgacgctttttttctggcaagatagtct<br>tgtaaatgcgggccaagatctgcacactggtatttcggtttttggggccgcgggcg<br>gcgacggggcccgtgcgtcccagcgcacatgttcggcgaggcggggcctgcgagcg<br>cggccaccgagaatcggacgggggtagtctcaagctggccggcctgctctggtgcc<br>tggcctcgcgccgccgtgtatcgccccgccctgggcggcaaggctggcccggtcgg<br>caccagttgcgtgagcggaaagatggccgcttcccggccctgctgcagggagctca<br>aaatggaggacgcggcgctcgggagagcgggcgggtgagtcacccacacaaaggaa<br>aagggcctttccgtcctcagccgtcgcttcatgtgactccacggagtaccgggcgc<br>cgtccaggcacctcgattagttctcgagcttttggagtacgtcgtctttaggttgg<br>ggggaggggttttatgcgatggagtttccccacactgagtgggtggagactgaagt<br>taggccagcttggcacttgatgtaattctccttggaatttgcccttttttgagtttg<br>gatcttggttcattctcaagcctcagacagtggttcaaagtttttttcttccattt<br>caggtgtcgtgaa | EF1 alpha promoter<br>(GenBank: J04617.1) |
| 70 | CGTGAGGCTCCGGTGCCCGTCAGTGGGCAGAGCGCACATCGCCCACAGTCCCCGAG<br>AAGTTGGGGGGAGGGGTCGGCAATTGAACCGGTGCCTAGAGAAGGTGGCGCGGGGT<br>AAACTGGGAAAGTGATGTCGTGTACTGGCTCCGCCTTTTTCCCGAGGGTGGGGGAG<br>AACCGTATATAAGTGCACTAGTCGCCGTGAACGTTCTTTTTCGCAACGGGTTTGCC<br>GCCAGAACACAGGTAAGTGCCGTGTGTGGTTCCCGCGGGCCTGGCCTCTTTACGGG<br>TTATGGCCCTTGCGTGCCTTGAATTACTTCCACCTGGCTGCAGTACGTGATTCTTG<br>ATCCCGAGCTTCGGGTTGGAAGTGGGTGGGAGAGTTCGTGGCCTTGCGCTTAAGGA<br>GCCCCTTCGCCTCGTGCTTGAGTTGTGGCCTGGCCTGGGCGCTGGGGCCGCCGCGT<br>GCGAATCTGGTGGCACCTTCGCGCCTGTCTCGCTGCTTTCGATAAGTCTCTAGCCA<br>TTTAAAATTTTTGATGACCTGCTGCGACGCTTTTTTTCTGGCAAGATAGTCTTGTA<br>AATGCGGGCCAAGATCAGCACACTGGTATTTCGGTTTTTGGGGCCGCGGGCGGCGA<br>CGGGGCCCGTGCGTCCCAGCGCACATGTTCGGCGAGGCGGGGCCTGCGAGCGCGGC<br>CACCGAGAATCGGACGGGGGTAGTCTCAAGCTGCCCGGCCTGCTCTGGTGCCTGGC<br>CTCGCGCCGCCGTGTATCGCCCCGCCCTGGGCGGCAAGGCTGGCCCGGTCGGCACC<br>AGTTGCGTGAGCGGAAAGATGGCCGCTTCCCGGCCCTGCTGCAGGGAGCACAAAAT<br>GGAGGACGCGGCGCTCGGGAGAGCGGGCGGGTGAGTCACCCACACAAAGGAAAAGG<br>GCCTTTCCGTCCTCAGCCGTCGCTTCATGTGACTCCACGGAGTACCGGGCGCCGTC<br>CAGGCACCTCGATTAGTTCTCCAGCTTTTGGAGTACGTCGTCTTTAGGTTGGGGGG<br>AGGGGTTTTATGCGATGGAGTTTCCCCACACTGAGTGGGTGGAGACTGAAGTTAGG<br>CCAGCTTGGCACTTGATGTAATTCTCCTTGGAATTTGCCCTTTTTGAGTTTGGATC<br>TTGGTTCATTCTCAAGCCTCAGACAGTGGTTCAAAGTTTTTTTCTTCCATTTCAGG<br>TGTCGTGAAAACTACCCCTAAAAGCCAAA | EF1 alpha promoter |

-continued

SEQUENCES

| SEQ ID NO: | Sequence | Description |
|---|---|---|
| 71 | gggtctctctggttagaccagatctgagcctgggagctctctggctaactagggaa cccactgcttaagcctcaataaagcttgccttgagtgcttcaagtagtgtgtgccc gtctgttgtgtgactctggtaactagagatccctcagacccttttagtcagtgtgg aaaatctctagca | MND promoter |
| 72 | atgcttctcctggtgacaagccttctgctctgtgagttaccacacccagcattcct cctgatccca | GMCSFR alpha chain leader sequence |
| 73 | MLLLVTSLLLCELPHPAFLL IP | GMCSFR alpha chain leader sequence |
| 74 | MALPVTALLLPLALLLHA | CD8 alpha chain leader sequence |
| 75 | MALPVTALLLPLALLLHAARP | CD8 alpha chain leader sequence |
| 76 | RKVCNGIGIGEFKDSLSINATNIKHFKNCTSISGDLHILPVAFRGDSFTHTPPLDP QELDILKTVKEITGFLLIQAWPENRTDLHAFENLEIIRGRTKQHGQFSLAVVSLNI TSLGLRSLKEISDGDVIISGNKNLCYANTINWKKLFGTSGQKTKIISNRGENSCKA TGQVCHALCSPEGCWGPEPRDCVSCRNVSRGRECVDKCNLLEGEPREFVENSECIQ CHPECLPQAMNITCTGRGPDNCIQCAHYIDGPHCVKTCPAGVMGENNTLVWKYADA GHVCHLCHPNCTYGCTGPGLEGCPTNGPKIPSIATGMVGALLLLLVVALGIGLFM | EGFRt |
| 77 | RVKFSRSADAPAYQQGQNQLFNELNLGRREEFDVLDKRRGRDPEMGGKPRRKNPQE GLFNELQKDKMAEAFSEIGMKGERRRGKGHDGLFQGLSTATKDTFDALHMQALPPR | CD3 zeta ITAM mutant |

The invention claimed is:

1. A method for assessing activity of a recombinant receptor, comprising:

a) incubating one or more of reporter T cells, each of said reporter T cells comprising:

(i) a nucleic acid sequence encoding a reporter molecule integrated in an endogenous Nur77 locus under the operable control of a transcriptional regulatory element of the endogenous locus encoding Nur77 and (ii) a recombinant receptor that is a chimeric antigen receptor (CAR) comprising an intracellular signaling region and a binding domain, wherein the T cell is a Jurkat cell line or a derivative thereof, and wherein the incubating is carried out in the presence or absence of an agent that binds to the binding domain of the recombinant receptor and/or an agent that induces or is capable of inducing a signal through the intracellular signaling region of the recombinant receptor; and b) assessing the one or more reporter T cells for expression of the reporter molecule.

2. The method of claim 1, wherein the one or more reporter T cells comprise a plurality of reporter T cells each comprising a polynucleotide encoding a distinct recombinant receptor, wherein the encoded distinct recombinant receptor in a reporter T cell in the plurality of reporter T cells is distinct from the encoded recombinant receptor present in at least one of the other reporter T cells in the plurality.

3. The method of claim 1, wherein the one or more reporter T cells are incubated in the presence of the agent that binds to the binding domain of the recombinant receptor and/or the agent that induces or is capable of inducing a signal through an intracellular signaling region of the recombinant receptor, thereby assessing antigen-specific activity of the recombinant receptor.

4. The method of claim 1, wherein the one or more reporter T cells are incubated in the absence of the agent that binds to the binding domain of the recombinant receptor and/or the agent that induces or is capable of inducing a signal through an intracellular signaling region of the recombinant receptor, thereby assessing tonic signaling and/or antigen independent activity of the recombinant receptor.

5. The method of claim 2, further comprising identifying one or more reporter T cells among the plurality that express the distinct recombinant receptor on the surface of the cell.

6. The method of claim 1, wherein the reporter molecule is or comprises a fluorescent protein, a luciferase, a β-galactosidase, a chloramphenicol acetyltransferase (CAT), or a β-glucuronidase (GUS).

7. The method of claim 1, wherein the agent comprises a target antigen or epitope specifically recognized by the recombinant receptor.

8. The method of claim 2, wherein the plurality of reporter T cells each comprise a polynucleotide encoding the CAR, wherein each polynucleotide is encoded from a vector backbone, wherein the vector backbone comprises a) regulatory elements for expression of components of the CAR, b) a nucleic acid sequence encoding a leader sequence comprising a molecular barcode, c) one or more site(s) for introduction of a nucleic acid sequence encoding the binding domain, d) a nucleic acid sequence encoding a spacer, and e) a nucleic acid sequence encoding the intracellular signaling region.

9. The method of claim 1, wherein prior to the incubating, the nucleic acid sequence encoding the reporter molecule is integrated by:

a) inducing a genetic disruption at one or more target site(s) at the endogenous locus encoding Nur77; and b) introducing a template polynucleotide comprising the nucleic acid encoding the reporter molecule for homology directed repair (HDR).

10. The method of claim 9, wherein the genetic disruption is induced by a fusion protein comprising a DNA-targeting protein and a nuclease or a RNA-guided nuclease that is or comprises a zinc finger nuclease (ZFN), a TAL-effector nuclease, or a CRISPR-Cas9 combination that specifically binds to, recognizes, or hybridizes to the target site.

11. The method of claim 1, wherein the nucleic acid encoding the reporter is present within the genome at a site that is at or near the final exon of the endogenous locus encoding Nur77.

12. The method of claim 9, wherein the one or more target site(s) comprise the nucleic acid sequence TCATTGACAAGATCTTCATG (SEQ ID NO:65) and/or GCCTGGGAACACGTGTGCA (SEQ ID NO:66).

13. The method of claim 9, wherein the template polynucleotide comprises the structure [5' homology arm]-[nucleic acid sequence encoding the reporter molecule]-[3' homology arm], wherein the 5' homology arm or 3' homology arm comprises nucleic acid sequences homologous to nucleic acid sequences present at and/or surrounding the one or more target site(s).

14. The method of claim 1, wherein the one or more reporter T cells comprise a plurality of reporter T cells, and the method, further comprises identifying a T cell from the one or more reporter T cells among the plurality that express the reporter molecule in the presence of the agent, and/or that do not express the reporter molecule in the absence of the agent.

15. The method of claim 1, wherein the one or more reporter T cells comprise a plurality of reporter T cells, and the method further comprises identifying a T cell from the one or more reporter T cells among the plurality that express the reporter molecule in the presence of the agent, and that do not express the reporter molecule in the absence of the agent or have low antigen-independent activity or low tonic signaling.

16. The method of claim 15, wherein the agent comprises a target antigen or epitope specifically recognized by the recombinant receptor.

17. The method of claim 16, wherein the target antigen is expressed by target cells.

18. The method of claim 1, wherein the one or more reporter T cells are incubated with cells lacking expression of a target antigen of the recombinant receptor, such that the agent that binds to the binding domain of the recombinant receptor is absent, thereby assessing antigen-independent activity of the recombinant receptor.

19. The method of claim 1, wherein the one or more reporter T cells are incubated with target cells that express a target antigen recognized by the recombinant receptor, wherein the target antigen is the agent that binds to the binding domain of the recombinant receptor, thereby assessing antigen-dependent activity of the recombinant receptor.

20. The method of claim 1, wherein the one or more reporter T cells are separately incubated with (i) target cells that express a target antigen recognized by the recombinant receptor, wherein the antigen is the agent that binds to the binding domain of the recombinant receptor, and (ii) non-target cells that do not express the target antigen, wherein the method further comprises comparing the expression of the reporter molecule in the reporter T cells incubated with the target cells to the expression of the reporter molecule in the reporter T cells incubated with the non-target cells to determine antigen-dependent signaling and antigen-independent signaling via the recombinant receptor.

21. The method of claim 20, wherein the target cells and the non-target cells are of the same cell type, and the target cells are engineered to express the target antigen and the non-target cells do not express the target antigen.

22. The method of claim 21, further comprising identifying T cells that have greater signaling when the T cells are incubated with the target cells than signaling when the T cells are incubated with the non-target cells.

23. The method of claim 20, wherein the reporter molecule is or comprises a fluorescent protein, a luciferase, a β-galactosidase, a chloramphenicol acetyltransferase (CAT), or a β-glucuronidase (GUS).

24. The method of claim 20, wherein the agent comprises a target antigen or epitope specifically recognized by the recombinant receptor.

25. The method of claim 20, wherein the one or more target site(s) comprise, and/or the nucleic acid is present within the genome at a site comprising, the nucleic acid sequence TCATTGACAAGATCTTCATG (SEQ ID NO:65) and/or GCCTGGGAACACGTGTGCA (SEQ ID NO:66).

26. The method of claim 20, wherein the nucleic acid encoding the reporter molecule is present within the genome at a site that is at or near the final exon of the endogenous locus encoding Nur77.

27. The method of claim 20, wherein the agent comprises a target antigen or epitope specifically recognized by the recombinant receptor.

28. The method of claim 20, the Jurkat cell line or a derivative thereof is Jurkat T cell clone E6-1.

* * * * *